US006210942B1

(12) United States Patent
Lewis et al.

(10) Patent No.: US 6,210,942 B1
(45) Date of Patent: Apr. 3, 2001

(54) RECOMBINANT PINORESINOL/ LARICIRESINOL REDUCTASE, RECOMBINANT DIRIGENT PROTEIN, AND METHODS OF USE

(75) Inventors: Norman G. Lewis; Laurence B. Davin, both of Pullman, WA (US); Albena T. Dinkova-Kostova, Baltimore, MD (US); Masayuki Fujita, Kagawa (JP); David R. Gang, Ann Arbor, MI (US); Simo Sarkanen, S. Minneapolis, MN (US); Joshua D. Ford, Pullman, WA (US)

(73) Assignees: Washington State University Research Foundation, Pullman, Washington; Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/475,316

(22) Filed: Dec. 30, 1999

Related U.S. Application Data

(63) Continuation-in-part of application No. 09/307,653, filed on May 7, 1999.
(60) Provisional application No. 60/054,380, filed on Jul. 31, 1997, and provisional application No. 60/030,522, filed on Nov. 8, 1996.

(51) Int. Cl.[7] .................................................. C12N 9/00
(52) U.S. Cl. .................. 435/183; 435/320.1; 435/325; 435/252.3; 435/254.11; 435/419; 435/254.2; 536/23.1; 536/23.2
(58) Field of Search ................... 435/183, 320.1, 435/325, 252.3, 254.11, 419, 254.2; 536/23.1, 23.2

(56) References Cited

PUBLICATIONS

Katayama, T. et al. "Novel Benzylic Ether Reductions in Lignan Biogenesis in *Forsythia Intermedia*," *Phytochemistry*, 33(3):581–591 (1993).

Katayama, T. et al. "A Extraordinary Accumulation of (−)–Pinoresinol in Cell–Free Extracts of *Forsythia Intermedia*: Evidence For Enantiospecific Reduction of (+)–Pinoresinol," *Phytochemistry*, 31(11):3875 (1992).

Chu, A. et al. "Sterospecificity of (+)–Pinorsinol and (+)–Lariciresinol Reductases from *Forsythia intermedia*," *The Journal of Biological Chemistry*, 268(36):27026–27033 (1993).

*Primary Examiner*—Ponnathapu Achutamurthy
*Assistant Examiner*—Kathleen Kerr
(74) *Attorney, Agent, or Firm*—Christensen O'Connor Johnson Kindness PLLC

(57) ABSTRACT

Dirigent proteins and pinoresinol/lariciresinol reductases have been isolated, together with cDNAs encoding dirigent proteins and pinoresinol/lariciresinol reductases. Accordingly, isolated DNA sequences are provided which code for the expression of dirigent proteins and pinoresinol/ lariciresinol reductases. In other aspects, replicable recombinant cloning vehicles are provided which code for dirigent proteins or pinoresinol/lariciresinol reductases or for a base sequence sufficiently complementary to at least a portion of dirigent protein or pinoresinol/lariciresinol reductase DNA or RNA to enable hybridization therewith. In yet other aspects, modified host cells are provided that have been transformed, transfected, infected and/or injected with a recombinant cloning vehicle and/or DNA sequence encoding dirigent protein or pinoresinol/lariciresinol reductase. Thus, systems and methods are provided for the recombinant expression of dirigent proteins and/or pinoresinol/ lariciresinol reductases.

38 Claims, 1 Drawing Sheet

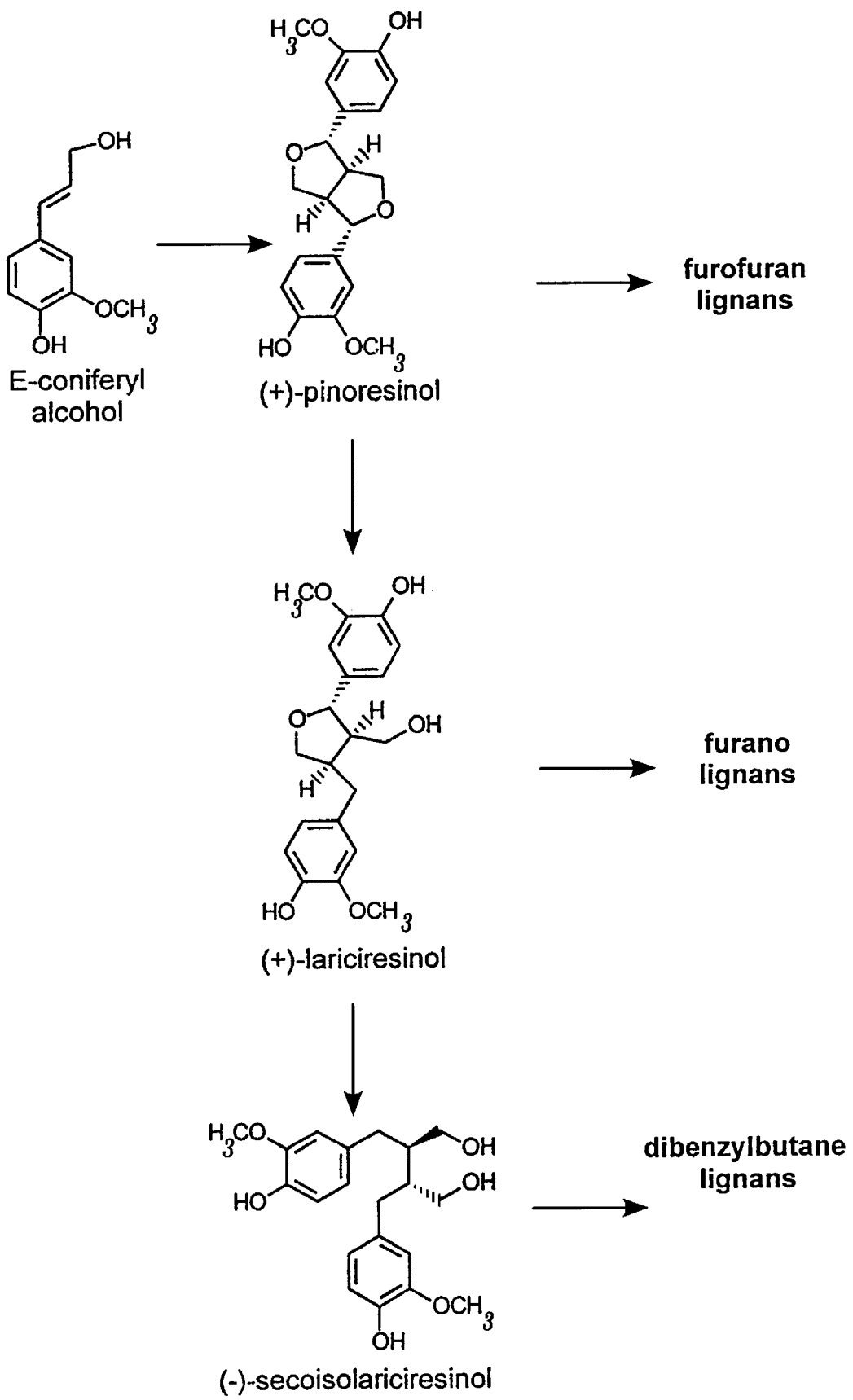

SEQUENCE LISTING

```
<160> NUMBER OF SEQ ID NOS:  122

<210> SEQ ID NO 1
<211> LENGTH: 28
<212> TYPE: PRT
<213> ORGANISM: Forsythia x intermedia
<220> FEATURE:
<221> NAME/KEY: PEPTIDE
<222> LOCATION: (1)..(28)
<223> OTHER INFORMATION: Peptide fragment, wherein Xaa = unknown amino
      acid

<400> SEQUENCE: 1

Lys Pro Arg Pro Xaa Arg Xaa Xaa Lys Glu Leu Val Phe Tyr Phe Xaa
  1               5                  10                  15

Asp Ile Leu Phe Lys Gly Xaa Asn Tyr Asn Xaa Ala
             20                  25

<210> SEQ ID NO 2
<211> LENGTH: 24
<212> TYPE: PRT
<213> ORGANISM: Forsythia x intermedia

<400> SEQUENCE: 2

Thr Ala Met Ala Val Pro Phe Asn Tyr Gly Asp Leu Val Val Phe Asp
  1               5                  10                  15

Asp Pro Ile Thr Leu Asp Asn Asn
             20

<210> SEQ ID NO 3
<211> LENGTH: 16
<212> TYPE: PRT
<213> ORGANISM: Forsythia x intermedia
<220> FEATURE:
<221> NAME/KEY: PEPTIDE
<222> LOCATION: (1)..(16)
<223> OTHER INFORMATION: Peptide fragment, wherein Xaa = unknown amino
      acid

<400> SEQUENCE: 3

Tyr Val Gly Thr Leu Asn Phe Ala Gly Ala Asp Pro Leu Leu Xaa Lys
  1               5                  10                  15

<210> SEQ ID NO 4
<211> LENGTH: 15
<212> TYPE: PRT
<213> ORGANISM: Forsythia x intermedia

<400> SEQUENCE: 4

Asp Ile Ser Val Ile Gly Gly Thr Gly Asp Phe Phe Met Ala Arg
  1               5                  10                  15

<210> SEQ ID NO 5
<211> LENGTH: 15
<212> TYPE: PRT
```

```
<213> ORGANISM: Forsythia x intermedia
<220> FEATURE:
<221> NAME/KEY: PEPTIDE
<222> LOCATION: (1)..(15)
<223> OTHER INFORMATION: Peptide fragment, wherein Xaa = unknown amino
      acid

<400> SEQUENCE: 5

Gly Val Ala Thr Leu Met Thr Asp Ala Phe Glu Gly Asp Xaa Tyr
 1               5                  10                  15

<210> SEQ ID NO 6
<211> LENGTH: 10
<212> TYPE: PRT
<213> ORGANISM: Forsythia x intermedia

<400> SEQUENCE: 6

Ala Gln Gly Met Tyr Phe Tyr Asp Gln Lys
 1               5                  10

<210> SEQ ID NO 7
<211> LENGTH: 5
<212> TYPE: PRT
<213> ORGANISM: Forsythia x intermedia

<400> SEQUENCE: 7

Tyr Asn Ala Trp Leu
 1               5

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(21)
<223> OTHER INFORMATION: PCR primer PSINT1, wherein N = any nucleic acid

<400> SEQUENCE: 8
aargarytng tnttytaytt y                                            21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(20)
<223> OTHER INFORMATION: PCR primer PSI1R, wherein N = any nucleic acid

<400> SEQUENCE: 9
tarttraang gnacngccat                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(20)
<223> OTHER INFORMATION: PCR primer PSI2R, wherein N = any nucleic acid

<400> SEQUENCE: 10
```

```
gtnatnggrt crtcraanac                                                    20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(19)
<223> OTHER INFORMATION: PCR primer PSI7R, wherein N = any nucleic acid

<400> SEQUENCE: 11
ccatraaraa rtcnccngt                                                     19

<210> SEQ ID NO 12
<211> LENGTH: 901
<212> TYPE: DNA
<213> ORGANISM: Forsythia x intermedia
<220> FEATURE:
<221> NAME/KEY: CDS
<222> LOCATION: (26)..(583)

<400> SEQUENCE: 12
atttcggcac gagattaaac caaac atg gtt tct aaa aca caa att gta gct         52
                            Met Val Ser Lys Thr Gln Ile Val Ala
                             1               5 ctt ttc ctt tgc ttc ctc act tcc acc tct tcc gcc acc tac ggc cgc        100
Leu Phe Leu Cys Phe Leu Thr Ser Thr Ser Ser Ala Thr Tyr Gly Arg
 10              15                  20                  25 aag cca cgc cct cgc cgg ccc tgc aaa gaa ttg gtg ttc tat ttc cac        148
Lys Pro Arg Pro Arg Arg Pro Cys Lys Glu Leu Val Phe Tyr Phe His
             30                  35                  40 gac gta ctt ttc aaa gga aat aat tac cac aat gcc act tcc gcc ata        196
Asp Val Leu Phe Lys Gly Asn Asn Tyr His Asn Ala Thr Ser Ala Ile
         45                  50                  55 gtc ggg tcc ccc caa tgg ggc aac aag act gcc atg gcc gtg cca ttc        244
Val Gly Ser Pro Gln Trp Gly Asn Lys Thr Ala Met Ala Val Pro Phe
     60                  65                  70 aat tat ggt gac cta gtt gtg ttc gac gat ccc att acc tta gac aac        292
Asn Tyr Gly Asp Leu Val Val Phe Asp Asp Pro Ile Thr Leu Asp Asn
 75                  80                  85 aat ctg cat tca ccc cca gtg ggt cgg gcg caa ggg atg tac ttc tat        340
Asn Leu His Ser Pro Pro Val Gly Arg Ala Gln Gly Met Tyr Phe Tyr
 90                  95                 100                 105 gat caa aaa aat aca tac aat gct tgg cta ggg ttc tca ttt ttg ttc        388
Asp Gln Lys Asn Thr Tyr Asn Ala Trp Leu Gly Phe Ser Phe Leu Phe
                110                 115                 120 aat tca act aag tat gtt gga acc ttg aac ttt gct ggg gct gat cca        436
Asn Ser Thr Lys Tyr Val Gly Thr Leu Asn Phe Ala Gly Ala Asp Pro
            125                 130                 135 ttg ttg aac aag act aga gac ata tca gtc att ggt gga act ggt gac        484
Leu Leu Asn Lys Thr Arg Asp Ile Ser Val Ile Gly Gly Thr Gly Asp
        140                 145                 150 ttt ttc atg gcg aga ggg gtt gcc act ttg atg acc gat gcc ttt gaa        532
Phe Phe Met Ala Arg Gly Val Ala Thr Leu Met Thr Asp Ala Phe Glu
    155                 160                 165 ggg gat gtg tat ttc cgc ctt cgt gtc gat att aat ttg tat gaa tgt        580
Gly Asp Val Tyr Phe Arg Leu Arg Val Asp Ile Asn Leu Tyr Glu Cys
170                 175                 180                 185 tgg taaacaattt agccgtatat atatatatat atggctatac atatttcata            633
```

Trp

```
gaatccagat tgctgtttc aaatgtgtgt ttctttagtt gtgccaccaa taaaaaatg      693 tacacattat ttaataaata taattattta atgtgttcat ttttgaagtt aaatttaagt    753
tgtatttatt tgattatgta taaattctct attagtaaaa tagtcaaagt gacacatatt    813
caagacgaca tatgtaactt tatttcatat cttcaacaag ttcaataatg tcatatatat    873
tgtactattg aaaaaaaaaa aaaaaaa                                         901
```

```
<210> SEQ ID NO 13
<211> LENGTH: 186
<212> TYPE: PRT
<213> ORGANISM: Forsythia x intermedia

<400> SEQUENCE: 13
```

```
Met Val Ser Lys Thr Gln Ile Val Ala Leu Phe Leu Cys Phe Leu Thr
 1               5                  10                  15

Ser Thr Ser Ser Ala Thr Tyr Gly Arg Lys Pro Arg Pro Arg Arg Pro
                20                  25                  30

Cys Lys Glu Leu Val Phe Tyr Phe His Asp Val Leu Phe Lys Gly Asn
            35                  40                  45

Asn Tyr His Asn Ala Thr Ser Ala Ile Val Gly Ser Pro Gln Trp Gly
        50                  55                  60

Asn Lys Thr Ala Met Ala Val Pro Phe Asn Tyr Gly Asp Leu Val Val
 65                  70                  75                  80

Phe Asp Asp Pro Ile Thr Leu Asp Asn Asn Leu His Ser Pro Pro Val
                85                  90                  95

Gly Arg Ala Gln Gly Met Tyr Phe Tyr Asp Gln Lys Asn Thr Tyr Asn
            100                 105                 110

Ala Trp Leu Gly Phe Ser Phe Leu Phe Asn Ser Thr Lys Tyr Val Gly
        115                 120                 125

Thr Leu Asn Phe Ala Gly Ala Asp Pro Leu Leu Asn Lys Thr Arg Asp
    130                 135                 140

Ile Ser Val Ile Gly Gly Thr Gly Asp Phe Phe Met Ala Arg Gly Val
145                 150                 155                 160

Ala Thr Leu Met Thr Asp Ala Phe Glu Gly Asp Val Tyr Phe Arg Leu
                165                 170                 175

Arg Val Asp Ile Asn Leu Tyr Glu Cys Trp
            180                 185
```

```
<210> SEQ ID NO 14
<211> LENGTH: 858
<212> TYPE: DNA
<213> ORGANISM: Forsythia x intermedia
<220> FEATURE:
<221> NAME/KEY: CDS
<222> LOCATION: (19)..(573)

<400> SEQUENCE: 14
```

```
aattcggcac gaggaaaa atg gca gct aaa aca caa acc aca gcc ctt ttc      51
                    Met Ala Ala Lys Thr Gln Thr Thr Ala Leu Phe
                     1               5                  10 ctc tgc ctc ctc atc tgc atc tcc gcc gtg tac ggc cac aaa acc agg      99
Leu Cys Leu Leu Ile Cys Ile Ser Ala Val Tyr Gly His Lys Thr Arg
            15                  20                  25 tct cga cgc ccc tgt aaa gag ctc gtt ttc ttc ttc cac gac atc ctc     147
Ser Arg Arg Pro Cys Lys Glu Leu Val Phe Phe Phe His Asp Ile Leu
        30                  35                  40
```

```
tac cta gga tac aat aga aac aat gcc acc gct gtc ata gta gcc tct       195
Tyr Leu Gly Tyr Asn Arg Asn Asn Ala Thr Ala Val Ile Val Ala Ser
         45                  50                  55 cct caa tgg gga aac aag act gcc atg gct aaa cct ttc aat ttt ggt       243
Pro Gln Trp Gly Asn Lys Thr Ala Met Ala Lys Pro Phe Asn Phe Gly
 60                  65                  70                  75 gat ttg gtt gtg ttt gat gat ccc att acc tta gac aac aac ctg cat       291
Asp Leu Val Val Phe Asp Asp Pro Ile Thr Leu Asp Asn Asn Leu His
                     80                  85                  90 tct cct ccg gtc ggc cgg gct cag gga act tat ttc tac gat caa tgg       339
Ser Pro Pro Val Gly Arg Ala Gln Gly Thr Tyr Phe Tyr Asp Gln Trp
                 95                 100                 105 agt att tat ggt gca tgg ctt gga ttt tca ttt ttg ttc aat tct act       387
Ser Ile Tyr Gly Ala Trp Leu Gly Phe Ser Phe Leu Phe Asn Ser Thr
            110                 115                 120 gat tat gtt gga act cta aat ttt gct gga gct gat cca ttg att aac       435
Asp Tyr Val Gly Thr Leu Asn Phe Ala Gly Ala Asp Pro Leu Ile Asn
        125                 130                 135 aaa act agg gac att tca gta att gga gga act ggt gat ttt ttc atg       483
Lys Thr Arg Asp Ile Ser Val Ile Gly Gly Thr Gly Asp Phe Phe Met
140                 145                 150                 155 gct aga ggg gta gcc act gtg tcg acc gat gct ttt gaa ggg gat gtt       531
Ala Arg Gly Val Ala Thr Val Ser Thr Asp Ala Phe Glu Gly Asp Val
                    160                 165                 170 tat ttc agg ctt cgt gtt gat att agg ttg tat gag tgt tgg               573
Tyr Phe Arg Leu Arg Val Asp Ile Arg Leu Tyr Glu Cys Trp
                175                 180                 185 taaatttacc ttattttttcc attttcttga gtttgactcg gatttgacta ataatgtctt    633
ctgtaatcct tgtttttgat caatttgtgg cgatttttatc aattagtgat tgtttggttc    693 atatttaat ctgttaaaaa aaattgtggt caaaagccaa taaccacaac cgtagggagt      753
tttttccgtt aagggaaaa aaaagtatgt ccatgtgtta ctacgttttc aatttcattc      813
aaaatttgct tttcaatcat cttcttcaaa aaaaaaaaaa aaaaa                     858

<210> SEQ ID NO 15
<211> LENGTH: 185
<212> TYPE: PRT
<213> ORGANISM: Forsythia x intermedia

<400> SEQUENCE: 15

Met Ala Ala Lys Thr Gln Thr Thr Ala Leu Phe Leu Cys Leu Leu Ile
 1               5                  10                  15

Cys Ile Ser Ala Val Tyr Gly His Lys Thr Arg Ser Arg Pro Cys
            20                  25                  30

Lys Glu Leu Val Phe Phe His Asp Ile Leu Tyr Leu Gly Tyr Asn
         35                  40                  45

Arg Asn Asn Ala Thr Ala Val Ile Val Ala Ser Pro Gln Trp Gly Asn
 50                  55                  60

Lys Thr Ala Met Ala Lys Pro Phe Asn Phe Gly Asp Leu Val Val Phe
 65                  70                  75                  80

Asp Asp Pro Ile Thr Leu Asp Asn Asn Leu His Ser Pro Pro Val Gly
                 85                  90                  95

Arg Ala Gln Gly Thr Tyr Phe Tyr Asp Gln Trp Ser Ile Tyr Gly Ala
            100                 105                 110

Trp Leu Gly Phe Ser Phe Leu Phe Asn Ser Thr Asp Tyr Val Gly Thr
        115                 120                 125

Leu Asn Phe Ala Gly Ala Asp Pro Leu Ile Asn Lys Thr Arg Asp Ile
```

```
                  130              135              140
Ser Val Ile Gly Gly Thr Gly Asp Phe Phe Met Ala Arg Gly Val Ala
145                 150                  155                 160

Thr Val Ser Thr Asp Ala Phe Glu Gly Asp Val Tyr Phe Arg Leu Arg
                    165                 170                 175

Val Asp Ile Arg Leu Tyr Glu Cys Trp
                180                  185

<210> SEQ ID NO 16
<211> LENGTH: 948
<212> TYPE: DNA
<213> ORGANISM: Tsuga heterophylla
<220> FEATURE:
<221> NAME/KEY: CDS
<222> LOCATION: (104)..(688)

<400> SEQUENCE: 16
gggcaccctc tcttgttaat tgagcccttc tcctcctact tctcttgtta gttctttgat     60
cccatatctt cttctataat cactttagtc tataagattg tca atg gca atc aag    115
                                             Met Ala Ile Lys
                                                  1 aat cgt aat aga gct gtg cac ttg tgt ttt cta tgg ctt cta ctg tcc    163
Asn Arg Asn Arg Ala Val His Leu Cys Phe Leu Trp Leu Leu Leu Ser
  5              10                  15                  20 tct gtg ttg ttg caa aca agt gat ggg aaa agc tgg aag aag cac cga    211
Ser Val Leu Leu Gln Thr Ser Asp Gly Lys Ser Trp Lys Lys His Arg
             25                  30                  35 ctc cga aag cct tgt agg aat ctg gtg ttg tat ttc cat gat gta atc    259
Leu Arg Lys Pro Cys Arg Asn Leu Val Leu Tyr Phe His Asp Val Ile
         40                  45                  50 tac aat ggc agc aac gcc aag aac gct aca tcc aca ctt gtg ggt gct    307
Tyr Asn Gly Ser Asn Ala Lys Asn Ala Thr Ser Thr Leu Val Gly Ala
     55                  60                  65 ccc cac ggg tct aac ctc aca ctt ctc gct gga aaa gac aac cac ttt    355
Pro His Gly Ser Asn Leu Thr Leu Leu Ala Gly Lys Asp Asn His Phe
 70                  75                  80 gga gat ctg gcg gtg ttt gac gat ccc atc act ctt gac aac aat ttc    403
Gly Asp Leu Ala Val Phe Asp Asp Pro Ile Thr Leu Asp Asn Asn Phe
 85                  90                  95                 100 cac tct cct ccg gtg ggc aga gct cag gga ttc tac ttt tat gac atg    451
His Ser Pro Pro Val Gly Arg Ala Gln Gly Phe Tyr Phe Tyr Asp Met
                105                 110                 115 aag aac acc ttc agc tcc tgg ctt gga ttc acg ttt gta ctc aac tct    499
Lys Asn Thr Phe Ser Ser Trp Leu Gly Phe Thr Phe Val Leu Asn Ser
            120                 125                 130 aca gat tac aaa ggc acc atc acg ttc tct gga gcc gat cca atc ctt    547
Thr Asp Tyr Lys Gly Thr Ile Thr Phe Ser Gly Ala Asp Pro Ile Leu
        135                 140                 145 act aaa tac aga gat ata tca gtg gtg gga gga act gga gat ttc ata    595
Thr Lys Tyr Arg Asp Ile Ser Val Val Gly Gly Thr Gly Asp Phe Ile
    150                 155                 160 atg gca aga gga atc gcc aca atc tcc acc gat gcg tat gaa ggc gac    643
Met Ala Arg Gly Ile Ala Thr Ile Ser Thr Asp Ala Tyr Glu Gly Asp
165                 170                 175                 180 gtt tac ttc cgt ctc tgc gtg aat atc aca ctc tat gag tgc tac        688
Val Tyr Phe Arg Leu Cys Val Asn Ile Thr Leu Tyr Glu Cys Tyr
                185                 190                 195 tgagtgctat aggtctattt tctccttcga ctatccattt atatgttcat tttagttgaa    748
ctagtgtttt cttgtgcgag agatatgcac gaagctctga gatattgtag cgtgaagttc    808
```

```
ctttagcagc cgaataatgt atttcgattt tgtcgaaggc catatctaat attgtcaagg      868
gaaaatgcag aattctatgt cggtcaagca cttttattta aaaataaaag aaatattggt      928
taaaaaaaaa aaaaaaaaa                                                   948
```

<210> SEQ ID NO 17
<211> LENGTH: 195
<212> TYPE: PRT
<213> ORGANISM: Tsuga heterophylla

<400> SEQUENCE: 17

```
Met Ala Ile Lys Asn Arg Asn Arg Ala Val His Leu Cys Phe Leu Trp
 1               5                  10                  15

Leu Leu Leu Ser Ser Val Leu Leu Gln Thr Ser Asp Gly Lys Ser Trp
             20                  25                  30

Lys Lys His Arg Leu Arg Lys Pro Cys Arg Asn Leu Val Leu Tyr Phe
         35                  40                  45

His Asp Val Ile Tyr Asn Gly Ser Asn Ala Lys Asn Ala Thr Ser Thr
     50                  55                  60

Leu Val Gly Ala Pro His Gly Ser Asn Leu Thr Leu Leu Ala Gly Lys
 65                  70                  75                  80

Asp Asn His Phe Gly Asp Leu Ala Val Phe Asp Asp Pro Ile Thr Leu
                 85                  90                  95

Asp Asn Asn Phe His Ser Pro Pro Val Gly Arg Ala Gln Gly Phe Tyr
            100                 105                 110

Phe Tyr Asp Met Lys Asn Thr Phe Ser Ser Trp Leu Gly Phe Thr Phe
        115                 120                 125

Val Leu Asn Ser Thr Asp Tyr Lys Gly Thr Ile Thr Phe Ser Gly Ala
    130                 135                 140

Asp Pro Ile Leu Thr Lys Tyr Arg Asp Ile Ser Val Val Gly Gly Thr
145                 150                 155                 160

Gly Asp Phe Ile Met Ala Arg Gly Ile Ala Thr Ile Ser Thr Asp Ala
                165                 170                 175

Tyr Glu Gly Asp Val Tyr Phe Arg Leu Cys Val Asn Ile Thr Leu Tyr
            180                 185                 190

Glu Cys Tyr
        195
```

<210> SEQ ID NO 18
<211> LENGTH: 849
<212> TYPE: DNA
<213> ORGANISM: Tsuga heterophylla
<220> FEATURE:
<221> NAME/KEY: CDS
<222> LOCATION: (71)..(625)

<400> SEQUENCE: 18

```
gttctgttcc aaattctaat tagccttcca ttcattccag gatcccactc ttcttccttc       60
aagattggca atg gct atc aag agt aat agg gct gtg cgt ttc tgc ttt        109
             Met Ala Ile Lys Ser Asn Arg Ala Val Arg Phe Cys Phe
               1               5                  10 gta tgg ctt ctg ttg ttg caa agt ggt ttt gta ttt cca ctc cca cag        157
Val Trp Leu Leu Leu Leu Gln Ser Gly Phe Val Phe Pro Leu Pro Gln
 15                  20                  25 cct tgt agg aat ctg gtt ttg tat ttc cac gat gta ctc tac aat ggc        205
Pro Cys Arg Asn Leu Val Leu Tyr Phe His Asp Val Leu Tyr Asn Gly
 30                  35                  40                  45
```

```
ttc aac gcc cac aac gct aca tct aca ctt gtg ggt gct cca cag ggg      253
Phe Asn Ala His Asn Ala Thr Ser Thr Leu Val Gly Ala Pro Gln Gly
                50                  55                  60 gct aac ctc aca ctt ctc gct gga aaa gac aac cac ttt gga gat ctg      301
Ala Asn Leu Thr Leu Leu Ala Gly Lys Asp Asn His Phe Gly Asp Leu
            65                  70                  75 gcg gtg ttc gac gat ccc atc act ctt gac aac aat ttc cag tct cct      349
Ala Val Phe Asp Asp Pro Ile Thr Leu Asp Asn Asn Phe Gln Ser Pro
        80                  85                  90 ccg gtg ggc aga gct cag gga ttc tac ttt tat gac atg aag aac acc      397
Pro Val Gly Arg Ala Gln Gly Phe Tyr Phe Tyr Asp Met Lys Asn Thr
    95                 100                 105 ttc agc tcc tgg ctt gga ttc acg ttt gta ctc aac tct aca gat tac      445
Phe Ser Ser Trp Leu Gly Phe Thr Phe Val Leu Asn Ser Thr Asp Tyr
110                 115                 120                 125 aaa ggc acc atc acg ttc tct gga gcc gat cca atc ctt act aaa tac      493
Lys Gly Thr Ile Thr Phe Ser Gly Ala Asp Pro Ile Leu Thr Lys Tyr
                130                 135                 140 aga gat ata tca gtg gtg gga gga act gga gat ttc ata atg gca aga      541
Arg Asp Ile Ser Val Val Gly Gly Thr Gly Asp Phe Ile Met Ala Arg
            145                 150                 155 gga atc gcc aca atc tcc acc gat gcg tat gaa gga gat gtt tac ttc      589
Gly Ile Ala Thr Ile Ser Thr Asp Ala Tyr Glu Gly Asp Val Tyr Phe
        160                 165                 170 cgt ctc cgc gtc aat atc aca ctc tat gaa tgc tac tgatattatt          635
Arg Leu Arg Val Asn Ile Thr Leu Tyr Glu Cys Tyr
    175                 180                 185 aagtagctac tgtttctcgt ctggtctcgc catttcgatg ctcttttttaa cattagtgct     695 ttccataaat tgttgtagcc tctcaataaa acccagtaaa atatttcttc tgtttattta     755
gcagcttcca aatcattgta ttagtatttt atattatttg gatttatac aagtccataa     815 aatatttctt cagctaaaaa aaaaaaaaaa aaaa                                 849

<210> SEQ ID NO 19
<211> LENGTH: 185
<212> TYPE: PRT
<213> ORGANISM: Tsuga heterophylla

<400> SEQUENCE: 19

Met Ala Ile Lys Ser Asn Arg Ala Val Arg Phe Cys Phe Val Trp Leu
 1                5                  10                  15

Leu Leu Leu Gln Ser Gly Phe Val Phe Pro Leu Pro Gln Pro Cys Arg
                20                  25                  30

Asn Leu Val Leu Tyr Phe His Asp Val Leu Tyr Asn Gly Phe Asn Ala
            35                  40                  45

His Asn Ala Thr Ser Thr Leu Val Gly Ala Pro Gln Gly Ala Asn Leu
        50                  55                  60

Thr Leu Leu Ala Gly Lys Asp Asn His Phe Gly Asp Leu Ala Val Phe
65                  70                  75                  80

Asp Asp Pro Ile Thr Leu Asp Asn Asn Phe Gln Ser Pro Pro Val Gly
                85                  90                  95

Arg Ala Gln Gly Phe Tyr Phe Tyr Asp Met Lys Asn Thr Phe Ser Ser
            100                 105                 110

Trp Leu Gly Phe Thr Phe Val Leu Asn Ser Thr Asp Tyr Lys Gly Thr
        115                 120                 125

Ile Thr Phe Ser Gly Ala Asp Pro Ile Leu Thr Lys Tyr Arg Asp Ile
130                 135                 140
```

```
Ser Val Val Gly Gly Thr Gly Asp Phe Ile Met Ala Arg Gly Ile Ala
145                 150                 155                 160

Thr Ile Ser Thr Asp Ala Tyr Glu Gly Asp Val Tyr Phe Arg Leu Arg
            165                 170                 175

Val Asn Ile Thr Leu Tyr Glu Cys Tyr
        180                 185

<210> SEQ ID NO 20
<211> LENGTH: 873
<212> TYPE: DNA
<213> ORGANISM: Thuja plicata
<220> FEATURE:
<221> NAME/KEY: CDS
<222> LOCATION: (25)..(591)

<400> SEQUENCE: 20
gttgcacgag ggatttcaag agat atg agt aga ata gca ttt cat ttg tgc         51
                          Met Ser Arg Ile Ala Phe His Leu Cys
                            1               5 ttc atg ggg ctt ctg ctc tct tcc acg gtg ctc aga aat gta gat ggg        99
Phe Met Gly Leu Leu Leu Ser Ser Thr Val Leu Arg Asn Val Asp Gly
 10                  15                  20                  25 cat gca tgg aag agg caa ctt cca atg cca tgt aag aat ttg gtg ctc       147
His Ala Trp Lys Arg Gln Leu Pro Met Pro Cys Lys Asn Leu Val Leu
                 30                  35                  40 tac ttt cat gat ata ctc tac aat ggc aaa aac att cac aat gca act       195
Tyr Phe His Asp Ile Leu Tyr Asn Gly Lys Asn Ile His Asn Ala Thr
             45                  50                  55 gct gcg ctg gtt gca gct cct gcg tgg ggc aat ctc act act ttc gct       243
Ala Ala Leu Val Ala Ala Pro Ala Trp Gly Asn Leu Thr Thr Phe Ala
         60                  65                  70 gaa cct ttc aag ttt gga gat gtg gtt gtg ttt gac gat ccc att act       291
Glu Pro Phe Lys Phe Gly Asp Val Val Val Phe Asp Asp Pro Ile Thr
 75                  80                  85 ctc gac aac aat ctt cac tct cct cct gtg gga aga gcg cag gga ttt       339
Leu Asp Asn Asn Leu His Ser Pro Pro Val Gly Arg Ala Gln Gly Phe
 90                  95                 100                 105 tat ttg tac aac atg aag act act tac aat gct tgg ttg ggg ttc aca       387
Tyr Leu Tyr Asn Met Lys Thr Thr Tyr Asn Ala Trp Leu Gly Phe Thr
                110                 115                 120 ttt gtg ctg aat tcg aca gat tat aag ggc aca atc acc ttc aat ggc       435
Phe Val Leu Asn Ser Thr Asp Tyr Lys Gly Thr Ile Thr Phe Asn Gly
            125                 130                 135 gcc gac ccc ccg ctg gtt aag tac aga gat ata tcc gtt gtt ggc ggt       483
Ala Asp Pro Pro Leu Val Lys Tyr Arg Asp Ile Ser Val Val Gly Gly
        140                 145                 150 acg ggt gat ttc ttg atg gcg aga gga att gcc acc ctt tct act gat       531
Thr Gly Asp Phe Leu Met Ala Arg Gly Ile Ala Thr Leu Ser Thr Asp
    155                 160                 165 gca atc gag gga aat gtt tat ttc cga ctc agg gtt aac atc aca ctc       579
Ala Ile Glu Gly Asn Val Tyr Phe Arg Leu Arg Val Asn Ile Thr Leu
170                 175                 180                 185 tac gag tgt tac tgatgattac taactaaatg gagagtcttt gtttagagaa          631
Tyr Glu Cys Tyr tagtgtgttg gctgtttac ttaaagtcga cgttctatgc agttgaagtc tttgtttaga      691
tgaatgcaat ggtgggtttt ctttcctcgt gagggttaac atcacactct acgagtgtta    751
ctgataattg ttaagtattt ggagagtctt gtaagttgag aataatgtat tttggctgtt    811
tattttgagt cgaaaaaaaa aaaaaaaaa aaaaaaaaa aaaaaaaaa aaaaaaaa         871
```

```
aa                                                                       873

<210> SEQ ID NO 21
<211> LENGTH: 189
<212> TYPE: PRT
<213> ORGANISM: Thuja plicata

<400> SEQUENCE: 21

Met Ser Arg Ile Ala Phe His Leu Cys Phe Met Gly Leu Leu Leu Ser
 1               5                  10                  15

Ser Thr Val Leu Arg Asn Val Asp Gly His Ala Trp Lys Arg Gln Leu
            20                  25                  30

Pro Met Pro Cys Lys Asn Leu Val Leu Tyr Phe His Asp Ile Leu Tyr
        35                  40                  45

Asn Gly Lys Asn Ile His Asn Ala Thr Ala Ala Leu Val Ala Ala Pro
    50                  55                  60

Ala Trp Gly Asn Leu Thr Thr Phe Ala Glu Pro Phe Lys Phe Gly Asp
 65                  70                  75                  80

Val Val Val Phe Asp Asp Pro Ile Thr Leu Asp Asn Asn Leu His Ser
                85                  90                  95

Pro Pro Val Gly Arg Ala Gln Gly Phe Tyr Leu Tyr Asn Met Lys Thr
            100                 105                 110

Thr Tyr Asn Ala Trp Leu Gly Phe Thr Phe Val Leu Asn Ser Thr Asp
        115                 120                 125

Tyr Lys Gly Thr Ile Thr Phe Asn Gly Ala Asp Pro Leu Val Lys
    130                 135                 140

Tyr Arg Asp Ile Ser Val Val Gly Gly Thr Gly Asp Phe Leu Met Ala
145                 150                 155                 160

Arg Gly Ile Ala Thr Leu Ser Thr Asp Ala Ile Glu Gly Asn Val Tyr
                165                 170                 175

Phe Arg Leu Arg Val Asn Ile Thr Leu Tyr Glu Cys Tyr
            180                 185

<210> SEQ ID NO 22
<211> LENGTH: 867
<212> TYPE: DNA
<213> ORGANISM: Thuja plicata
<220> FEATURE:
<221> NAME/KEY: CDS
<222> LOCATION: (80)..(655)

<400> SEQUENCE: 22
gcaatattgt gctggttcag taatctatgt cttgttgacc tgtagtgtat acccaaacat    60
ttctccttct tttgcaaaa atg gca atg aag gct gca aaa ttt ctg cat ttc   112
                        Met Ala Met Lys Ala Ala Lys Phe Leu His Phe
                          1               5                  10 tta ttt atc tgg ctt cta gtc tgc act gtg ttg ctc aaa tct gca gac   160
Leu Phe Ile Trp Leu Leu Val Cys Thr Val Leu Leu Lys Ser Ala Asp
            15                  20                  25 tgt cat aga tgg aag aag aaa att cca gag cca tgt aag aat ctg gta   208
Cys His Arg Trp Lys Lys Lys Ile Pro Glu Pro Cys Lys Asn Leu Val
        30                  35                  40 ttg tac ttt cat gat atc ctc tac aat gga tcc aac aaa cac aat gca   256
Leu Tyr Phe His Asp Ile Leu Tyr Asn Gly Ser Asn Lys His Asn Ala
    45                  50                  55 aca tct gca att gtt gga gca ccc aaa gga gcc aat ctc act att ttg   304
Thr Ser Ala Ile Val Gly Ala Pro Lys Gly Ala Asn Leu Thr Ile Leu
 60                  65                  70                  75
```

```
act ggt aac aac cat ttt gga gat gtg gtt gtg ttt gat gat cct att      352
Thr Gly Asn Asn His Phe Gly Asp Val Val Val Phe Asp Asp Pro Ile
                 80                  85                  90 act ctt gac aac aat ctt cac tct act cct gtg gga aga gct cag ggc      400
Thr Leu Asp Asn Asn Leu His Ser Thr Pro Val Gly Arg Ala Gln Gly
         95                 100                 105 ttt tat ttc tat gac atg aag aat aca ttc aat tct tgg ctt ggg ttt      448
Phe Tyr Phe Tyr Asp Met Lys Asn Thr Phe Asn Ser Trp Leu Gly Phe
            110                 115                 120 aca ttt gtg ttg aat tca aca aat tat aag ggc acc atc acc ttc aat      496
Thr Phe Val Leu Asn Ser Thr Asn Tyr Lys Gly Thr Ile Thr Phe Asn
        125                 130                 135 ggg gct gac cca att ctg act aag tac aga gat ata tct gtt gtg ggt      544
Gly Ala Asp Pro Ile Leu Thr Lys Tyr Arg Asp Ile Ser Val Val Gly
140                 145                 150                 155 ggt acg ggt gat ttc ttg atg gcc aga gga atc gcc acc att tct act      592
Gly Thr Gly Asp Phe Leu Met Ala Arg Gly Ile Ala Thr Ile Ser Thr
                160                 165                 170 gat gca tac gag gga gat gtt tat ttc cgt ctt agg gtg aat atc act      640
Asp Ala Tyr Glu Gly Asp Val Tyr Phe Arg Leu Arg Val Asn Ile Thr
            175                 180                 185 ctc tat gag tgt tac tgattcgaat ttgatttcct gttctaatct ctaatttgag      695
Leu Tyr Glu Cys Tyr
            190 aggatgaaca ttcaataaac tttatagaag catatataaa taggtgcagg aaaataagag    755 gtaagggatg agattatttc agcctcatat cttattctgc atcagttttg tatgctcatt    815 tgtttaataa aatttgacca gtttcatcat gttgaaaaaa aaaaaaaaaa aa            867

<210> SEQ ID NO 23
<211> LENGTH: 192
<212> TYPE: PRT
<213> ORGANISM: Thuja plicata

<400> SEQUENCE: 23

Met Ala Met Lys Ala Ala Lys Phe Leu His Phe Leu Phe Ile Trp Leu
 1               5                  10                  15

Leu Val Cys Thr Val Leu Leu Lys Ser Ala Asp Cys His Arg Trp Lys
                20                  25                  30

Lys Lys Ile Pro Glu Pro Cys Lys Asn Leu Val Leu Tyr Phe His Asp
            35                  40                  45

Ile Leu Tyr Asn Gly Ser Asn Lys His Asn Ala Thr Ser Ala Ile Val
        50                  55                  60

Gly Ala Pro Lys Gly Ala Asn Leu Thr Ile Leu Thr Gly Asn Asn His
65                  70                  75                  80

Phe Gly Asp Val Val Phe Asp Pro Ile Thr Leu Asp Asn Asn
                85                  90                  95

Leu His Ser Thr Pro Val Gly Arg Ala Gln Gly Phe Tyr Phe Tyr Asp
                100                 105                 110

Met Lys Asn Thr Phe Asn Ser Trp Leu Gly Phe Thr Phe Val Leu Asn
            115                 120                 125

Ser Thr Asn Tyr Lys Gly Thr Ile Thr Phe Asn Gly Ala Asp Pro Ile
        130                 135                 140

Leu Thr Lys Tyr Arg Asp Ile Ser Val Val Gly Gly Thr Gly Asp Phe
145                 150                 155                 160

Leu Met Ala Arg Gly Ile Ala Thr Ile Ser Thr Asp Ala Tyr Glu Gly
                165                 170                 175
```

―continued

```
Asp Val Tyr Phe Arg Leu Arg Val Asn Ile Thr Leu Tyr Glu Cys Tyr
        180                 185                 190

<210> SEQ ID NO 24
<211> LENGTH: 914
<212> TYPE: DNA
<213> ORGANISM: Thuja plicata
<220> FEATURE:
<221> NAME/KEY: CDS
<222> LOCATION: (94)..(669)

<400> SEQUENCE: 24
cgtaggaaat atctcagagg gagccgaaaa ttgagataat tgttgtacga aatatataaa        60
agattagatt cagaggaatt tgcagatgtt gtt gta tct aaa aca gct gct aga       114
                                 Val Ser Lys Thr Ala Ala Arg
                                   1               5 gtt ctg cat tta tgc ttt cta tgg ctt cta gta tct gca atc ttc ata        162
Val Leu His Leu Cys Phe Leu Trp Leu Leu Val Ser Ala Ile Phe Ile
         10                  15                  20 aaa tct gca gat tgc cgt agc tgg aaa aag aag ctt cca aag ccc tgt        210
Lys Ser Ala Asp Cys Arg Ser Trp Lys Lys Lys Leu Pro Lys Pro Cys
 25                  30                  35 aga aat ctt gtg tta tat ttt cat gat ata atc tac aat ggc aaa aat        258
Arg Asn Leu Val Leu Tyr Phe His Asp Ile Ile Tyr Asn Gly Lys Asn
 40                  45                  50                  55 gca gag aat gca aca tct gca ctt gtt tca gcc cct caa gga gct aat        306
Ala Glu Asn Ala Thr Ser Ala Leu Val Ser Ala Pro Gln Gly Ala Asn
                 60                  65                  70 ctc acc att atg act ggt aat aac cat ttt ggg aat ctt gca gtg ttt        354
Leu Thr Ile Met Thr Gly Asn Asn His Phe Gly Asn Leu Ala Val Phe
             75                  80                  85 gat gat cct att act ctt gac aac aat ctt cac tct cct cct gtt gga        402
Asp Asp Pro Ile Thr Leu Asp Asn Asn Leu His Ser Pro Pro Val Gly
         90                  95                 100 aga gct cag ggc ttt tac ttc tat gac atg aag aac acc ttc agt gcc        450
Arg Ala Gln Gly Phe Tyr Phe Tyr Asp Met Lys Asn Thr Phe Ser Ala
105                 110                 115 tgg ctt ggc ttc aca ttt gtg ctc aat tca act gat cac aag ggc tcc        498
Trp Leu Gly Phe Thr Phe Val Leu Asn Ser Thr Asp His Lys Gly Ser
120                 125                 130                 135 att act ttc aat gga gca gat ccc atc tta aca aag tac aga gac ata        546
Ile Thr Phe Asn Gly Ala Asp Pro Ile Leu Thr Lys Tyr Arg Asp Ile
                140                 145                 150 tct gtt gtg ggt gga aca ggg gat ttc ttg atg gca aga gga att gct        594
Ser Val Val Gly Gly Thr Gly Asp Phe Leu Met Ala Arg Gly Ile Ala
            155                 160                 165 acc att tct act gac tca tat gag gga gat gtt tat ttc agg ctt agg        642
Thr Ile Ser Thr Asp Ser Tyr Glu Gly Asp Val Tyr Phe Arg Leu Arg
        170                 175                 180 gtc aat atc aca ctc tat gag tgt tac tgaacaaatt ccttgctctg              689
Val Asn Ile Thr Leu Tyr Glu Cys Tyr
    185                 190 tatttctagt ttttgggacc ttttaaagat agttgtttac ttcaatgtct ctatatgtaa      749
taacactgtg tgaagattat atacgatgga ctatagaaac tatgttgaat tctgttctgt      809
agctaattta tgtatatgat ccactcatat ctcttaatat gataccgatt tgtaattatc      869
ccagataaag tatgtcatgt gctttgacaa aaaaaaaaaa aaaaa                      914

<210> SEQ ID NO 25
<211> LENGTH: 192
```

-continued

```
<212> TYPE: PRT
<213> ORGANISM: Thuja plicata

<400> SEQUENCE: 25

Val Ser Lys Thr Ala Ala Arg Val Leu His Leu Cys Phe Leu Trp Leu
 1               5                  10                  15

Leu Val Ser Ala Ile Phe Ile Lys Ser Ala Asp Cys Arg Ser Trp Lys
            20                  25                  30

Lys Lys Leu Pro Lys Pro Cys Arg Asn Leu Val Leu Tyr Phe His Asp
        35                  40                  45

Ile Ile Tyr Asn Gly Lys Asn Ala Glu Asn Ala Thr Ser Ala Leu Val
    50                  55                  60

Ser Ala Pro Gln Gly Ala Asn Leu Thr Ile Met Thr Gly Asn Asn His
65                  70                  75                  80

Phe Gly Asn Leu Ala Val Phe Asp Asp Pro Ile Thr Leu Asp Asn Asn
                85                  90                  95

Leu His Ser Pro Pro Val Gly Arg Ala Gln Gly Phe Tyr Phe Tyr Asp
            100                 105                 110

Met Lys Asn Thr Phe Ser Ala Trp Leu Gly Phe Thr Phe Val Leu Asn
        115                 120                 125

Ser Thr Asp His Lys Gly Ser Ile Thr Phe Asn Gly Ala Asp Pro Ile
    130                 135                 140

Leu Thr Lys Tyr Arg Asp Ile Ser Val Val Gly Gly Thr Gly Asp Phe
145                 150                 155                 160

Leu Met Ala Arg Gly Ile Ala Thr Ile Ser Thr Asp Ser Tyr Glu Gly
                165                 170                 175

Asp Val Tyr Phe Arg Leu Arg Val Asn Ile Thr Leu Tyr Glu Cys Tyr
            180                 185                 190

<210> SEQ ID NO 26
<211> LENGTH: 704
<212> TYPE: DNA
<213> ORGANISM: Thuja plicata
<220> FEATURE:
<221> NAME/KEY: CDS
<222> LOCATION: (3)..(416)

<400> SEQUENCE: 26 ag aat gcc cac aat gca aca tct gca ctt gtt gca gcc cct gag gga          47
   Asn Ala His Asn Ala Thr Ser Ala Leu Val Ala Ala Pro Glu Gly
    1               5                  10                  15 gcc aat ctc acc att atg act ggt aat aac cat ttt ggg aat att gct         95
Ala Asn Leu Thr Ile Met Thr Gly Asn Asn His Phe Gly Asn Ile Ala
                20                  25                  30 gtg ttt gat gat cct att act ctt gac aac aat ctt cac tct cct tct        143
Val Phe Asp Asp Pro Ile Thr Leu Asp Asn Asn Leu His Ser Pro Ser
            35                  40                  45 gtt gga aga gct cag ggc ttt tac ttc tat gac atg aag gat acc ttc        191
Val Gly Arg Ala Gln Gly Phe Tyr Phe Tyr Asp Met Lys Asp Thr Phe
        50                  55                  60 aat gct tgg ctt ggt ttt aca ttt gtg ctg aat tca act gat cac aag        239
Asn Ala Trp Leu Gly Phe Thr Phe Val Leu Asn Ser Thr Asp His Lys
65                  70                  75 ggc acc att act ttc aat gga gca gat cca atc ctg acc aag tac aga        287
Gly Thr Ile Thr Phe Asn Gly Ala Asp Pro Ile Leu Thr Lys Tyr Arg
    80                  85                  90                  95 gat ata tct gtt gtg ggt gga aca ggg gat ttc ttg atg gcc aga gga        335
Asp Ile Ser Val Val Gly Gly Thr Gly Asp Phe Leu Met Ala Arg Gly
                100                 105                 110
```

```
att gcc acc att tct act gat tca tat gag gga gat gtt tat ttc agg      383
Ile Ala Thr Ile Ser Thr Asp Ser Tyr Glu Gly Asp Val Tyr Phe Arg
            115                 120                 125 ctt agg gtc aat atc aca ctc tat gag tgt tac taaaaatgaa tttcctctgt    436
Leu Arg Val Asn Ile Thr Leu Tyr Glu Cys Tyr
        130                 135 attactagct tataggagtc attccctggt tcaatgtcta ggcatggaa taaaagaatt      496 tgaagatggt tttgaaatat ggagcatgta ttctaatttg aagagccctc aaggaagtgc    556
attttacaga gtttagtttt gccctctaga atattatgtt ttcaaaatgc tctatgaaag    616
tcatatgatg tatggagtac catttggaat aattaaagca agcatatttt attaaaaaaa    676
aaaaaaaaaa aaaaaaaaa aaaaaaaa                                        704

<210> SEQ ID NO 27
<211> LENGTH: 138
<212> TYPE: PRT
<213> ORGANISM: Thuja plicata

<400> SEQUENCE: 27

Asn Ala His Asn Ala Thr Ser Ala Leu Val Ala Ala Pro Glu Gly Ala
 1               5                  10                  15

Asn Leu Thr Ile Met Thr Gly Asn Asn His Phe Gly Asn Ile Ala Val
            20                  25                  30

Phe Asp Asp Pro Ile Thr Leu Asp Asn Asn Leu His Ser Pro Ser Val
        35                  40                  45

Gly Arg Ala Gln Gly Phe Tyr Phe Tyr Asp Met Lys Asp Thr Phe Asn
    50                  55                  60

Ala Trp Leu Gly Phe Thr Phe Val Leu Asn Ser Thr Asp His Lys Gly
65                  70                  75                  80

Thr Ile Thr Phe Asn Gly Ala Asp Pro Ile Leu Thr Lys Tyr Arg Asp
                85                  90                  95

Ile Ser Val Val Gly Gly Thr Gly Asp Phe Leu Met Ala Arg Gly Ile
            100                 105                 110

Ala Thr Ile Ser Thr Asp Ser Tyr Glu Gly Asp Val Tyr Phe Arg Leu
        115                 120                 125

Arg Val Asn Ile Thr Leu Tyr Glu Cys Tyr
    130                 135

<210> SEQ ID NO 28
<211> LENGTH: 820
<212> TYPE: DNA
<213> ORGANISM: Thuja plicata
<220> FEATURE:
<221> NAME/KEY: CDS
<222> LOCATION: (43)..(612)

<400> SEQUENCE: 28
gtctaattga gagaaaattc caataatttt ttaccaatag ca atg aaa gcc att      54
                                              Met Lys Ala Ile
                                               1 aga gtt ctg cat tta tgc ttt cta tgt ctt cta gtg tct gca atc ttg    102
Arg Val Leu His Leu Cys Phe Leu Cys Leu Leu Val Ser Ala Ile Leu
  5                  10                  15                  20 cta aaa tct gca gat tgc cat agc tgg aaa aag aag ctt cca aag ccc    150
Leu Lys Ser Ala Asp Cys His Ser Trp Lys Lys Lys Leu Pro Lys Pro
                25                  30                  35 tgc aag aat ctt gtg tta tat ttc cat gat ata atc tac aat ggc aaa    198
Cys Lys Asn Leu Val Leu Tyr Phe His Asp Ile Ile Tyr Asn Gly Lys
```

```
aat gca gag aat gca aca tct gca ctt gtt gca gcc cct gag gga gcc    246
Asn Ala Glu Asn Ala Thr Ser Ala Leu Val Ala Ala Pro Glu Gly Ala
            55                  60                  65 aat ctc acc att atg act ggt aat aac cat ttt ggg aat ctt gct gtg    294
Asn Leu Thr Ile Met Thr Gly Asn Asn His Phe Gly Asn Leu Ala Val
     70                  75                  80 ttt gat gat cct att act ctt gac aac aat ctc cac tct cct cct gtg    342
Phe Asp Asp Pro Ile Thr Leu Asp Asn Asn Leu His Ser Pro Pro Val
 85                  90                  95                 100 gga aga gct cag gga ttt tac ttc tat gac atg aag aac acc ttc agt    390
Gly Arg Ala Gln Gly Phe Tyr Phe Tyr Asp Met Lys Asn Thr Phe Ser
                105                 110                 115 gct tgg ctt ggc ttc aca ttt gtg ctg aat tca act gat cac aag ggc    438
Ala Trp Leu Gly Phe Thr Phe Val Leu Asn Ser Thr Asp His Lys Gly
            120                 125                 130 acc att act ttc aat gga gca gac cca atc ctg acc aag tac aga gac    486
Thr Ile Thr Phe Asn Gly Ala Asp Pro Ile Leu Thr Lys Tyr Arg Asp
     135                 140                 145 ata tct gtt gtg ggt gga aca ggg gat ttc ttg atg gcc aga gga att    534
Ile Ser Val Val Gly Gly Thr Gly Asp Phe Leu Met Ala Arg Gly Ile
 150                 155                 160 gcc acc att tct act gat tca tat gag gga gaa gtt tat ttc agg ctt    582
Ala Thr Ile Ser Thr Asp Ser Tyr Glu Gly Glu Val Tyr Phe Arg Leu
165                 170                 175                 180 agg gtc aat atc aca ctc tat gag tgt tac tgagcaaatg cctgtcttct      632
Arg Val Asn Ile Thr Leu Tyr Glu Cys Tyr
                185                 190 tcctctgtag ttcttgtttt gggtgccttt gaggaatagt tcttggcttc aatgtctctg  692
tatgtagtaa catggtcaat ggagtctatt ttgaagatta tgaagatata gtctctatat  752
atatatatat tgaagagaat gagatctgtt ttaggtagct cttttcattc aaaaaaaaaa  812
aaaaaaaa                                                           820

<210> SEQ ID NO 29
<211> LENGTH: 190
<212> TYPE: PRT
<213> ORGANISM: Thuja plicata

<400> SEQUENCE: 29

Met Lys Ala Ile Arg Val Leu His Leu Cys Phe Leu Cys Leu Leu Val
  1               5                  10                  15

Ser Ala Ile Leu Leu Lys Ser Ala Asp Cys His Ser Trp Lys Lys Lys
             20                  25                  30

Leu Pro Lys Pro Cys Lys Asn Leu Val Leu Tyr Phe His Asp Ile Ile
         35                  40                  45

Tyr Asn Gly Lys Asn Ala Glu Asn Ala Thr Ser Ala Leu Val Ala Ala
     50                  55                  60

Pro Glu Gly Ala Asn Leu Thr Ile Met Thr Gly Asn Asn His Phe Gly
 65                  70                  75                  80

Asn Leu Ala Val Phe Asp Asp Pro Ile Thr Leu Asp Asn Asn Leu His
                 85                  90                  95

Ser Pro Pro Val Gly Arg Ala Gln Gly Phe Tyr Phe Tyr Asp Met Lys
            100                 105                 110

Asn Thr Phe Ser Ala Trp Leu Gly Phe Thr Phe Val Leu Asn Ser Thr
        115                 120                 125

Asp His Lys Gly Thr Ile Thr Phe Asn Gly Ala Asp Pro Ile Leu Thr
```

```
                130             135             140
Lys Tyr Arg Asp Ile Ser Val Val Gly Gly Thr Gly Asp Phe Leu Met
145                 150                 155                 160

Ala Arg Gly Ile Ala Thr Ile Ser Thr Asp Ser Tyr Glu Gly Glu Val
                165                 170                 175

Tyr Phe Arg Leu Arg Val Asn Ile Thr Leu Tyr Glu Cys Tyr
            180                 185                 190

<210> SEQ ID NO 30
<211> LENGTH: 1013
<212> TYPE: DNA
<213> ORGANISM: Thuja plicata
<220> FEATURE:
<221> NAME/KEY: CDS
<222> LOCATION: (47)..(616)

<400> SEQUENCE: 30
ctcagtctaa ttgagagaaa attccaataa ttttttccca atagca atg aaa gcc         55
                                                Met Lys Ala
                                                  1 att aga gtt ctg caa tta tgc ttt cta tgg ctt cta gta tct gca atc       103
Ile Arg Val Leu Gln Leu Cys Phe Leu Trp Leu Leu Val Ser Ala Ile
    5                  10                  15 ttg cta aaa tct gca gat tgc cat agc tgg aaa aag aag ctt cca aag       151
Leu Leu Lys Ser Ala Asp Cys His Ser Trp Lys Lys Lys Leu Pro Lys
 20                  25                  30                  35 ccc tgc aag aat ctt gtg tta tat ttc cat gat ata atc tac aat ggc       199
Pro Cys Lys Asn Leu Val Leu Tyr Phe His Asp Ile Ile Tyr Asn Gly
                 40                  45                  50 aaa aat gca gag aat gca aca tct gca ctt gtt gca gcc cct gag gga       247
Lys Asn Ala Glu Asn Ala Thr Ser Ala Leu Val Ala Ala Pro Glu Gly
             55                  60                  65 gcc aat ctc acc att atg act ggt aat aac cat ttt ggg aat ctt gct       295
Ala Asn Leu Thr Ile Met Thr Gly Asn Asn His Phe Gly Asn Leu Ala
         70                  75                  80 gtg ttt gat gat cct att act ctt gac aac aat ctc cac tct cct cct       343
Val Phe Asp Asp Pro Ile Thr Leu Asp Asn Asn Leu His Ser Pro Pro
     85                  90                  95 gtg gga aga gct cag ggc ttt tac ttc tat gac atg aag aac acc ttc       391
Val Gly Arg Ala Gln Gly Phe Tyr Phe Tyr Asp Met Lys Asn Thr Phe
100                 105                 110                 115 agt gct tgg ctt ggc ttc aca ttt gtg ctg aat tca act gat cac aag       439
Ser Ala Trp Leu Gly Phe Thr Phe Val Leu Asn Ser Thr Asp His Lys
                120                 125                 130 ggc acc att act ttc aat gga gca gac cca atc ctg acc aag tac aga       487
Gly Thr Ile Thr Phe Asn Gly Ala Asp Pro Ile Leu Thr Lys Tyr Arg
            135                 140                 145 gat ata tct gtt gtg ggt gga aca ggg gat ttc ttg atg gcc aga gga       535
Asp Ile Ser Val Val Gly Gly Thr Gly Asp Phe Leu Met Ala Arg Gly
        150                 155                 160 att gcc acc att tct act gat tca tat gag gga gat gtt tat ttc agg       583
Ile Ala Thr Ile Ser Thr Asp Ser Tyr Glu Gly Asp Val Tyr Phe Arg
    165                 170                 175 ctt agg gtc aat atc aca ctc tat aag tgt tac tgagcaaatg cctgtcttct     636
Leu Arg Val Asn Ile Thr Leu Tyr Lys Cys Tyr
180                 185                 190 tcctctgtag ttcttgtttt gggtgccttt gaggaatagt tcttggcttc aatgtctctg     696
tatgtagtaa catggtcaat ggagtctatt ttgaagatta tgaagatata gtctctctat     756
atatatatat tgaagagaat gagatctgtt ttaggtagct cttttcattc atatatatgg     816
```

```
gttaacttgg atttcatgtt tggttcaaag atcagttatg gaggatttcc ttttagtggt      876
tttatgggat ttttgacata ttagattact ttcatctcaa atatatgtta aatcagttat      936
atatgaaact aatcatatat aagttcagaa atatcagaac aaccatttta tggaaaaaaa      996
aaaaaaaaaa aaaaaaa                                                    1013

<210> SEQ ID NO 31
<211> LENGTH: 190
<212> TYPE: PRT
<213> ORGANISM: Thuja plicata

<400> SEQUENCE: 31

Met Lys Ala Ile Arg Val Leu Gln Leu Cys Phe Leu Trp Leu Leu Val
  1               5                  10                  15

Ser Ala Ile Leu Leu Lys Ser Ala Asp Cys His Ser Trp Lys Lys Lys
                 20                  25                  30

Leu Pro Lys Pro Cys Lys Asn Leu Val Leu Tyr Phe His Asp Ile Ile
             35                  40                  45

Tyr Asn Gly Lys Asn Ala Glu Asn Ala Thr Ser Ala Leu Val Ala Ala
 50                  55                  60

Pro Glu Gly Ala Asn Leu Thr Ile Met Thr Gly Asn Asn His Phe Gly
 65                  70                  75                  80

Asn Leu Ala Val Phe Asp Asp Pro Ile Thr Leu Asp Asn Asn Leu His
                 85                  90                  95

Ser Pro Pro Val Gly Arg Ala Gln Gly Phe Tyr Phe Tyr Asp Met Lys
            100                 105                 110

Asn Thr Phe Ser Ala Trp Leu Gly Phe Thr Phe Val Leu Asn Ser Thr
        115                 120                 125

Asp His Lys Gly Thr Ile Thr Phe Asn Gly Ala Asp Pro Ile Leu Thr
130                 135                 140

Lys Tyr Arg Asp Ile Ser Val Val Gly Gly Thr Gly Asp Phe Leu Met
145                 150                 155                 160

Ala Arg Gly Ile Ala Thr Ile Ser Thr Asp Ser Tyr Glu Gly Asp Val
                165                 170                 175

Tyr Phe Arg Leu Arg Val Asn Ile Thr Leu Tyr Lys Cys Tyr
            180                 185                 190

<210> SEQ ID NO 32
<211> LENGTH: 913
<212> TYPE: DNA
<213> ORGANISM: Thuja plicata
<220> FEATURE:
<221> NAME/KEY: CDS
<222> LOCATION: (77)..(652)

<400> SEQUENCE: 32
gcaagctcaa atacccgact tctttctcta cttcagagct cttctttctt caaacatttt       60
tgatatattt tgcaca atg gca atc tgg aat gga aga gtt ctg aat ttg tgc      112
                Met Ala Ile Trp Asn Gly Arg Val Leu Asn Leu Cys
                  1               5                  10 att ctg tgg ctt ctg gtc tcc ata gtt ttg ctg aat ggt ata gat tgc        160
Ile Leu Trp Leu Leu Val Ser Ile Val Leu Leu Asn Gly Ile Asp Cys
         15                  20                  25 cat agt aga aaa aag aag ctt cca aag cca tgt agg aat ctt gtt ttg        208
His Ser Arg Lys Lys Lys Leu Pro Lys Pro Cys Arg Asn Leu Val Leu
         30                  35                  40 tat ttt cat gat att atc tac aat ggt aaa aat gca ggc aat gca aca        256
```

|  |  |  |  |  |  |  |  |  |  |  |  | |
|---|---|---|---|---|---|---|---|---|---|---|---|---|
| Tyr | Phe | His | Asp | Ile | Ile | Tyr | Asn | Gly | Lys | Asn | Ala | Gly | Asn | Ala | Thr |
|  | 45 |  |  |  | 50 |  |  |  |  | 55 |  |  |  |  | 60 |

```
tct acg ctt gtt gca gcc cct caa gga gct aat ctc acc att atg act      304
Ser Thr Leu Val Ala Ala Pro Gln Gly Ala Asn Leu Thr Ile Met Thr
             65                  70                  75 ggc aat tac cat ttt gga gat ctg tct gtg ttt gat gat cct att act      352
Gly Asn Tyr His Phe Gly Asp Leu Ser Val Phe Asp Asp Pro Ile Thr
         80                  85                  90 gtt gac aac aat ctt cat tct cct cct gtg gga aga gct cag ggc ttt      400
Val Asp Asn Asn Leu His Ser Pro Pro Val Gly Arg Ala Gln Gly Phe
         95                 100                 105 tac ttc tat gac atg aag aat aca ttc agt gct tgg ctt ggg ttc aca      448
Tyr Phe Tyr Asp Met Lys Asn Thr Phe Ser Ala Trp Leu Gly Phe Thr
    110                 115                 120 ttt gtg ctg aac tca aca gat tat aaa ggc act att act ttc ggt gga      496
Phe Val Leu Asn Ser Thr Asp Tyr Lys Gly Thr Ile Thr Phe Gly Gly
125                 130                 135                 140 gca gac cca att ttg gct aag tac aga gat ata tct gtt gtg ggt ggt      544
Ala Asp Pro Ile Leu Ala Lys Tyr Arg Asp Ile Ser Val Val Gly Gly
                145                 150                 155 act gga gat ttc ttg atg gca aga gga att gct aca atc gat act gat      592
Thr Gly Asp Phe Leu Met Ala Arg Gly Ile Ala Thr Ile Asp Thr Asp
            160                 165                 170 gca tat gag gga gat gtt tat ttc agg cta agg gtg aat atc aca ctc      640
Ala Tyr Glu Gly Asp Val Tyr Phe Arg Leu Arg Val Asn Ile Thr Leu
        175                 180                 185 tat gag tgt tac tgatccatgg gtattctatg tagaatagct caatctgata          692
Tyr Glu Cys Tyr
    190 tggctatatt attttgagag cataggtagt taagttttat aactaagtag tgaaccatga    752 gatcattgaa aacttgggtg ctcatgcaca gttttcatat tttctaaata agtctgctcg    812 actattacat ttatggattg ttgagaattg tgtcgcttat tactttatga ataagctatt    872 ttaaacaaag ttttcacaag tttaaaaaaa aaaaaaaaaa a                        913

<210> SEQ ID NO 33
<211> LENGTH: 192
<212> TYPE: PRT
<213> ORGANISM: Thuja plicata

<400> SEQUENCE: 33

Met Ala Ile Trp Asn Gly Arg Val Leu Asn Leu Cys Ile Leu Trp Leu
 1               5                  10                  15

Leu Val Ser Ile Val Leu Leu Asn Gly Ile Asp Cys His Ser Arg Lys
            20                  25                  30

Lys Lys Leu Pro Lys Pro Cys Arg Asn Leu Val Leu Tyr Phe His Asp
        35                  40                  45

Ile Ile Tyr Asn Gly Lys Asn Ala Gly Asn Ala Thr Ser Thr Leu Val
    50                  55                  60

Ala Ala Pro Gln Gly Ala Asn Leu Thr Ile Met Thr Gly Asn Tyr His
65                  70                  75                  80

Phe Gly Asp Leu Ser Val Phe Asp Asp Pro Ile Thr Val Asp Asn Asn
                85                  90                  95

Leu His Ser Pro Pro Val Gly Arg Ala Gln Gly Phe Tyr Phe Tyr Asp
            100                 105                 110

Met Lys Asn Thr Phe Ser Ala Trp Leu Gly Phe Thr Phe Val Leu Asn
        115                 120                 125
```

```
Ser Thr Asp Tyr Lys Gly Thr Ile Thr Phe Gly Gly Ala Asp Pro Ile
        130                 135                 140

Leu Ala Lys Tyr Arg Asp Ile Ser Val Val Gly Gly Thr Gly Asp Phe
145                 150                 155                 160

Leu Met Ala Arg Gly Ile Ala Thr Ile Asp Thr Asp Ala Tyr Glu Gly
                165                 170                 175

Asp Val Tyr Phe Arg Leu Arg Val Asn Ile Thr Leu Tyr Glu Cys Tyr
            180                 185                 190

<210> SEQ ID NO 34
<211> LENGTH: 890
<212> TYPE: DNA
<213> ORGANISM: Thuja plicata
<220> FEATURE:
<221> NAME/KEY: CDS
<222> LOCATION: (44)..(619)

<400> SEQUENCE: 34
cagagctctt ctttcttcaa acatttttga tatattttgc aca atg gca atc tgg      55
                                            Met Ala Ile Trp
                                              1 aat gga aga gtt ctg aat ttg tgc att ctg tgg ctt ctg gtc tcc ata     103
Asn Gly Arg Val Leu Asn Leu Cys Ile Leu Trp Leu Leu Val Ser Ile
  5              10                  15                  20 gtt ttg ctg aat ggt ata gat tgc cat agt aga aaa aag aag ctt cca     151
Val Leu Leu Asn Gly Ile Asp Cys His Ser Arg Lys Lys Lys Leu Pro
                 25                  30                  35 aag cca tgt agg aat ctt gtt ttg tat ttt cat gat att atc tac aat     199
Lys Pro Cys Arg Asn Leu Val Leu Tyr Phe His Asp Ile Ile Tyr Asn
             40                  45                  50 ggt aaa aat gca ggc aat gca aca tct acg ctt gtt gca gcc cct caa     247
Gly Lys Asn Ala Gly Asn Ala Thr Ser Thr Leu Val Ala Ala Pro Gln
         55                  60                  65 gga gct aat ctc acc att atg act ggc aat tac cat ttt gga gat ctg     295
Gly Ala Asn Leu Thr Ile Met Thr Gly Asn Tyr His Phe Gly Asp Leu
     70                  75                  80 gct gtg ttt gat gat cct att act gtt gac aac aat ctt cat tct cct     343
Ala Val Phe Asp Asp Pro Ile Thr Val Asp Asn Asn Leu His Ser Pro
 85                  90                  95                 100 cct gtg gga aga gct cag ggc ttt tac ttc tat gac atg aag aat aca     391
Pro Val Gly Arg Ala Gln Gly Phe Tyr Phe Tyr Asp Met Lys Asn Thr
                105                 110                 115 ttc agt gct tgg ctt ggg ttc aca ttt gtg ctg aac tca aca gat tat     439
Phe Ser Ala Trp Leu Gly Phe Thr Phe Val Leu Asn Ser Thr Asp Tyr
            120                 125                 130 aaa ggc act att act ttc ggt gga gca gac cca att ttg gct aag tac     487
Lys Gly Thr Ile Thr Phe Gly Gly Ala Asp Pro Ile Leu Ala Lys Tyr
        135                 140                 145 aga gat ata tct gtt gtg ggt ggt act gga gat ttc ttg atg gca aga     535
Arg Asp Ile Ser Val Val Gly Gly Thr Gly Asp Phe Leu Met Ala Arg
150                 155                 160 gga att gct aca atc gat act gat gca tat gag gga gat gtt tat ttc     583
Gly Ile Ala Thr Ile Asp Thr Asp Ala Tyr Glu Gly Asp Val Tyr Phe
165                 170                 175                 180 agg cta agg gtg aat atc aca ctc tat gag tgt tac tgatccatgg          629
Arg Leu Arg Val Asn Ile Thr Leu Tyr Glu Cys Tyr
                185                 190 gtattctatg tagaatagct caatctgata tggctatatt attttgagag cataggtagt   689
taagttttat aactaagtag tgaaccatga gatcattgaa aacttgggtg ctcatgcaca   749
```

```
gttttcatat ttctaaata agtctgctcg actattacat ttatggattg ttgagaattg   809
tgtcgcttat tactttatga ataagctatt ttaaacaaag ttttcacaag tttaaaagtt   869
gtcaaaaaaa aaaaaaaaaa a                                             890
```

<210> SEQ ID NO 35
<211> LENGTH: 192
<212> TYPE: PRT
<213> ORGANISM: Thuja plicata

<400> SEQUENCE: 35

```
Met Ala Ile Trp Asn Gly Arg Val Leu Asn Leu Cys Ile Leu Trp Leu
 1               5                  10                  15

Leu Val Ser Ile Val Leu Leu Asn Gly Ile Asp Cys His Ser Arg Lys
            20                  25                  30

Lys Lys Leu Pro Lys Pro Cys Arg Asn Leu Val Leu Tyr Phe His Asp
        35                  40                  45

Ile Ile Tyr Asn Gly Lys Asn Ala Gly Asn Ala Thr Ser Thr Leu Val
    50                  55                  60

Ala Ala Pro Gln Gly Ala Asn Leu Thr Ile Met Thr Gly Asn Tyr His
65                  70                  75                  80

Phe Gly Asp Leu Ala Val Phe Asp Asp Pro Ile Thr Val Asp Asn Asn
                85                  90                  95

Leu His Ser Pro Pro Val Gly Arg Ala Gln Gly Phe Tyr Phe Tyr Asp
            100                 105                 110

Met Lys Asn Thr Phe Ser Ala Trp Leu Gly Phe Thr Phe Val Leu Asn
        115                 120                 125

Ser Thr Asp Tyr Lys Gly Thr Ile Thr Phe Gly Ala Asp Pro Ile
    130                 135                 140

Leu Ala Lys Tyr Arg Asp Ile Ser Val Val Gly Gly Thr Gly Asp Phe
145                 150                 155                 160

Leu Met Ala Arg Gly Ile Ala Thr Ile Asp Thr Asp Ala Tyr Glu Gly
                165                 170                 175

Asp Val Tyr Phe Arg Leu Arg Val Asn Ile Thr Leu Tyr Glu Cys Tyr
            180                 185                 190
```

<210> SEQ ID NO 36
<211> LENGTH: 30
<212> TYPE: PRT
<213> ORGANISM: Forsythia x intermedia

<400> SEQUENCE: 36

```
Gly Lys Ser Lys Val Leu Ile Ile Gly Gly Thr Gly Tyr Leu Gly Arg
 1               5                  10                  15

Arg Leu Val Lys Ala Ser Leu Ala Gln Gly His Glu Thr Tyr
            20                  25                  30
```

<210> SEQ ID NO 37
<211> LENGTH: 16
<212> TYPE: PRT
<213> ORGANISM: Forsythia x intermedia
<220> FEATURE:
<221> NAME/KEY: PEPTIDE
<222> LOCATION: (1)..(16)
<223> OTHER INFORMATION: Peptide fragment, wherein Xaa = unknown amino
      acid

<400> SEQUENCE: 37

```
Phe Met Asp Ile Ala Met Xaa Pro Gly Lys Val Thr Leu Asp Glu Lys
 1               5                  10                  15
```

<210> SEQ ID NO 38
<211> LENGTH: 13
<212> TYPE: PRT
<213> ORGANISM: Forsythia x intermedia
<220> FEATURE:
<221> NAME/KEY: PEPTIDE
<222> LOCATION: (1)..(13)
<223> OTHER INFORMATION: Peptide fragment, wherein Xaa = unknown amino
      acid

<400> SEQUENCE: 38

Leu Pro Xaa Glu Phe Gly Met Asp Pro Ala Lys Phe Met
 1               5                  10

<210> SEQ ID NO 39
<211> LENGTH: 8
<212> TYPE: PRT
<213> ORGANISM: Forsythia x intermedia
<220> FEATURE:
<221> NAME/KEY: PEPTIDE
<222> LOCATION: (1)..(8)
<223> OTHER INFORMATION: Peptide fragment, wherein Xaa = unknown amino
      acid

<400> SEQUENCE: 39

Glu Val Val Gln Xaa Xaa Glu Lys
 1               5

<210> SEQ ID NO 40
<211> LENGTH: 10
<212> TYPE: PRT
<213> ORGANISM: Forsythia x intermedia
<220> FEATURE:
<221> NAME/KEY: PEPTIDE
<222> LOCATION: (1)..(10)
<223> OTHER INFORMATION: Peptide fragment, wherein Xaa = unknown amino
      acid

<400> SEQUENCE: 40

Tyr Xaa Ser Val Glu Glu Tyr Leu Lys Arg
 1               5                  10

<210> SEQ ID NO 41
<211> LENGTH: 12
<212> TYPE: PRT
<213> ORGANISM: Forsythia x intermedia

<400> SEQUENCE: 41

Met Glu Pro Gly Lys Val Thr Leu Asp Glu Lys Met
 1               5                  10

<210> SEQ ID NO 42
<211> LENGTH: 7
<212> TYPE: PRT
<213> ORGANISM: Forsythia x intermedia

<400> SEQUENCE: 42

Met Asp Pro Ala Lys Phe Met
 1               5

<210> SEQ ID NO 43
<211> LENGTH: 7
<212> TYPE: PRT
<213> ORGANISM: Forsythia x intermedia

<400> SEQUENCE: 43

```
Met Leu Ile Ser Phe Lys Met
 1               5
```

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(20)
<223> OTHER INFORMATION: PCR primer PLRN5, wherein N = any nucleic acid

<400> SEQUENCE: 44
athathggng gnacnggnta                                               20

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(19)
<223> OTHER INFORMATION: PCR primer PLR14R, wherein N = any nucleic acid

<400> SEQUENCE: 45
gytccatngc natrtccat                                                19

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(20)
<223> OTHER INFORMATION: PCR primer PLR15R, wherein N = any nucleic acid

<400> SEQUENCE: 46
tcytcnarng tnacyttncc                                               20

<210> SEQ ID NO 47
<211> LENGTH: 1060
<212> TYPE: DNA
<213> ORGANISM: Forsythia x intermedia
<220> FEATURE:
<221> NAME/KEY: CDS
<222> LOCATION: (28)..(963)

<400> SEQUENCE: 47

```
aattcggcac gagaaaaaca gagagag atg gga aaa agc aaa gtt ttg atc att    54
                            Met Gly Lys Ser Lys Val Leu Ile Ile
                              1               5 ggg ggt aca ggg tac tta ggg agg aga ttg gtt aag gca agt tta gct    102
Gly Gly Thr Gly Tyr Leu Gly Arg Arg Leu Val Lys Ala Ser Leu Ala
 10              15                  20                  25 caa ggt cat gaa aca tac att ctg cat agg cct gaa att ggt gtt gat    150
Gln Gly His Glu Thr Tyr Ile Leu His Arg Pro Glu Ile Gly Val Asp
                 30                  35                  40 att gat aaa gtt gaa atg cta ata tca ttt aaa atg caa gga gct cat    198
Ile Asp Lys Val Glu Met Leu Ile Ser Phe Lys Met Gln Gly Ala His
             45                  50                  55 ctt gta tct ggt tct ttc aag gat ttc aac agt ctg gtc gag gct gtc    246
```

```
Leu Val Ser Gly Ser Phe Lys Asp Phe Asn Ser Leu Val Glu Ala Val
            60                  65                  70 aag ctc gta gac gta gta atc agc gcc att tct ggt gtt cat att cga      294
Lys Leu Val Asp Val Val Ile Ser Ala Ile Ser Gly Val His Ile Arg
 75                  80                  85 agc cat caa att ctt ctt caa ctc aag ctt gtt gaa gct att aaa gag      342
Ser His Gln Ile Leu Leu Gln Leu Lys Leu Val Glu Ala Ile Lys Glu
 90                  95                 100                 105 gct gga aat gtc aag aga ttt tta cca tct gag ttt gga atg gat cct      390
Ala Gly Asn Val Lys Arg Phe Leu Pro Ser Glu Phe Gly Met Asp Pro
                110                 115                 120 gca aaa ttt atg gat acg gcc atg gaa ccc gga aag gta aca ctt gat      438
Ala Lys Phe Met Asp Thr Ala Met Glu Pro Gly Lys Val Thr Leu Asp
            125                 130                 135 gag aag atg gtg gta agg aaa gca att gaa aag gct ggg att cct ttc      486
Glu Lys Met Val Val Arg Lys Ala Ile Glu Lys Ala Gly Ile Pro Phe
        140                 145                 150 aca tat gtc tct gca aat tgc ttt gct ggt tat ttc ttg gga ggt ctc      534
Thr Tyr Val Ser Ala Asn Cys Phe Ala Gly Tyr Phe Leu Gly Gly Leu
    155                 160                 165 tgt caa ttt ggc aaa att ctt cct tct aga gat ttt gtc att ata cat      582
Cys Gln Phe Gly Lys Ile Leu Pro Ser Arg Asp Phe Val Ile Ile His
170                 175                 180                 185 gga gat ggt aac aaa aaa gca ata tat aac aat gaa gat gat ata gca      630
Gly Asp Gly Asn Lys Lys Ala Ile Tyr Asn Asn Glu Asp Asp Ile Ala
                190                 195                 200 act tat gcc atc aaa aca att aat gat cca aga acc ctc aac aag aca      678
Thr Tyr Ala Ile Lys Thr Ile Asn Asp Pro Arg Thr Leu Asn Lys Thr
            205                 210                 215 atc tac att agt cct cca aaa aac atc ctt tca caa aga gaa gtt gtt      726
Ile Tyr Ile Ser Pro Pro Lys Asn Ile Leu Ser Gln Arg Glu Val Val
        220                 225                 230 cag aca tgg gag aag ctt att ggg aaa gaa ctg cag aaa att aca ctc      774
Gln Thr Trp Glu Lys Leu Ile Gly Lys Glu Leu Gln Lys Ile Thr Leu
    235                 240                 245 tcg aag gaa gat ttt tta gcc tcc gtg aaa gag ctc gag tat gct cag      822
Ser Lys Glu Asp Phe Leu Ala Ser Val Lys Glu Leu Glu Tyr Ala Gln
250                 255                 260                 265 caa gtg gga tta agc cat tat cat gat gtc aac tat cag gga tgc ctt      870
Gln Val Gly Leu Ser His Tyr His Asp Val Asn Tyr Gln Gly Cys Leu
                270                 275                 280 acg agt ttt gag ata gga gat gaa gaa gag gca tct aaa ctt tat cca      918
Thr Ser Phe Glu Ile Gly Asp Glu Glu Glu Ala Ser Lys Leu Tyr Pro
            285                 290                 295 gag gtt aag tat acc agt gtg gaa gag tac ctc aag cgt tac gtg          963
Glu Val Lys Tyr Thr Ser Val Glu Glu Tyr Leu Lys Arg Tyr Val
        300                 305                 310 tagttgaaag ctttccatta ttattgtaat aatatttaaa tcagtatgta gttttaaatt   1023
tcgttaaata atatgtgttg aattttgctt ccaaaaa                            1060

<210> SEQ ID NO 48
<211> LENGTH: 312
<212> TYPE: PRT
<213> ORGANISM: Forsythia x intermedia

<400> SEQUENCE: 48

Met Gly Lys Ser Lys Val Leu Ile Ile Gly Gly Thr Gly Tyr Leu Gly
 1               5                  10                  15

Arg Arg Leu Val Lys Ala Ser Leu Ala Gln Gly His Glu Thr Tyr Ile
```

```
                      20                     25                        30
Leu His Arg Pro Glu Ile Gly Val Asp Ile Asp Lys Val Glu Met Leu
         35                      40                      45
Ile Ser Phe Lys Met Gln Gly Ala His Leu Val Ser Gly Ser Phe Lys
    50                      55                      60
Asp Phe Asn Ser Leu Val Glu Ala Val Lys Leu Val Asp Val Val Ile
65                      70                      75                      80
Ser Ala Ile Ser Gly Val His Ile Arg Ser His Gln Ile Leu Leu Gln
                    85                      90                      95
Leu Lys Leu Val Glu Ala Ile Lys Glu Ala Gly Asn Val Lys Arg Phe
                100                     105                     110
Leu Pro Ser Glu Phe Gly Met Asp Pro Ala Lys Phe Met Asp Thr Ala
            115                     120                     125
Met Glu Pro Gly Lys Val Thr Leu Asp Glu Lys Met Val Val Arg Lys
        130                     135                     140
Ala Ile Glu Lys Ala Gly Ile Pro Phe Thr Tyr Val Ser Ala Asn Cys
145                     150                     155                     160
Phe Ala Gly Tyr Phe Leu Gly Gly Leu Cys Gln Phe Gly Lys Ile Leu
                    165                     170                     175
Pro Ser Arg Asp Phe Val Ile Ile His Gly Asp Gly Asn Lys Lys Ala
                180                     185                     190
Ile Tyr Asn Asn Glu Asp Asp Ile Ala Thr Tyr Ala Ile Lys Thr Ile
            195                     200                     205
Asn Asp Pro Arg Thr Leu Asn Lys Thr Ile Tyr Ile Ser Pro Pro Lys
        210                     215                     220
Asn Ile Leu Ser Gln Arg Glu Val Val Gln Thr Trp Glu Lys Leu Ile
225                     230                     235                     240
Gly Lys Glu Leu Gln Lys Ile Thr Leu Ser Lys Glu Asp Phe Leu Ala
                    245                     250                     255
Ser Val Lys Glu Leu Glu Tyr Ala Gln Gln Val Gly Leu Ser His Tyr
                260                     265                     270
His Asp Val Asn Tyr Gln Gly Cys Leu Thr Ser Phe Glu Ile Gly Asp
            275                     280                     285
Glu Glu Glu Ala Ser Lys Leu Tyr Pro Glu Val Lys Tyr Thr Ser Val
        290                     295                     300
Glu Glu Tyr Leu Lys Arg Tyr Val
305                     310

<210> SEQ ID NO 49
<211> LENGTH: 1112
<212> TYPE: DNA
<213> ORGANISM: Forsythia x intermedia
<220> FEATURE:
<221> NAME/KEY: CDS
<222> LOCATION: (44)..(979)

<400> SEQUENCE: 49
aattcggcac gagctcgtgc cgcacagaga aaaacagaga gag atg gga aaa agc      55
                                                Met Gly Lys Ser
                                                  1 aaa gtt ttg atc att ggg ggt aca ggg tac tta ggg agg aga ttg gtt     103
Lys Val Leu Ile Ile Gly Gly Thr Gly Tyr Leu Gly Arg Arg Leu Val
  5                  10                  15                  20 aag gca agt tta gct caa ggt cat gaa aca tac att ctg cat agg cct    151
Lys Ala Ser Leu Ala Gln Gly His Glu Thr Tyr Ile Leu His Arg Pro
                25                  30                  35
```

-continued

```
gaa att ggt gtt gat att gat aaa gtt gaa atg cta ata tca ttt aaa      199
Glu Ile Gly Val Asp Ile Asp Lys Val Glu Met Leu Ile Ser Phe Lys
             40                  45                  50 atg caa gga gct cat ctt gta tct ggt tct ttc aag gat ttc aac agt      247
Met Gln Gly Ala His Leu Val Ser Gly Ser Phe Lys Asp Phe Asn Ser
         55                  60                  65 ctg gtc gag gct gtc aag ctc gta gac gta gta atc agc gcc att tct      295
Leu Val Glu Ala Val Lys Leu Val Asp Val Val Ile Ser Ala Ile Ser
 70                  75                  80 ggt gtt cat att cga agc cat caa att ctt ctt caa ctc aag ctt gtt      343
Gly Val His Ile Arg Ser His Gln Ile Leu Leu Gln Leu Lys Leu Val
 85                  90                  95                 100 gaa gct att aaa gag gct gga aat gtc aag aga ttt tta cca tct gag      391
Glu Ala Ile Lys Glu Ala Gly Asn Val Lys Arg Phe Leu Pro Ser Glu
                105                 110                 115 ttt gga atg gat cct gca aaa ttt atg gat acg gcc atg gaa ccc gga      439
Phe Gly Met Asp Pro Ala Lys Phe Met Asp Thr Ala Met Glu Pro Gly
            120                 125                 130 aag gta aca ctt gat gag aag atg gtg gta agg aaa gca att gaa aag      487
Lys Val Thr Leu Asp Glu Lys Met Val Val Arg Lys Ala Ile Glu Lys
        135                 140                 145 gct ggg att cct ttc aca tat gtc tct gca aat tgc ttt gct ggt tat      535
Ala Gly Ile Pro Phe Thr Tyr Val Ser Ala Asn Cys Phe Ala Gly Tyr
150                 155                 160 ttc ttg gga ggt ctc tgt caa ttt ggc aaa att ctt cct tct aga gat      583
Phe Leu Gly Gly Leu Cys Gln Phe Gly Lys Ile Leu Pro Ser Arg Asp
165                 170                 175                 180 ttt gtc att ata cat gga gat ggt aac aaa aaa gca ata tat aac aat      631
Phe Val Ile Ile His Gly Asp Gly Asn Lys Lys Ala Ile Tyr Asn Asn
                185                 190                 195 gaa gat gat ata gca act tat gcc atc aaa aca att aat gat cca aga      679
Glu Asp Asp Ile Ala Thr Tyr Ala Ile Lys Thr Ile Asn Asp Pro Arg
            200                 205                 210 acc ctc aac aag aca atc tac att agt cct cca aaa aac atc ctt tca      727
Thr Leu Asn Lys Thr Ile Tyr Ile Ser Pro Pro Lys Asn Ile Leu Ser
        215                 220                 225 caa aga gaa gtt gtt cag aca tgg gag aag ctt att ggg aaa gaa ctg      775
Gln Arg Glu Val Val Gln Thr Trp Glu Lys Leu Ile Gly Lys Glu Leu
    230                 235                 240 cag aaa att aca ctc tcg aag gaa gat ttt tta gcc tcc gtg aaa gag      823
Gln Lys Ile Thr Leu Ser Lys Glu Asp Phe Leu Ala Ser Val Lys Glu
245                 250                 255                 260 ctc gag tat gct cag caa gtg gga tta agc cat tat cat gat gtc aac      871
Leu Glu Tyr Ala Gln Gln Val Gly Leu Ser His Tyr His Asp Val Asn
                265                 270                 275 tat cag gga tgc ctt acg agt ttt gag ata gga gat gaa gag gca      919
Tyr Gln Gly Cys Leu Thr Ser Phe Glu Ile Gly Asp Glu Glu Ala
            280                 285                 290 tct aaa ctt tat cca gag gtt aag tat acc agt gtg gaa gag tac ctc      967
Ser Lys Leu Tyr Pro Glu Val Lys Tyr Thr Ser Val Glu Glu Tyr Leu
        295                 300                 305 aag cgt tac gtg tagttgaaag ctttccatta ttattgtaat aatatttaaa         1019
Lys Arg Tyr Val
        310 tcagtatgta gttttaaatt tcgttaaata atatgtgttg aattttgctt caaacgagtg   1079 gtcgattgaa atggaatttt gaagtcaaaa aaa                                 1112

<210> SEQ ID NO 50
<211> LENGTH: 312
```

```
<212> TYPE: PRT
<213> ORGANISM: Forsythia x intermedia

<400> SEQUENCE: 50

Met Gly Lys Ser Lys Val Leu Ile Ile Gly Thr Gly Tyr Leu Gly
  1               5                  10                  15

Arg Arg Leu Val Lys Ala Ser Leu Ala Gln Gly His Glu Thr Tyr Ile
             20                  25                  30

Leu His Arg Pro Glu Ile Gly Val Asp Ile Asp Lys Val Glu Met Leu
         35                  40                  45

Ile Ser Phe Lys Met Gln Gly Ala His Leu Val Ser Gly Ser Phe Lys
     50                  55                  60

Asp Phe Asn Ser Leu Val Glu Ala Val Lys Leu Val Asp Val Val Ile
 65                  70                  75                  80

Ser Ala Ile Ser Gly Val His Ile Arg Ser His Gln Ile Leu Leu Gln
                 85                  90                  95

Leu Lys Leu Val Glu Ala Ile Lys Glu Ala Gly Asn Val Lys Arg Phe
            100                 105                 110

Leu Pro Ser Glu Phe Gly Met Asp Pro Ala Lys Phe Met Asp Thr Ala
        115                 120                 125

Met Glu Pro Gly Lys Val Thr Leu Asp Glu Lys Met Val Val Arg Lys
130                 135                 140

Ala Ile Glu Lys Ala Gly Ile Pro Phe Thr Tyr Val Ser Ala Asn Cys
145                 150                 155                 160

Phe Ala Gly Tyr Phe Leu Gly Gly Leu Cys Gln Phe Gly Lys Ile Leu
                165                 170                 175

Pro Ser Arg Asp Phe Val Ile Ile His Gly Asp Gly Asn Lys Lys Ala
            180                 185                 190

Ile Tyr Asn Asn Glu Asp Asp Ile Ala Thr Tyr Ala Ile Lys Thr Ile
        195                 200                 205

Asn Asp Pro Arg Thr Leu Asn Lys Thr Ile Tyr Ile Ser Pro Pro Lys
    210                 215                 220

Asn Ile Leu Ser Gln Arg Glu Val Val Gln Thr Trp Glu Lys Leu Ile
225                 230                 235                 240

Gly Lys Glu Leu Gln Lys Ile Thr Leu Ser Lys Glu Asp Phe Leu Ala
                245                 250                 255

Ser Val Lys Glu Leu Glu Tyr Ala Gln Gln Val Gly Leu Ser His Tyr
            260                 265                 270

His Asp Val Asn Tyr Gln Gly Cys Leu Thr Ser Phe Glu Ile Gly Asp
        275                 280                 285

Glu Glu Glu Ala Ser Lys Leu Tyr Pro Glu Val Lys Tyr Thr Ser Val
    290                 295                 300

Glu Glu Tyr Leu Lys Arg Tyr Val
305                 310

<210> SEQ ID NO 51
<211> LENGTH: 1124
<212> TYPE: DNA
<213> ORGANISM: Forsythia x intermedia
<220> FEATURE:
<221> NAME/KEY: CDS
<222> LOCATION: (29)..(964)

<400> SEQUENCE: 51
aattcggcac gaggaaaaac agagagag atg gga aaa agc aaa gtt ttg atc      52
                            Met Gly Lys Ser Lys Val Leu Ile
                              1               5
```

-continued

```
att ggg ggt aca ggg tac tta ggg agg aga ttg gtt aag gca agt tta      100
Ile Gly Gly Thr Gly Tyr Leu Gly Arg Arg Leu Val Lys Ala Ser Leu
     10              15                  20 gct caa ggt cat gaa aca tac att ctg cat agg cct gaa att ggt gtt      148
Ala Gln Gly His Glu Thr Tyr Ile Leu His Arg Pro Glu Ile Gly Val
 25              30                  35                  40 gat att gat aaa gtt gaa atg cta ata tca ttt aaa atg caa gga gct      196
Asp Ile Asp Lys Val Glu Met Leu Ile Ser Phe Lys Met Gln Gly Ala
             45                  50                  55 cat ctt gta tct ggt tct ttc aag gat ttc aac agt ctg gtc gag gct      244
His Leu Val Ser Gly Ser Phe Lys Asp Phe Asn Ser Leu Val Glu Ala
         60                  65                  70 gtc aag ctc gta gac gta gta atc agc gcc att tct ggt gtt cat att      292
Val Lys Leu Val Asp Val Val Ile Ser Ala Ile Ser Gly Val His Ile
     75                  80                  85 cga agc cat caa att ctt ctt caa ctc aag ctt gtt gaa gct att aaa      340
Arg Ser His Gln Ile Leu Leu Gln Leu Lys Leu Val Glu Ala Ile Lys
 90                  95                 100 gag gct gga aat gtc aag aga ttt tta cca tct gag ttt gga atg gat      388
Glu Ala Gly Asn Val Lys Arg Phe Leu Pro Ser Glu Phe Gly Met Asp
105                 110                 115                 120 cct gca aaa ttt atg gat acg gcc atg gaa ccc gga aag gta aca ctt      436
Pro Ala Lys Phe Met Asp Thr Ala Met Glu Pro Gly Lys Val Thr Leu
                125                 130                 135 gat gag aag atg gtg gta agg aaa gca att gaa aag gct ggg att cct      484
Asp Glu Lys Met Val Val Arg Lys Ala Ile Glu Lys Ala Gly Ile Pro
            140                 145                 150 ttc aca tat gtc tct gca aat tgc ttt gct ggt tat ttc ttg gga ggt      532
Phe Thr Tyr Val Ser Ala Asn Cys Phe Ala Gly Tyr Phe Leu Gly Gly
        155                 160                 165 ctc tgt caa ttt ggc aaa att ctt cct tct aga gat ttt gtc att ata      580
Leu Cys Gln Phe Gly Lys Ile Leu Pro Ser Arg Asp Phe Val Ile Ile
    170                 175                 180 cat gga gat ggt aac aaa aaa gca ata tat aac aat gaa gat gat ata      628
His Gly Asp Gly Asn Lys Lys Ala Ile Tyr Asn Asn Glu Asp Asp Ile
185                 190                 195                 200 gca act tat gcc atc aaa aca att aat gat cca aga acc ctc aac aag      676
Ala Thr Tyr Ala Ile Lys Thr Ile Asn Asp Pro Arg Thr Leu Asn Lys
                205                 210                 215 aca atc tac att agt cct cca aaa aac atc ctt tca caa aga gaa gtt      724
Thr Ile Tyr Ile Ser Pro Pro Lys Asn Ile Leu Ser Gln Arg Glu Val
            220                 225                 230 gtt cag aca tgg gag aag ctt att ggg aaa gaa ctg cag aaa att aca      772
Val Gln Thr Trp Glu Lys Leu Ile Gly Lys Glu Leu Gln Lys Ile Thr
        235                 240                 245 ctc tcg aag gaa gat ttt tta gcc tcc gtg aaa gag ctc gag tat gct      820
Leu Ser Lys Glu Asp Phe Leu Ala Ser Val Lys Glu Leu Glu Tyr Ala
    250                 255                 260 cag caa gtg gga tta agc cat tat cat gat gtc aac tat cag gga tgc      868
Gln Gln Val Gly Leu Ser His Tyr His Asp Val Asn Tyr Gln Gly Cys
265                 270                 275                 280 ctt acg agt ttt gag ata gga gat gaa gaa gag gca tct aaa ctt tat      916
Leu Thr Ser Phe Glu Ile Gly Asp Glu Glu Glu Ala Ser Lys Leu Tyr
                285                 290                 295 cca gag gtt aag tat acc agt gtg gaa gag tac ctc aag cgt tac gtg      964
Pro Glu Val Lys Tyr Thr Ser Val Glu Glu Tyr Leu Lys Arg Tyr Val
            300                 305                 310 tagttgaaag ctttccatta ttattgtaat aatatttaaa tcagtatgta gtttttaaatt  1024
```

-continued

```
tcgttaaata atatgtgttg aattttgctt caaacgagtg gtcgattgaa atgaattttt    1084
gaagtcatct tctccacaat attagtccaa ataaaaaaaa                          1124
```

```
<210> SEQ ID NO 52
<211> LENGTH: 312
<212> TYPE: PRT
<213> ORGANISM: Forsythia x intermedia

<400> SEQUENCE: 52

Met Gly Lys Ser Lys Val Leu Ile Ile Gly Gly Thr Gly Tyr Leu Gly
 1               5                  10                  15

Arg Arg Leu Val Lys Ala Ser Leu Ala Gln Gly His Glu Thr Tyr Ile
            20                  25                  30

Leu His Arg Pro Glu Ile Gly Val Asp Ile Asp Lys Val Glu Met Leu
        35                  40                  45

Ile Ser Phe Lys Met Gln Gly Ala His Leu Val Ser Gly Ser Phe Lys
    50                  55                  60

Asp Phe Asn Ser Leu Val Glu Ala Val Lys Leu Val Asp Val Val Ile
65                  70                  75                  80

Ser Ala Ile Ser Gly Val His Ile Arg Ser His Gln Ile Leu Leu Gln
                85                  90                  95

Leu Lys Leu Val Glu Ala Ile Lys Glu Ala Gly Asn Val Lys Arg Phe
            100                 105                 110

Leu Pro Ser Glu Phe Gly Met Asp Pro Ala Lys Phe Met Asp Thr Ala
        115                 120                 125

Met Glu Pro Gly Lys Val Thr Leu Asp Glu Lys Met Val Val Arg Lys
    130                 135                 140

Ala Ile Glu Lys Ala Gly Ile Pro Phe Thr Tyr Val Ser Ala Asn Cys
145                 150                 155                 160

Phe Ala Gly Tyr Phe Leu Gly Gly Leu Cys Gln Phe Gly Lys Ile Leu
                165                 170                 175

Pro Ser Arg Asp Phe Val Ile His Gly Asp Gly Asn Lys Lys Ala
            180                 185                 190

Ile Tyr Asn Asn Glu Asp Asp Ile Ala Thr Tyr Ala Ile Lys Thr Ile
        195                 200                 205

Asn Asp Pro Arg Thr Leu Asn Lys Thr Ile Tyr Ile Ser Pro Pro Lys
    210                 215                 220

Asn Ile Leu Ser Gln Arg Glu Val Val Gln Thr Trp Glu Lys Leu Ile
225                 230                 235                 240

Gly Lys Glu Leu Gln Lys Ile Thr Leu Ser Lys Glu Asp Phe Leu Ala
                245                 250                 255

Ser Val Lys Glu Leu Glu Tyr Ala Gln Gln Val Gly Leu Ser His Tyr
            260                 265                 270

His Asp Val Asn Tyr Gln Gly Cys Leu Thr Ser Phe Glu Ile Gly Asp
        275                 280                 285

Glu Glu Glu Ala Ser Lys Leu Tyr Pro Glu Val Lys Tyr Thr Ser Val
    290                 295                 300

Glu Glu Tyr Leu Lys Arg Tyr Val
305                 310

<210> SEQ ID NO 53
<211> LENGTH: 1097
<212> TYPE: DNA
<213> ORGANISM: Forsythia x intermedia
<220> FEATURE:
<221> NAME/KEY: CDS
```

<222> LOCATION: (29)..(964)

<400> SEQUENCE: 53

```
aattcggcac gaggaaaaac agagagag atg gga aaa agc aaa gtt ttg atc         52
                                Met Gly Lys Ser Lys Val Leu Ile
                                  1               5 att ggg ggt aca ggg tac tta ggg agg aga ttg gtt aag gca agt tta       100
Ile Gly Gly Thr Gly Tyr Leu Gly Arg Arg Leu Val Lys Ala Ser Leu
 10                  15                  20 gct caa ggt cat gaa aca tac att ctg cat agg cct gaa att ggt gtt       148
Ala Gln Gly His Glu Thr Tyr Ile Leu His Arg Pro Glu Ile Gly Val
 25                  30                  35                  40 gat att gat aaa gtt gaa atg cta ata tca ttt aaa atg caa gga gct       196
Asp Ile Asp Lys Val Glu Met Leu Ile Ser Phe Lys Met Gln Gly Ala
                 45                  50                  55 cat ctt gta tct ggt tct ttc aag gat ttc aac agt ctg gtc gag gct       244
His Leu Val Ser Gly Ser Phe Lys Asp Phe Asn Ser Leu Val Glu Ala
             60                  65                  70 gtc aag ctc gta gac gta gta atc agc gcc att tct ggt gtt cat att       292
Val Lys Leu Val Asp Val Val Ile Ser Ala Ile Ser Gly Val His Ile
         75                  80                  85 cga agc cat caa att ctt ctt caa ctc aag ctt gtt gaa gct att aaa       340
Arg Ser His Gln Ile Leu Leu Gln Leu Lys Leu Val Glu Ala Ile Lys
 90                  95                 100 gag gct gga aat gtc aag aga ttt tta cca tct gag ttt gga atg gat       388
Glu Ala Gly Asn Val Lys Arg Phe Leu Pro Ser Glu Phe Gly Met Asp
105                 110                 115                 120 cct gca aaa ttt atg gat acg gcc atg gaa ccc gga aag gta aca ctt       436
Pro Ala Lys Phe Met Asp Thr Ala Met Glu Pro Gly Lys Val Thr Leu
                125                 130                 135 gat gag aag atg gtg gta agg aaa gca att gaa aag gct ggg att cct       484
Asp Glu Lys Met Val Val Arg Lys Ala Ile Glu Lys Ala Gly Ile Pro
            140                 145                 150 ttc aca tat gtc tct gca aat tgc ttt gct ggt tat ttc ttg gga ggt       532
Phe Thr Tyr Val Ser Ala Asn Cys Phe Ala Gly Tyr Phe Leu Gly Gly
        155                 160                 165 ctc tgt caa ttt ggc aaa att ctt cct tct aga gat ttt gtc att ata       580
Leu Cys Gln Phe Gly Lys Ile Leu Pro Ser Arg Asp Phe Val Ile Ile
170                 175                 180 cat gga gat ggt aac aaa aaa gca ata tat aac aat gaa gat gat ata       628
His Gly Asp Gly Asn Lys Lys Ala Ile Tyr Asn Asn Glu Asp Asp Ile
185                 190                 195                 200 gca act tat gcc atc aaa aca att aat gat cca aga acc ctc aac aag       676
Ala Thr Tyr Ala Ile Lys Thr Ile Asn Asp Pro Arg Thr Leu Asn Lys
                205                 210                 215 aca atc tac att agt cct cca aaa aac atc ctt tca caa aga gaa gtt       724
Thr Ile Tyr Ile Ser Pro Pro Lys Asn Ile Leu Ser Gln Arg Glu Val
            220                 225                 230 gtt cag aca tgg gag aag ctt att ggg aaa gaa ctg cag aaa att aca       772
Val Gln Thr Trp Glu Lys Leu Ile Gly Lys Glu Leu Gln Lys Ile Thr
        235                 240                 245 ctc tcg aag gaa gat ttt tta gcc tcc gtg aaa gag ctc gag tat gct       820
Leu Ser Lys Glu Asp Phe Leu Ala Ser Val Lys Glu Leu Glu Tyr Ala
250                 255                 260 cag caa gtg gga tta agc cat tat cat gat gtc aac tat cag gga tgc       868
Gln Gln Val Gly Leu Ser His Tyr His Asp Val Asn Tyr Gln Gly Cys
265                 270                 275                 280 ctt acg agt ttt gag ata gga gat gaa gaa gag gca tct aaa ctt tat       916
Leu Thr Ser Phe Glu Ile Gly Asp Glu Glu Glu Ala Ser Lys Leu Tyr
                285                 290                 295
```

```
cca gag gtt aag tat acc agt gtg gaa gag tac ctc aag cgt tac gtg        964
Pro Glu Val Lys Tyr Thr Ser Val Glu Glu Tyr Leu Lys Arg Tyr Val
        300                 305                 310 tagttgaaag ctttccatta ttattgtaat aatatttaaa tcagtatgta gttttaaatt     1024
tcgttaaata atatgtgttg aattttgctt caaacgagtg gtcgattgaa atggaatttt     1084
gaaaaaaaaa aaa                                                         1097
```

<210> SEQ ID NO 54
<211> LENGTH: 312
<212> TYPE: PRT
<213> ORGANISM: Forsythia x intermedia

<400> SEQUENCE: 54

```
Met Gly Lys Ser Lys Val Leu Ile Ile Gly Gly Thr Gly Tyr Leu Gly
 1               5                  10                  15

Arg Arg Leu Val Lys Ala Ser Leu Ala Gln Gly His Glu Thr Tyr Ile
                20                  25                  30

Leu His Arg Pro Glu Ile Gly Val Asp Ile Asp Lys Val Glu Met Leu
            35                  40                  45

Ile Ser Phe Lys Met Gln Gly Ala His Leu Val Ser Gly Ser Phe Lys
    50                  55                  60

Asp Phe Asn Ser Leu Val Glu Ala Val Lys Leu Val Asp Val Val Ile
65                  70                  75                  80

Ser Ala Ile Ser Gly Val His Ile Arg Ser His Gln Ile Leu Leu Gln
                85                  90                  95

Leu Lys Leu Val Glu Ala Ile Lys Glu Ala Gly Asn Val Lys Arg Phe
            100                 105                 110

Leu Pro Ser Glu Phe Gly Met Asp Pro Ala Lys Phe Met Asp Thr Ala
        115                 120                 125

Met Glu Pro Gly Lys Val Thr Leu Asp Glu Lys Met Val Val Arg Lys
    130                 135                 140

Ala Ile Glu Lys Ala Gly Ile Pro Phe Thr Tyr Val Ser Ala Asn Cys
145                 150                 155                 160

Phe Ala Gly Tyr Phe Leu Gly Gly Leu Cys Gln Phe Gly Lys Ile Leu
                165                 170                 175

Pro Ser Arg Asp Phe Val Ile Ile His Gly Asp Gly Asn Lys Lys Ala
            180                 185                 190

Ile Tyr Asn Asn Glu Asp Asp Ile Ala Thr Tyr Ala Ile Lys Thr Ile
        195                 200                 205

Asn Asp Pro Arg Thr Leu Asn Lys Thr Ile Tyr Ile Ser Pro Pro Lys
    210                 215                 220

Asn Ile Leu Ser Gln Arg Glu Val Val Gln Thr Trp Glu Lys Leu Ile
225                 230                 235                 240

Gly Lys Glu Leu Gln Lys Ile Thr Leu Ser Lys Glu Asp Phe Leu Ala
                245                 250                 255

Ser Val Lys Glu Leu Glu Tyr Ala Gln Gln Val Gly Leu Ser His Tyr
            260                 265                 270

His Asp Val Asn Tyr Gln Gly Cys Leu Thr Ser Phe Glu Ile Gly Asp
        275                 280                 285

Glu Glu Glu Ala Ser Lys Leu Tyr Pro Glu Val Lys Tyr Thr Ser Val
    290                 295                 300

Glu Glu Tyr Leu Lys Arg Tyr Val
305                 310
```

```
<210> SEQ ID NO 55
<211> LENGTH: 1109
<212> TYPE: DNA
<213> ORGANISM: Forsythia x intermedia
<220> FEATURE:
<221> NAME/KEY: CDS
<222> LOCATION: (31)..(966)

<400> SEQUENCE: 55
```

| | | |
|---|---|---|
| aattcggcac gaggagaaaa acagagagag atg gga aaa agc aaa gtt ttg atc<br>                                                  Met Gly Lys Ser Lys Val Leu Ile<br>                                                  1               5 | 54 |

```
att ggg ggt aca ggg tac tta ggg agg aga ttg gtt aag gca agt tta        102
Ile Gly Gly Thr Gly Tyr Leu Gly Arg Arg Leu Val Lys Ala Ser Leu
     10                  15                  20 gct caa ggt cat gaa aca tac att ctg cat agg cct gaa att ggt gtt        150
Ala Gln Gly His Glu Thr Tyr Ile Leu His Arg Pro Glu Ile Gly Val
 25                  30                  35                  40 gat att gat aaa gtt gaa atg cta ata tca ttt aaa atg caa gga gct        198
Asp Ile Asp Lys Val Glu Met Leu Ile Ser Phe Lys Met Gln Gly Ala
                 45                  50                  55 cat ctt gta tct ggt tct ttc aag gat ttc aac agt ctg gtc gag gct        246
His Leu Val Ser Gly Ser Phe Lys Asp Phe Asn Ser Leu Val Glu Ala
             60                  65                  70 gtc aag ctc gta gac gta gta atc agc gcc att tct ggt gtt cat att        294
Val Lys Leu Val Asp Val Val Ile Ser Ala Ile Ser Gly Val His Ile
         75                  80                  85 cga agc cat caa att ctt ctt caa ctc aag ctt gtt gaa gct att aaa        342
Arg Ser His Gln Ile Leu Leu Gln Leu Lys Leu Val Glu Ala Ile Lys
     90                  95                 100 gag gct gga aat gtc aag aga ttt tta cca tct gag ttt gga atg gat        390
Glu Ala Gly Asn Val Lys Arg Phe Leu Pro Ser Glu Phe Gly Met Asp
105                 110                 115                 120 cct gca aaa ttt atg gat acg gcc atg gaa ccc gga aag gta aca ctt        438
Pro Ala Lys Phe Met Asp Thr Ala Met Glu Pro Gly Lys Val Thr Leu
                125                 130                 135 gat gag aag atg gtg gta agg aaa gca att gaa aag gct ggg att cct        486
Asp Glu Lys Met Val Val Arg Lys Ala Ile Glu Lys Ala Gly Ile Pro
            140                 145                 150 ttc aca tat gtc tct gca aat tgc ttt gct ggt tat ttc ttg gga ggt        534
Phe Thr Tyr Val Ser Ala Asn Cys Phe Ala Gly Tyr Phe Leu Gly Gly
        155                 160                 165 ctc tgt caa ttt ggc aaa att ctt cct tct aga gat ttt gtc att ata        582
Leu Cys Gln Phe Gly Lys Ile Leu Pro Ser Arg Asp Phe Val Ile Ile
    170                 175                 180 cat gga gat ggt aac aaa aaa gca ata tat aac aat gaa gat gat ata        630
His Gly Asp Gly Asn Lys Lys Ala Ile Tyr Asn Asn Glu Asp Asp Ile
185                 190                 195                 200 gca act tat gcc atc aaa aca att aat gat cca aga acc ctc aac aag        678
Ala Thr Tyr Ala Ile Lys Thr Ile Asn Asp Pro Arg Thr Leu Asn Lys
                205                 210                 215 aca atc tac att agt cct cca aaa aac atc ctt tca caa aga gaa gtt        726
Thr Ile Tyr Ile Ser Pro Pro Lys Asn Ile Leu Ser Gln Arg Glu Val
            220                 225                 230 gtt cag aca tgg gag aag ctt att ggg aaa gaa ctg cag aaa att aca        774
Val Gln Thr Trp Glu Lys Leu Ile Gly Lys Glu Leu Gln Lys Ile Thr
        235                 240                 245 ctc tcg aag gaa gat ttt tta gcc tcc gtg aaa gag ctc gag tat gct        822
Leu Ser Lys Glu Asp Phe Leu Ala Ser Val Lys Glu Leu Glu Tyr Ala
    250                 255                 260
```

```
cag caa gtg gga tta agc cat tat cat gat gtc aac tat cag gga tgc      870
Gln Gln Val Gly Leu Ser His Tyr His Asp Val Asn Tyr Gln Gly Cys
265                 270                 275                 280 ctt acg agt ttt gag ata gga gat gaa gaa gag gca tct aaa ctt tat      918
Leu Thr Ser Phe Glu Ile Gly Asp Glu Glu Glu Ala Ser Lys Leu Tyr
                285                 290                 295 cca gag gtt aag tat acc agt gtg gaa gag tac ctc aag cgt tac gtg      966
Pro Glu Val Lys Tyr Thr Ser Val Glu Glu Tyr Leu Lys Arg Tyr Val
            300                 305                 310 tagttgaaag ctttccatta ttattgtaat aatatttaaa tcagtatgta gttttaaatt   1026
tcgttaaata atatgtgttg aatttgctt caaacgagtg gtcgattgaa atggaatttt    1086
gaagtcatct tctccaaaaa aaa                                           1109
```

<210> SEQ ID NO 56
<211> LENGTH: 312
<212> TYPE: PRT
<213> ORGANISM: Forsythia x intermedia

<400> SEQUENCE: 56

```
Met Gly Lys Ser Lys Val Leu Ile Ile Gly Thr Gly Tyr Leu Gly
 1               5                  10                  15

Arg Arg Leu Val Lys Ala Ser Leu Ala Gln Gly His Glu Thr Tyr Ile
                20                  25                  30

Leu His Arg Pro Glu Ile Gly Val Asp Ile Asp Lys Val Glu Met Leu
            35                  40                  45

Ile Ser Phe Lys Met Gln Gly Ala His Leu Val Ser Gly Ser Phe Lys
        50                  55                  60

Asp Phe Asn Ser Leu Val Glu Ala Val Lys Leu Val Asp Val Val Ile
65                  70                  75                  80

Ser Ala Ile Ser Gly Val His Ile Arg Ser His Gln Ile Leu Leu Gln
                85                  90                  95

Leu Lys Leu Val Glu Ala Ile Lys Glu Ala Gly Asn Val Lys Arg Phe
            100                 105                 110

Leu Pro Ser Glu Phe Gly Met Asp Pro Ala Lys Phe Met Asp Thr Ala
        115                 120                 125

Met Glu Pro Gly Lys Val Thr Leu Asp Glu Lys Met Val Val Arg Lys
130                 135                 140

Ala Ile Glu Lys Ala Gly Ile Pro Phe Thr Tyr Val Ser Ala Asn Cys
145                 150                 155                 160

Phe Ala Gly Tyr Phe Leu Gly Gly Leu Cys Gln Phe Gly Lys Ile Leu
                165                 170                 175

Pro Ser Arg Asp Phe Val Ile His Gly Asp Gly Asn Lys Lys Ala
            180                 185                 190

Ile Tyr Asn Asn Glu Asp Asp Ile Ala Thr Tyr Ala Ile Lys Thr Ile
        195                 200                 205

Asn Asp Pro Arg Thr Leu Asn Lys Thr Ile Tyr Ile Ser Pro Pro Lys
210                 215                 220

Asn Ile Leu Ser Gln Arg Glu Val Val Gln Thr Trp Glu Lys Leu Ile
225                 230                 235                 240

Gly Lys Glu Leu Gln Lys Ile Thr Leu Ser Lys Glu Asp Phe Leu Ala
                245                 250                 255

Ser Val Lys Glu Leu Glu Tyr Ala Gln Gln Val Gly Leu Ser His Tyr
            260                 265                 270

His Asp Val Asn Tyr Gln Gly Cys Leu Thr Ser Phe Glu Ile Gly Asp
        275                 280                 285
```

-continued

```
Glu Glu Glu Ala Ser Lys Leu Tyr Pro Glu Val Lys Tyr Thr Ser Val
    290                 295                 300
Glu Glu Tyr Leu Lys Arg Tyr Val
305                 310

<210> SEQ ID NO 57
<211> LENGTH: 1107
<212> TYPE: DNA
<213> ORGANISM: Forsythia x intermedia
<220> FEATURE:
<221> NAME/KEY: CDS
<222> LOCATION: (27)..(962)

<400> SEQUENCE: 57
aattcggcac gagaaaacag agagag atg gga aaa agc aaa gtt ttg atc att        53
                            Met Gly Lys Ser Lys Val Leu Ile Ile
                              1               5 ggg ggt aca ggg tac tta ggg agg aga ttg gtt aag gca agt tta gct       101
Gly Gly Thr Gly Tyr Leu Gly Arg Arg Leu Val Lys Ala Ser Leu Ala
 10              15                  20                  25 caa ggt cat gaa aca tac att ctg cat agg cct gaa att ggt gtt gat       149
Gln Gly His Glu Thr Tyr Ile Leu His Arg Pro Glu Ile Gly Val Asp
                 30                  35                  40 att gat aaa gtt gaa atg cta ata tca ttt aaa atg caa gga gct cat       197
Ile Asp Lys Val Glu Met Leu Ile Ser Phe Lys Met Gln Gly Ala His
             45                  50                  55 ctt gta tct ggt tct ttc aag gat ttc aac agt ctg gtc gag gct gtc       245
Leu Val Ser Gly Ser Phe Lys Asp Phe Asn Ser Leu Val Glu Ala Val
         60                  65                  70 aag ctc gta gac gta gta atc agc gcc att tct ggt gtt cat att cga       293
Lys Leu Val Asp Val Val Ile Ser Ala Ile Ser Gly Val His Ile Arg
     75                  80                  85 agc cat caa att ctt ctt caa ctc aag ctt gtt gaa gct att aaa gag       341
Ser His Gln Ile Leu Leu Gln Leu Lys Leu Val Glu Ala Ile Lys Glu
 90                  95                 100                 105 gct gga aat gtc aag aga ttt tta cca tct gag ttt gga atg gat cct       389
Ala Gly Asn Val Lys Arg Phe Leu Pro Ser Glu Phe Gly Met Asp Pro
                110                 115                 120 gca aaa ttt atg gat acg gcc atg gaa ccc gga aag gta aca ctt gat       437
Ala Lys Phe Met Asp Thr Ala Met Glu Pro Gly Lys Val Thr Leu Asp
                125                 130                 135 gag aag atg gtg gta agg aaa gca att gaa aag gct ggg att cct ttc       485
Glu Lys Met Val Val Arg Lys Ala Ile Glu Lys Ala Gly Ile Pro Phe
            140                 145                 150 aca tat gtc tct gca aat tgc ttt gct ggt tat ttc ttg gga ggt ctc       533
Thr Tyr Val Ser Ala Asn Cys Phe Ala Gly Tyr Phe Leu Gly Gly Leu
            155                 160                 165 tgt caa ttt ggc aaa att ctt cct tct aga gat ttt gtc att ata cat       581
Cys Gln Phe Gly Lys Ile Leu Pro Ser Arg Asp Phe Val Ile Ile His
170                 175                 180                 185 gga gat ggt aac aaa aaa gca ata tat aac aat gaa gat gat ata gca       629
Gly Asp Gly Asn Lys Lys Ala Ile Tyr Asn Asn Glu Asp Asp Ile Ala
                190                 195                 200 act tat gcc atc aaa aca att aat gat cca aga acc ctc aac aag aca       677
Thr Tyr Ala Ile Lys Thr Ile Asn Asp Pro Arg Thr Leu Asn Lys Thr
                205                 210                 215 atc tac att agt cct cca aaa aac atc ctt tca caa aga gaa gtt gtt       725
Ile Tyr Ile Ser Pro Pro Lys Asn Ile Leu Ser Gln Arg Glu Val Val
            220                 225                 230 cag aca tgg gag aag ctt att ggg aaa gaa ctg cag aaa att aca ctc       773
```

```
              Gln Thr Trp Glu Lys Leu Ile Gly Lys Glu Leu Gln Lys Ile Thr Leu
                  235                 240                 245 tcg aag gaa gat ttt tta gcc tcc gtg aaa gag ctc gag tat gct cag        821
Ser Lys Glu Asp Phe Leu Ala Ser Val Lys Glu Leu Glu Tyr Ala Gln
250                 255                 260                 265 caa gtg gga tta agc cat tat cat gat gtc aac tat cag gga tgc ctt        869
Gln Val Gly Leu Ser His Tyr His Asp Val Asn Tyr Gln Gly Cys Leu
                270                 275                 280 acg agt ttt gag ata gga gat gaa gaa gag gca tct aaa ctt tat cca        917
Thr Ser Phe Glu Ile Gly Asp Glu Glu Glu Ala Ser Lys Leu Tyr Pro
            285                 290                 295 gag gtt aag tat acc agt gtg gaa gag tac ctc aag cgt tac gtg            962
Glu Val Lys Tyr Thr Ser Val Glu Glu Tyr Leu Lys Arg Tyr Val
        300                 305                 310 tagttgaaag ctttccatta ttattgtaat aatatttaaa tcagtatgta gttttaaatt     1022
tcgttaaata atatgtgttg aattttgctt caaacgagtg gtcgattgaa atggaatttt     1082
gaagtcatct tctccacaaa aaaaa                                           1107

<210> SEQ ID NO 58
<211> LENGTH: 312
<212> TYPE: PRT
<213> ORGANISM: Forsythia x intermedia

<400> SEQUENCE: 58

Met Gly Lys Ser Lys Val Leu Ile Ile Gly Gly Thr Gly Tyr Leu Gly
1               5                   10                  15

Arg Arg Leu Val Lys Ala Ser Leu Ala Gln Gly His Glu Thr Tyr Ile
                20                  25                  30

Leu His Arg Pro Glu Ile Gly Val Asp Ile Asp Lys Val Glu Met Leu
            35                  40                  45

Ile Ser Phe Lys Met Gln Gly Ala His Leu Val Ser Gly Ser Phe Lys
        50                  55                  60

Asp Phe Asn Ser Leu Val Glu Ala Val Lys Leu Val Asp Val Val Ile
65                  70                  75                  80

Ser Ala Ile Ser Gly Val His Ile Arg Ser His Gln Ile Leu Leu Gln
                85                  90                  95

Leu Lys Leu Val Glu Ala Ile Lys Glu Ala Gly Asn Val Lys Arg Phe
            100                 105                 110

Leu Pro Ser Glu Phe Gly Met Asp Pro Ala Lys Phe Met Asp Thr Ala
        115                 120                 125

Met Glu Pro Gly Lys Val Thr Leu Asp Glu Lys Met Val Val Arg Lys
130                 135                 140

Ala Ile Glu Lys Ala Gly Ile Pro Phe Thr Tyr Val Ser Ala Asn Cys
145                 150                 155                 160

Phe Ala Gly Tyr Phe Leu Gly Gly Leu Cys Gln Phe Gly Lys Ile Leu
                165                 170                 175

Pro Ser Arg Asp Phe Val Ile His Gly Asp Gly Asn Lys Lys Ala
            180                 185                 190

Ile Tyr Asn Asn Glu Asp Asp Ile Ala Thr Tyr Ala Ile Lys Thr Ile
        195                 200                 205

Asn Asp Pro Arg Thr Leu Asn Lys Thr Ile Tyr Ile Ser Pro Pro Lys
210                 215                 220

Asn Ile Leu Ser Gln Arg Glu Val Val Gln Thr Trp Glu Lys Leu Ile
225                 230                 235                 240

Gly Lys Glu Leu Gln Lys Ile Thr Leu Ser Lys Glu Asp Phe Leu Ala
```

-continued

```
                    245                 250                 255
Ser Val Lys Glu Leu Glu Tyr Ala Gln Gln Val Gly Leu Ser His Tyr
                260                 265                 270

His Asp Val Asn Tyr Gln Gly Cys Leu Thr Ser Phe Glu Ile Gly Asp
            275                 280                 285

Glu Glu Glu Ala Ser Lys Leu Tyr Pro Glu Val Lys Tyr Thr Ser Val
    290                 295                 300

Glu Glu Tyr Leu Lys Arg Tyr Val
305                 310

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(26)
<223> OTHER INFORMATION: cDNA synthesis linker primer

<400> SEQUENCE: 59
gtctcgagtt tttttttttt tttttt                                          26

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(21)
<223> OTHER INFORMATION: cDNA synthesis primer

<400> SEQUENCE: 60
gcacataaga gtatggataa g                                               21

<210> SEQ ID NO 61
<211> LENGTH: 1190
<212> TYPE: DNA
<213> ORGANISM: Thuja plicata
<220> FEATURE:
<221> NAME/KEY: CDS
<222> LOCATION: (13)..(951)

<400> SEQUENCE: 61
gcacataaga gt atg gat aag aag agc aga gtt ctg ata gtg ggg ggc act     51
              Met Asp Lys Lys Ser Arg Val Leu Ile Val Gly Gly Thr
                1               5                   10 ggt tat ata ggc aaa aga att gtg aat gcc agt ata tct ctt ggc cat       99
Gly Tyr Ile Gly Lys Arg Ile Val Asn Ala Ser Ile Ser Leu Gly His
 15                  20                  25 ccc act tat gtt ttg ttc aga cca gaa gtg gtc tct aac att gac aaa      147
Pro Thr Tyr Val Leu Phe Arg Pro Glu Val Val Ser Asn Ile Asp Lys
 30                  35                  40                  45 gtg cag atg ctg tta tac ttc aaa cag ctt ggt gcc aaa ctt att gag      195
Val Gln Met Leu Leu Tyr Phe Lys Gln Leu Gly Ala Lys Leu Ile Glu
                 50                  55                  60 gct tca ttg gat gac cac caa agg ctt gtg gat gct ctg aaa caa gtg      243
Ala Ser Leu Asp Asp His Gln Arg Leu Val Asp Ala Leu Lys Gln Val
             65                  70                  75 gat gtt gtc ata agt gct ttg gca gga ggt gtt cta agc cac cat ata      291
Asp Val Val Ile Ser Ala Leu Ala Gly Gly Val Leu Ser His His Ile
         80                  85                  90
```

```
ctt gaa cag ctc aaa cta gtg gaa gcc atc aaa gaa gct gga aat att    339
Leu Glu Gln Leu Lys Leu Val Glu Ala Ile Lys Glu Ala Gly Asn Ile
         95                 100                 105 aag aga ttt ctt cca tct gag ttt ggc atg gat cca gat att atg gag    387
Lys Arg Phe Leu Pro Ser Glu Phe Gly Met Asp Pro Asp Ile Met Glu
110                 115                 120                 125 cat gca ttg caa cct ggt agc att aca ttc atc gat aag aga aag gtt    435
His Ala Leu Gln Pro Gly Ser Ile Thr Phe Ile Asp Lys Arg Lys Val
                130                 135                 140 cgg cgt gcc att gaa gca gca tcc att cct tac aca tat gtg tct tca    483
Arg Arg Ala Ile Glu Ala Ala Ser Ile Pro Tyr Thr Tyr Val Ser Ser
            145                 150                 155 aat atg ttt gct ggt tac ttt gct gga agt tta gct caa ctt gat ggt    531
Asn Met Phe Ala Gly Tyr Phe Ala Gly Ser Leu Ala Gln Leu Asp Gly
        160                 165                 170 cat atg atg cct cct cga gac aag gtc ctc atc tat gga gat gga aat    579
His Met Met Pro Pro Arg Asp Lys Val Leu Ile Tyr Gly Asp Gly Asn
175                 180                 185 gtt aaa ggt att tgg gtg gat gaa gat gat gtt gga aca tac aca atc    627
Val Lys Gly Ile Trp Val Asp Glu Asp Asp Val Gly Thr Tyr Thr Ile
190                 195                 200                 205 aaa tca att gat gat cca caa acc ctt aac aag act atg tat att agg    675
Lys Ser Ile Asp Asp Pro Gln Thr Leu Asn Lys Thr Met Tyr Ile Arg
                210                 215                 220 cca cct atg aat atc ctt tca cag aag gaa gtt ata caa ata tgg gag    723
Pro Pro Met Asn Ile Leu Ser Gln Lys Glu Val Ile Gln Ile Trp Glu
            225                 230                 235 aga tta tca gaa caa aac ctg gat aaa ata tac att tct tct caa gac    771
Arg Leu Ser Glu Gln Asn Leu Asp Lys Ile Tyr Ile Ser Ser Gln Asp
        240                 245                 250 ttt ctt gca gat atg aaa gat aaa tca tat gaa gag aag att gta cga    819
Phe Leu Ala Asp Met Lys Asp Lys Ser Tyr Glu Glu Lys Ile Val Arg
255                 260                 265 tgt cat ctc tac caa att ttc ttt aga gga gat ctt tac aac ttt gaa    867
Cys His Leu Tyr Gln Ile Phe Phe Arg Gly Asp Leu Tyr Asn Phe Glu
270                 275                 280                 285 att ggc ccc aat gct att gaa gct acc aaa ctt tat cca gaa gtg aaa    915
Ile Gly Pro Asn Ala Ile Glu Ala Thr Lys Leu Tyr Pro Glu Val Lys
                290                 295                 300 tac gta acc atg gat tca tat tta gag cgc tat gtt tgaatatctt         961
Tyr Val Thr Met Asp Ser Tyr Leu Glu Arg Tyr Val
            305                 310 tctagttttg tatattgttt ttctacatga taatgtgaga ggtactattt caaataattt  1021
agacttatgg ctcaatttta aaactagagt acactttatt ccaaattact tacactattt  1081
tttacttcat attgtactca atatagactt ggtataaaga atatggaatc ataatgatat  1141
tataattatt tatagatctt atttttaaata aaaaaaaaaa aaaaaaaa              1190

<210> SEQ ID NO 62
<211> LENGTH: 313
<212> TYPE: PRT
<213> ORGANISM: Thuja plicata

<400> SEQUENCE: 62

Met Asp Lys Lys Ser Arg Val Leu Ile Val Gly Gly Thr Gly Tyr Ile
  1               5                  10                  15

Gly Lys Arg Ile Val Asn Ala Ser Ile Ser Leu Gly His Pro Thr Tyr
             20                  25                  30
```

```
Val Leu Phe Arg Pro Glu Val Val Ser Asn Ile Asp Lys Val Gln Met
         35                  40                  45

Leu Leu Tyr Phe Lys Gln Leu Gly Ala Lys Leu Ile Glu Ala Ser Leu
     50                  55                  60

Asp Asp His Gln Arg Leu Val Asp Ala Leu Lys Gln Val Asp Val Val
 65                  70                  75                  80

Ile Ser Ala Leu Ala Gly Gly Val Leu Ser His His Ile Leu Glu Gln
                 85                  90                  95

Leu Lys Leu Val Glu Ala Ile Lys Glu Ala Gly Asn Ile Lys Arg Phe
                100                 105                 110

Leu Pro Ser Glu Phe Gly Met Asp Pro Asp Ile Met Glu His Ala Leu
            115                 120                 125

Gln Pro Gly Ser Ile Thr Phe Ile Asp Lys Arg Lys Val Arg Arg Ala
        130                 135                 140

Ile Glu Ala Ala Ser Ile Pro Tyr Thr Tyr Val Ser Ser Asn Met Phe
145                 150                 155                 160

Ala Gly Tyr Phe Ala Gly Ser Leu Ala Gln Leu Asp Gly His Met Met
                165                 170                 175

Pro Pro Arg Asp Lys Val Leu Ile Tyr Gly Asp Gly Asn Val Lys Gly
            180                 185                 190

Ile Trp Val Asp Glu Asp Val Gly Thr Tyr Thr Ile Lys Ser Ile
        195                 200                 205

Asp Asp Pro Gln Thr Leu Asn Lys Thr Met Tyr Ile Arg Pro Pro Met
    210                 215                 220

Asn Ile Leu Ser Gln Lys Glu Val Ile Gln Ile Trp Glu Arg Leu Ser
225                 230                 235                 240

Glu Gln Asn Leu Asp Lys Ile Tyr Ile Ser Ser Gln Asp Phe Leu Ala
                245                 250                 255

Asp Met Lys Asp Lys Ser Tyr Glu Glu Lys Ile Val Arg Cys His Leu
            260                 265                 270

Tyr Gln Ile Phe Phe Arg Gly Asp Leu Tyr Asn Phe Glu Ile Gly Pro
        275                 280                 285

Asn Ala Ile Glu Ala Thr Lys Leu Tyr Pro Glu Val Lys Tyr Val Thr
    290                 295                 300

Met Asp Ser Tyr Leu Glu Arg Tyr Val
305                 310
```

<210> SEQ ID NO 63
<211> LENGTH: 1151
<212> TYPE: DNA
<213> ORGANISM: Thuja plicata
<220> FEATURE:
<221> NAME/KEY: CDS
<222> LOCATION: (61)..(996)

<400> SEQUENCE: 63

```
gataagcagc atttcttcac caaagtggtc cgccattaaa ggaatagttt gaaagcagag      60 atg gaa gag agt agc agg gtt ttg ata gtg gga ggc aca gga tac ata     108
Met Glu Glu Ser Ser Arg Val Leu Ile Val Gly Gly Thr Gly Tyr Ile
  1               5                  10                  15 ggc aga agg att gtg aaa gcc agc att gct ctg ggc cat cct act ttc     156
Gly Arg Arg Ile Val Lys Ala Ser Ile Ala Leu Gly His Pro Thr Phe
                 20                  25                  30 att ttg ttt agg aaa gaa gtt gtt tct gat gta gag aaa gtg gag atg     204
Ile Leu Phe Arg Lys Glu Val Val Ser Asp Val Glu Lys Val Glu Met
             35                  40                  45
```

-continued

```
tta ttg tcc ttc aaa aag aat ggt gcc aaa tta ctg gag gct tca ttt      252
Leu Leu Ser Phe Lys Lys Asn Gly Ala Lys Leu Leu Glu Ala Ser Phe
     50                  55                  60 gat gat cac gaa agc ctt gta gat gct gtg aag cag gtt gat gtt gtg      300
Asp Asp His Glu Ser Leu Val Asp Ala Val Lys Gln Val Asp Val Val
 65                  70                  75                  80 ata agt gca gtt gca gga aac cac atg cgg cat cac atc ctt caa cag      348
Ile Ser Ala Val Ala Gly Asn His Met Arg His His Ile Leu Gln Gln
                 85                  90                  95 ctc aaa tta gtg gag gcc att aaa gaa gct gga aat att aag agg ttt      396
Leu Lys Leu Val Glu Ala Ile Lys Glu Ala Gly Asn Ile Lys Arg Phe
            100                 105                 110 gtt cct tca gaa ttt ggg atg gat cca ggg tta atg gag cat gca atg      444
Val Pro Ser Glu Phe Gly Met Asp Pro Gly Leu Met Glu His Ala Met
        115                 120                 125 gca cct ggc aac att gta ttt att gat aaa ata aaa gtt cga gag gcc      492
Ala Pro Gly Asn Ile Val Phe Ile Asp Lys Ile Lys Val Arg Glu Ala
    130                 135                 140 ata gaa gct gca tcc att cct cac act tat atc tct gcc aac ata ttt      540
Ile Glu Ala Ala Ser Ile Pro His Thr Tyr Ile Ser Ala Asn Ile Phe
145                 150                 155                 160 gct ggc tac ttg gtt ggt gga tta gct caa ctt ggt cgt gtg atg cct      588
Ala Gly Tyr Leu Val Gly Gly Leu Ala Gln Leu Gly Arg Val Met Pro
                165                 170                 175 cct tca gaa aaa gta att ctc tat gga gat gga aat gtc aaa gct gtt      636
Pro Ser Glu Lys Val Ile Leu Tyr Gly Asp Gly Asn Val Lys Ala Val
            180                 185                 190 tgg gta gat gaa gat gat gtt gga ata tac aca atc aaa gca att gat      684
Trp Val Asp Glu Asp Asp Val Gly Ile Tyr Thr Ile Lys Ala Ile Asp
        195                 200                 205 gac cct cac acc cta aat aag act atg tac atc agg cca cct ttg aat      732
Asp Pro His Thr Leu Asn Lys Thr Met Tyr Ile Arg Pro Pro Leu Asn
    210                 215                 220 att ctt tct cag aag gaa gtg gtt gaa aaa tgg gaa aag tta tca gga      780
Ile Leu Ser Gln Lys Glu Val Val Glu Lys Trp Glu Lys Leu Ser Gly
225                 230                 235                 240 aag agc tta aat aaa ata aat att tct gtt gaa gat ttt ctt gca ggc      828
Lys Ser Leu Asn Lys Ile Asn Ile Ser Val Glu Asp Phe Leu Ala Gly
                245                 250                 255 atg gaa ggt caa tca tat gga gag cag att gga ata tca cat ttc tac      876
Met Glu Gly Gln Ser Tyr Gly Glu Gln Ile Gly Ile Ser His Phe Tyr
            260                 265                 270 caa atg ttc tat agg ggt gat ctt tat aat ttt gaa att gga cct aat      924
Gln Met Phe Tyr Arg Gly Asp Leu Tyr Asn Phe Glu Ile Gly Pro Asn
        275                 280                 285 gga gta gaa gct tcc caa ctt tat cca gaa gta aaa tat aca aca gtg      972
Gly Val Glu Ala Ser Gln Leu Tyr Pro Glu Val Lys Tyr Thr Thr Val
    290                 295                 300 gat tca tac atg gaa cgc tac cta tgaaaatctt cttcacgaag atatctaaat    1026
Asp Ser Tyr Met Glu Arg Tyr Leu
305                 310 ttaatttaag ctttctaaaa gttttttatat tttgacatta tgctaaataa aaatggagag   1086
tatctagata ataatattga ccaatcatat taaaaattat tgggattaaa aaaaaaaaaa   1146
aaaaa                                                                1151
```

<210> SEQ ID NO 64
<211> LENGTH: 312
<212> TYPE: PRT

-continued

```
<213> ORGANISM: Thuja plicata

<400> SEQUENCE: 64

Met Glu Glu Ser Ser Arg Val Leu Ile Val Gly Gly Thr Gly Tyr Ile
 1               5                  10                  15

Gly Arg Arg Ile Val Lys Ala Ser Ile Ala Leu Gly His Pro Thr Phe
                20                  25                  30

Ile Leu Phe Arg Lys Glu Val Ser Asp Val Glu Lys Val Glu Met
            35                  40                  45

Leu Leu Ser Phe Lys Lys Asn Gly Ala Lys Leu Leu Glu Ala Ser Phe
        50                  55                  60

Asp Asp His Glu Ser Leu Val Asp Ala Val Lys Gln Val Asp Val Val
 65                  70                  75                  80

Ile Ser Ala Val Ala Gly Asn His Met Arg His His Ile Leu Gln Gln
                85                  90                  95

Leu Lys Leu Val Glu Ala Ile Lys Glu Ala Gly Asn Ile Lys Arg Phe
            100                 105                 110

Val Pro Ser Glu Phe Gly Met Asp Pro Gly Leu Met Glu His Ala Met
        115                 120                 125

Ala Pro Gly Asn Ile Val Phe Ile Asp Lys Ile Lys Val Arg Glu Ala
130                 135                 140

Ile Glu Ala Ala Ser Ile Pro His Thr Tyr Ile Ser Ala Asn Ile Phe
145                 150                 155                 160

Ala Gly Tyr Leu Val Gly Gly Leu Ala Gln Leu Gly Arg Val Met Pro
                165                 170                 175

Pro Ser Glu Lys Val Ile Leu Tyr Gly Asp Gly Asn Val Lys Ala Val
            180                 185                 190

Trp Val Asp Glu Asp Val Gly Ile Tyr Thr Ile Lys Ala Ile Asp
        195                 200                 205

Asp Pro His Thr Leu Asn Lys Thr Met Tyr Ile Arg Pro Pro Leu Asn
210                 215                 220

Ile Leu Ser Gln Lys Glu Val Val Glu Lys Trp Glu Lys Leu Ser Gly
225                 230                 235                 240

Lys Ser Leu Asn Lys Ile Asn Ile Ser Val Glu Asp Phe Leu Ala Gly
                245                 250                 255

Met Glu Gly Gln Ser Tyr Gly Glu Gln Ile Gly Ile Ser His Phe Tyr
            260                 265                 270

Gln Met Phe Tyr Arg Gly Asp Leu Tyr Asn Phe Glu Ile Gly Pro Asn
        275                 280                 285

Gly Val Glu Ala Ser Gln Leu Tyr Pro Glu Val Lys Tyr Thr Thr Val
290                 295                 300

Asp Ser Tyr Met Glu Arg Tyr Leu
305                 310

<210> SEQ ID NO 65
<211> LENGTH: 1308
<212> TYPE: DNA
<213> ORGANISM: Thuja plicata
<220> FEATURE:
<221> NAME/KEY: CDS
<222> LOCATION: (164)..(1105)

<400> SEQUENCE: 65
aaaaactctt agacttattt tcatttttac ccagttcata agtgtttgtt gggtctcttc      60
aaaaaaagcc ccctctcgtt agaggcaaag aacagcatgc tcagatatat gtaagaagca    120
```

-continued

```
aaatgcccaa aatttgactg tgaaagtgga tgcacataag aat atg gat aag aag       175
                                              Met Asp Lys Lys
                                                1 agc aga gtt cta ata gtg ggg ggt act ggt ttt ata ggc aaa aga att       223
Ser Arg Val Leu Ile Val Gly Gly Thr Gly Phe Ile Gly Lys Arg Ile
  5                  10                  15                  20 gtg aag gcc agt ttg gct ctt ggc cat cct act tat gtt ttg ttc agg       271
Val Lys Ala Ser Leu Ala Leu Gly His Pro Thr Tyr Val Leu Phe Arg
                     25                  30                  35 cca gaa gcc ctc tct tac att gac aaa gtg cag atg ttg ata tcc ttc       319
Pro Glu Ala Leu Ser Tyr Ile Asp Lys Val Gln Met Leu Ile Ser Phe
                 40                  45                  50 aaa cag ctt ggg gcc aaa ctt ctt gag gct tca ttg gat gac cac caa       367
Lys Gln Leu Gly Ala Lys Leu Leu Glu Ala Ser Leu Asp Asp His Gln
             55                  60                  65 ggg ctt gtg gat gtt gtg aaa caa gta gat gtt gtg atc agt gct gtt       415
Gly Leu Val Asp Val Val Lys Gln Val Asp Val Val Ile Ser Ala Val
         70                  75                  80 tca gga ggt ctg gtg cgc cac cat ata ctt gac cag ctc aag cta gtg       463
Ser Gly Gly Leu Val Arg His His Ile Leu Asp Gln Leu Lys Leu Val
 85                  90                  95                 100 gag gca att aaa gaa gct ggc aat att aag aga ttt ctt cct tca gaa       511
Glu Ala Ile Lys Glu Ala Gly Asn Ile Lys Arg Phe Leu Pro Ser Glu
                    105                 110                 115 ttt ggg atg gac cca gat gtt gta gaa gat cca ttg gaa cct ggt aac       559
Phe Gly Met Asp Pro Asp Val Val Glu Asp Pro Leu Glu Pro Gly Asn
                120                 125                 130 att aca ttc att gat aaa aga aaa gtt aga cgt gcc att gaa gca gca       607
Ile Thr Phe Ile Asp Lys Arg Lys Val Arg Arg Ala Ile Glu Ala Ala
            135                 140                 145 acc att cct tac aca tat gtg tct tca aat atg ttt gct ggg ttc ttt       655
Thr Ile Pro Tyr Thr Tyr Val Ser Ser Asn Met Phe Ala Gly Phe Phe
150                 155                 160 gct gga agc tta gca caa ctg caa gat gct ccc cgc atg atg cct gct       703
Ala Gly Ser Leu Ala Gln Leu Gln Asp Ala Pro Arg Met Met Pro Ala
165                 170                 175                 180 cga gat aaa gtt ctc ata tat gga gat gga aat gtt aaa ggt gtt tat       751
Arg Asp Lys Val Leu Ile Tyr Gly Asp Gly Asn Val Lys Gly Val Tyr
                    185                 190                 195 gta gat gaa gat gat gct gga ata tac ata gtc aaa tca att gat gat       799
Val Asp Glu Asp Asp Ala Gly Ile Tyr Ile Val Lys Ser Ile Asp Asp
                200                 205                 210 cct cgc aca ctc aac aag act gtg tat atc agg cca cca atg aat ata       847
Pro Arg Thr Leu Asn Lys Thr Val Tyr Ile Arg Pro Pro Met Asn Ile
            215                 220                 225 ctt tca cag aaa gaa gta gtt gaa ata tgg gag aga cta tca ggt ttg       895
Leu Ser Gln Lys Glu Val Val Glu Ile Trp Glu Arg Leu Ser Gly Leu
230                 235                 240 agc cta gaa aaa atc tac gtt tct gag gac caa ctt ctt aat atg aaa       943
Ser Leu Glu Lys Ile Tyr Val Ser Glu Asp Gln Leu Leu Asn Met Lys
245                 250                 255                 260 gat aaa tct tat gtg gag aag atg gca cga tgt cat ctc tat cat ttt       991
Asp Lys Ser Tyr Val Glu Lys Met Ala Arg Cys His Leu Tyr His Phe
                265                 270                 275 ttt atc aaa ggg gat ctt tac aat ttt gaa att gga ccc aat gct act      1039
Phe Ile Lys Gly Asp Leu Tyr Asn Phe Glu Ile Gly Pro Asn Ala Thr
            280                 285                 290 gaa ggc aca aaa ctt tat cca gaa gtc aaa tac aca acc atg gat tca      1087
Glu Gly Thr Lys Leu Tyr Pro Glu Val Lys Tyr Thr Thr Met Asp Ser
295                 300                 305
```

-continued

```
tat atg gag cgt tat cta tagctaatag attttctta aataatagct          1135
Tyr Met Glu Arg Tyr Leu
        310 tgaaatattc tatactcaat aagagtgtat tcataaataa tacacaacac ttgctctttt  1195 atagattact tttttaatag gtggctttta taaaacatgt ataaaaaaaa ttgcaaacaa  1255 tatttttaaa ttagcaataa taaccacctt taaataaaaa aaaaaaaaaa aaa         1308

<210> SEQ ID NO 66
<211> LENGTH: 314
<212> TYPE: PRT
<213> ORGANISM: Thuja plicata

<400> SEQUENCE: 66

Met Asp Lys Lys Ser Arg Val Leu Ile Val Gly Gly Thr Gly Phe Ile
 1               5                  10                  15

Gly Lys Arg Ile Val Lys Ala Ser Leu Ala Leu Gly His Pro Thr Tyr
            20                  25                  30

Val Leu Phe Arg Pro Glu Ala Leu Ser Tyr Ile Asp Lys Val Gln Met
        35                  40                  45

Leu Ile Ser Phe Lys Gln Leu Gly Ala Lys Leu Leu Glu Ala Ser Leu
    50                  55                  60

Asp Asp His Gln Gly Leu Val Asp Val Val Lys Gln Val Asp Val Val
65                  70                  75                  80

Ile Ser Ala Val Ser Gly Gly Leu Val Arg His His Ile Leu Asp Gln
                85                  90                  95

Leu Lys Leu Val Glu Ala Ile Lys Glu Ala Gly Asn Ile Lys Arg Phe
            100                 105                 110

Leu Pro Ser Glu Phe Gly Met Asp Pro Asp Val Val Glu Asp Pro Leu
        115                 120                 125

Glu Pro Gly Asn Ile Thr Phe Ile Asp Lys Arg Lys Val Arg Arg Ala
    130                 135                 140

Ile Glu Ala Ala Thr Ile Pro Tyr Thr Tyr Val Ser Ser Asn Met Phe
145                 150                 155                 160

Ala Gly Phe Phe Ala Gly Ser Leu Ala Gln Leu Gln Asp Ala Pro Arg
                165                 170                 175

Met Met Pro Ala Arg Asp Lys Val Leu Ile Tyr Gly Asp Gly Asn Val
            180                 185                 190

Lys Gly Val Tyr Val Asp Glu Asp Ala Gly Ile Tyr Ile Val Lys
        195                 200                 205

Ser Ile Asp Asp Pro Arg Thr Leu Asn Lys Thr Val Tyr Ile Arg Pro
    210                 215                 220

Pro Met Asn Ile Leu Ser Gln Lys Glu Val Val Glu Ile Trp Glu Arg
225                 230                 235                 240

Leu Ser Gly Leu Ser Leu Glu Lys Ile Tyr Val Ser Glu Asp Gln Leu
                245                 250                 255

Leu Asn Met Lys Asp Lys Ser Tyr Val Glu Lys Met Ala Arg Cys His
            260                 265                 270

Leu Tyr His Phe Phe Ile Lys Gly Asp Leu Tyr Asn Phe Glu Ile Gly
        275                 280                 285

Pro Asn Ala Thr Glu Gly Thr Lys Leu Tyr Pro Glu Val Lys Tyr Thr
    290                 295                 300

Thr Met Asp Ser Tyr Met Glu Arg Tyr Leu
305                 310
```

-continued

```
<210> SEQ ID NO 67
<211> LENGTH: 1287
<212> TYPE: DNA
<213> ORGANISM: Thuja plicata
<220> FEATURE:
<221> NAME/KEY: CDS
<222> LOCATION: (11)..(946)

<400> SEQUENCE: 67
```

| | | | | | | | | | | | | | | | |
|---|---|---|---|---|---|---|---|---|---|---|---|---|---|---|---|
| gaaagcagag | atg | gaa | gag | agt | agc | agg | att | ttg | gta | gtg | gga | ggc | aca | | 49 |
| | Met | Glu | Glu | Ser | Ser | Arg | Ile | Leu | Val | Val | Gly | Gly | Thr | | |
| | 1 | | | 5 | | | | | 10 | | | | | | |
| gga | tac | ata | ggc | aga | agg | att | gtg | aaa | gcc | agc | att | gct | ctg | ggc cat | 97 |
| Gly | Tyr | Ile | Gly | Arg | Arg | Ile | Val | Lys | Ala | Ser | Ile | Ala | Leu | Gly His | |
| 15 | | | | | 20 | | | | | 25 | | | | | |
| cct | act | ttc | att | ttg | ttt | agg | aaa | gaa | gtt | gtt | tct | gat | gta | gag aaa | 145 |
| Pro | Thr | Phe | Ile | Leu | Phe | Arg | Lys | Glu | Val | Val | Ser | Asp | Val | Glu Lys | |
| 30 | | | | | 35 | | | | | 40 | | | | | 45 |
| gtg | gag | atg | tta | ttg | tcc | ttc | aaa | aag | aat | ggt | gcc | aaa | tta | ctg gag | 193 |
| Val | Glu | Met | Leu | Leu | Ser | Phe | Lys | Lys | Asn | Gly | Ala | Lys | Leu | Leu Glu | |
| | | | | 50 | | | | | 55 | | | | | 60 | |
| gct | tca | ttt | gat | gat | cac | gaa | agc | ctt | gta | gat | gct | gtg | aag | cag gtt | 241 |
| Ala | Ser | Phe | Asp | Asp | His | Glu | Ser | Leu | Val | Asp | Ala | Val | Lys | Gln Val | |
| | | | | 65 | | | | | 70 | | | | | 75 | |
| gat | gtt | gtc | ata | agt | gca | gtt | gca | gga | aac | cac | atg | cgg | cat | cac atc | 289 |
| Asp | Val | Val | Ile | Ser | Ala | Val | Ala | Gly | Asn | His | Met | Arg | His | His Ile | |
| | | 80 | | | | | 85 | | | | | 90 | | | |
| ctt | caa | cag | ctc | aaa | tta | gtg | gag | gcc | att | aaa | gaa | gct | gga | aat att | 337 |
| Leu | Gln | Gln | Leu | Lys | Leu | Val | Glu | Ala | Ile | Lys | Glu | Ala | Gly | Asn Ile | |
| | 95 | | | | | 100 | | | | | 105 | | | | |
| aag | agg | ttt | gtc | cct | tca | gaa | ttt | ggg | atg | gat | cca | ggg | tta | atg gac | 385 |
| Lys | Arg | Phe | Val | Pro | Ser | Glu | Phe | Gly | Met | Asp | Pro | Gly | Leu | Met Asp | |
| 110 | | | | | 115 | | | | | 120 | | | | | 125 |
| cat | gca | atg | gca | cca | gga | aac | att | gta | ttt | att | gat | aaa | ata | aaa gtt | 433 |
| His | Ala | Met | Ala | Pro | Gly | Asn | Ile | Val | Phe | Ile | Asp | Lys | Ile | Lys Val | |
| | | | | 130 | | | | | 135 | | | | | 140 | |
| cga | gag | gcc | att | gaa | gct | gca | gct | att | cct | cac | act | tat | att | tct gcc | 481 |
| Arg | Glu | Ala | Ile | Glu | Ala | Ala | Ala | Ile | Pro | His | Thr | Tyr | Ile | Ser Ala | |
| | | | 145 | | | | | 150 | | | | | 155 | | |
| aat | ata | ttt | gct | ggc | tac | ttg | gtt | ggt | gga | tta | gct | caa | ctt | ggt cgt | 529 |
| Asn | Ile | Phe | Ala | Gly | Tyr | Leu | Val | Gly | Gly | Leu | Ala | Gln | Leu | Gly Arg | |
| | | 160 | | | | | 165 | | | | | 170 | | | |
| gtg | atg | cct | cct | tca | gac | aaa | gta | ttt | ctc | tat | gga | gat | gga | aat gtc | 577 |
| Val | Met | Pro | Pro | Ser | Asp | Lys | Val | Phe | Leu | Tyr | Gly | Asp | Gly | Asn Val | |
| | 175 | | | | | 180 | | | | | 185 | | | | |
| aaa | gct | gtt | tgg | ata | gat | gaa | gaa | gat | gtt | gga | ata | tac | aca | atc aaa | 625 |
| Lys | Ala | Val | Trp | Ile | Asp | Glu | Glu | Asp | Val | Gly | Ile | Tyr | Thr | Ile Lys | |
| 190 | | | | | 195 | | | | | 200 | | | | | 205 |
| gca | att | gat | gac | cct | cgc | acc | cta | aat | aag | act | gtg | tac | atc | agg cca | 673 |
| Ala | Ile | Asp | Asp | Pro | Arg | Thr | Leu | Asn | Lys | Thr | Val | Tyr | Ile | Arg Pro | |
| | | | | 210 | | | | | 215 | | | | | 220 | |
| cct | ttg | aat | gtt | ctt | tcc | cag | aag | gaa | gtg | gtt | gaa | aaa | tgg | gaa aaa | 721 |
| Pro | Leu | Asn | Val | Leu | Ser | Gln | Lys | Glu | Val | Val | Glu | Lys | Trp | Glu Lys | |
| | | | | 225 | | | | | 230 | | | | | 235 | |
| tta | tca | aga | aag | agc | ttg | gat | aaa | ata | tat | atg | tct | gtt | gag | gat ttt | 769 |
| Leu | Ser | Arg | Lys | Ser | Leu | Asp | Lys | Ile | Tyr | Met | Ser | Val | Glu | Asp Phe | |
| | | 240 | | | | | 245 | | | | | 250 | | | |
| ctc | gca | ggc | atg | gaa | ggt | caa | tca | tat | gga | gag | aag | att | gga | ata tca | 817 |
| Leu | Ala | Gly | Met | Glu | Gly | Gln | Ser | Tyr | Gly | Glu | Lys | Ile | Gly | Ile Ser | |
| | 255 | | | | | 260 | | | | | 265 | | | | |

```
cat ttc tat cag atg ttc tat aag ggg gat ctt tat aat ttt gaa att         865
His Phe Tyr Gln Met Phe Tyr Lys Gly Asp Leu Tyr Asn Phe Glu Ile
270                 275                 280                 285 gga cct aat gga gta gaa gct tcc caa ctt tac cca gga gta aaa tac         913
Gly Pro Asn Gly Val Glu Ala Ser Gln Leu Tyr Pro Gly Val Lys Tyr
                290                 295                 300 aca aca gtg gac tca tac atg gag cgc tac cta tgaaatctt cttcatgaag        966
Thr Thr Val Asp Ser Tyr Met Glu Arg Tyr Leu
                305                 310 atatttaaat tcaatttaat gctttctaaa agttttata ttttgacata atgctaaata       1026
tagatgtaga gtatctagat aataatattc aattgataat attcaacaat cagttgagat      1086 gacttttcc ctttaactgc atgctcaaca tattttatac aaacaagcta atgtcttta        1146 aggttgagaa actaaatatg gttttgtatt acatggaaaa accatatttt gatatttgag      1206
attgtattta ttttgaatgt tatgattttg ataaaatttg aaattgatta tgaacattgt      1266
tttaaaaaaa aaaaaaaaaa a                                                1287
```

<210> SEQ ID NO 68
<211> LENGTH: 312
<212> TYPE: PRT
<213> ORGANISM: Thuja plicata

<400> SEQUENCE: 68

```
Met Glu Glu Ser Ser Arg Ile Leu Val Val Gly Gly Thr Gly Tyr Ile
1               5                   10                  15

Gly Arg Arg Ile Val Lys Ala Ser Ile Ala Leu Gly His Pro Thr Phe
            20                  25                  30

Ile Leu Phe Arg Lys Glu Val Val Ser Asp Val Glu Lys Val Glu Met
        35                  40                  45

Leu Leu Ser Phe Lys Lys Asn Gly Ala Lys Leu Leu Glu Ala Ser Phe
    50                  55                  60

Asp Asp His Glu Ser Leu Val Asp Ala Val Lys Gln Val Asp Val Val
65                  70                  75                  80

Ile Ser Ala Val Ala Gly Asn His Met Arg His Ile Leu Gln Gln
                85                  90                  95

Leu Lys Leu Val Glu Ala Ile Lys Glu Ala Gly Asn Ile Lys Arg Phe
            100                 105                 110

Val Pro Ser Glu Phe Gly Met Asp Pro Gly Leu Met Asp His Ala Met
        115                 120                 125

Ala Pro Gly Asn Ile Val Phe Ile Asp Lys Ile Lys Val Arg Glu Ala
    130                 135                 140

Ile Glu Ala Ala Ala Ile Pro His Thr Tyr Ile Ser Ala Asn Ile Phe
145                 150                 155                 160

Ala Gly Tyr Leu Val Gly Gly Leu Ala Gln Leu Gly Arg Val Met Pro
                165                 170                 175

Pro Ser Asp Lys Val Phe Leu Tyr Gly Asp Gly Asn Val Lys Ala Val
            180                 185                 190

Trp Ile Asp Glu Glu Asp Val Gly Ile Tyr Thr Ile Lys Ala Ile Asp
        195                 200                 205

Asp Pro Arg Thr Leu Asn Lys Thr Val Tyr Ile Arg Pro Pro Leu Asn
    210                 215                 220

Val Leu Ser Gln Lys Glu Val Val Glu Lys Trp Glu Lys Leu Ser Arg
225                 230                 235                 240

Lys Ser Leu Asp Lys Ile Tyr Met Ser Val Glu Asp Phe Leu Ala Gly
                245                 250                 255
```

```
Met Glu Gly Gln Ser Tyr Gly Glu Lys Ile Gly Ile Ser His Phe Tyr
        260                 265                 270

Gln Met Phe Tyr Lys Gly Asp Leu Tyr Asn Phe Glu Ile Gly Pro Asn
        275                 280                 285

Gly Val Glu Ala Ser Gln Leu Tyr Pro Gly Val Lys Tyr Thr Thr Val
    290                 295                 300

Asp Ser Tyr Met Glu Arg Tyr Leu
305                 310

<210> SEQ ID NO 69
<211> LENGTH: 1282
<212> TYPE: DNA
<213> ORGANISM: Tsuga heterophylla
<220> FEATURE:
<221> NAME/KEY: CDS
<222> LOCATION: (2)..(922)

<400> SEQUENCE: 69 c aga gtt cta ata gtg ggt ggc aca gga tac ata ggt aga aaa ttt gta        49
  Arg Val Leu Ile Val Gly Gly Thr Gly Tyr Ile Gly Arg Lys Phe Val
    1               5                  10                  15 aaa gct agc tta gct cta ggc cac cca aca ttc gtt ttg tcc agg cca        97
Lys Ala Ser Leu Ala Leu Gly His Pro Thr Phe Val Leu Ser Arg Pro
             20                  25                  30 gaa gta ggg ttt gac att gag aag gtg cac atg ttg ctc tcc ttc aaa       145
Glu Val Gly Phe Asp Ile Glu Lys Val His Met Leu Leu Ser Phe Lys
         35                  40                  45 caa gcg ggt gcc aga ctt ttg gag ggt tca ttt gag gat ttc caa agc       193
Gln Ala Gly Ala Arg Leu Leu Glu Gly Ser Phe Glu Asp Phe Gln Ser
     50                  55                  60 ctt gtg gca gcc ttg aag cag gtt gat gtt gtg ata agt gca gtg gca       241
Leu Val Ala Ala Leu Lys Gln Val Asp Val Val Ile Ser Ala Val Ala
 65                  70                  75                  80 gga aac cat ttc aga aac ctt ata ctt caa cag ctt aaa ttg gtg gaa       289
Gly Asn His Phe Arg Asn Leu Ile Leu Gln Gln Leu Lys Leu Val Glu
                 85                  90                  95 gcc ata aaa gaa gct ggc aac att aag aga ttt ctt cct tct gaa ttt       337
Ala Ile Lys Glu Ala Gly Asn Ile Lys Arg Phe Leu Pro Ser Glu Phe
            100                 105                 110 gga atg gaa cca gac ctc atg gag cac gct ttg gaa cct ggt aac gct       385
Gly Met Glu Pro Asp Leu Met Glu His Ala Leu Glu Pro Gly Asn Ala
        115                 120                 125 gtc ttc att gat aag aga aag gtt cgg cgc gcc att gaa gca gca ggc       433
Val Phe Ile Asp Lys Arg Lys Val Arg Arg Ala Ile Glu Ala Ala Gly
    130                 135                 140 att cct tac acg tat gtc tct tca aat ata ttt gct ggg tat tta gca       481
Ile Pro Tyr Thr Tyr Val Ser Ser Asn Ile Phe Ala Gly Tyr Leu Ala
145                 150                 155                 160 gga ggg ttg gca caa att ggc cgg ctt atg cct cct cgt gat gaa gta       529
Gly Gly Leu Ala Gln Ile Gly Arg Leu Met Pro Pro Arg Asp Glu Val
                165                 170                 175 gtt atc tat gga gat ggt aac gtt aaa gct gtt tgg gtg gac gaa gat       577
Val Ile Tyr Gly Asp Gly Asn Val Lys Ala Val Trp Val Asp Glu Asp
            180                 185                 190 gat gtc gga ata tac aca ctg aaa aca atc gat gat cca cgc act ctg       625
Asp Val Gly Ile Tyr Thr Leu Lys Thr Ile Asp Asp Pro Arg Thr Leu
        195                 200                 205 aac aag act gta tat atc agg cca ctc aaa aat att ctc tct cag aag       673
Asn Lys Thr Val Tyr Ile Arg Pro Leu Lys Asn Ile Leu Ser Gln Lys
    210                 215                 220
```

```
gag ctt gtg gca aag tgg gaa aaa ctc tca gga aag tgt ttg aag aaa       721
Glu Leu Val Ala Lys Trp Glu Lys Leu Ser Gly Lys Cys Leu Lys Lys
225                 230                 235                 240 aca tac att tct gct gag gat ttt ctt gca ggc atc gaa gat caa cct       769
Thr Tyr Ile Ser Ala Glu Asp Phe Leu Ala Gly Ile Glu Asp Gln Pro
                245                 250                 255 tac gaa cat cag gtc gga ata tct cac ttc tat caa atg ttt tac agt       817
Tyr Glu His Gln Val Gly Ile Ser His Phe Tyr Gln Met Phe Tyr Ser
            260                 265                 270 gga gat ctc tat aat ttt gag att ggg cca gac ggt aga gaa gca aca       865
Gly Asp Leu Tyr Asn Phe Glu Ile Gly Pro Asp Gly Arg Glu Ala Thr
        275                 280                 285 gtg cta tac cct gaa gtt caa tac act acc atg gat tct tat ttg aag       913
Val Leu Tyr Pro Glu Val Gln Tyr Thr Thr Met Asp Ser Tyr Leu Lys
    290                 295                 300 cgc tac tta taagcaggat gaaggttaat gttctacgac atgaatccca              962
Arg Tyr Leu
305 cgagaaatac cagaaatctt cattcaagat caaataatgg ataaataatt caacattagt    1022 tccatcagaa ataccagaaa tttctaatcg agttcaaata atggataaat aattcattat    1082 ttaagtttta tttatcgaaa tagggctgga cgaattgaat atatattcat ctgatatgga    1142 cgggcaggtt gtaaaattgc aagctgtaca gtaactacgt cttgtcgcga aaagctacta    1202 tatcgatata actgatgtga aaagttacca tttcgtaata actatgcttg aatttatttt    1262 tgacaaaaaa aaaaaaaaaa                                                1282

<210> SEQ ID NO 70
<211> LENGTH: 307
<212> TYPE: PRT
<213> ORGANISM: Tsuga heterophylla

<400> SEQUENCE: 70

Arg Val Leu Ile Val Gly Gly Thr Gly Tyr Ile Gly Arg Lys Phe Val
1               5                   10                  15

Lys Ala Ser Leu Ala Leu Gly His Pro Thr Phe Val Leu Ser Arg Pro
            20                  25                  30

Glu Val Gly Phe Asp Ile Glu Lys Val His Met Leu Leu Ser Phe Lys
        35                  40                  45

Gln Ala Gly Ala Arg Leu Leu Glu Gly Ser Phe Glu Asp Phe Gln Ser
    50                  55                  60

Leu Val Ala Ala Leu Lys Gln Val Asp Val Val Ile Ser Ala Val Ala
65                  70                  75                  80

Gly Asn His Phe Arg Asn Leu Ile Leu Gln Gln Leu Lys Leu Val Glu
                85                  90                  95

Ala Ile Lys Glu Ala Gly Asn Ile Lys Arg Phe Leu Pro Ser Glu Phe
            100                 105                 110

Gly Met Glu Pro Asp Leu Met Glu His Ala Leu Glu Pro Gly Asn Ala
        115                 120                 125

Val Phe Ile Asp Lys Arg Lys Val Arg Arg Ala Ile Glu Ala Ala Gly
    130                 135                 140

Ile Pro Tyr Thr Tyr Val Ser Ser Asn Ile Phe Ala Gly Tyr Leu Ala
145                 150                 155                 160

Gly Gly Leu Ala Gln Ile Gly Arg Leu Met Pro Pro Arg Asp Glu Val
                165                 170                 175

Val Ile Tyr Gly Asp Gly Asn Val Lys Ala Val Trp Val Asp Glu Asp
```

-continued

```
                    180                 185                 190
Asp Val Gly Ile Tyr Thr Leu Lys Thr Ile Asp Asp Pro Arg Thr Leu
                195                 200                 205

Asn Lys Thr Val Tyr Ile Arg Pro Leu Lys Asn Ile Leu Ser Gln Lys
            210                 215                 220

Glu Leu Val Ala Lys Trp Glu Lys Leu Ser Gly Lys Cys Leu Lys Lys
225                 230                 235                 240

Thr Tyr Ile Ser Ala Glu Asp Phe Leu Ala Gly Ile Glu Asp Gln Pro
                    245                 250                 255

Tyr Glu His Gln Val Gly Ile Ser His Phe Tyr Gln Met Phe Tyr Ser
                260                 265                 270

Gly Asp Leu Tyr Asn Phe Glu Ile Gly Pro Asp Gly Arg Glu Ala Thr
            275                 280                 285

Val Leu Tyr Pro Glu Val Gln Tyr Thr Thr Met Asp Ser Tyr Leu Lys
        290                 295                 300

Arg Tyr Leu
305

<210> SEQ ID NO 71
<211> LENGTH: 1328
<212> TYPE: DNA
<213> ORGANISM: Tsuga heterophylla
<220> FEATURE:
<221> NAME/KEY: CDS
<222> LOCATION: (20)..(946)

<400> SEQUENCE: 71
gaattcggca cgagctaac atg agc aga gtt cta ata gtg ggt ggc aca gga      52
                    Met Ser Arg Val Leu Ile Val Gly Gly Thr Gly
                      1               5                  10 tac ata ggt aga aaa ttt gta aaa gct agc tta gct cta ggc cac cca     100
Tyr Ile Gly Arg Lys Phe Val Lys Ala Ser Leu Ala Leu Gly His Pro
             15                  20                  25 aca ttc gtt ttg tcc agg cca gaa gta ggg ttt gac att gag aag gtg     148
Thr Phe Val Leu Ser Arg Pro Glu Val Gly Phe Asp Ile Glu Lys Val
         30                  35                  40 cac atg ttg ctc tcc ttc aaa caa gcg ggt gcc aga ctt ttg gag ggt     196
His Met Leu Leu Ser Phe Lys Gln Ala Gly Ala Arg Leu Leu Glu Gly
     45                  50                  55 tca ttt gag gat ttc caa agc ctt gtg gca gcc ttg aag cag gtt gat     244
Ser Phe Glu Asp Phe Gln Ser Leu Val Ala Ala Leu Lys Gln Val Asp
 60                  65                  70                  75 gtt gtg ata agt gca gtg gca gga aac cat ttc aga aac ctt ata ctt     292
Val Val Ile Ser Ala Val Ala Gly Asn His Phe Arg Asn Leu Ile Leu
                 80                  85                  90 caa cag ctt aaa ttg gtg gaa gcc ata aaa gag gct cgc aac att aag     340
Gln Gln Leu Lys Leu Val Glu Ala Ile Lys Glu Ala Arg Asn Ile Lys
             95                 100                 105 aga ttt ctt cct tct gaa ttt gga atg gac cca gac ctc atg gag cac     388
Arg Phe Leu Pro Ser Glu Phe Gly Met Asp Pro Asp Leu Met Glu His
        110                 115                 120 gct ttg gaa cct ggt aac gct gtc ttc att gat aag aga aag gtt cgg     436
Ala Leu Glu Pro Gly Asn Ala Val Phe Ile Asp Lys Arg Lys Val Arg
    125                 130                 135 cgc gcc att gaa gca gca ggt att cct tac acg tat gtc tct tca aat     484
Arg Ala Ile Glu Ala Ala Gly Ile Pro Tyr Thr Tyr Val Ser Ser Asn
140                 145                 150                 155 ata ttt gct ggg tat tta gca gga ggg ttg gca caa att ggc cgg ctt     532
Ile Phe Ala Gly Tyr Leu Ala Gly Gly Leu Ala Gln Ile Gly Arg Leu
```

```
                      160                 165                 170
atg cct cct cgt gat gaa gta gtt atc tat gga gat ggt aac gtt aaa          580
Met Pro Pro Arg Asp Glu Val Val Ile Tyr Gly Asp Gly Asn Val Lys
            175                 180                 185 gct gtt tgg gtg gac gaa gat gat gtc gga ata tac aca ctg aaa aca          628
Ala Val Trp Val Asp Glu Asp Asp Val Gly Ile Tyr Thr Leu Lys Thr
        190                 195                 200 atc gat gat cca cgc act ctg aac aag act gta tat atc agg cca ctc          676
Ile Asp Asp Pro Arg Thr Leu Asn Lys Thr Val Tyr Ile Arg Pro Leu
    205                 210                 215 aaa aat ata ctc tct cag aag gag ctt gtg gca aag tgg gaa aaa ctc          724
Lys Asn Ile Leu Ser Gln Lys Glu Leu Val Ala Lys Trp Glu Lys Leu
220                 225                 230                 235 tca gga aag ttt ttg aag aaa aca tac att tct gct gag gat ttt ctt          772
Ser Gly Lys Phe Leu Lys Lys Thr Tyr Ile Ser Ala Glu Asp Phe Leu
                240                 245                 250 gca ggc atc gaa gat caa cct tac gaa cat cag gtc gga ata tct cac          820
Ala Gly Ile Glu Asp Gln Pro Tyr Glu His Gln Val Gly Ile Ser His
            255                 260                 265 ttc tat caa atg ttt tac agt gga gat ctc tat aat ttt gag att ggg          868
Phe Tyr Gln Met Phe Tyr Ser Gly Asp Leu Tyr Asn Phe Glu Ile Gly
        270                 275                 280 cca gac ggt aga gaa gca aca atg cta tac cct gaa gtt caa tac act          916
Pro Asp Gly Arg Glu Ala Thr Met Leu Tyr Pro Glu Val Gln Tyr Thr
    285                 290                 295 acc atg gat tct tat ttg aag cgc tac tta taagcaggat gaaggttaat            966
Thr Met Asp Ser Tyr Leu Lys Arg Tyr Leu
300                 305 gttctacgac atgaatccca cgagaaatac cagaaatctt cattcaagat caaataatgg       1026
ataaataatt caacattagt tccatcagaa atatcagaaa tttctaatca agttcaaata       1086
atggataaat aattcattat ttaagtttta tttattgaaa tagggctgga cgaagccttt       1146
aatcagtatt gaatatatat tcatctgata tggacgggca ggttgtaaaa ttgcaagccg       1206
tacagtaact acgtcttgtc gcgaaaagct accatatcga tataactaag tcttgtcgcg       1266
taaagctacc atatcgatat aactgatgtg accatttcgt aataactatg cttgtgcagg       1326
aa                                                                      1328
```

<210> SEQ ID NO 72
<211> LENGTH: 309
<212> TYPE: PRT
<213> ORGANISM: Tsuga heterophylla

<400> SEQUENCE: 72

Met Ser Arg Val Leu Ile Val Gly Gly Thr Gly Tyr Ile Gly Arg Lys
1               5                   10                  15

Phe Val Lys Ala Ser Leu Ala Leu Gly His Pro Thr Phe Val Leu Ser
            20                  25                  30

Arg Pro Glu Val Gly Phe Asp Ile Glu Lys Val His Met Leu Leu Ser
        35                  40                  45

Phe Lys Gln Ala Gly Ala Arg Leu Leu Glu Gly Ser Phe Glu Asp Phe
    50                  55                  60

Gln Ser Leu Val Ala Ala Leu Lys Gln Val Asp Val Val Ile Ser Ala
65                  70                  75                  80

Val Ala Gly Asn His Phe Arg Asn Leu Ile Leu Gln Gln Leu Lys Leu
                85                  90                  95

Val Glu Ala Ile Lys Glu Ala Arg Asn Ile Lys Arg Phe Leu Pro Ser

```
                    100                 105                 110
Glu Phe Gly Met Asp Pro Asp Leu Met Glu His Ala Leu Glu Pro Gly
                115                 120                 125
Asn Ala Val Phe Ile Asp Lys Arg Lys Val Arg Ala Ile Glu Ala
            130                 135                 140
Ala Gly Ile Pro Tyr Thr Tyr Val Ser Ser Asn Ile Phe Ala Gly Tyr
145                 150                 155                 160
Leu Ala Gly Gly Leu Ala Gln Ile Gly Arg Leu Met Pro Pro Arg Asp
                165                 170                 175
Glu Val Val Ile Tyr Gly Asp Gly Asn Val Lys Ala Val Trp Val Asp
                180                 185                 190
Glu Asp Asp Val Gly Ile Tyr Thr Leu Lys Thr Ile Asp Asp Pro Arg
                195                 200                 205
Thr Leu Asn Lys Thr Val Tyr Ile Arg Pro Leu Lys Asn Ile Leu Ser
            210                 215                 220
Gln Lys Glu Leu Val Ala Lys Trp Glu Lys Leu Ser Gly Lys Phe Leu
225                 230                 235                 240
Lys Lys Thr Tyr Ile Ser Ala Glu Asp Phe Leu Ala Gly Ile Glu Asp
                245                 250                 255
Gln Pro Tyr Glu His Gln Val Gly Ile Ser His Phe Tyr Gln Met Phe
                260                 265                 270
Tyr Ser Gly Asp Leu Tyr Asn Phe Glu Ile Gly Pro Asp Gly Arg Glu
                275                 280                 285
Ala Thr Met Leu Tyr Pro Glu Val Gln Tyr Thr Thr Met Asp Ser Tyr
            290                 295                 300
Leu Lys Arg Tyr Leu
305

<210> SEQ ID NO 73
<211> LENGTH: 355
<212> TYPE: DNA
<213> ORGANISM: Forsythia x intermedia

<400> SEQUENCE: 73
aaggagctgg tgttctactt ccacgacata cttttcaaag gggataatta caacaatgcc      60
actgccacca tagtcgggtc cccccaatgg ggcaacaaga ctgccatggc cgtgccattc     120
aattttggtg acctaatggt gttcgacgat cccattacct agacaacaa tctgcattca      180 cccccagtgg gtcgggcaca aggatgtac ttctatgatc aaaaaagtac atacaatgct      240
tggctcgggt tctcattttt gttcaattca actaagtatg ttggaacctt gaactttgct     300
ggggctgatc cattgttgaa caagactagg gacgtatcag tcattggtgg aacca          355

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(20)
<223> OTHER INFORMATION: PCR primer R20

<400> SEQUENCE: 74
cagctatgac catgattacg                                                   20

<210> SEQ ID NO 75
```

-continued

```
<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(19)
<223> OTHER INFORMATION: PCR primer U19

<400> SEQUENCE: 75
gttttcccag tcacgacgt                                                    19

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: conserved
      domain
<221> NAME/KEY: PEPTIDE
<222> LOCATION: (1)..(6)
<223> OTHER INFORMATION: peptide (NADPH) binding motif

<400> SEQUENCE: 76

Gly Xaa Gly Xaa Xaa Gly
  1               5

<210> SEQ ID NO 77
<211> LENGTH: 582
<212> TYPE: DNA
<213> ORGANISM: Thuja plicata
<220> FEATURE:
<221> NAME/KEY: CDS
<222> LOCATION: (1)..(582)

<400> SEQUENCE: 77 atg gca atc tgg aat ggt aga gtt ctg aac ttg tgc att ctg tgg ctt     48
Met Ala Ile Trp Asn Gly Arg Val Leu Asn Leu Cys Ile Leu Trp Leu
  1               5                  10                  15 ctg gtc tcc aca gtt ttg ctg aat gat gca gat tgc cat agc tgg aaa     96
Leu Val Ser Thr Val Leu Leu Asn Asp Ala Asp Cys His Ser Trp Lys
             20                  25                  30 aag aag ctt cca aag ccc cgt aag aat ctt gtt ttg tat ttc cat gac    144
Lys Lys Leu Pro Lys Pro Arg Lys Asn Leu Val Leu Tyr Phe His Asp
         35                  40                  45 ata atc tac aat ggg caa aat gca gag aat gca act tct aca att gtt    192
Ile Ile Tyr Asn Gly Gln Asn Ala Glu Asn Ala Thr Ser Thr Ile Val
     50                  55                  60 gca gcc cct gaa gga gcc aat ctc act att ttg act ggc aac aac cat    240
Ala Ala Pro Glu Gly Ala Asn Leu Thr Ile Leu Thr Gly Asn Asn His
 65                  70                  75                  80 ttt ggg aat att gct gtg ttt gat gat cct att act ctt gac aac aat    288
Phe Gly Asn Ile Ala Val Phe Asp Asp Pro Ile Thr Leu Asp Asn Asn
                 85                  90                  95 ctt cat tct cct cca gtg ggt aga cct cag ggc ttt tac ttc tat gac    336
Leu His Ser Pro Pro Val Gly Arg Pro Gln Gly Phe Tyr Phe Tyr Asp
            100                 105                 110 atg aag aat aca ttc agt tct tgg ctt ggc ttc aca ttt gtg ctg aat    384
Met Lys Asn Thr Phe Ser Ser Trp Leu Gly Phe Thr Phe Val Leu Asn
        115                 120                 125 tca acg gac tat aag ggc acc att act ttc aat gga gca gac cca att    432
Ser Thr Asp Tyr Lys Gly Thr Ile Thr Phe Asn Gly Ala Asp Pro Ile
    130                 135                 140 ttg gtt aag tac aga gat ata tct gtt gtg ggt gga acg ggg gat ttg    480
```

```
tta atg gcc aga gga att gct gca atc aat act gat gca tat gag gga    528
Leu Met Ala Arg Gly Ile Ala Ala Ile Asn Thr Asp Ala Tyr Glu Gly
            165                 170                 175 gat gtt tat ttc cgt ctt aga gtg aat att aca ctg tat gag tgc tac    576
Asp Val Tyr Phe Arg Leu Arg Val Asn Ile Thr Leu Tyr Glu Cys Tyr
        180                 185                 190 tac tga                                                             582
Tyr
```

<210> SEQ ID NO 78
<211> LENGTH: 193
<212> TYPE: PRT
<213> ORGANISM: Thuja plicata

<400> SEQUENCE: 78

```
Met Ala Ile Trp Asn Gly Arg Val Leu Asn Leu Cys Ile Leu Trp Leu
 1               5                  10                  15

Leu Val Ser Thr Val Leu Leu Asn Asp Ala Asp Cys His Ser Trp Lys
            20                  25                  30

Lys Lys Leu Pro Lys Pro Arg Lys Asn Leu Val Leu Tyr Phe His Asp
        35                  40                  45

Ile Ile Tyr Asn Gly Gln Asn Ala Glu Asn Ala Thr Ser Thr Ile Val
    50                  55                  60

Ala Ala Pro Glu Gly Ala Asn Leu Thr Ile Leu Thr Gly Asn Asn His
65                  70                  75                  80

Phe Gly Asn Ile Ala Val Phe Asp Asp Pro Ile Thr Leu Asp Asn Asn
                85                  90                  95

Leu His Ser Pro Pro Val Gly Arg Pro Gln Gly Phe Tyr Phe Tyr Asp
            100                 105                 110

Met Lys Asn Thr Phe Ser Ser Trp Leu Gly Phe Thr Phe Val Leu Asn
        115                 120                 125

Ser Thr Asp Tyr Lys Gly Thr Ile Thr Phe Asn Gly Ala Asp Pro Ile
    130                 135                 140

Leu Val Lys Tyr Arg Asp Ile Ser Val Val Gly Gly Thr Gly Asp Leu
145                 150                 155                 160

Leu Met Ala Arg Gly Ile Ala Ala Ile Asn Thr Asp Ala Tyr Glu Gly
                165                 170                 175

Asp Val Tyr Phe Arg Leu Arg Val Asn Ile Thr Leu Tyr Glu Cys Tyr
            180                 185                 190

Tyr
```

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(25)
<223> OTHER INFORMATION: PCR primer CS1-895N

<400> SEQUENCE: 79
agagtggaga ttgttgtcaa gagta                                         25

<210> SEQ ID NO 80
<211> LENGTH: 39

```
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(39)
<223> OTHER INFORMATION: Oligo dt anchor primer

<400> SEQUENCE: 80
gaccacgcgt atcgatgtcg actttttttt tttttttv                              39

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(22)
<223> OTHER INFORMATION: PCR anchor primer

<400> SEQUENCE: 81
gaccacgcgt atcgatgtcg ac                                               22

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(21)
<223> OTHER INFORMATION: Primer CS1-874N

<400> SEQUENCE: 82
agtaatagga tcatcaaaca c                                                21

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(24)
<223> OTHER INFORMATION: primer RT-CS-C1(-)50s

<400> SEQUENCE: 83
ccaacttctt tctctacttc agaa                                             24

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(24)
<223> OTHER INFORMATION: primer RT-CS-C1(-)31s

<400> SEQUENCE: 84
cagaaccctg ttttctgatt tatt                                             24

<210> SEQ ID NO 85
```

```
<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(24)
<223> OTHER INFORMATION: primerRT-CS-C1(-)13s

<400> SEQUENCE: 85
tttatttttg cacaatggca atct                                              24

<210> SEQ ID NO 86
<211> LENGTH: 576
<212> TYPE: DNA
<213> ORGANISM: Thuja plicata
<220> FEATURE:
<221> NAME/KEY: CDS
<222> LOCATION: (1)..(576)

<400> SEQUENCE: 86
```

| atg gca atg aaa gct gct aga gtt ctg cat tta tgc ttt cta tgg ctt | 48 |
|---|---|
| Met Ala Met Lys Ala Ala Arg Val Leu His Leu Cys Phe Leu Trp Leu | |
| 1               5                   10                  15 | |

| cta gta tct gca atc ttc ata aaa tct gca gat tgc cgt agc tgg aaa | 96 |
|---|---|
| Leu Val Ser Ala Ile Phe Ile Lys Ser Ala Asp Cys Arg Ser Trp Lys | |
|             20                  25                  30 | |

| aag aag ctt cca aag ccc tgt aga aat ctt gtg tta tat ttt cat gat | 144 |
|---|---|
| Lys Lys Leu Pro Lys Pro Cys Arg Asn Leu Val Leu Tyr Phe His Asp | |
|         35                  40                  45 | |

| ata atc tac aat ggc aaa aat gca gag aat gca aca tct gca ctt gtt | 192 |
|---|---|
| Ile Ile Tyr Asn Gly Lys Asn Ala Glu Asn Ala Thr Ser Ala Leu Val | |
|     50                  55                  60 | |

| tca gcc cct caa gga gct aat ctc acc att atg act ggt aat aac cat | 240 |
|---|---|
| Ser Ala Pro Gln Gly Ala Asn Leu Thr Ile Met Thr Gly Asn Asn His | |
| 65                  70                  75                  80 | |

| ttt ggg aat ctt gca gtg ttt gat gat cct att act ctt gac aac aat | 288 |
|---|---|
| Phe Gly Asn Leu Ala Val Phe Asp Asp Pro Ile Thr Leu Asp Asn Asn | |
|                 85                  90                  95 | |

| ctt cac tct cct cct gtt gga aga gct cag ggc ttt tac ttc tat gac | 336 |
|---|---|
| Leu His Ser Pro Pro Val Gly Arg Ala Gln Gly Phe Tyr Phe Tyr Asp | |
|             100                 105                 110 | |

| atg aag aac acc ttc agt gcc tgg ctt ggc ttc aca ttt gtg ctc aat | 384 |
|---|---|
| Met Lys Asn Thr Phe Ser Ala Trp Leu Gly Phe Thr Phe Val Leu Asn | |
|         115                 120                 125 | |

| tca act gat cac aag ggc tcc att act ttc aat gga gca gat ccc atc | 432 |
|---|---|
| Ser Thr Asp His Lys Gly Ser Ile Thr Phe Asn Gly Ala Asp Pro Ile | |
|     130                 135                 140 | |

| tta aca aag tac aga gac ata tct gtt gtg ggt gga aca ggg gat ttc | 480 |
|---|---|
| Leu Thr Lys Tyr Arg Asp Ile Ser Val Val Gly Gly Thr Gly Asp Phe | |
| 145                 150                 155                 160 | |

| ttg atg gca aga gga att gct acc att tct act gac tca tat gag gga | 528 |
|---|---|
| Leu Met Ala Arg Gly Ile Ala Thr Ile Ser Thr Asp Ser Tyr Glu Gly | |
|                 165                 170                 175 | |

| gat gtt tat ttc agg ctt agg gtc aat atc aca ctc tat gag tgt tac | 576 |
|---|---|
| Asp Val Tyr Phe Arg Leu Arg Val Asn Ile Thr Leu Tyr Glu Cys Tyr | |
|             180                 185                 190 | |

```
<210> SEQ ID NO 87
<211> LENGTH: 192
<212> TYPE: PRT
<213> ORGANISM: Thuja plicata
```

<400> SEQUENCE: 87

| | | | | | | | | | | | | | | | |
|---|---|---|---|---|---|---|---|---|---|---|---|---|---|---|---|
| Met | Ala | Met | Lys | Ala | Ala | Arg | Val | Leu | His | Leu | Cys | Phe | Leu | Trp | Leu |
| 1 | | | | 5 | | | | 10 | | | | | 15 | | |
| Leu | Val | Ser | Ala | Ile | Phe | Ile | Lys | Ser | Ala | Asp | Cys | Arg | Ser | Trp | Lys |
| | | | 20 | | | | | 25 | | | | | 30 | | |
| Lys | Lys | Leu | Pro | Lys | Pro | Cys | Arg | Asn | Leu | Val | Leu | Tyr | Phe | His | Asp |
| | | 35 | | | | | 40 | | | | | 45 | | | |
| Ile | Ile | Tyr | Asn | Gly | Lys | Asn | Ala | Glu | Asn | Ala | Thr | Ser | Ala | Leu | Val |
| | 50 | | | | | 55 | | | | | 60 | | | | |
| Ser | Ala | Pro | Gln | Gly | Ala | Asn | Leu | Thr | Ile | Met | Thr | Gly | Asn | Asn | His |
| 65 | | | | | 70 | | | | | 75 | | | | | 80 |
| Phe | Gly | Asn | Leu | Ala | Val | Phe | Asp | Asp | Pro | Ile | Thr | Leu | Asp | Asn | Asn |
| | | | | 85 | | | | | 90 | | | | | 95 | |
| Leu | His | Ser | Pro | Pro | Val | Gly | Arg | Ala | Gln | Gly | Phe | Tyr | Phe | Tyr | Asp |
| | | | 100 | | | | | 105 | | | | | 110 | | |
| Met | Lys | Asn | Thr | Phe | Ser | Ala | Trp | Leu | Gly | Phe | Thr | Phe | Val | Leu | Asn |
| | | 115 | | | | | 120 | | | | | 125 | | | |
| Ser | Thr | Asp | His | Lys | Gly | Ser | Ile | Thr | Phe | Asn | Gly | Ala | Asp | Pro | Ile |
| | 130 | | | | | 135 | | | | | 140 | | | | |
| Leu | Thr | Lys | Tyr | Arg | Asp | Ile | Ser | Val | Val | Gly | Gly | Thr | Gly | Asp | Phe |
| 145 | | | | | 150 | | | | | 155 | | | | | 160 |
| Leu | Met | Ala | Arg | Gly | Ile | Ala | Thr | Ile | Ser | Thr | Asp | Ser | Tyr | Glu | Gly |
| | | | | 165 | | | | | 170 | | | | | 175 | |
| Asp | Val | Tyr | Phe | Arg | Leu | Arg | Val | Asn | Ile | Thr | Leu | Tyr | Glu | Cys | Tyr |
| | | | 180 | | | | | 185 | | | | | 190 | | |

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(22)
<223> OTHER INFORMATION: primer AP1

<400> SEQUENCE: 88
gtaatacgac tcactatagg gc                                              22

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(28)
<223> OTHER INFORMATION: primer TpS4-213n

<400> SEQUENCE: 89
agattagctc cttgaggggc tgaaacaa                                        28

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature

```
<222> LOCATION: (1)..(19)
<223> OTHER INFORMATION: primer ap2

<400> SEQUENCE: 90
actatagggc acgcgtggt                                                    19

<210> SEQ ID NO 91
<211> LENGTH: 28
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(28)
<223> OTHER INFORMATION: primer TpS4-199n

<400> SEQUENCE: 91
aggggctgaa acaagtgcag atgttgca                                          28

<210> SEQ ID NO 92
<211> LENGTH: 29
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(29)
<223> OTHER INFORMATION: primer TpS4-188n

<400> SEQUENCE: 92
caagtgtgca gatgttgcat tctctgcat                                         29

<210> SEQ ID NO 93
<211> LENGTH: 576
<212> TYPE: DNA
<213> ORGANISM: Thuja plicata
<220> FEATURE:
<221> NAME/KEY: CDS
<222> LOCATION: (1)..(576)

<400> SEQUENCE: 93 atg gca atg aaa tct gaa aga gct ttg cag tta tgc ctt ctg tgg ctt        48
Met Ala Met Lys Ser Glu Arg Ala Leu Gln Leu Cys Leu Leu Trp Leu
 1               5                  10                  15 ctg atg tct gca atc ttg cta aaa cct gca gat tgc cat gga agg aag        96
Leu Met Ser Ala Ile Leu Leu Lys Pro Ala Asp Cys His Gly Arg Lys
             20                  25                  30 aag agg ctt ccc aag ccc tgc aag cat ctt gtg ttg tat ttc cat gat       144
Lys Arg Leu Pro Lys Pro Cys Lys His Leu Val Leu Tyr Phe His Asp
         35                  40                  45 ata ctc tac aat ggc aag aat gcc cac aat gca aca tct gca ctt gtt       192
Ile Leu Tyr Asn Gly Lys Asn Ala His Asn Ala Thr Ser Ala Leu Val
 50                  55                  60 gca gcc cct gag gga gcc aat ctc acc att atg act ggt aat aac cat       240
Ala Ala Pro Glu Gly Ala Asn Leu Thr Ile Met Thr Gly Asn Asn His
 65                  70                  75                  80 ttt ggg aat att gct gtg ttt gat gat cct att act ctt gac aac aat       288
Phe Gly Asn Ile Ala Val Phe Asp Asp Pro Ile Thr Leu Asp Asn Asn
                 85                  90                  95 ctt cac tct cct tct gtt gga aga gct cag ggc ttt tac ttc tat gac       336
Leu His Ser Pro Ser Val Gly Arg Ala Gln Gly Phe Tyr Phe Tyr Asp
            100                 105                 110 atg aag gat acc ttc aat gct tgg ctt ggt ttt aca ttt gtg ctg aat       384
```

```
                    Met Lys Asp Thr Phe Asn Ala Trp Leu Gly Phe Thr Phe Val Leu Asn
                            115                 120                 125 tca act gat cac aag ggc acc att act ttc aat gga gca gat cca atc            432
Ser Thr Asp His Lys Gly Thr Ile Thr Phe Asn Gly Ala Asp Pro Ile
    130                 135                 140 ctg acc aag tac aga gat ata tct gtt gtg ggt gga aca ggg gat ttc            480
Leu Thr Lys Tyr Arg Asp Ile Ser Val Val Gly Gly Thr Gly Asp Phe
145                 150                 155                 160 ttg atg gcc aga gga att gcc acc att tct act gat tca tat gag gga            528
Leu Met Ala Arg Gly Ile Ala Thr Ile Ser Thr Asp Ser Tyr Glu Gly
                165                 170                 175 gat gtt tat ttc agg ctt agg gtc aat atc aca ctc tat gag tgt tac            576
Asp Val Tyr Phe Arg Leu Arg Val Asn Ile Thr Leu Tyr Glu Cys Tyr
            180                 185                 190

<210> SEQ ID NO 94
<211> LENGTH: 192
<212> TYPE: PRT
<213> ORGANISM: Thuja plicata

<400> SEQUENCE: 94

Met Ala Met Lys Ser Glu Arg Ala Leu Gln Leu Cys Leu Leu Trp Leu
  1               5                  10                  15

Leu Met Ser Ala Ile Leu Leu Lys Pro Ala Asp Cys His Gly Arg Lys
             20                  25                  30

Lys Arg Leu Pro Lys Pro Cys Lys His Leu Val Leu Tyr Phe His Asp
         35                  40                  45

Ile Leu Tyr Asn Gly Lys Asn Ala His Asn Ala Thr Ser Ala Leu Val
     50                  55                  60

Ala Ala Pro Glu Gly Ala Asn Leu Thr Ile Met Thr Gly Asn Asn His
 65                  70                  75                  80

Phe Gly Asn Ile Ala Val Phe Asp Asp Pro Ile Thr Leu Asp Asn Asn
                 85                  90                  95

Leu His Ser Pro Ser Val Gly Arg Ala Gln Gly Phe Tyr Phe Tyr Asp
            100                 105                 110

Met Lys Asp Thr Phe Asn Ala Trp Leu Gly Phe Thr Phe Val Leu Asn
        115                 120                 125

Ser Thr Asp His Lys Gly Thr Ile Thr Phe Asn Gly Ala Asp Pro Ile
    130                 135                 140

Leu Thr Lys Tyr Arg Asp Ile Ser Val Val Gly Gly Thr Gly Asp Phe
145                 150                 155                 160

Leu Met Ala Arg Gly Ile Ala Thr Ile Ser Thr Asp Ser Tyr Glu Gly
                165                 170                 175

Asp Val Tyr Phe Arg Leu Arg Val Asn Ile Thr Leu Tyr Glu Cys Tyr
            180                 185                 190

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(27)
<223> OTHER INFORMATION: primer CS10-826N

<400> SEQUENCE: 95
cagtcataat ggtgagattg gctccct                                              27
```

-continued

```
<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(27)
<223> OTHER INFORMATION: primer CS10-814N

<400> SEQUENCE: 96
tgagattggc tccctcaggg gctgcaa                                          27

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(27)
<223> OTHER INFORMATION: primer CS10-795N

<400> SEQUENCE: 97
ggctgcaaca agtgcagatg ttgcatt                                          27

<210> SEQ ID NO 98
<211> LENGTH: 552
<212> TYPE: DNA
<213> ORGANISM: Eucommia ulmoides
<220> FEATURE:
<221> NAME/KEY: CDS
<222> LOCATION: (1)..(552)

<400> SEQUENCE: 98 atg gca aac ctt gtt gag aaa tct tat tac att atc ttc atg ctt gtt       48
Met Ala Asn Leu Val Glu Lys Ser Tyr Tyr Ile Ile Phe Met Leu Val
 1               5                  10                  15 cta aca tca tcc tat gtt gtt gtc tcc tcc aag tcc aag aca atc cga       96
Leu Thr Ser Ser Tyr Val Val Val Ser Ser Lys Ser Lys Thr Ile Arg
                20                  25                  30 ccc gaa aac cca tgc aac cgt atc gtc ctc tac tac cac gac atc ctc      144
Pro Glu Asn Pro Cys Asn Arg Ile Val Leu Tyr Tyr His Asp Ile Leu
            35                  40                  45 ttc aac ggc acc aac acc gtt aat gcc aca tca gca aaa gcc gcc aaa      192
Phe Asn Gly Thr Asn Thr Val Asn Ala Thr Ser Ala Lys Ala Ala Lys
        50                  55                  60 gag acc cgc ctc ggg tcc cac gaa ttt ggg atg ctc gtg gtt ttt gac      240
Glu Thr Arg Leu Gly Ser His Glu Phe Gly Met Leu Val Val Phe Asp
 65                  70                  75                  80 gat ccg gtg acg gca gac cgc gag ctc cag tcg cct ccg ttg ggc cgg      288
Asp Pro Val Thr Ala Asp Arg Glu Leu Gln Ser Pro Pro Leu Gly Arg
                 85                  90                  95 gct cag ggg ttc tac ttt tat gat atg aag agc gag tac aat gct tgg      336
Ala Gln Gly Phe Tyr Phe Tyr Asp Met Lys Ser Glu Tyr Asn Ala Trp
            100                 105                 110 ttt gca tat acg ttg gtg ttt aac tcg agc gag cat aaa ggg acg atc      384
Phe Ala Tyr Thr Leu Val Phe Asn Ser Ser Glu His Lys Gly Thr Ile
        115                 120                 125 acg ata atg ggg gcc gat atg atg ggg gag aaa aca cgg gat ctt ccg      432
Thr Ile Met Gly Ala Asp Met Met Gly Glu Lys Thr Arg Asp Leu Pro
    130                 135                 140
```

```
gtg gtt gga gga acg ggg gat ttt ttc atg gca aga ggg att gcc acg        480
Val Val Gly Gly Thr Gly Asp Phe Phe Met Ala Arg Gly Ile Ala Thr
145             150                 155                 160 ttt cga acc gat gct ttt gag ggg ttc aat tat ttt cgg ctt gag atg        528
Phe Arg Thr Asp Ala Phe Glu Gly Phe Asn Tyr Phe Arg Leu Glu Met
                165                 170                 175 gat gtc aag ttg tac gag tgt tat                                        552
Asp Val Lys Leu Tyr Glu Cys Tyr
            180
```

<210> SEQ ID NO 99
<211> LENGTH: 184
<212> TYPE: PRT
<213> ORGANISM: Eucommia ulmoides

<400> SEQUENCE: 99

```
Met Ala Asn Leu Val Glu Lys Ser Tyr Tyr Ile Ile Phe Met Leu Val
 1               5                  10                  15

Leu Thr Ser Ser Tyr Val Val Ser Ser Lys Ser Lys Thr Ile Arg
            20                  25                  30

Pro Glu Asn Pro Cys Asn Arg Ile Val Leu Tyr Tyr His Asp Ile Leu
            35                  40                  45

Phe Asn Gly Thr Asn Thr Val Asn Ala Thr Ser Ala Lys Ala Ala Lys
        50                  55                  60

Glu Thr Arg Leu Gly Ser His Glu Phe Gly Met Leu Val Val Phe Asp
 65                 70                  75                  80

Asp Pro Val Thr Ala Asp Arg Glu Leu Gln Ser Pro Leu Gly Arg
                85                  90                  95

Ala Gln Gly Phe Tyr Phe Tyr Asp Met Lys Ser Glu Tyr Asn Ala Trp
            100                 105                 110

Phe Ala Tyr Thr Leu Val Phe Asn Ser Ser Glu His Lys Gly Thr Ile
            115                 120                 125

Thr Ile Met Gly Ala Asp Met Met Gly Glu Lys Thr Arg Asp Leu Pro
        130                 135                 140

Val Val Gly Gly Thr Gly Asp Phe Phe Met Ala Arg Gly Ile Ala Thr
145             150                 155                 160

Phe Arg Thr Asp Ala Phe Glu Gly Phe Asn Tyr Phe Arg Leu Glu Met
                165                 170                 175

Asp Val Lys Leu Tyr Glu Cys Tyr
            180
```

<210> SEQ ID NO 100
<211> LENGTH: 28
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(28)
<223> OTHER INFORMATION: E ulmoides n-terminal primer

<400> SEQUENCE: 100
garttggtgt tctatttcca cgacatmc                                          28

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence:

```
        oligonucleotide
<221> NAME/KEY: misc_feature
<222> LOCATION: (1)..(25)
<223> OTHER INFORMATION: E ulmoides c-terminal primer

<400> SEQUENCE: 101
caaagtggca acccctgtcg ccatg                                          25

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(22)
<223> OTHER INFORMATION: primer Sp2

<400> SEQUENCE: 102
cccccgttcc tccaaccacc gg                                             22

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(26)
<223> OTHER INFORMATION: primer SpN1

<400> SEQUENCE: 103
ggcccatgcg gttaagcata ttctcc                                         26

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(29)
<223> OTHER INFORMATION: primer SpN2

<400> SEQUENCE: 104
cctctataaa aacataattc ttttccccc                                      29

<210> SEQ ID NO 105
<211> LENGTH: 588
<212> TYPE: DNA
<213> ORGANISM: Schisandra chinensis
<220> FEATURE:
<221> NAME/KEY: CDS
<222> LOCATION: (1)..(588)

<400> SEQUENCE: 105 atg gaa ggg aga aag ctg atc atc act atc cct ctc ctc ctc ttc ttc       48
Met Glu Gly Arg Lys Leu Ile Ile Thr Ile Pro Leu Leu Leu Phe Phe
  1               5                  10                  15 att gcc ttc ttc tca gtg cct ccg gct gcg ttt ggc cgg aaa gtg aca       96
Ile Ala Phe Phe Ser Val Pro Pro Ala Ala Phe Gly Arg Lys Val Thr
             20                  25                  30 ctt ccc cgt aaa agg atg ccg caa cca tgc atg aac ttg gtg ttt tac      144
Leu Pro Arg Lys Arg Met Pro Gln Pro Cys Met Asn Leu Val Phe Tyr
         35                  40                  45
```

```
ttc cac gac atc tta tac aac ggc aag aat gct gcc aat gca act tcg    192
Phe His Asp Ile Leu Tyr Asn Gly Lys Asn Ala Ala Asn Ala Thr Ser
    50                  55                  60 gcg att gtc ggg tcg ccg gca tgg ggg aac cgg acc att cta gct gga    240
Ala Ile Val Gly Ser Pro Ala Trp Gly Asn Arg Thr Ile Leu Ala Gly
65                  70                  75                  80 caa agc aat ttt ggt gac atg gtc gta ttt gat gac ccg att act ctt    288
Gln Ser Asn Phe Gly Asp Met Val Val Phe Asp Asp Pro Ile Thr Leu
                85                  90                  95 gac aac aat ctg cat tcg ccc ccc gtt ggt cgt gcg cag gga ttc tac    336
Asp Asn Asn Leu His Ser Pro Pro Val Gly Arg Ala Gln Gly Phe Tyr
            100                 105                 110 ttc tac gac agg aag gat gta ttt acc gcg tgg cta ggc ttc agt ttc    384
Phe Tyr Asp Arg Lys Asp Val Phe Thr Ala Trp Leu Gly Phe Ser Phe
        115                 120                 125 gtc ttc aac aat tca gac tac agg ggg agt ata aat ttt gct ggc gca    432
Val Phe Asn Asn Ser Asp Tyr Arg Gly Ser Ile Asn Phe Ala Gly Ala
    130                 135                 140 gat cca ctt ttg atc aag acg agg gac atc tct gtg atc ggt ggc acc    480
Asp Pro Leu Leu Ile Lys Thr Arg Asp Ile Ser Val Ile Gly Gly Thr
145                 150                 155                 160 ggc gat ttt ttc atg gct aga ggg atc gcg aca ttg atg aca gat gcc    528
Gly Asp Phe Phe Met Ala Arg Gly Ile Ala Thr Leu Met Thr Asp Ala
                165                 170                 175 ttc gag ggt gag gtg tat ttc agg ctg agg aca gat atc aag ctg tat    576
Phe Glu Gly Glu Val Tyr Phe Arg Leu Arg Thr Asp Ile Lys Leu Tyr
            180                 185                 190 gaa tgc tac tga                                                    588
Glu Cys Tyr
        195

<210> SEQ ID NO 106
<211> LENGTH: 195
<212> TYPE: PRT
<213> ORGANISM: Schisandra chinensis

<400> SEQUENCE: 106

Met Glu Gly Arg Lys Leu Ile Ile Thr Ile Pro Leu Leu Phe Phe
1               5                   10                  15

Ile Ala Phe Phe Ser Val Pro Pro Ala Ala Phe Gly Arg Lys Val Thr
                20                  25                  30

Leu Pro Arg Lys Arg Met Pro Gln Pro Cys Met Asn Leu Val Phe Tyr
            35                  40                  45

Phe His Asp Ile Leu Tyr Asn Gly Lys Asn Ala Ala Asn Ala Thr Ser
    50                  55                  60

Ala Ile Val Gly Ser Pro Ala Trp Gly Asn Arg Thr Ile Leu Ala Gly
65                  70                  75                  80

Gln Ser Asn Phe Gly Asp Met Val Val Phe Asp Asp Pro Ile Thr Leu
                85                  90                  95

Asp Asn Asn Leu His Ser Pro Val Gly Arg Ala Gln Gly Phe Tyr
            100                 105                 110

Phe Tyr Asp Arg Lys Asp Val Phe Thr Ala Trp Leu Gly Phe Ser Phe
        115                 120                 125

Val Phe Asn Asn Ser Asp Tyr Arg Gly Ser Ile Asn Phe Ala Gly Ala
    130                 135                 140

Asp Pro Leu Leu Ile Lys Thr Arg Asp Ile Ser Val Ile Gly Gly Thr
145                 150                 155                 160
```

```
Gly Asp Phe Phe Met Ala Arg Gly Ile Ala Thr Leu Met Thr Asp Ala
                165                 170                 175

Phe Glu Gly Glu Val Tyr Phe Arg Leu Arg Thr Asp Ile Lys Leu Tyr
            180                 185                 190

Glu Cys Tyr
        195

<210> SEQ ID NO 107
<211> LENGTH: 939
<212> TYPE: DNA
<213> ORGANISM: Linum usitatissimum
<220> FEATURE:
<221> NAME/KEY: CDS
<222> LOCATION: (1)..(939)

<400> SEQUENCE: 107 atg ggg cgg tgc aga gtt ctg gtg gtg gga ggt acc ggg tac ata ggc     48
Met Gly Arg Cys Arg Val Leu Val Val Gly Gly Thr Gly Tyr Ile Gly
  1               5                  10                  15 aag cgg atc gtc aag gct agc atc gaa cac ggc cac gac act tac gtc     96
Lys Arg Ile Val Lys Ala Ser Ile Glu His Gly His Asp Thr Tyr Val
             20                  25                  30 ctc aag cga cct gag acg ggc ctc gat att gaa aaa ttc cag ctc ttg    144
Leu Lys Arg Pro Glu Thr Gly Leu Asp Ile Glu Lys Phe Gln Leu Leu
         35                  40                  45 ttg tct ttc aag aaa cag ggc gcc cac ctc gtc gag gcc tcc ttc tct    192
Leu Ser Phe Lys Lys Gln Gly Ala His Leu Val Glu Ala Ser Phe Ser
     50                  55                  60 gac cac gag agc ctt gtt cga gcg gtg aag cta gtc gat gtc gtg ata    240
Asp His Glu Ser Leu Val Arg Ala Val Lys Leu Val Asp Val Val Ile
 65                  70                  75                  80 tgt acc gtc tcg ggg gct cat tca cgc agc ctc ctc ctc cag ctc aag    288
Cys Thr Val Ser Gly Ala His Ser Arg Ser Leu Leu Leu Gln Leu Lys
                 85                  90                  95 ttg gtc gag gcc atc aaa gag gcc gga aat gtt aag aga ttc att ccg    336
Leu Val Glu Ala Ile Lys Glu Ala Gly Asn Val Lys Arg Phe Ile Pro
            100                 105                 110 tct gag ttt ggg atg gac ccg gcg agg atg ggg gat gca ttg gag cca    384
Ser Glu Phe Gly Met Asp Pro Ala Arg Met Gly Asp Ala Leu Glu Pro
        115                 120                 125 ggg agg gag acg ttc gat ctg aag atg gtg gtg agg aaa gcg atc gag    432
Gly Arg Glu Thr Phe Asp Leu Lys Met Val Val Arg Lys Ala Ile Glu
    130                 135                 140 gac gcg aat atc ccc cac act tac atc tcg gcc aac tgc ttt gga ggt    480
Asp Ala Asn Ile Pro His Thr Tyr Ile Ser Ala Asn Cys Phe Gly Gly
145                 150                 155                 160 tat ttc gtc ggc aat ctt tcg caa ctc gga cct cta acc cct cct tcc    528
Tyr Phe Val Gly Asn Leu Ser Gln Leu Gly Pro Leu Thr Pro Pro Ser
                165                 170                 175 gat aag gtc acc atc tat gga gat ggc aac gtc aaa gtg gtg tac atg    576
Asp Lys Val Thr Ile Tyr Gly Asp Gly Asn Val Lys Val Val Tyr Met
            180                 185                 190 gat gaa gat gat gtc gcc act tac acg atc atg acg ata gag gat gac    624
Asp Glu Asp Asp Val Ala Thr Tyr Thr Ile Met Thr Ile Glu Asp Asp
        195                 200                 205 cgg aca ctt aac aag acg atg tac ttc cgg cca ccg gaa aat gtg att    672
Arg Thr Leu Asn Lys Thr Met Tyr Phe Arg Pro Pro Glu Asn Val Ile
    210                 215                 220 act cat agg caa tta gtg gag act tgg gaa aag ctc tca ggc aac caa    720
Thr His Arg Gln Leu Val Glu Thr Trp Glu Lys Leu Ser Gly Asn Gln
225                 230                 235                 240
```

```
ctt caa aag act gag ctt tct tca caa gac ttt ctt gca ctc atg gaa      768
Leu Gln Lys Thr Glu Leu Ser Ser Gln Asp Phe Leu Ala Leu Met Glu
                245                 250                 255 ggg aag gac gta gcg gag cag atc gta ata ggg cac ctc tac cac att      816
Gly Lys Asp Val Ala Glu Gln Ile Val Ile Gly His Leu Tyr His Ile
            260                 265                 270 tac tac gaa gga tgt ctc act aac ttt gac atc gat gct gac caa gat      864
Tyr Tyr Glu Gly Cys Leu Thr Asn Phe Asp Ile Asp Ala Asp Gln Asp
        275                 280                 285 caa gta gaa gct tca agt tta tac cct gaa gtt gaa tac act cgt atg      912
Gln Val Glu Ala Ser Ser Leu Tyr Pro Glu Val Glu Tyr Thr Arg Met
    290                 295                 300 aaa gat tat ctg atg atc tac ctt tga                                  939
Lys Asp Tyr Leu Met Ile Tyr Leu
305                 310
```

<210> SEQ ID NO 108
<211> LENGTH: 312
<212> TYPE: PRT
<213> ORGANISM: Linum usitatissimum

<400> SEQUENCE: 108

```
Met Gly Arg Cys Arg Val Leu Val Gly Gly Thr Gly Tyr Ile Gly
  1               5                  10                  15

Lys Arg Ile Val Lys Ala Ser Ile Glu His Gly His Asp Thr Tyr Val
                 20                  25                  30

Leu Lys Arg Pro Glu Thr Gly Leu Asp Ile Glu Lys Phe Gln Leu Leu
             35                  40                  45

Leu Ser Phe Lys Lys Gln Gly Ala His Leu Val Glu Ala Ser Phe Ser
     50                  55                  60

Asp His Glu Ser Leu Val Arg Ala Val Lys Leu Val Asp Val Ile
 65                  70                  75                  80

Cys Thr Val Ser Gly Ala His Ser Arg Ser Leu Leu Gln Leu Lys
                 85                  90                  95

Leu Val Glu Ala Ile Lys Glu Ala Gly Asn Val Lys Arg Phe Ile Pro
                100                 105                 110

Ser Glu Phe Gly Met Asp Pro Ala Arg Met Gly Asp Ala Leu Glu Pro
            115                 120                 125

Gly Arg Glu Thr Phe Asp Leu Lys Met Val Val Arg Lys Ala Ile Glu
130                 135                 140

Asp Ala Asn Ile Pro His Thr Tyr Ile Ser Ala Asn Cys Phe Gly Gly
145                 150                 155                 160

Tyr Phe Val Gly Asn Leu Ser Gln Leu Gly Pro Leu Thr Pro Pro Ser
                165                 170                 175

Asp Lys Val Thr Ile Tyr Gly Asp Gly Asn Val Lys Val Val Tyr Met
            180                 185                 190

Asp Glu Asp Asp Val Ala Thr Tyr Thr Ile Met Thr Ile Glu Asp Asp
        195                 200                 205

Arg Thr Leu Asn Lys Thr Met Tyr Phe Arg Pro Pro Glu Asn Val Ile
    210                 215                 220

Thr His Arg Gln Leu Val Glu Thr Trp Glu Lys Leu Ser Gly Asn Gln
225                 230                 235                 240

Leu Gln Lys Thr Glu Leu Ser Ser Gln Asp Phe Leu Ala Leu Met Glu
                245                 250                 255

Gly Lys Asp Val Ala Glu Gln Ile Val Ile Gly His Leu Tyr His Ile
            260                 265                 270
```

Tyr Tyr Glu Gly Cys Leu Thr Asn Phe Asp Ile Asp Ala Asp Gln Asp
        275                 280                 285

Gln Val Glu Ala Ser Ser Leu Tyr Pro Glu Val Glu Tyr Thr Arg Met
    290                 295                 300

Lys Asp Tyr Leu Met Ile Tyr Leu
305                 310

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(24)
<223> OTHER INFORMATION: primer PLR4 wherein n at positions 3, 6, 15 and
      24 represents inosine

<400> SEQUENCE: 109
ccntcngagt tcggnatgga tccn                                               24

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(21)
<223> OTHER INFORMATION: primer PLR 6 wherein n at positions 1, 10 and
      16 represents inosine

<400> SEQUENCE: 110
ngtatatttn acttcngggt a                                                  21

<210> SEQ ID NO 111
<211> LENGTH: 603
<212> TYPE: DNA
<213> ORGANISM: Linum usitatissimum

<400> SEQUENCE: 111
tctgagtttg ggatggaccc ggcgaggatg ggggatgcat tggagccagg gagggagacg         60
ttcgatctga agatggtggt gaggaaagcg atcgaggacg cgaatatccc ccacacttac        120
atctcggcca actgctttgg aggttatttc gtcggcaatc tttcgcaact cggacctcta        180
accccttctt ccgataaggt caccatctat ggagatggca acgtcaaagt ggtgtacatg        240
gatgaagatg atgtcgccac ttacacgatc atgacgatag aggatgaccg gacacttaac        300
aagacgatgt acttccggcc accggaaaat gtgattactc ataggcaatt agtggagact        360
tgggaaaagc tctcaggcaa ccaacttcaa aagactgagc tttcttcaca agactttctt        420
gcactcatgg aagggaagga cgtagcggag cagatcgtaa tagggcacct ctaccacatt        480
tactacgaag gatgtctcac taactttgac atcgatgctg accaagatca agtagaagct        540
tcaagtttat accctgaagt tgaatacact cgtatgaaag attatctgat gatctacctt        600
tga                                                                     603

<210> SEQ ID NO 112
<211> LENGTH: 681
<212> TYPE: DNA
<213> ORGANISM: Linum usitatissimum -continued

<400> SEQUENCE: 112

| cattcacgca gcctcctcct ccagctcaag ttggtcgagg ccatcaaaga ggccggaaat | 60 |
| gttaagagat tcattccgtc tgagtttggg atggacccgg cgaggatggg ggatgcattg | 120 |
| gagccaggga gggagacgtt cgatctgaag atggtggtga ggaaagcgat cgaggacgcg | 180 |
| aatatccccc acacttacat ctcggccaac tgctttggag gttatttcgt cggcaatctt | 240 |
| tcgcaactcg gacctctaac ccctccttcc gataaggtca ccatctatgg agatggcaac | 300 |
| gtcaaagtgg tgtacatgga tgaagatgat gtcgccactt acacgatcat gacgatagag | 360 |
| gatgaccgga cacttaacaa gacgatgtac ttccggccac cggaaaatgt gattactcat | 420 |
| aggcaattag tggagacttg ggaaaagctc tcaggcaacc aacttcaaaa gactgagctt | 480 |
| tcttcacaag actttcttgc actcatggaa gggaaggacg tagcggagca gatcgtaata | 540 |
| gggcacctct accacattta ctacgaagga tgtctcacta actttgacat cgatgctgac | 600 |
| caagatcaag tagaagcttc aagtttatac cctgaagttg aatacactcg tatgaaagat | 660 |
| tatctgatga tctacctttg a | 681 |

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: oligonucleotide
<221> NAME/KEY: misc_feature
<222> LOCATION: (1)..(30)
<223> OTHER INFORMATION: primer 1

<400> SEQUENCE: 113

| aacatttccg gcctctttga tggcctcgac | 30 |

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: oligonucleotide
<221> NAME/KEY: misc_feature
<222> LOCATION: (1)..(30)
<223> OTHER INFORMATION: primer 2

<400> SEQUENCE: 114

| aaggtagatc atcagataat ctttcatacg | 30 |

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: oligonucleotide
<221> NAME/KEY: misc_feature
<222> LOCATION: (1)..(22)
<223> OTHER INFORMATION: T7 primer

<400> SEQUENCE: 115

| gtaatacgac tcactatagg gc | 22 |

<210> SEQ ID NO 116
<211> LENGTH: 20
<212> TYPE: DNA

```
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(20)
<223> OTHER INFORMATION: T3 primer

<400> SEQUENCE: 116
aattaaccct cactaaaggg                                                    20

<210> SEQ ID NO 117
<211> LENGTH: 942
<212> TYPE: DNA
<213> ORGANISM: Schisandra chinensis
<220> FEATURE:
<221> NAME/KEY: CDS
<222> LOCATION: (1)..(942)

<400> SEQUENCE: 117 atg acg aag ttg agt gag agc aag gtt ctg att gtg ggt ggc aca ggc        48
Met Thr Lys Leu Ser Glu Ser Lys Val Leu Ile Val Gly Gly Thr Gly
  1               5                  10                  15 cac ata ggg agg agg ctg gtt aga gcc agt ctt gcc ctt aat cac cca        96
His Ile Gly Arg Arg Leu Val Arg Ala Ser Leu Ala Leu Asn His Pro
             20                  25                  30 act tac gtc ctg ttt cga gag gag aat ttg aat gat atc gag aag atc       144
Thr Tyr Val Leu Phe Arg Glu Glu Asn Leu Asn Asp Ile Glu Lys Ile
         35                  40                  45 gag ctt ctt ctg gat ttc aag caa aac ggt gct cgt ctt gtg atg gga       192
Glu Leu Leu Leu Asp Phe Lys Gln Asn Gly Ala Arg Leu Val Met Gly
     50                  55                  60 tcg ttc gac aac cgg gag agc ctg ctg aat gca gtt aag cag gtg gac       240
Ser Phe Asp Asn Arg Glu Ser Leu Leu Asn Ala Val Lys Gln Val Asp
 65                  70                  75                  80 atc gtc ata tcc gcc ttg gct gca aac cat gtc cgc cat gag atc atc       288
Ile Val Ile Ser Ala Leu Ala Ala Asn His Val Arg His Glu Ile Ile
                 85                  90                  95 acg caa ttg aaa ctc ctg gat gtc atc ata gaa gcc ggt cat atc aag       336
Thr Gln Leu Lys Leu Leu Asp Val Ile Ile Glu Ala Gly His Ile Lys
            100                 105                 110 agg ttc ata cct tca gag ttt gga atg gac cca gat ata atg gtt ggt       384
Arg Phe Ile Pro Ser Glu Phe Gly Met Asp Pro Asp Ile Met Val Gly
        115                 120                 125 gct cta cct cca ggc aat aag aca ttt ata gat aaa agc aag gtc agg       432
Ala Leu Pro Pro Gly Asn Lys Thr Phe Ile Asp Lys Ser Lys Val Arg
    130                 135                 140 cgt gca ata gaa gct gca gga gtt ccc cat acc tat gtc tct gca aat       480
Arg Ala Ile Glu Ala Ala Gly Val Pro His Thr Tyr Val Ser Ala Asn
145                 150                 155                 160 tgc tac gct gca tat ttc gtc ggt ggc ctg ggc caa atc ggc cct ggt       528
Cys Tyr Ala Ala Tyr Phe Val Gly Gly Leu Gly Gln Ile Gly Pro Gly
                165                 170                 175 tta atc cca tca cag gaa aaa gtt gcc ctc ttt gga gat gga gag gcc       576
Leu Ile Pro Ser Gln Glu Lys Val Ala Leu Phe Gly Asp Gly Glu Ala
            180                 185                 190 aaa gtg ata tgg aat gat gag atg gac ata gca aca tat gtt ctt aaa       624
Lys Val Ile Trp Asn Asp Glu Met Asp Ile Ala Thr Tyr Val Leu Lys
        195                 200                 205 gca gca gac gat cca cgg aca tta aac aag gca ata ttt atc aga cct       672
Ala Ala Asp Asp Pro Arg Thr Leu Asn Lys Ala Ile Phe Ile Arg Pro
    210                 215                 220
```

-continued

```
cca gac aat ata ctt tct cag aga gag ctt gtg caa ata tgg gag aaa      720
Pro Asp Asn Ile Leu Ser Gln Arg Glu Leu Val Gln Ile Trp Glu Lys
225                 230                 235                 240 cta att ggc cat gaa tta aag aaa aca aat att tca tct caa gag tgg      768
Leu Ile Gly His Glu Leu Lys Lys Thr Asn Ile Ser Ser Gln Glu Trp
            245                 250                 255 ttg aaa tct atg gaa ggg atg ccc gag ggg ctg caa tta gca atg gca      816
Leu Lys Ser Met Glu Gly Met Pro Glu Gly Leu Gln Leu Ala Met Ala
        260                 265                 270 cac aac ttt cat ata ttc tat gaa ggg tgt tta aca aat ttc cca gtt      864
His Asn Phe His Ile Phe Tyr Glu Gly Cys Leu Thr Asn Phe Pro Val
    275                 280                 285 ggt gat gat caa gaa gct tcg aag ctt tac cca gaa gtc aga tac aca      912
Gly Asp Asp Gln Glu Ala Ser Lys Leu Tyr Pro Glu Val Arg Tyr Thr
290                 295                 300 tct atg gaa gaa tat ttg aag cga tat cta                              942
Ser Met Glu Glu Tyr Leu Lys Arg Tyr Leu
305                 310
```

<210> SEQ ID NO 118
<211> LENGTH: 314
<212> TYPE: PRT
<213> ORGANISM: Schisandra chinensis

<400> SEQUENCE: 118

```
Met Thr Lys Leu Ser Glu Ser Lys Val Leu Ile Val Gly Gly Thr Gly
1               5                   10                  15

His Ile Gly Arg Arg Leu Val Arg Ala Ser Leu Ala Leu Asn His Pro
            20                  25                  30

Thr Tyr Val Leu Phe Arg Glu Glu Asn Leu Asn Asp Ile Glu Lys Ile
        35                  40                  45

Glu Leu Leu Leu Asp Phe Lys Gln Asn Gly Ala Arg Leu Val Met Gly
    50                  55                  60

Ser Phe Asp Asn Arg Glu Ser Leu Leu Asn Ala Val Lys Gln Val Asp
65                  70                  75                  80

Ile Val Ile Ser Ala Leu Ala Ala Asn His Val Arg His Glu Ile Ile
                85                  90                  95

Thr Gln Leu Lys Leu Leu Asp Val Ile Ile Glu Ala Gly His Ile Lys
            100                 105                 110

Arg Phe Ile Pro Ser Glu Phe Gly Met Asp Pro Asp Ile Met Val Gly
        115                 120                 125

Ala Leu Pro Pro Gly Asn Lys Thr Phe Ile Asp Lys Ser Lys Val Arg
    130                 135                 140

Arg Ala Ile Glu Ala Ala Gly Val Pro Thr Tyr Val Ser Ala Asn
145                 150                 155                 160

Cys Tyr Ala Ala Tyr Phe Val Gly Gly Leu Gly Gln Ile Gly Pro Gly
                165                 170                 175

Leu Ile Pro Ser Gln Glu Lys Val Ala Leu Phe Gly Asp Gly Glu Ala
            180                 185                 190

Lys Val Ile Trp Asn Asp Glu Met Asp Ile Ala Thr Tyr Val Leu Lys
        195                 200                 205

Ala Ala Asp Asp Pro Arg Thr Leu Asn Lys Ala Ile Phe Ile Arg Pro
    210                 215                 220

Pro Asp Asn Ile Leu Ser Gln Arg Glu Leu Val Gln Ile Trp Glu Lys
225                 230                 235                 240

Leu Ile Gly His Glu Leu Lys Lys Thr Asn Ile Ser Ser Gln Glu Trp
                245                 250                 255
```

Leu Lys Ser Met Glu Gly Met Pro Glu Gly Leu Gln Leu Ala Met Ala
        260                 265                 270

His Asn Phe His Ile Phe Tyr Glu Gly Cys Leu Thr Asn Phe Pro Val
    275                 280                 285

Gly Asp Asp Gln Glu Ala Ser Lys Leu Tyr Pro Glu Val Arg Tyr Thr
    290                 295                 300

Ser Met Glu Glu Tyr Leu Lys Arg Tyr Leu
305                 310

<210> SEQ ID NO 119
<211> LENGTH: 944
<212> TYPE: DNA
<213> ORGANISM: Schisandra chinensis

<400> SEQUENCE: 119

| | | | | | | |
|---|---|---|---|---|---|---|
| atgacgaagc | tgagtgagag | caaggttctg | attgtgggtg | gcacaggcca | catagggagg | 60 |
| aggctggtta | gagccagtct | tgcccttaat | cacccaactt | acgtcctgtt | tcgagaggag | 120 |
| aatttgaatg | atatcgagaa | gatcgagctt | cttctggatt | tcaagcaaaa | cggtgctcgt | 180 |
| cttgtgatgg | gatcgttcga | caaccgggag | agcctgctga | atgcagttaa | gcaggtggac | 240 |
| atcgtcatat | ccgccttggc | tgcaaaccat | gtccgccatg | agatcatcac | gcaactgaag | 300 |
| ctcctggatg | tcatcataga | agccggtcat | atcaagaggt | tcataccttc | agagtttgga | 360 |
| atggacccag | atataatgtt | tggtgctcta | cctccaggca | ataagacatt | tatagataaa | 420 |
| agcaaggtca | ggcgtgcaat | agaagctgca | ggagttcccc | ataccctatgt | ctctgcaaat | 480 |
| tgctacgctg | catatttcgt | cggtggcctg | ggccaaatcg | gccctggttt | aatcccatca | 540 |
| caggaaaaag | ttgccctctt | tggagatgga | gaggccaagt | gatatggaat | gatgagatgg | 600 |
| acatagcaac | atatgttctt | aaagcagcag | acgatccacg | gacattaaac | aaggcaatat | 660 |
| ttatcagacc | tccagacaat | atactttctc | agagagagct | tgtgcaaata | tgggagaaac | 720 |
| taattggcca | tgaattaaag | aaaacaaata | tttcatctca | agagtggttg | aaatctatgg | 780 |
| aagggatgcc | cgagggggctg | caattagcaa | tggcacacaa | ctttcatata | ttctatgaag | 840 |
| ggtgtttaac | aaatttccca | gttggtgatg | atcaagaagc | ttcgaagctt | tacccagaag | 900 |
| tcagatacac | atctatggaa | gaatatttga | agcgatatct | atga | | 944 |

<210> SEQ ID NO 120
<211> LENGTH: 31
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(31)
<223> OTHER INFORMATION: PCR primer PS-6For

<400> SEQUENCE: 120
kgtgttygay gatccyatta cybtwgacaa c                                      31

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(30)

-continued

```
<223> OTHER INFORMATION: PCR primer PS2-rev

<400> SEQUENCE: 121
tgrctamgta wactycctct acaaataaag                                30

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(18)
<223> OTHER INFORMATION: Linker primer

<400> SEQUENCE: 122
ctcgagtttt tttttttt                                             18
```

RECOMBINANT PINORESINOL/LARICIRESINOL REDUCTASE, RECOMBINANT DIRIGENT PROTEIN, AND METHODS OF USE

RELATED APPLICATIONS

The present application is a continuation-in-part of copending U.S. patent application Ser. No. 09/307,653, filed May 7, 1999, which claims the benefit of priority of international application PCT/US97/20391, filed Nov. 7, 1997, which claims the benefit of priority of U.S. provisional application serial No. 60/030,522, filed Nov. 8, 1996, and of U.S. provisional application serial No. 60/054,380, filed Jul. 31, 1997, the benefit of which is hereby claimed under 35 U.S.C., sections 119 and 120.

GOVERNMENT RIGHTS

This invention was funded in part by grant number DE-FG03-97ER20259 from the United States Department of Energy, by grant number MCB09631980 from the National Science Foundation, by grant number NAG100164 from the National Aeronautics and Space Administration, and by grant number 96-35103-3358 from the United States Department of Agriculture. The government has certain rights in this invention.

FIELD OF THE INVENTION

The present invention relates to isolated dirigent proteins from *Forsythia intermedia, Tsuga heterophylla, Thuja plicata, Eucommia ulmoides*, and *Schisandra chinensis* and to isolated pinoresinol/lariciresinol reductases from *Forsythia intermedia, Tsuga heterophylla, Linum usitatissimum*, and *Schisandra chinensis*. The present invention also relates to nucleic acid sequences which code for dirigent proteins from *Forsythia intermedia, Tsuga heterophylla, Thuja plicata, Eucommia ulmoides*, and *Schisandra chinensis* and to nucleic acid sequences which code for pinoresinol/lariciresinol reductases from *Forsythia intermedia, Tsuga heterophylla, Thuja plicata, Eucommia ulmoides*, and *Schisandra chinensis*. The present invention also relates to vectors containing the sequences, host cells containing the sequences and methods of producing recombinant pinoresinol/lariciresinol reductases, recombinant dirigent proteins and their mutants.

BACKGROUND OF THE INVENTION

Lignans are a large, structurally diverse, class of vascular plant metabolites having a wide range of physiological functions and pharmacologically important properties (Ayres, D. C., and Loike, J. D. in *Chemistry and Pharmacology of Natural Products. Lignans. Chemical, Biological and Clinical Properties*, Cambridge University Press, Cambridge, England (1990); Lewis et al., in Chemistry of the Amazon, Biodiversity Natural Products, and Environmental Issues, 588, (P. R. Seidl, O. R. Gottlieb and M. A. C. Kaplan) 135–167, ACS Symposium Series, Washington D.C. (1995)). Because of their pronounced antibiotic properties (Markkanen, T. et al., *Drugs Exptl. Clin. Res.* 7:711–718 (1981)), antioxidant properties (Fauré, M. et al., *Phytochemistry* 29:3773–3775 (1990); Osawa, T. et al., *Agric. Biol. Chem.* 49:3351–3352 (1985)) and antifeedant properties (Harmatha, J., and Nawrot, J., *Biochem. Syst. Ecol.* 12:95–98 (1984)), a major role of lignans in vascular plants is to help confer resistance against various opportunistic biological pathogens and predators. Lignans have also been proposed as cytokinins (Binns, A. N. et al., *Proc. Natl. Acad. Sci. USA* 84:980–984 (1987)) and as intermediates in lignification (Rahman, M. M. A. et al., *Phytochemistry* 29:1861–1866 (1990)), suggesting a critical role in plant growth and development. It is widely held that elaboration of biochemical pathways to lignins/lignans and related substances from phenylalanine (tyrosine) was essential for the successful transition of aquatic plants to their vascular dry-land counterparts (Lewis, N. G., and Davin, L. B., in *Isoprenoids and Other Natural Products. Evolution and Function*, 562 (W. D. Nes, ed) 202–246, ACS Symposium Series: Washington, DC (1994)), some four hundred and eighty million years ago (Graham, L. E., *Origin of Land Plants*, John Wiley & Sons, Inc., New York, N.Y. (1993)).

Based on existing chemotaxonomic data, lignans are present in "primitive" plants, such as the fern *Blechnum orientate* (Wada, H. et al., *Chem. Pharm. Bull.* 40:2099–2101 (1992)) and the hornworts, e.g., *Dendroceros japonicus* and *Megaceros flagellaris* (Takeda, R. et al., in *Bryophytes. Their Chemistry and Chemical Taxonomy*, Vol. 29 (Zinsmeister, H. D. and Mues, R. eds) pp. 201–207, Oxford University Press: New York, N.Y. (1990); Takeda, R. et al., *Tetrahedron Lett.* 31:4159–4162 (1990)), with the latter recently being classified as originating in the Silurian period (Graham, L. E., *J. Plant Res.* 109: 241–252 (1996)). Interestingly, evolution of both gymnosperms and angiosperms was accompanied by major changes in the structural complexity and oxidative modifications of the lignans (Lewis, N. G., and Davin, L. B., in *Isoprenoids and Other Natural Products, Evolution and Function*, 562 (W. D. Nes, ed) 202–246, ACS Symposium Series: Washington, DC (1994); Gottlieb, O. R., and Yoshida, M., in *Natural Products of Woody Plants. Chemicals Extraneous to the Lignocellulosic Cell Wall* (Rowe, J. W. and Kirk, C. H. eds) pp. 439–511, Springer Verlag: Berlin (1989)). Indeed, in some species, such as Western Red Cedar (*Thuja plicata*), lignans can contribute extensively to heartwood formation/generation by enhancing the resulting heartwood color, quality, fragrance and durability.

In addition to their functions in plants, lignans also have important pharmacological roles. For example, podophyllotoxin, as its etoposide and teniposide derivatives, is an example of a plant compound that has been successfully employed as an anticancer agent (Ayres, D. C., and Loike, J. D. in *Chemistry and Pharmacology of Natural Products. Lignans. Chemical, Biological and Clinical Properties*, Cambridge University Press, Cambridge, England (1990)). Antiviral properties have also been reported for selected lignans. For example, (−)-arctigenin (Schröder, H. C. et al., *Z. Naturforsch.* 45c, 1215–1221 (1990)), (−)-trachelogenin (Schröder, H. C. et al., *Z. Naturforsch.* 45c, 1215–1221 (1990)) and nordihydroguaiaretic acid (Gnabre, J. N. et al., *Proc. Natl. Acad. Sci. USA* 92:11239–11243 (1995)) are each effective against HIV due to their pronounced reverse transcriptase inhibitory activities. Some lignans, e.g., matairesinol (Nikaido, T. et al., *Chem. Pharm. Bull.* 29:3586–3592 (1981)), inhibit cAMP-phosphodiesterase, whereas others enhance cardiovascular activity, e.g., syringaresinol β-D-glucoside (Nishibe, S. et al., *Chem. Pharm. Bull.* 38:1763–1765 (1990)). There is also a high correlation between the presence, in the diet, of the "mammalian" lignans or "phytoestrogens", enterolactone and enterodiol, formed following digestion of high fiber diets, and reduced incidence rates of breast and prostate cancers (so-called chemoprevention) (Axelson, M., and Setchell, K. D. R., *FEBS Lett.* 123:337–342 (1981); Adlercreutz et al., *J. Steroid Biochem. Molec. Biol.* 41:3–8 (1992);

Adlercreutz et al., *J. Steroid Biochem. Molec. Biol.* 52:97–103 (1995)). The "mammalian lignans," in turn, are considered to be derived from lignans such as matairesinol and secoisolariciresinol (Boriello et al., *J. Applied Bacteriol.*, 58:37–43 (1985)).

The biosynthetic pathways to the lignans are only now being defined, although there are no prior art reports of the isolation of enzymes or genes involved in the lignan biosynthetic pathway. Based on radiolabeling experiments with crude enzyme extracts from *Forsythia intermedia*, it was first established that entry into the 8,8'-linked lignans, which represent the most prevalent dilignol linkage known (Davin, L. B., and Lewis, N. G., in *Rec. Adv. Phytochemistry*, Vol. 26 (Stafford, H. A., and Ibrahim, R. K., eds), pp. 325–375, Plenum Press, New York, N.Y. (1992)), occurs via stereoselective coupling of two achiral coniferyl alcohol molecules, in the form of oxygenated free radicals, to afford the furofuran lignan (+)-pinoresinol (Davin, L. B., Bedgar, D. L., Katayama, T., and Lewis, N. G., *Phytochemistry* 31:3869–3874 (1992); Paré, P. W. et al., *Tetrahedron Lett.* 35:4731–4734 (1994)) (FIG. 1).

Bimolecular phenoxy radical coupling reactions, such as the stereoselective coupling of two achiral coniferyl alcohol molecules to afford the furofuran lignan (+)-pinoresinol, are involved in numerous biological processes. These are presumed to include lignin formation in vascular plants (M. Nose et al., *Phytochemistry* 39:71 (1995)), lignan formation in vascular plants (N. G. Lewis and L. B. Davin, *ACS Symp. Ser.* 562:202 (1994); P. W. Paré et al., *Tetrahedron Lett.* 35:4731 (1994)), suberin formation in vascular plants (M. A. Bernards et al., *J. Biol. Chem.* 270:7382 (1995)), fruiting body development in fungi (J. D. Bu'Lock et al., *J. Chem. Soc.* 2085 (1962)), insect cuticle melanization and sclerotization (M. Miessner et al., *Helv. Chim. Acta* 74:1205 (1991); V. J. Marmaras et al., *Arch. Insect Biochem. Physiol.* 31:119 (1996)), the formation of aphid pigments (D. W. Cameron and Lord Todd, in *Organic Substances of Natural Origin. Oxidative Coupling of Phenols*, W. I. Taylor and A. R. Battersby, Eds. (Dekker, New York, 1967), Vol. 1, p.203), and the formation of algal cell wall polymers (M. A. Ragan, *Phytochemistry* 23:2029 (1984)).

In contrast to the marked regiochemical and/or stereochemical specificities observed in the biosynthesis of the foregoing lignin and lignan substances in vivo, all previously described chemical (J. Iqbal et al., *Chem. Rev.* 94:519 (1994)) and enzymatic (K. Freudenberg, *Science* 148:595 (1965)) bimolecular phenoxy radical coupling reactions in vitro have lacked strict regio- and stereospecific control. That is, if chiral centers are introduced during coupling in vitro, the products are racemic, and different regiochemistries can result if more than one potential coupling site is present. Thus, the ability to generate a particular enantiomeric form or a specific coupling product in vitro is not under explicit control. Consequently, it is inferred that a mechanism exists in vivo to control the regiochemistry and stereochemistry of bimolecular phenoxy radical coupling reactions leading to the formation of, for example, lignans.

In *Forsythia intermedia*, and presumably other species, (+)-pinoresinol, the product of the stereospecific coupling of two E-coniferyl alcohol molecules, undergoes sequential reduction to generate (+)-lariciresinol and then (−)-secoisolariciresinol (Katayama, T. et al., *Phytochemistry* 32:581–591 (1993); Chu, A. et al., *J. Biol. Chem.* 268:27026–27033 (1993)) (FIG. 1). While it has hitherto been unclear whether more than one reductase is required to catalyze the sequential steps, the reductions proceed via abstraction of the pro-R hydride of NADPH, resulting in an "inversion" of configuration at both the C-7 and C-7' positions of the products, (+)-lariciresinol and (−)-secoisolariciresinol (Chu, A., et al., *J. Biol. Chem.* 268:27026–27033 (1993)). (−)-Matairesinol is subsequently formed via dehydrogenation of (−)-secoisolariciresinol, further metabolism of which presumably affords lignans such as the antiviral (−)-trachelogenin in *Ipomoea cairica* and (−)-podophyllotoxin in *Podophyllum peltatum*.

Thus, the stereospecific formation of (+)-pinoresinol and the subsequent reductive steps giving (+)-lariciresinol and (−)-secoisolariciresinol are pivotal points in lignan metabolism, since they represent entry into the furano, dibenzylbutane, dibenzylbutyrolactone and aryltetrahydronaphthalene lignan subclasses. Additionally, it should be noted that while lignans are normally optically active, the particular enantiomer present may differ between plant species. For example, (−)-pinoresinol occurs in *Xanthoxylum ailanthoides* (Ishii et al., *Yakugaku Zasshi*, 103:279–292 (1983)), and (−)-lariciresinol is present in *Daphne tangutica* (Lin-Gen, et al., *Planta Medica*, 45:172–176 (1982)). The optical activity of a particular lignan may have important ramifications regarding biological activity. For example, (−)-trachelogenin inhibits the in vitro replication of HIV-1, whereas its (+)-enantiomer is much less effective (Schroder et al., *Naturforsch.* 45c:1215–1221(1990)).

SUMMARY OF THE INVENTION

In accordance with the foregoing, in one aspect of the invention it has now been discovered that a 78-kD dirigent protein is involved in conferring stereospecificity in 8,8'-linked lignan formation. This protein has no detectable catalytically active oxidative center and apparently serves only to bind and orient coniferyl alcohol-derived free radicals, which then undergo stereoselective coupling to form (+)-pinoresinol. The formation of free-radicals, in the first instance, requires the oxidative capacity of either a nonspecific oxidase or even a non-enzymatic electron oxidant. In another aspect of the invention, it has been discovered that a single enzyme, designated pinoresinol/lariciresinol reductase, catalyzes the conversion of pinoresinol to lariciresinol and then to secoisolariciresinol. Thus, one aspect of the invention relates to isolated dirigent proteins and to isolated pinoresinol/lariciresinol reductases, such as, for example, those from *Forsythia intermedia, Thuja plicata, Tsuga heterophylla, Eucommia ulmoides, Schisandra chinensis,* and *Linum usitatissimum*.

In other aspects of the invention, cDNAs encoding dirigent protein from several plant species have been isolated and sequenced, and the corresponding amino acid sequences have been deduced. Also, cDNAs encoding pinoresinol/lariciresinol reductase from several plant species have been isolated and sequenced, and the corresponding amino acid sequences have been deduced.

Thus, the present invention relates to isolated proteins and to isolated DNA sequences which code for the expression of dirigent protein or pinoresinol/lariciresinol reductase. In other aspects, the present invention is directed to replicable vectors comprising a nucleic acid sequence which codes for a pinoresinol/lariciresinol reductase or for a dirigent protein. The present invention is also directed to a base sequence sufficiently complementary to at least a portion of a pinoresinol/lariciresinol reductase DNA or RNA, or to at least a portion of a dirigent protein DNA or RNA, to enable hybridization therewith. The aforesaid complementary base sequences include, but are not limited to: antisense pinoresinol/lariciresinol reductase RNA; antisense dirigent protein RNA; fragments of DNA that are complementary to a pinoresinol/lariciresinol reductase DNA, or to a dirigent protein DNA, and which are therefore useful as polymerase chain reaction primers, or as probes for pinoresinol/lariciresinol reductase genes, dirigent protein genes, or related genes.

In yet other aspects of the invention, modified host cells are provided that have been transformed, transfected, infected and/or injected with a replicable vector and/or DNA sequence of the invention. Thus, the present invention provides for the recombinant expression of pinoresinol/lariciresinol reductases and dirigent proteins in plants, animals, microbes and in cell cultures. The inventive concepts described herein may be used to facilitate the production, isolation and purification of significant quantities of recombinant pinoresinol/lariciresinol reductase or dirigent protein, or of their enzyme products, in plants, animals, microbes or cell cultures.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 shows the stereospecific conversion of E-coniferyl alcohol to (+)-pinoresinol in *Forsythia intermedia*. The stereoselectivity of this reaction is controlled by dirigent protein. (+)-Pinoresinol is then sequentially converted to (+)-lariciresinol and (−)-secoisolariciresinol by (+)-pinoresinol/(+)-lariciresinol reductase. (+)-pinoresinol, (+)-lariciresinol and (−)-secoisolariciresinol are the precursors of the furofuran, furano and dibenzylbutane families of lignans, respectively.

DETAILED DESCRIPTION OF THE PREFERRED EMBODIMENT

As used herein, the terms "amino acid" and "amino acids" refer to all naturally occurring L-α-amino acids or their residues. The amino acids are identified by either the single-letter or three-letter designations:

| Asp | D | aspartic acid | Ile | I | isoleucine |
| Thr | T | threonine | Leu | L | leucine |
| Ser | S | serine | Tyr | Y | tyrosine |
| Glu | F | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C") and thymine ("T"). Inosine ("I") is a synthetic base that can be used to substitute for any of the four, naturally-occurring bases (A, C, G or T). The four RNA bases are A,G,C and uracil ("U"). The nucleotide sequences described herein comprise a linear array of nucleotides connected by phosphodiester bonds between the 3' and 5' carbons of adjacent pentoses.

The term "percent identity" (% I) means the percentage of amino acids or nucleotides that occupy the same relative position when two amino acid sequences, or two nucleic acid sequences, are aligned side by side.

The term "percent similarity" (% S) is a statistical measure of the degree of relatedness of two compared protein sequences. The percent similarity is calculated by a computer program that assigns a numerical value to each compared pair of amino acids based on chemical similarity (e.g., whether the compared amino acids are acidic, basic, hydrophobic, aromatic, etc.) and/or evolutionary distance as measured by the minimum number of base pair changes that would be required to convert a codon encoding one member of a pair of compared amino acids to a codon encoding the other member of the pair. Calculations are made after a best fit alignment of the two sequences has been made empirically by iterative comparison of all possible alignments. (Henikoff, S. and Henikoff, J. G., *Proc. Nat'l Acad Sci USA* 89:10915–10919 (1992)).

"Oligonucleotide" refers to short length single or double stranded sequences of deoxyribonucleotides linked via phosphodiester bonds. The oligonucleotides are chemically synthesized by known methods and purified, for example, on polyacrylamide gels.

The term "pinoresinol/lariciresinol reductase" is used herein to mean an enzyme capable of catalyzing two reduction reactions: the reduction of pinoresinol to lariciresinol, and the reduction of lariciresinol to secoisolariciresinol. The products of these reactions, lariciresinol and secoisolariciresinol, can be either the (+)- or (−)-enantiomers.

The term "dirigent protein" is used herein to mean a protein capable of guiding a bimolecular phenoxy radical coupling reaction thereby determining the stereochemistry and regiochemistry of the product of the reaction and/or its polymeric derivatives.

The term "stringent wash conditions" refers to the conditions used to wash a nucleic acid blot, such as a Southern blot. The following are representative hybridization and stringent wash conditions useful for identifying (by Southern blotting) nucleic acid molecules of the invention that are capable of hybridizing to a nucleic acid molecule selected from the group consisting of SEQ ID NOS:12, 14, 16, 18, 20, 22, 28, 30, 32, 34, 77, 86, 93, 98 and 105, or to the antisense complement of a nucleic acid molecule selected from the group consisting of SEQ ID NOS:12, 14, 16, 18, 20, 22, 28, 30, 32, 34, 77, 86, 93, 98 and 105: hybridization in 6×SSC, 5×Denhardt's, 0.5% SDS at 55–58° C. for 12 hours, followed by washing in 2×SSC, 0.5% SDS at 55–58° C. for 30 minutes. An optional further wash can be conducted in 1×SSC, 0.5% SDS at 55–58° C. for 30 minutes, followed by an additional, optional wash in 0.5×SSC, 0.5% SDS at 55–58° C. for 30 minutes.

The following are representative hybridization and stringent wash conditions useful for identifying (by Southern blotting) nucleic acid molecules of the invention that are capable of hybridizing to a nucleic acid molecule selected from the group consisting of SEQ ID NOS:47, 49, 51, 53, 55, 57, 61, 63, 65, 67, 69, 71, 107 and 117, or to the antisense complement of a nucleic acid molecule selected from the group consisting of SEQ ID NOS:47, 49, 51, 53, 55, 57, 61, 63, 65, 67, 69, 71, 107 and 117: hybridization in 6×SSC, 5×Denhardt's, 0.5% SDS at 57–58° C. for 12 hours, followed by one wash in 4×SSC, 0.5% SDS at room temperature (typically 20° C. to 30° C.) for 5 minutes, followed by one wash in 2×SSC, 0.5% SDS at 57–58° C. for 20 minutes.

An optional further wash can be conducted in 1×SSC, 0.5% SDS at 57–58° C. for 30 minutes, followed by an additional, optional wash in 0.5×SSC, 0.5% SDS at 57–58° C. for 30 minutes.

The terms "alteration", "amino acid sequence alteration", "variant" and "amino acid sequence variant" refer to dirigent protein or pinoresinol/lariciresinol reductase molecules with some differences in their amino acid sequences as compared to the corresponding native dirigent protein or pinoresinol/lariciresinol reductase. Ordinarily, the variants will possess at least about 70% homology with the corresponding, native dirigent protein or pinoresinol/lariciresinol reductase, and preferably they will be at least about 80% homologous with the corresponding, native dirigent protein or pinoresinol/lariciresinol reductase. The amino acid sequence variants of dirigent protein or pinoresinol/lariciresinol reductase falling within this invention possess substitutions, deletions, and/or insertions at certain positions. Sequence variants of dirigent protein or pinoresinol/lariciresinol reductase may be used to attain desired enhanced or reduced enzymatic activity, modified regiochemistry or stereochemistry, or altered substrate utilization or product distribution.

Substitutional dirigent protein variants or pinoresinol/lariciresinol reductase variants are those that have at least one amino acid residue in the corresponding native dirigent protein sequence or pinoresinol/lariciresinol reductase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the dirigent protein or pinoresinol/lariciresinol reductase molecule may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the dirigent protein or pinoresinol/lariciresinol reductase molecule would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional dirigent protein variants or pinoresinol/lariciresinol reductase variants are those with one or more amino acids inserted immediately adjacent to an amino acid at a particular position in the native dirigent protein or pinoresinol/lariciresinol reductase molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native dirigent protein or pinoresinol/lariciresinol reductase molecule have been removed. Ordinarily, deletional variants will have one or two amino acids deleted in a particular region of the dirigent protein or pinoresinol/lariciresinol reductase molecule.

The term "antisense" or "antisense RNA" or "antisense nucleic acid" is used herein to mean a nucleic acid molecule that is complementary to all or part of a messenger RNA molecule. Antisense nucleic acid molecules are typically used to inhibit the expression, in vivo, of complementary, expressed messenger RNA molecules.

The terms "biological activity", "biologically active", "activity" and "active" when used with reference to a pinoresinol/lariciresinol reductase molecule refer to the ability of the pinoresinol/lariciresinol reductase molecule to reduce pinoresinol and lariciresinol to yield lariciresinol and secoisolariciresinol, respectively, as measured in an enzyme activity assay, such as the assay described in Example 8 below.

The terms "biological activity", "biologically active", "activity" and "active" when used with reference to a dirigent protein refer to the ability of the dirigent protein to guide a bimolecular phenoxy radical coupling reaction thereby determining the stereochemistry and regiochemistry of the product of the reaction and of its polymeric derivatives.

Amino acid sequence variants of dirigent protein or pinoresinol/lariciresinol reductase may have desirable altered biological activity including, for example, altered reaction kinetics, substrate utilization, product distribution or other characteristics such as regiochemistry and stereochemistry.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The term "replicable vector" refers to a piece of DNA, usually double-stranded, which may have inserted into it a piece of foreign DNA. Foreign DNA is defined as heterologous DNA, which is DNA not naturally found in the host. The vector is used to transport the foreign or heterologous DNA into a suitable host cell. Once in the host cell, the vector can replicate independently of or coincidentally with the host chromosomal DNA, and several copies of the vector and its inserted (foreign) DNA may be generated. The term "replicable vector" includes replicable expression vectors that contain the necessary elements that permit translating the foreign DNA into a polypeptide. Many molecules of the polypeptide encoded by the foreign DNA can thus be rapidly synthesized. Replicable vectors can also include insert DNA that is normally found in the host.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of *E. coli*. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

In accordance with the present invention, cDNAs encoding dirigent protein and pinoresinol/lariciresinol reductase from several plant species, including *Forsythia intermedia, Thuja plicata Tsuga heterophylla, Eucommia ulmoides, Schisandra chinensis,* and *Linum usitatissimum* were isolated, sequenced and expressed in the following manner.

With respect to the cDNAs encoding dirigent protein from *Forsythia intermedia*, an empirically-determined purification protocol was developed to isolate the Forsythia dirigent protein. This procedure yielded at least six isoforms of the dirigent protein. Amino acid sequencing of the amino terminus of each of these isoforms revealed that the sequence of each isoform was identical. Sequencing of the N-terminus of a mixture of these isoforms yielded a 28 amino acid sequence (SEQ ID NO:1). Tryptic digestion of a mixture of these isoforms yielded six peptide fragments which were purified in sufficient quantity to permit sequencing SEQ ID NOS:2–7.

A primer designated PSINT1 (SEQ ID NO:8) was synthesized based on the sequence of amino acids 9 to 15 of the N-terminal peptide (SEQ ID NO:1). A primer designated PSI1R (SEQ ID NO:9) was synthesized based on the sequence of amino acids 3 to 9 of the internal peptide sequence set forth in (SEQ ID NO:2). A primer designated PSI2R (SEQ ID NO:10) was synthesized based on the sequence of amino acids 13 to 20 of the internal peptide sequence set forth in (SEQ ID NO:2). A primer designated PSI7R (SEQ ID NO:11) was synthesized based on the sequence of amino acids 6 to 12 of the internal peptide sequence set forth in (SEQ ID NO:3).

Forsythia total RNA was isolated by means of a protocol adapted from a method specifically designed for woody tissues which contain a large concentration of polyphenols. Poly A+RNA was isolated and a cDNA library constructed using standard means. A PCR reaction utilizing primers PSINT1 (SEQ ID NO:8) and one of PSI7R, (SEQ ID NO:11) PSI2R (SEQ ID NO:10) or PSI1R (SEQ ID NO:9), together with an aliquot of Forsythia cDNA as substrate, each yielded a single cDNA band of ~370 bp, ~155 bp and ~125 bp, respectively. The ~370 bp product of the PSINT1 (SEQ ID NO:8)-PSI7R (SEQ ID NO:11) reaction was amplified by PCR and utilized as a probe to screen approximately 600,000 PFU of a *Forsythia intermedia* cDNA library. Two distinct cDNAs were identified, called pPSDFi1 (SEQ ID NO:12) and pPSDFi2 (SEQ ID NO:14). The cDNA insert encoding dirigent protein was excised from plasmid pPSDFi1 and cloned into the baculovirus transfer vector pBlueBac4. The resulting construct was used to transform *Spodoptera frugiperda* from which functional dirigent protein was purified.

In another aspect, Forsythia cDNAs were used as probes to isolate two dirigent protein clones from *Tsuga heterophylla* (SEQ ID NOS:16, 18), and eight dirigent protein cDNA clones from *Thuja plicata* (SEQ ID NOS:20, 22, 24, 26, 28, 30, 32, 34).

With respect to the cDNAs encoding (+)-pinoresinol/(+)-lariciresinol reductase from *Forsythia intermedia*, an empirically-determined purification protocol, consisting of eight chromatographic steps, was developed to isolate the Forsythia (+)-pinoresinol/(+)-lariciresinol reductase protein. This procedure yielded two isoforms of (+)-pinoresinol/(+)-lariciresinol reductase which were both capable of catalyzing the reduction of (+)-pinoresinol and (+)-lariciresinol. Sequencing of the N-terminus of each of these isoforms yielded an identical 30 amino acid sequence (SEQ ID NO:36). Tryptic digestion of a mixture of both of these isoforms yielded four peptide fragments which were purified in sufficient quantity to permit sequencing (SEQ ID Nos:37–40). Additionally, cyanogen bromide cleavage of a mixture of both of these isoforms yielded three peptide fragments which were purified in sufficient quantity to permit sequencing (SEQ ID Nos:41–43).

A primer designated PLRN5 (SEQ ID NO:44) was synthesized based on the sequence of amino acids 7 to 13 of the N-terminal peptide (SEQ ID NO:36). A primer designated PLR14R (SEQ ID NO:45) was synthesized based on the sequence of amino acids 2 to 8 of the internal peptide sequence set forth in SEQ ID NO:37. A primer designated PLR15R (SEQ ID NO:46) was synthesized based on the sequence of amino acids 9 to 15 of the internal peptide sequence set forth in SEQ ID NO:37. The sequence of amino acids 9 to 15 of the internal peptide sequence set forth in SEQ ID NO:37, upon which the sequence of primer PLR15R (SEQ ID NO:46) was based, also corresponded to the sequence of amino acids 4 to 10 of the cyanogen bromide-generated, internal fragment set forth in SEQ ID NO:41.

Forsythia total RNA was isolated by means of a protocol adapted from a method specifically designed for woody tissues which contain a large concentration of polyphenols. Poly A+RNA was isolated and a cDNA library constructed using standard means. A PCR reaction utilizing primers PLRN5 (SEQ ID NO:44) and either PLR14R (SEQ ID NO:45) or PLR15R (SEQ ID NO:46), together with an aliquot of Forsythia cDNA as substrate, yielded two, amplified bands of 380 bp and 400 bp. One 400 bp cDNA insert was utilized as a probe with which to screen the Forsythia cDNA library. The 400 bp probe corresponded to bases 22 to 423 of SEQ ID NO:47. Six cDNA clones were isolated and sequenced (SEQ ID Nos:47, 49, 51, 53, 55, 57). The clones shared a common coding region, many had a different 5'-untranslated region and the 3'-untranslated region of each terminated at a different point. One of these cDNAs (SEQ ID NO:47), expressed as a β-galactosidase fusion protein in *E. coli*, catalyzed the same enantiomer-specific reactions as the native plant protein.

In another aspect, (+)-pinoresinol/(+)-lariciresinol reductase and (−)-pinoresinol/(−)-lariciresinol reductase from *Thuja plicata* were isolated by synthesizing *Thuja plicata* cDNA which was utilized as a template in a PCR reaction in which the primers were a 3' linker-primer (SEQ ID NO:59) and a 5' primer, designated CR6-NT, (SEQ ID NO:60). At least two bands of the expected length (1.2 kb) were generated and cloned into a plasmid vector. One clone, designated plr-Tp1, (SEQ ID NO:61) was completely sequenced and expressed as a β-galactosidase fusion protein in *E. coli*. plr-Tp1 (SEQ ID NO:61) encodes a (−)-pinoresinol/(−)-lariciresinol reductase.

The cDNA insert of clone plr-Tp1 (SEQ ID NO:61) was used to screen the *T. plicata* cDNA library and identified an additional, unique clone, designated plr-Tp2, (SEQ ID NO:63). plr-Tp2 (SEQ ID NO:63) has high homology to plr-Tp1 (SEQ ID NO:61) but encodes a (+)-pinoresinol/(+)-lariciresinol reductase. The cDNA insert of clone plr-Tp1 (SEQ ID NO:61) was used to screen the *T. plicata* cDNA library and identify an additional two pinoresinol/lariciresinol reductase cDNAs (SEQ ID NOS:65, 67).

Two cDNAs encoding pinoresinol/lariciresinol reductases from *Tsuga heterophylla* (SEQ ID Nos:69, 71) were isolated by screening a *Tsuga heterophylla* cDNA library with the plr-Tp1 cDNA insert (SEQ ID NO:61). Additional pinoresinol/lariciresinol reductase cDNAs and dirigent protein cDNAs were isolated as described in Examples 17–22 herein.

The isolation of cDNAs encoding dirigent proteins, (+)-pinoresinol/(+)-lariciresinol reductase and (−)-pinoresinol/(−)-lariciresinol reductase permits the development of an efficient expression system for these functional enzymes; provides useful tools for examining the developmental regulation of lignan biosynthesis and permits the isolation of other dirigent proteins and pinoresinol/lariciresinol reductases. The isolation of the dirigent protein and pinoresinol/lariciresinol reductase cDNAs also permits the transformation of a wide range of organisms in order to enhance or modify lignan biosynthesis.

The proteins and nucleic acids of the present invention can be utilized to predetermine the stereochemistry, regiochemistry, or both, of the products of bimolecular phenoxy coupling reactions, such as the furofuran, furano and dibenzylbutane lignans. By way of non-limiting examples, the proteins and nucleic acids of the present invention can be utilized to: elevate or otherwise alter the levels of health-protecting lignans, such as podophyllotoxin, in plant species, including but not limited to vegetables, grains and fruits, and to food items incorporating material derived from such genetically altered plants; genetically alter plant species to provide an abundant, natural supply of lignans useful for a variety of purposes, for example as neutriceuticals and dietary supplements; to genetically alter living organisms to produce an abundant supply of optically pure lignans having desirable biological properties, for example (−)-arctigenin which possesses antiviral properties. In particular, characterization of the dirigent protein binding site and mechanism of action permits the development of synthetic proteins consisting of an array of dirigent protein binding sites which serve as templates for stereochemically-controlled polymeric assembly.

N-terminal transport sequences well known in the art (see, e.g., von Heijne, G. et al., *Eur. J. Biochem* 180:535–545 (1989); Stryer, Biochemistry W. H. Freeman and Company, New York, N.Y., p. 769 (1988)) may be employed to direct the dirigent protein or pinoresinol/lariciresinol reductase to a variety of cellular or extracellular locations.

Sequence variants of wild-type dirigent protein clones and pinoresinol/lariciresinol clones that can be produced by deletions, substitutions, mutations and/or insertions are intended to be within the scope of the invention except insofar as limited by the prior art. Dirigent protein or pinoresinol/lariciresinol reductase amino acid sequence variants may be constructed by mutating the DNA sequence that encodes wild-type dirigent protein or wild-type pinoresinol/lariciresinol reductase, such as by using techniques commonly referred to as site-directed mutagenesis. Various polymerase chain reaction (PCR) methods now well known in the field, such as a two primer system like the Transformer Site-Directed Mutagenesis kit from Clontech, may be employed for this purpose.

Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis on Mutation Detection Enhancement gel (J. T. Baker) to confirm that no other alterations in the sequence have occurred (by band shift comparison to the unmutagenized control).

The verified mutant duplexes can be cloned into a replicable expression vector, if not already cloned into a vector of this type, and the resulting expression construct used to transform *E. coli*, such as strain *E. coli* BL21(DE3)pLysS, for high level production of the mutant protein, and subsequent purification thereof. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS agrees with prediction. If necessary to verify a changed residue, CAD-tandem MS/MS can be employed to sequence the peptides of the mixture in question, or the target peptide purified for subtractive Edman degradation or carboxypeptidase Y digestion depending on the location of the modification.

In the design of a particular site directed mutant, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native enzyme. If the residue is by this means demonstrated to be important by activity impairment, or knockout, then conservative substitutions can be made, such as Asp for Glu to alter side chain length, Ser for Cys, or Arg for His. For hydrophobic segments, it is largely size that will be altered, although aromatics can also be substituted for alkyl side chains. Changes in the normal product distribution can indicate which step(s) of the reaction sequence have been altered by the mutation.

Other site directed mutagenesis techniques may also be employed with the nucleotide sequences of the invention. For example, restriction endonuclease digestion of DNA followed by ligation may be used to generate dirigent protein or pinoresinol/lariciresinol reductase deletion variants, as described in Section 15.3 of Sambrook et al. (*Molecular Cloning: A Laboratory Manual*, 2nd Ed., Cold Spring Harbor Laboratory Press, New York, N.Y. (1989)). A similar strategy may be used to construct insertion variants, as described in Section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (*DNA* 2:183 (1983)). Generally, oligonucleotides of at least 25 nucleotides in length are used to insert, delete or substitute two or more nucleotides in the dirigent protein gene or pinoresinol/lariciresinol reductase gene. An optimal oligonucleotide will have 12 to 15 perfectly matched nucleotides on either side of the nucleotides coding for the mutation. To mutagenize the wild-type dirigent protein or wild-type pinoresinol/lariciresinol reductase, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type dirigent protein or pinoresinol/lariciresinol reductase inserted in the vector, and the second strand of DNA encodes the mutated form of dirigent protein or pinoresinol/lariciresinol reductase inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

An alternative method involves two or more rounds of mutagenesis to produce the desired mutant. The first round is as described for the single mutants: wild-type dirigent protein or pinoresinol/lariciresinol reductase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Eukaryotic expression systems may be utilized for dirigent protein or pinoresinol/lariciresinol reductase production since they are capable of carrying out any required posttranslational modifications and of directing the enzyme to the proper membrane location. A representative eukaryotic expression system for this purpose uses the recombinant baculovirus, *Autographa californica* nuclear polyhedrosis virus (AcNPV; M. D. Summers and G. E. Smith, *A Manual of Methods for Baculovirus Vectors and Insect Cell Culture Procedures* (1986); Luckow et al., *Bio-technology* 6:47–55 (1987)) for expression of the dirigent protein or pinoresinol/lariciresinol reductases of the invention. Infection of insect cells (such as cells of the species *Spodoptera frugiperda*) with the recombinant baculoviruses allows for the production of large amounts of the dirigent protein or pinoresinol/lariciresinol reductase protein. In addition, the baculovirus system has other important advantages for the production of recombinant dirigent protein or pinoresinol/lariciresinol reductase. For example, baculoviruses do not infect humans and can therefore be safely handled in large quantities. In the baculovirus system, a DNA construct is prepared including a DNA segment encoding dirigent protein or pinoresinol/lariciresinol reductase and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably-linked or "downstream" or "under the control of") to the polyhedron gene promoter and (ii) the promoter/pinoresinol/lariciresinol reductase, or promoter/dirigent protein, combination is flanked on both sides by 200–300 base pairs of baculovirus DNA (the flanking sequences).

To produce a dirigent protein DNA construct, or a pinoresinol/lariciresinol reductase DNA construct, a cDNA clone encoding a full length dirigent protein or pinoresinol/lariciresinol reductase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full dirigent protein or pinoresinol/lariciresinol reductase. For example, an insect host cell can be cotransfected or transfected separately with the DNA construct and a functional baculovirus. Resulting recombinant baculoviruses can then be isolated and used to infect cells to effect production of dirigent protein or pinoresinol/lariciresinol reductase. Host insect cells include, for example, *Spodoptera frugiperda* cells. Insect host cells infected with a recombinant baculovirus of the present invention are then cultured under conditions allowing expression of the baculovirus-encoded dirigent protein or pinoresinol/lariciresinol reductase. Recombinant protein thus produced is then extracted from the cells using methods known in the art.

Other eukaryotic microbes such as yeasts may also be used to practice this invention. The baker's yeast *Saccharomyces cerevisiae*, is a commonly used yeast, although several other strains are available. The plasmid YRp7 (Stinchcomb et al., *Nature* 282:39 (1979); Kingsman et al., *Gene* 7:141 (1979); Tschemper et al., *Gene* 10:157 (1980)) is commonly used as an expression vector in Saccharomyces. This plasmid contains the trpl gene that provides a selection marker for a mutant strain of yeast lacking the ability to grow in tryptophan, such as strains ATCC No. 44,076 and PEP4-1 (Jones, *Genetics* 85:12 (1977)). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA* 75:1929 (1978)). Additional yeast transformation protocols are set forth in Gietz et al., *N.A.R.* 20(17):1425 (1992); Reeves et al., *FEMS* 99:193–197 (1992).

Suitable promoting sequences in yeast vectors include the promoters for 3-phosphoglycerate kinase (Hitzeman et al.,*J. Biol. Chem.* 255:2073 (1980)) or other glycolytic enzymes (Hess et al., *J. Adv. Enzyme Reg.* 7:149 (1968); Holland et al., *Biochemistry* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms, such as plants, may be used as hosts to practice this invention. Transgenic plants can be obtained, for example, by transferring plasmids that encode pinoresinol/lariciresinol reductase, and/or dirigent protein, and a selectable marker gene, e.g., the kan gene encoding resistance to kanamycin, into *Agrobacterium tumifaciens* containing a helper Ti plasmid as described in Hoeckema et al., *Nature* 303:179–181 (1983) and culturing the Agrobacterium cells with leaf slices of the plant to be transformed as described by An et al., *Plant Physiology* 81:301–305 (1986). Transformation of cultured plant host cells is normally accomplished through *Agrobacterium tumifaciens*, as described above. Cultures of mammalian host cells and other host cells that do not have rigid cell membrane barriers are usually transformed using the calcium phosphate method as originally described by Graham and Van der Eb (*Virology* 52:546 (1978)) and modified as described in Sections 16.32–16.37 of Sambrook et al., supra. However, other methods for introducing DNA into cells such as Polybrene (Kawai and Nishizawa, *Mol. Cell. Bio l.* 4:1172 (1984)), protoplast fusion (Schaffner, *Proc. Natl. Acad. Sci. USA* 77:2163 (1980)), electroporation (Neumann et al., *EMBO J.* 1:841 (1982)), and direct microinjection into nuclei (Capecchi, *Cell* 22:479 (1980)) may also be used. Additionally, animal transformation strategies are reviewed in Monastersky G. M. and Robl, J. M., *Strategies in Transgenic Animal Science*, ASM Press, Washington, D.C. (1995). Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating pinoresinol/lariciresinol reductase production, or dirigent protein production, can be incorporated into the plant along with a necessary promoter which is inducible. In the practice of this embodiment of the invention, a promoter that only responds to a specific external or internal stimulus is fused to the target cDNA. Thus, the gene will not be transcribed except in response to the specific stimulus. As long as the gene is not being transcribed, its gene product is not produced.

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology* 7:235–243 (1986)). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a pinoresinol/lariciresinol reductase gene, or a dirigent protein gene, that previously has had its native promoter removed. This engineered gene is the combination of a promoter that responds to an external chemical stimulus and a gene responsible for successful production of pinoresinol/lariciresinol reductase or dirigent protein.

In addition to the methods described above, several methods are known in the art for transferring cloned DNA into a wide variety of plant species, including gymnosperms, angiosperms, monocots and dicots (see, e.g., Glick and Thompson, eds., *Methods in Plant Molecular Biology*, CRC Press, Boca Raton, Fla. (1993)). Representative examples include electroporation-facilitated DNA uptake by protoplasts (Rhodes et al., *Science* 240(4849):204–207 (1988)); treatment of protoplasts with polyethylene glycol (Lyznik et al., *Plant Molecular Biology* 13:151–161 (1989)); and bombardment of cells with DNA laden microprojectiles (Klein et al., *Plant Physiol.* 91:440–444 (1989) and Boynton et al., *Science* 240(4858):1534–1538 (1988)). Numerous methods now exist, for example, for the transformation of cereal crops (see, e.g., McKinnon, G. E. and Henry, R. J.,*J. Cereal Science*, 22(3):203–210 (1995); Mendel, R. R. and Teeri, T. H., *Plant and Microbial Biotechnology Research Series*, 3:81–98, Cambridge University Press (1995); McElroy, D. and Brettell, R. I. S., *Trends in Biotechnology*, 12(2):62–68 (1994); Christou et al., *Trends in Biotechnology*, 10(7):239–246 (1992); Christou, P. and Ford, T. L., Annals of Botany, 75(5): 449–454 (1995); Park et al.,*Plant Molecular Biology*, 32(6):1135–1148 (1996); Altpeter et al., *Plant Cell Reports*, 16:12–17 (1996)). Additionally, plant transformation strategies and techniques are reviewed in Birch, R. G., *Ann Rev Plant Phys Plant Mol Biol* 48:297 (1997); Forester et al., *Exp. Agric.* 33:15–33 (1997). Minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue. Preferably, the plasmid will contain both selectable and screenable marker genes.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., *J. Gen. Virol.* 36:59 (1977)); baby hamster kidney cells (BHK, ATCC CCL 10); Chinese hamster ovary cells (Urlab and Chasin, *Proc. Natl. Acad. Sci USA* 77:4216 (1980)); mouse sertoli cells (TM4, Mather, *Biol. Reprod.* 23:243 (1980)); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.* 85:1 (1980)); and TRI cells (Mather et al., *Annals N.Y. Acad. Sci.* 383:44 (1982)). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus 2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature* 273:113 (1978)). Smaller or larger SV40 DNA fragments may also be used, provided they contain the approximately 250-bp sequence extending from the HindIII site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

The use of a secondary DNA coding sequence can enhance production levels of pinoresinol/lariciresinol reductase or dirigent protein in transformed cell lines. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-Kl cell line (ATCC No. CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 294 (ATCC No. 31,446), *E. coli* strain W3110 (ATCC No.27,325) *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in Genetic Engineering, Principles and Methods, 12:275–296, Plenum Publishing Corp. (1990); Hanahan et al., *Meth. Enxymol.*, 204:63 (1991).

As a representative example, cDNA sequences encoding dirigent protein or pinoresinol/lariciresinol reductase may be transferred to the $(His)_6$·Tag pET vector commercially available (from Novagen) for overexpression in *E. coli* as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block" of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein with thrombin, and the dirigent protein or pinoresinol/lariciresinol reductase eluted. This overexpression-purification system has high capacity, excellent resolving power and is fast, and the chance of a contaminating *E. coli* protein exhibiting similar binding behavior (before and after thrombin proteolysis) is extremely small.

As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCI18, pUC119, and Bluescript M13, all of which are described in Sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature* 375:615 (1978); Itakura et al., *Science* 198:1056 (1977); Goeddel et al., *Nature* 281:544 (1979)) and a tryptophan (trp) promoter system (Goeddel et al., *Nucl. Acids Res.* 8:4057 (1980); EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell* 20:269 (1980)).

Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, *Biochemistry* W.H. Freeman and Company, New York, N.Y., p. 769 (1988)), and can be used as signal sequences in appropriate eukaryotic host cells. Yeast signal sequences, as for example acid phosphatase (Arima et al., *Nucleic Acids Res.* 11:1657 (1983)), alpha-factor, alkaline phosphatase and invertase may be used to direct secretion from yeast host cells. Prokaryotic signal sequences from genes encoding, for example, LamB or OmpF (Wong et al., *Gene* 68:193 (1988)), MalE, PhoA, or beta-lactamase, as well as other genes, may be used to target proteins from prokaryotic cells into the culture medium.

Trafficking sequences from plants, animals and microbes can be employed in the practice of the invention to direct the gene product to the cytoplasm, endoplasmic reticulum, mitochondria or other cellular components, or to target the protein for export to the medium. These considerations apply to the overexpression of pinoresinol/lariciresinol reductase or dirigent protein, and to direction of expression within cells or intact organisms to permit gene product function in any desired location.

The construction of suitable vectors containing DNA encoding replication sequences, regulatory sequences, phenotypic selection genes and the dirigent protein DNA or pinoresinol/lariciresinol reductase DNA of interest are prepared using standard recombinant DNA procedures. Isolated plasmids and DNA fragments are cleaved, tailored, and ligated together in a specific order to generate the desired vectors, as is well known in the art (see, for example, Sambrook et al., supra).

As discussed above, pinoresinol/lariciresinol reductase variants, or dirigent protein variants, are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

A dirigent protein gene and/or pinoresinol/lariciresinol reductase gene, or an antisense nucleic acid fragment complementary to all or part of a dirigent protein gene or pinoresinol/lariciresinol reductase gene, may be introduced, as appropriate, into any plant species for a variety of purposes including, but not limited to: altering or improving the color, texture, durability and pest-resistance of wood tissue, especially heartwood tissue; reducing the formation of lignans and/or lignins in plant species, such as corn, which are useful as animal fodder, thereby enhancing the availability of the cellulose fraction of the plant material to the digestive system of animals ingesting the plant material; reducing the lignan/lignin content of plant species utilized in pulp and paper production, thereby making pulp and paper production easier and cheaper; improving the defensive capability of a plant against predators and pathogens by enhancing the production of defensive lignans or lignins; the alteration of other ecological interactions mediated by lignans or lignins; producing elevated levels of optically-pure lignan enantiomers as medicines or food additives; introducing, enhancing or inhibiting the production of dirigent proteins or pinoresinol/lariciresinol reductases, or the production of pinoresinol or lariciresinol and their derivatives. A dirigent protein and/or pinoresinol/lariciresinol reductase gene may be introduced into any organism for a variety of purposes including, but not limited to: introducing, enhancing or inhibiting the production of dirigent protein and/or pinoresinol/lariciresinol reductase, or the production of pinoresinol or lariciresinol and their derivatives.

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also Sections 1.60–1.61 and Sections 3.38–3.39 of Sambrook et al., supra.)

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (*Nucleic Acids Res.* 9:6103–6114 (1982)), and Goeddel et al. (*Nucleic Acids Res.*, supra).

The following examples merely illustrate the best mode now contemplated for practicing the invention, but should not be construed to limit the invention. All literature citations herein are expressly incorporated by reference.

EXAMPLE 1

Purification of Dirigent Protein from *Forsythia intermedia*

Plant Materials. *Forsythia intermedia* plants were either obtained from Bailey's Nursery (var. Lynwood Gold, St., Paul, Minn.), and maintained in Washington State University greenhouse facilities, or were gifts from the local community.

Initial Extraction and Ammonium Sulphate Precipitation. Solubilization of bound proteins was carried out at 4° C. Frozen *Forsythia intermedia* stems (2 kg) were pulverized in a Waring Blendor (Model CB6) in the presence of liquid nitrogen. The resulting powder was homogenized with 0.1 M $KH_2PO_4$-$K_2HPO_4$ buffer (pH 7.0, 4 liters) containing 5 mM dithiothreitol, and filtered through four layers of cheesecloth. The insoluble residue was consecutively extracted, with continuous agitation at 250 rpm, as follows: with chilled (−20° C.) re-distilled acetone (4 liters, 3×30 min); 0.1 M $KH_2PO_4$-$K_2HPO_4$ buffer (pH 6.5) containing 0.1% β-mercaptoethanol (solution A, 8 liters, 30 min); solution A containing 1% Triton X100 (8 liters, 4 hours) and finally solution A (8 liters, 16 hours). Between each extraction, the residue was filtered through one layer of Miracloth (Calbiochem). Solubilization of the (+)-pinoresinol forming system was achieved by mechanically stirring the residue in solution A containing 1 M NaCl (8 liters, 4 hours). The homogenate was decanted and the resulting solution consecutively filtered through Miracloth (Calbiochem) and glass fiber (G6, Fisher Sci.). The filtrate was concentrated in an Amicon cell (Model 2000, YM 30 membrane) to a final volume of ~800 ml, and subjected to $(NH_4)_2SO_4$ fractionation. Proteins precipitating between 40 and 80% saturation were recovered by centrifugation (15,000 g, 30 min) and the $(NH_4)_2SO_4$ pellet stored at −20° C. until required.

Mono S Column Chromatography. Purification of 78-kD dirigent protein and partial purification of oxidase. The ammonium sulfate pellet (obtained from 2 kg of *F intermedia* stems) was reconstituted in 40 mM MES [2-(N-Morpholino)ethanesulfonic acid] buffer, adjusted to pH 5.0 with 6 M NaOH (solution B, 30 ml), the slurry being centrifuged (3,600 g, 5 min), and the supernatant dialyzed overnight against solution B (4 liters). The dialyzed extract was filtered (0.22 μm) and the sample (35 to 40 mg proteins) was applied to a MonoS HR5/5 (50 mm by 5 mm) column equilibrated in solution B at 4° C. After eluting (flow rate 5 ml $min^{-1}$ $cm^{-2}$) with solution B (13 ml), proteins were desorbed with $Na_2SO_4$ in solution B, using a linear gradient from 0 to 100 mM in 8 ml and holding at this concentration for 32 ml, then implementing a series of step gradients at 133 mM for 50 ml, 166 mM for 50 ml, 200 mM for 40 ml, 233 mM for 40 ml and finally 333 mM $Na_2SO_4$ for 40 ml. Fractions capable of forming (+)-pinoresinol from E-coniferyl alcohol were eluted with 333 mM $Na_2SO_4$, combined and stored (−80° C.) until needed.

POROS SP-M Matrix Column Chromatography (First Column). Fractions from 15 individual elutions from the MonoS HR5/5 column (33 mM $Na_2SO_4$) were combined (18.5 mg proteins, 180 ml) and dialyzed overnight against solution C. The dialyzed enzyme solution (190 ml) was filtered (0.22 μm) and an aliquot (47 ml) was applied to the POROS SP-M column. All separations on a POROS SP-M matrix (100 mm by 4.6 mm), previously equilibrated in 25 mM MES-HEPES-sodium acetate buffer (pH 5.0, solution C), were performed at a flow rate of 60 ml $min^{-1}$ $cm^{-2}$ and at room temperature. After elution with solution C (12 ml), the proteins were desorbed with a linear $Na_2SO_4$ gradient (0 to 0.7 M in 66.5 ml) in solution C, whereupon the concentration established was held for an additional 16.6 ml. Under these conditions, separation of four fractions (I, II, III and IV) was achieved at ~40, 47, 55 and 61 mS, respectively. This purification step was repeated three times with the remaining dialyzed enzymatic extract, and fractions I, II, III, and IV from each experiment were separately combined. When protease inhibitors [that is, phenylmethanesulfonyl fluoride (0.1 mmol $ml^{-1}$), EDTA (0.5 nmol $ml^{-1}$), pepstatin A (1 μg $ml^{-1}$), and antipain (1 μg $ml^{-1}$)] were added during the solubilization and all subsequent purification stages, no differences were observed in the elution profiles of fractions I, II, III, and IV.

POROS SP-M Matrix Column Chromatography (Second Column). Fraction I from the first POROS SP-M Matrix column chromatography step (2.62 mg proteins, 40 ml, ~24.6 mS) was diluted in filtered, cold distilled water until the conductivity reached ~8 mS (final volume=150 ml). The diluted protein solution was then applied onto a POROS SP-M column (100 mm by 4.6 mm). After elution with solution C (12 ml), fraction I was desorbed using a linear $Na_2SO_4$ gradient from 0 to 0.25 M in 20 ml, whereupon the concentration established was held for another 25 ml. This was followed by another linear $Na_2SO_4$ gradient from 0.25 to 0.7 M in 26 ml which was then held at 0.7 M for an additional 16.6 ml. Fractions eluted at ~30 mS (the ionic strength of the eluent was measured with a flow-through detector) were combined (15 ml, 1.3 mg), diluted with water and rechromatographed. The resulting protein (eluted at ~30 mS with the gradient described above) was stored (−80° C.) until needed.

Gel filtration. An aliquot from fraction I (595.5 μg proteins, 3 ml, eluted at ~30 mS), was concentrated to 0.6 ml (Centricon 10, Amicon) and loaded onto a S200 (73.2 cm by 1.6 cm, Pharmacia-LKB) gel chromatographic column equilibrated in 0.1 M MES-HEPES-sodium acetate buffer (pH 5.0) containing 50 mM $Na_2SO_4$ at 4° C. An apparently homogenous 78-kD dirigent protein (242 μg) was eluted (flow rate 0.25 ml $min^{-1}$ $cm^{-2}$) as a single component at 133 ml (Vo=105 ml). Molecular weights were estimated by comparison of their elution profiles with the standard proteins, β-amylase (200,000), alcohol dehydrogenase (150,000), bovine serum albumin (66,000), ovalbumin (45,000), carbonic anhydrase (29,000) and cytochrome c (12,400).

EXAMPLE 2

Characterization of the Purified Dirigent Protein

Molecular Weight and Isoelectric Point Determination. Polyacrylamide gel electrophoresis (PAGE) was performed in Laemmli's buffer system with gradient (4 to 15% acrylamide, Bio-Rad) gels under denaturing and reducing conditions. Proteins were visualized by silver staining. Gel filtration (S200) chromatography of fraction I gave a protein of native molecular weight ~78 kD, whereas SDS-polyacrylamide gel electrophoresis showed a single band at ~27 kD, suggesting that the native protein exists as a trimer. Isoelectric focusing of the native protein on a polyacrylamide gel (pH 3 to 10 gradient) revealed the presence of six bands. After isoelectric focusing, each of these bands was electroblotted onto a polyvinylidene fluoride (PVDF) membrane and subjected to amino terminal sequencing, which established that all had similar sequences indicating a series of isoforms. The ultraviolet-visible spectrum of the protein had only a characteristic protein absorbance at 280 nm with a barely perceptible shoulder at ~330 nm. Inductively coupled plasma (ICP) analysis gave no indication of any metal being present in the protein. Thus, the 78-kD dirigent protein lacks any detectable catalytically active oxidative center.

Assay of the Ability of the Purified Dirigent Protein to Form (+)Pinoresinol from E-Coniferyl alcohol. The four fractions (I to IV) from the first POROS SP-M chromatographic step (Example 1) were individually rechromatographed, with each fraction subsequently assayed for (+)-pinoresinol-forming activity with E-[9-$^3$H] coniferyl alcohol as substrate for one hour. Fraction I (containing dirigent protein) had very little (+)-pinoresinol-forming activity (<5% of total activity loaded onto the POROS SP-M column), whereas fraction III catalyzed nonspecific oxidative coupling to give (±)-dehydrodiconiferyl alcohols, (±)-pinoresinols, and (±)-erythro/threo guaiacylglycerol 8-O-4'-coniferyl alcohol ethers. Thus, Fraction III appeared to contain an endogenous plant oxygenating protein.

Although the putative oxidase preparation (Fraction III) was not purified to electrophoretic homogeneity, the electron paramagnetic resonance (EPR) spectrum of this protein preparation resembled that of a typical plant laccase, i.e., a class of naturally-occurring plant oxygenase proteins. We then studied the fate of E-[9-$^3$H]coniferyl alcohol (2 μmol $ml^{-1}$, 14.7 kBq) in the presence of, respectively, the oxidase (fraction III), the 78-kD dirigent protein (Fraction I), and both fraction III and the 78-kD protein together. With the fraction III preparation alone, only nonspecific bimolecular radical coupling occurs to give (±)-dehydrodiconiferyl alcohols, (±)-pinoresinols and (±)-erythro/threo guaiacylglycerol 8-O-4'-coniferyl alcohol ethers. With the 78-kD protein by itself, however, a small amount of (+)-pinoresinol formation (<5% over 10 hours) was observed, this being presumed to result from residual traces of oxidizing capacity in the preparation. When both fraction III and the 78-kD protein were combined, full catalytic activity and regio- and stereo-specificity in the product was reestablished, whereby essentially only (+)-pinoresinol was formed. Additionally, with fraction III alone, and when fraction III was combined with the 78-kD protein, the rates of substrate depletion and dimeric product formation were nearly identical. Moreover, essentially no turnover of the dimeric lignan products occurred in either case in the presence of the oxidase, over the time-period (8 hours) examined: subsequent dimer oxidation does not occur when E-coniferyl alcohol, the preferred substrate, is still present in the assay mixture. The 78-kD protein therefore appears to determine the specificity of the bimolecular phenoxy radical coupling reaction.

Gel filtration studies were also carried out with mixtures of the dirigent and fraction III proteins, in order to establish if any detectable protein-protein interaction might account for the stereoselectivity. But no evidence in support of complex formation (i.e., to higher molecular size entities) was observed.

EXAMPLE 3

Effect of the 78-KD Dirigent Protein on Plant Laccase-Catalyzed Monolignol Coupling E-coniferyl alcohol coupling assay. E-[9-$^3$H]Coniferyl alcohol (4 μmol $ml^{-1}$, 29.3 kBq) was incubated with a 120-kD laccase (previously purified from *Forsythia intermedia* stem tissue) over a 24-hour period, in the presence and absence of the dirigent protein, as follows. Each assay consisted of E-[9-$^3$H]coniferyl alcohol (4 μmol $ml^{-1}$, 29.3 kBq, 7.3 MBq mole $liter^{-1}$; or 2 μmol $ml^{-1}$, 14.7 kBq with fraction III), the 78-kD dirigent protein, an oxidase or oxidant, or both [final concentrations: 770 pmol $ml^{-1}$ dirigent protein; 10.7 pmol protein $ml^{-1}$ *Forsythia laccase*; 12 μg protein $ml^{-1}$ fraction III; 0.5 μmol $ml^{-1}$ FMN; 0.5 μmol $ml^{-1}$ FAD; 1 and 10 μmol $ml^{-1}$ ammonium peroxydisulfate] in buffer (0.1 M MES-HEPES-sodium acetate, pH 5.0) to a total volume of 250 μl. The enzymatic reaction was initiated by addition of E-[9-$^3$H]coniferyl alcohol. Controls were performed in the presence of buffer alone.

After one hour incubation at 30° C. while shaking, the assay mixture was extracted with ethyl acetate (EtOAc, 500 μl) containing (±)-pinoresinols (7.5 μg), (±)-dehydrodiconiferyl alcohols (3.5 μg) and erythro/threo (±)-guaiacylglycerol 8-O-4-coniferyl alcohol ethers (7.5 μg) as radiochemical carriers and ferulic acid (15.0 μg) as an internal standard. After centrifugation (13,800 g, 5 min), the EtOAc soluble components were removed and the extraction procedure repeated with EtOAc (500 μl). The EtOAc soluble components from each assay were combined, the solutions evaporated to dryness in vacuo, redissolved in methanol-water solution (1:1; 100 μl) with an aliquot (50 μl) thereof subjected to reversed-phase column chromatography (Waters, Nova-Pak $C_{18}$, 150 mm by 3.8 mm). The elution conditions were as follows: acetonitrile/3% acetic acid in $H_2O$ (5:95) from 0 to 5 min, then linear gradients to ratios of 10:90 between 5 and 20 min, then to 20:80 between 20 and 45 min and finally to 50:50 between 45 and 60 min, at a flow rate of 8.8 ml $min^{-1}$ $cm^{-2}$.

Fractions corresponding to E-coniferyl alcohol, erythro/threo (±)-guaiacylglycerol 8-O-4'-coniferyl alcohol ethers, (±)-dehydrodiconiferyl alcohols and (±)-pinoresinols were individually collected, aliquots removed for liquid scintillation counting, and the remainder freeze-dried. Pinoresinol-containing fractions were redissolved in methanol (100 μl) and subjected to chiral column chromatography (Daicel, Chiralcel OD, 50 mm by 4.6 mm) with a solution of hexanes and ethanol (1:1) as the mobile phase (flow rate 3 ml min$^{-1}$ cm$^{-2}$), whereas dehydrodiconiferyl alcohol fractions were subjected to Chiralcel OF (250 mm by 4.6 mm) column chromatography eluted with a solution of hexanes and isopropanol (9:1) as the mobile phase (flow rate 2.4 ml min$^{-1}$ cm$^{-2}$), the radioactivity of the eluent being measured with a flow-through detector (Radiomatic, Model A120).

Results of E-coniferyl alcohol coupling assay. Incubation with laccase alone gave only racemic dimeric products, with (±)-dehydrodiconiferyl alcohols predominating. In the presence of the dirigent protein, however, the process was now primarily stereoselective, affording (+)-pinoresinol, rather than being nonspecific as observed when only laccase was present. The rates of both E-coniferyl alcohol (substrate) depletion and the formation of the dimeric lignans were similar with and without the dirigent protein. A substantial difference was noted in the subsequent turnover of the lignan products observed after E-coniferyl alcohol depletion. With the laccase alone no turnover occurred, but when both proteins were present the disappearance of the products was significant. In order to understand the difference, assays were conducted where bovine serum albumin (BSA) and ovalbumin were individually added to the laccase-containing solutions at levels matching the weight concentrations of the dirigent protein. In this way, it was established that the differences in product turnover were simply due to stabilization of laccase activity at the higher protein concentrations, although interestingly the dirigent protein, BSA and ovalbumin afforded somewhat different degrees of protection. The findings were quite comparable when a fungal laccase (from *Trametes versicolor*) was used in place of the plant laccase. When the oxidizing capacity (i.e., laccase concentration) was lowered five-fold, only (+)-pinoresinol formation was observed. Thus, complete stereoselectivity is preserved when the oxidative capacity does not exceed a point where the dirigent protein is saturated.

Stereoselective E-coniferyl alcohol coupling Assays were also conducted with E-[9-$^2$H$_2$, OC$^2$H$_3$]coniferyl alcohol and the dirigent protein in the presence of laccase as follows. E-[9-$^2$H$_2$, OC$^2$H$_3$]coniferyl alcohol (2 μmol ml$^{-1}$) was incubated in the presence of dirigent protein (770 pmol ml$^{-1}$), the purified plant laccase (4.1 pmol ml$^{-1}$) and buffer (0.1 M MES-HEPES-sodium acetate, pH 5.0) in a total volume of 250 μl. After one hour incubation, the reaction mixture was extracted with EtOAc, but with the addition of an internal standard and radiochemical carriers omitted. After reversed-phase column chromatography, the enzymatically formed pinoresinol was collected, freeze-dried, redissolved in methanol (100 μl) and subjected to chiral column chromatography (Daicel, Chiralcel OD, 50 mm by 4.6 mm) with detection at 280 nm and analysis by mass spectral fragmentation in the EI mode (Waters, Integrity System). Liquid chromatography-mass spectrometry (LC-MS) analysis of the resulting (+)-pinoresinol (>99% enantiomeric excess) gave a molecular ion with a mass to charge ratio (m/z) 368, thus establishing the presence of 10 $^2$H atoms and verifying that together the laccase and dirigent protein catalyzed stereoselective coupling of E-[9-$^2$H$_2$, OC$^2$H$_3$]coniferyl alcohol.

Other auxiliary one-electron oxidants can also facilitate stereoselective coupling with the dirigent protein. Ammonium peroxydisulfate readily undergoes homolytic cleavage (A. Usaitis, R. Makuska, *Polymer* 35:4896 (1994)) and is routinely used as an one-electron oxidant in acrylamide polymerization. Ammonium peroxydisulfate was first incubated with E-[9-$^3$H]coniferyl alcohol (4 μmol ml$^{-1}$, 29.3 kBq) for 6 hours using the E-coniferyl alcohol coupling assay procedure described above. Nonspecific bimolecular radical coupling was observed, to afford predominantly (±)-dehydrodiconiferyl alcohols as well as the other racemic lignans (Table 1). However, when the dirigent protein was added, the stereoselectivity of coupling was dramatically altered to give primarily (+)-pinoresinol at both concentrations of oxidant, together with small amounts of racemic lignans. This established that even an inorganic oxidant, such as ammonium peroxydisulfate, could promote (+)-pinoresinol synthesis in the presence of the dirigent protein, even if it was not oxidatively as selective toward the monolignol as was the fraction III oxidase or laccase.

TABLE 1

Effect of dirigent protein on product distribution from E-coniferyl alcohol oxidized by ammonium peroxydisulfate (6 hour assay).

| Oxidant | Dirigent protein (770 pmol ml$^{-1}$) | E-Coniferyl alcohol in dimer equivalents depleted (nmol ml$^{-1}$) | (±)-Guaiacyl-glycerol 8-O-4'-coniferyl alcohol ethers (nmol ml$^{-1}$) | (±)-Dehydro-diconiferyl alcohols (nmol ml$^{-1}$) | (±)-Pinoresinols (nmol ml$^{-1}$) | (+)-Pinoresinol (nmol ml$^{-1}$) | Total dimers (nmol ml$^{-1}$) |
|---|---|---|---|---|---|---|---|
| Ammonium peroxydisulfate (1 μmol ml$^{-1}$) | absent | 200 ± 4 | 10 ± 1 | 35 ± 2 | 16 ± 0 | 0 | 61 ± 3 |
|  | present | 250 ± 55 | 6 ± 0 | 13 ± 1 | 0 | 130 ± 10 | 149 ± 11 |
| Ammonium peroxydisulfate (10 μmol ml$^{-1}$) | absent | 860 ± 30 | 90 ± 4 | 250 ± 10 | 135 ± 4 | 0 | 475 ± 17 |
|  | present | 1030 ± 25 | 30 ± 1 | 90 ± 3 | 0 | 450 ± 10 | 570 ± 14 |
| Dirigent protein | present | 61 ± 20 | 5 ± 1 | 8 ± 1 | 0 | 55 ± 1 | 68 ± 3 |

Effect of Other Oxygenating Agents on the Stereospecific Conversion of E-Coniferyl Alcohol to (+)-pinoresinol. The effects of incubating E-coniferyl alcohol (4 μmol ml$^{-1}$, 29.3 kBq) with flavin mononucleotide (FMN) and flavin adenine dinucleotide (FAD) were investigated since, in addition to their roles as enzyme cofactors, they can also oxidize various organic substrates (T. C. Bruice, *Acc. Chem. Res.* 13:256 (1980)). E-[9-$^3$H]coniferyl alcohol was respectively incubated with FMN and FAD for 48 hours. To obtain the FMN, snake (*Naja naja atra*, Formosan cobra) venom was added to a solution of FAD (5 μmol ml$^{-1}$ in H$_2$O) and, after 30 min incubation at 30° C., the enzymatically formed FMN was separated from the protein mixture by filtration through a Centricon 10 (Amicon) microconcentrator. In every instance, E-coniferyl alcohol oxidation was more rapid in the presence of FMN than FAD. Although these differences between the FMN and FAD catalyzed rates of E-coniferyl alcohol oxidation were not anticipated, a consistent pattern was sustained: racemic lignan products were obtained, with the (±)-dehydrodiconiferyl alcohols predominating as before. When the time courses were repeated in the presence of the dirigent protein, a dramatic change in stereoselectivity was observed, where essentially only (+)-pinoresinol formation occurred. Again, the rates of E-coniferyl alcohol depletion, when adjusted for the traces of residual oxidizing capacity (<5% over 10 hours) in the dirigent protein preparation, were dependent only upon [FMN] and [FAD], as were the total amounts of dimers formed. When full depletion of E-coniferyl alcohol occurs, the corresponding lignan dimers can begin to undergo oxidative changes as a function of time; specifically, FMN is able subsequently to oxidize pinoresinol, in open solution, after the E-coniferyl alcohol has been fully depleted.

Investigation of Substrate-Specific Stereoselectivity. The coupling stereoselectivity was substrate specific. Neither E-p-[9-$^3$H]coumaryl (4 µmol ml$^{-1}$, 44.5 kBq) or E-[8-$^{14}$C] sinapyl alcohols (4 µmol ml$^{-1}$, 8.3 kBq), which differ from E-coniferyl alcohol only by a methoxyl group substituent on the aromatic ring, yielded stereoselective products when incubated for 6 hours with FMN and ammonium peroxydisulfate respectively, in the presence and absence of the dirigent protein. Incubations were carried out as described above with the following modifications: E-p-[9-$^3$H] coumaryl (4 µmol ml$^{-1}$, 44.5 kBq) or E-[8-$^{14}$C]sinapyl alcohols (4 µml$^{-1}$, 8.3 kBq) were used as substrates and, after 6 hour incubation at 30° C., the reaction mixture was extracted with EtOAc but without addition of radiochemical carriers. E-Sinapyl alcohol readily underwent coupling to afford syringaresinol, but chiral HPLC analysis revealed that the resulting products were, in every instance, racemic (Table 2). Interestingly, by itself, the 78-kD dirigent protein preparation catalyzed a low level of dimer formation, as previously noted, but only gave rise to racemic (±)-syringaresinol formation, which is presumably a consequence of the residual traces of contaminating oxidizing capacity present in the protein preparation.

In an analogous manner, no stereoselective coupling was observed with E-p-coumaryl alcohol as substrate. That is, only E-coniferyl alcohol undergoes stereoselective coupling in the presence of the dirigent protein. Given the marked substrate specificity of the dirigent protein for E-coniferyl alcohol, it will be of considerable interest to determine, in the future, how it differs from that affording (+)-syringaresinol in *Eucommia ulmoides* (T. Deyama, *Chem. Pharm. Bull.* 31, 2993 (1983)).

substrates that bind to the dirigent protein prior to coupling. The other two possibilities would require that E-coniferyl alcohol molecules are bound and oriented on the dirigent protein, thereby ensuring that only (+)-pinoresinol formation occurs upon subsequent oxidative coupling: this could occur either if both substrate phenolic hydroxyl groups were exposed so that they could readily be oxidized by an oxidase or oxidant, or if an electron transfer mechanism were operative between the oxidase or oxidant and an electron acceptor site or sites on the dirigent protein.

Among the three alternative mechanisms, three lines of evidence suggest "capture" of phenoxy radical intermediates by the dirigent protein. First, the rates of both substrate depletion and product formation are largely unaffected by the presence of the dirigent protein. If capture of the free-radical intermediates is the operative mechanism, the dirigent protein would only affect the specificity of coupling when single-electron oxidation of coniferyl alcohol is rate-determining. Second, an electron transfer mechanism is currently ruled out, since we observed no new ultraviolet-visible chromophores in either the presence or absence of an auxiliary oxidase or oxidant, under oxidizing conditions. Third, preliminary kinetic data (as disclosed in Example 4) support the concept of free-radical capture based on the formal values of Michaelis constant ($K_m$) and maximum velocity ($V_{max}$) characterizing the conversion of E-coniferyl alcohol into (+)-pinoresinol, with the dirigent protein alone and in the presence of the various oxidases or oxidants.

EXAMPLE 4

Kinetic Characterization of the Conversion of E-Coniferyl Alcohol to (+)-pinoresinol in the Presence of Dirigent Protein and an Oxygenating Agent Assays were carried out as described in Example 3 by incubating a series of E-[9-$^3$H]coniferyl alcohol concentrations (between 8.00 and 0.13 µmol ml$^{-1}$, 7.3 MBq mole liter$^{-1}$) with dirigent protein (770 pmol ml$^{-1}$) alone and in presence of Forsythia laccase (2.1 pmol ml$^{-1}$), fraction III (12 µg protein ml$^{-1}$), or FMN (0.5 µmol ml$^{-1}$). Assays with dirigent protein, in presence or absence of FMN, were incubated at 30° C. for 1 hour, whereas assays with Forsythia laccase or fraction III in presence or absence of dirigent protein were incubated at 30° C. for 15 min. If free-radical capture by the dirigent protein is the operative

TABLE 2

Effect of dirigent protein on coupling of E-sinapyl alcohol (6 hour assay)

| | Dirigent protein (770 pmol ml$^{-1}$) | E-Sinapyl alcohol in dimer equivalents depleted (nmol ml$^{-1}$) | Racemic (±)-syringaresinols (nmol ml$^{-1}$) |
|---|---|---|---|
| FMN (0.5 µmol ml$^{-1}$) | absent | 570 ± 100 | 290 ± 40 |
| | present | 610 ± 110 | 340 ± 40 |
| Ammonium peroxydisulfate (10 µmol ml$^{-1}$) | absent | 1400 ± 120 | 1020 ± 40 |
| | present | 1520 ± 10 | 1060 ± 30 |
| Dirigent protein | present | 110 ± 10 | 50 ± 10 |

Although the inventors do not intend to be bound by any particular mechanism for stereoselective coupling, three distinct possibilities can be envisaged. The most likely is that the oxidase or oxidant generates free-radical species from E-coniferyl alcohol, and that the latter are the true mechanism, the Michaelis-Menten parameters obtained will only represent formal rather than true values, because the highest free-energy intermediate state during the conversion of E-coniferyl alcohol into (+)-pinoresinol is still unknown and the relation between the concentration of substrate and that of the corresponding intermediate free-radical in open solution has not been delineated.

Bearing these qualifications in mind, we estimated formal $K_m$ and $V_{max}$ values for the dirigent protein preparation. As noted earlier, it was capable of engendering formation of low levels of both (+)-pinoresinol from E-coniferyl alcohol, and racemic (±)-syringaresinols from E-sinapyl alcohol, because of traces of contaminating oxidizing capacity. With this preparation (Table 3), a formal $K_m$ of 10±6 mM and $V_{max}$ of 0.02±0.02 mol s$^{-1}$ mol$^{-1}$ were obtained. However, with addition of fraction III, laccase, and FMN, the formal $K_m$ values (mM) were reduced to 1.6±0.3, 0.100±0.003, and 0.10±0.01, respectively, whereas the $V_{max}$ values were far less affected at these concentrations of auxiliary oxidase/oxidant.

Formal $K_m$ and $V_{max}$ values were calculated for the laccase and fraction III oxidase with respect to E-coniferyl alcohol conversion into the three racemic lignans. However, no direct comparisons can be made to the 78-kD protein, since the formal $K_m$ values involve only the corresponding oxidases. For completeness, the $K_m$ (mM) and $V_{max}$ (mol s$^{-1}$ mol$^{-1}$ enzyme) were as follows: with respect to the laccase, 0.200±0.001 and 3.9±0.2 for (±)-erythro/threo guaiacylglycerol 8-O-4'-coniferyl alcohol ethers, 0.3000±0.0003 and 13.1±0.6 for (±)-dehydrodiconiferyl alcohols, and 0.300±0.002 and 7.54±0.50 for (±)-pinoresinols; with respect to the fraction III oxidase (estimated to have a native molecular weight of 80 kDa), 2.2±0.3 and 0.20±0.03 for (±)-erythro/threo guaiacylglycerol 8-O-4'-coniferyl alcohol ethers, 2.2±0.2 and 0.7±0.1 for (±)-dehydrodiconiferyl alcohols, and 3.7±0.7 and 0.6±0.1 for (±)-pinoresinols.

These preliminary kinetic parameters are in harmony with the finding that dirigent protein does not substantially affect the rate of E-coniferyl alcohol depletion in the presence of fraction III, laccase and FMN. Both sets of results are together in accord with the working hypothesis that the dirigent protein functions by capturing free-radical intermediates which then undergo stereoselective coupling.

TABLE 3

Effect of various oxidants on formal $K_m$ and $V_{max}$ values for the dirigent protein (770 pmol ml$^{-1}$) during (+)-pinoresinol formation from E-coniferyl alcohol

| Oxidase/Oxidant | Formal $K_m$ (mM) | $V_{max}$ (mol s$^{-1}$ mol$^{-1}$ dirigent protein) |
|---|---|---|
| Dirigent protein | 10 ± 6 | 0.02 ± 0.02 |
| Fraction III (12 µg protein ml$^{-1}$) | 1.6 ± 0.3 | 0.10 ± 0.03 |
| Laccase (2.07 pmol ml$^{-1}$) | 0.100 ± 0.003 | 0.0600 ± 0.0002 |
| FMN (0.5 µmol ml$^{-1}$) | 0.10 ± 0.01 | 0.024 ± 0.001 |

EXAMPLE 5

Cloning of the Dirigent Protein cDNA from *Forsythia intermedia*

Plant Materials—*Forsythia intermedia* plants were either obtained from Bailey's Nursery (var. Lynwood Gold, St. Paul, Minn.), and maintained in Washington State University greenhouse facilities, or were gifts from the local community.

Materials—All solvents and chemicals used were reagent or HPLC grade. Taq thermostable DNA polymerase was obtained from Promega, whereas restriction enzymes were from Gibco BRL (HaeIII), Boehringer Mannheim (Sau3a) and Promega (TaqI). pT7Blue T-vector and competent NovaBlue cells were purchased from Novagen and radiolabeled nucleotide ([α-$^{32}$P]dCTP) was from DuPont NEN.

Oligonucleotide primers for polymerase chain reaction (PCR) and sequencing were synthesized by Gibco BRL Life Technologies. GENECLEAN II® kits (BIO 101 Inc.) were used for purification of PCR fragments, with the gel-purified DNA concentrations determined by comparison to a low DNA mass ladder (Gibco BRL) in 1.5% agarose gels.

Instrumentation—UV (including RNA and DNA determinations at OD$_{260}$) spectra were recorded on a Lambda 6 UV/VIS spectrophotometer. A Temptronic II thermocycler (Thermolyne) was used for all PCR amplifications. Purification of DNA for sequencing employed a QIAwell Plus plasmid purification system (QIAGEN) followed by PEG precipitation (Sambrook, J., Fritsch, E. F., and Maniatis, T. (1994) *Molecular Cloning: A Laboratory Manual*, 3 volumes, 3rd Ed., Cold Spring Harbor Laboratory, Cold Spring Harbor, N.Y.), with DNA sequences determined using an Applied Biosystems Model 373A automated sequencer. Amino acid sequences were obtained using an Applied Biosystems protein sequencer with on-line HPLC detection, according to the manufacturer's instructions.

Dirigent Protein Amino Acid Sequencing—The dirigent protein N-terminal amino acid sequence (SEQ ID NO:1) was obtained from the purified protein using an Applied Biosystems protein sequencer with on-line HPLC detection. For trypsin digestion, the purified enzyme (150 pmol) was suspended in 0.1 M Tris-HCl (50 µl, pH 8.5, Boehringer Mannheim, sequencing grade), with urea added to give a final concentration of 8 M in 77.5 µl. The mixture was incubated for 15 min at 50° C., following which 100 mM iodoacetamide (2.5 µl) was added, with the whole kept at room temperature for 15 min. Trypsin (1 µg in 20 µl) was then added, with the mixture digested for 24 h at 37° C., following which TFA (4 µl) was added to stop the enzymatic reaction. The resulting mixture was subjected to reversed phase HPLC analysis (C-8 column, Applied Biosytems), this being eluted with a linear gradient over 2 h from 0 to 100% acetonitrile (in 0.1% TFA) at a flow rate of 0.2 ml/min with detection at 280 nm. Fractions containing individual oligopeptide peaks were collected manually and directly submitted to amino acid sequencing (SEQ ID Nos:2–7).

*Forsythia intermedia* stem cDNA Library Synthesis—Total RNA (~300 µg/g fresh weight) was obtained (Dong, Z. D., and Dunstan, D. I. (1996) *Plant Cell Reports* 15:516–521) from young green stems of greenhouse-grown *Forsythia intermedia* plants (var. Lynwood Gold). A *Forsythia intermedia* stem cDNA library was constructed using 5 µg of purified poly A$^+$ mRNA (Oligotex-d™ Suspension, QIAGEN) with the ZAP-cDNA® synthesis kit, the Uni-ZAP™ XR vector and the Gigapack® II Gold packaging extract (Stratagene), with a titer of 1.2×10$^6$ PFU for the primary library. A portion (30 ml) of the amplified library (1.2×10$^{10}$ PFU/ml; 158 ml total) (Sambrook, J. et al., supra) was used to obtain pure cDNA library DNA (Ausubel, F. M., Brent, R., Kingston, R. E., Moore, D. D., Seidman, J. G., Smith, J. A., and Struhl, K. (1991) *Current Protocols in Molecular Biology*, 2 volumes, Greene Publishing Associates and Wiley-Interscience, John Wiley & Sons, N.Y.) for PCR.

Dirigent Protein DNA Probe Synthesis—The N-terminal and internal peptide amino acid sequences were used to construct the degenerate oligonucleotide primers. Purified *F. intermedia* cDNA library DNA (5 ng) was used as the template in 100 µl PCR reactions (10 mM Tris-HCl [pH 9.0], 50 mM KCl, 0.1% Triton X-100, 2.5 mM MgCl$_2$, 0.2 mM each dNTP and 2.5 units Taq DNA polymerase) with primer PSINT1 (SEQ ID NO:8) (100 pmol) and either primer PSI7R (SEQ ID NO:11) (20 pmol), primer PSI2R (SEQ ID NO:10) (20 pmol) or primer PSI1R (SEQ ID NO:9) (20 pmol). PCR amplification was carried out in a thermocycler as follows: 35 cycles of 1 min at 94° C., 2 min at 50° C. and 3 min at 72° C.; with 5 min at 72° C. and an indefinite hold at 4° C. after the final cycle. Single-primer, template-only and primer-only reactions were performed as controls. PCR products were resolved in 1.5% agarose gels, where a single band (~370-, ~155- or ~125-bp, respectively) was observed for each reaction.

To determine the nucleotide sequence of the amplified bands, five 100 μl PCR reactions were performed as above with PSINT1 (SEQ ID NO:8) +PSI7R (SEQ ID NO:11), PSINT1 (SEQ ID NO:8) +PSI2R (SEQ ID NO:10) and PSINT1 (SEQ ID NO:8) +PSI1R (SEQ ID NO:9) primer pairs. The 5 reactions from each primer pair were concentrated (Microcon 30, Amicon Inc.) and washed with TE buffer (10 mM Tris-HCl, pH 8.0, 1 mM EDTA; 2×200 μl), with the PCR products subsequently recovered in TE buffer (2×50 μl). These were resolved in preparative 1.5% agarose gels. Each gel-purified PCR product (~0.2 pmol) was then ligated into the pT7Blue T-vector and transformed into competent NovaBlue cells, according to Novagen's instructions. Insert sizes were determined using the rapid boiling lysis and PCR technique (with R20mer and U19mer primers) according to the manufacturer's instructions. Restriction analyses were performed to determine whether all inserts from the reactions utilizing each of the foregoing primer pairs were the same, as follows: to 20 μl each of a 100 μl PCR reaction (insert of interest amplified with R20mer (SEQ ID NO:74) and U19mer(SEQ ID NO:75) primers) were added 4 units HaeIII, 1.5 units Sau3a or 5 units TaqI restriction enzyme. Restriction digestions were allowed to proceed for 60 min at 37° C. for HaeIII and Sau3A and at 65° C. for TaqI reactions. Restriction products were resolved in 1.5% agarose gels giving one restriction group for each insert tested. Five recombinant plasmids from PSINT1 (SEQ ID NO:8) +PSI7R (SEQ ID NO:11) (called pT7PSI1-pT7PSI5) and 2 recombinant plasmids from PSINT1 (SEQ ID NO:8) +PSI2R (SEQ ID NO:10) (called pT7PSI6 and pT7PSI7) PCR products were selected for DNA sequencing; all contained the same open reading frame (ORF) (SEQ ID NO:69). The dirigent protein probe was next constructed as follows: five 100 μl PCR reactions were performed as above with 10 ng pT7PSI1 DNA (SEQ ID NO:69) with primers PSINT1 (SEQ ID NO:8) and PSI7R (SEQ ID NO:11). Gel-purified pT7PSI1 insert (50 ng) was used with Pharmacia's $^{T7}$QuickPrime® kit and [α-$^{32}$P]dCTP, according to kit instructions, to produce a radiolabeled probe (in 0.1 ml), which was purified over BioSpin 6 columns (Bio-Rad) and added to carrier DNA (0.5 mg/ml sheared salmon sperm DNA [Sigma], 0.9 ml).

Library Screening—600,000 PFU of *F. intermedia* amplified cDNA library were plated for primary screening, according to Stratagene's instructions. Plaques were blotted onto Magna Nylon membrane circles (Micron Separations Inc.), which were then allowed to air dry. The membranes were placed between two layers of Whatman® 3MM Chr paper. cDNA library phage DNA was fixed to the membranes and denatured in one step by autoclaving for 2 min at 100° C. with fast exhaust. The membranes were washed for 30 min at 37° C. in 6×standard saline citrate (SSC) and 0.1% SDS and prehybridized for 5 h with gentle shaking at 57–58° C. in preheated 6×SSC, 0.5% SDS and 5×Denhardt's reagent (hybridization solution, 300 ml) in a crystallization dish (190×75 mm). The [$^{32}$P]radiolabeled probe was denatured (boiling, 10 min), quickly cooled (ice, 15 min) and added to a preheated fresh hybridization solution (60 ml, 58° C.) in a crystallization dish (150×75 mm). The prehybridized membranes were next added to this dish, which was then covered with plastic wrap. Hybridization was performed for 18 h at 57–58° C. with gentle shaking. The membranes were washed in 4×SSC and 0.5% SDS for 5 min at room temperature, transferred to 2×SSC and 0.5% SDS (at room temperature) and incubated at 57–58° C. for 20 min with gentle shaking, wrapped with plastic wrap to prevent drying and finally exposed to Kodak X-OMAT AR film for 24 h at −80° C. with intensifying screens. Twenty positive plaques were purified through two more rounds of screening with hybridization conditions as above.

In vivo Excision and Sequencing of Dirigent Protein cDNA-containing Phagemids—Purified cDNA clones were rescued from the phage following Stratagene's in vivo excision protocol. Both strands of several different cDNAs that coded for dirigent protein were completely sequenced using overlapping sequencing primers. Two distinct cDNAs were identified, called pPSD_Fi1(SEQ ID NO:12) and pPSD_Fi2(SEQ ID NO:14).

Sequence Analysis—DNA and amino acid sequence analyses were performed using the Unix-based GCG Wisconsin Package (Program Manual for the Wisconsin Package, Version 8, September 1994, Genetics Computer Group, 575 Science Drive, Madison, Wis., USA 53711; Rice, P. (1996) Program Manual for the EGCG Package, Peter Rice, The Sanger Centre, Hinxton Hall, Cambridge, CB10 1Rq, England) and the ExPASy World Wide Web molecular biology server (Geneva University Hospital and University of Geneva, Geneva, Switzerland).

EXAMPLE 6

Expression of Functional Dirigent Protein in *Spodoptera frugiperda*

Attempts to express functional dirigent protein in *Escherichia coli* failed. Consequently, we expressed the dirigent protein in *Spodoptera frugiperda* utilizing a baculovirus expression system. The full-length 1.2 kb cDNA clone for the dirigent protein (PSD) in *F. intermedia*, containing both the 5' and 3' untranslated regions, was excised from the pBlueScript (Stratagene) derived plasmid pPSD_Fi1 (SEQ ID NO:12) using the restriction endonucleases BamH I and Xho I. This 1.2 kb fragment was directionally subcloned into these same restriction sites in the multiple cloning site of the baculovirus transfer vector pBlueBac4 (Invitrogen, San Diego, Calif.). This produced the 6.0 kb construct pBB4/PSD which generates a non-fusion dirigent protein with translation being initiated at the dirigent protein cDNA start codon. This construct was then co-transfected with linearized Bac-N-Blue DNA (Invitrogen) into *Spodoptera frugiperda* Sf9 cells by the technique of cationic liposome mediated transfection to produce, by means of homologous recombination, the recombinant *Autographa californica* nuclear polyhedrosis viral (AcMNPV) DNA Bac-N-Blue dirigent protein (BB/PSD) which was purified from plaques according to procedures described by Invitrogen. The final recombinant AcMNPV-BB/PSD contains the PSD gene under the polyhedrin promoter control and the essential sequence needed for replication of the recombinant virus. To verify that the dirigent protein was successfully expressed in the insect cell culture, log phase Sf9 cells infected with the AcMNPV-PSD recombinant viral high titer stock were used to obtain heterologous protein production. Maximal dirigent protein yield occurred by 48–70 hours post-infection. As determined by SDS-PAGE and (+)-pinoresinol forming activity, the protein was found secreted into the medium and showed a molecular mass and activity which corresponded to the indigenous protein originally isolated from *Forsythia intermedia*.

EXAMPLE 7

Isolation of Dirigent Protein Clones from *Thuja plicata* and *Tsuga heterophylla*

The coding region of a Forsythia dirigent protein cDNA, psd-Fi1 (SEQ ID NO:12), was used to screen cDNA libraries from *Thuja plicata* and *Tsuga heterophylla*. The conditions and methods were as disclosed in Example 5, except that hybridization was carried out at 45–50° C. Two dirigent protein cDNAs were isolated from *Tsuga heterophylla* (SEQ ID Nos:16, 18), and eight dirigent protein cDNAs were isolated from *Thuja plicata* (SEQ ID Nos:20, 22, 24, 26, 28, 30, 32, 34).

EXAMPLE 8

Purification of Pinoresinol/lariciresinol Reductases from Forsythia Intermedia

Plant Materials. *Forsythia intermedia* plants were either obtained from Bailey's Nursery (var. Lynwood Gold, St., Paul, Minn.), and maintained in Washington State University greenhouse facilities, or were gifts from the local community.

Materials. All solvents and chemicals used were reagent or HPLC grade. Unlabeled (±)-pinoresinols and (±)-lariciresinols were synthesized as described (Katayama, T. et al., *Phytochemistry* 32:581–591 (1993)). [4R-3H]NADPH was obtained as previously reported (Chu, A. et al., *J. Biol. Chem.* 268:27026–27033 (1993)) by modification of the procedure of Moran et al. (Moran, R. G. et al., *Anal. Biochem.* 138:196–204 (1984)), and [4R-2H]NADPH was prepared according to Anderson and Lin (Anderson, J. A., and Lin B. K., *Phytochemistry* 32:811–812 (1993)). Yeast glucose-6-phosphate dehydrogenase (Type IX,22.32. mmol $h^{-1}$ $mg^{-1}$) and yeast hexokinase (Type F300, 15.12 $mmol^{-1}$ $mg^{-1}$) were purchased from Sigma and dihydrofolate reductase (Lactobacillus casei, 33.48 mmol $h^{-1}$ $mg^{-1}$) was obtained from Biopure Co. Affi-Gel Blue Gel (100–200 mesh) and Bio-Gel HT Hydroxyapatite were purchased from Bio-Rad, whereas Phenyl Sepharose CL-4B, MonoQ HR 5/5, MonoP HR 5/20, Superose 6, Superose 12, Superdex 75, PD-10 columns, molecular weight standards and Polybuffer 74 were obtained from Pharmacia LKB Biotechnology, Inc. Adenosine 2',5'-diphosphate Sepharose and Reactive Yellow 3 Agarose were from Sigma Chemical Co.

Instrumentation. $^1$H Nuclear magnetic resonance spectra (300 and 500 MHz) were recorded on Brüker AMX300 and Varian VXR500S spectrometers, respectively, using $CDCl_3$ as solvent with chemical shifts (δ ppm) reported downfield from tetramethylsilane (internal standard). UV (including RNA and DNA determinations at $OD_{260}$) and mass spectra were obtained on Lambda 6 UV/VIS and VG 7070E (ionizing voltage 70 eV) spectrophotometers, respectively. High performance liquid chromatography was carried out using either reversed-phase (Waters, Nova-pak C 18, 150× 3.9 mm inner diameter) or chiral (Daicel, Chiralcel OD or Chiralcel OC, 240×4.6 mm inner diameter) columns, with detection at 280 nm (Chu, A. et al., *J. Biol. Chem.* 268:27026–27033 (1993)). Radioactive samples were analyzed in Ecolume (ICN) and measured using a liquid scintillation counter (Packard, Tricarb 2000 CA). Amino acid sequences were obtained using an Applied Biosystems protein sequencer with on-line HPLC detection, according to the manufacturer's instructions.

Enzyme Assays. Pinoresinol and lariciresinol reductase activities were assayed by monitoring the formation of (+)-[$^3$H]lariciresinol and (−)-[$^3$H]secoisolariciresinol (Chu, A. et al., *J. Biol. Chem.* 268:27026–27033 (1993)).

Briefly, each assay for pinoresinol reductase activity consisted of (±)-pinoresinols (5 mM in MeOH, 20 μl), the enzyme preparation at the corresponding stage of purity (100 μl), and buffer (20 mM Tris-HCl, pH 8.0, 110 μl). The enzymatic reaction was initiated by addition of [4R-$^3$H] NADPH (10 mM, 6.79 kBq/mmol in 20 μl of double-distilled $H_2O$). After 30 min incubation at 30° C. with shaking, the assay mixture was extracted with EtOAc (500 μl) containing (±)-lariciresinols (20 μg) and (±)-secoisolariciresinols (20 μg) as radiochemical carriers. After centrifugation (13,800×g, 5 min), the EtOAc solubles were removed and the extraction procedure was repeated. For each assay, the EtOAc solubles were combined with an aliquot (100 μl) removed for determination of its radioactivity using liquid scintillation counting. The remainder of the combined EtOAc solubles was evaporated to dryness in vacuo, reconstituted in MeOH/3% acetic acid in $H_2O$ (30:70, 100 μl) and subjected to reversed phase and chiral column HPLC. Controls were performed using either denatured enzyme (boiled for 10 min) or in the absence of (±)-pinoresinols as substrate.

Lariciresinol reductase activity was assayed by monitoring the formation of (−)-[$^3$H]secoisolariciresinol. These assays were carried out exactly as described above, except that (±)-lariciresinols (5 mM in MeOH, 20 μl) were used as substrates, with (±)-secoisolariciresinols (20 μg) added as radiochemical carriers.

General Procedures for Enzyme Purification. Protein purification procedures were carried out at 4° C. with chromatographic eluents monitored at 280 nm, unless otherwise stated. Protein concentrations were determined by the method of Bradford (Bradford, M. M., *Anal. Biochem.* 72:248–254 (1976)) using γ-globulin as standard. Polyacrylamide gel electrophoresis used gradient (4–15%, Bio-Rad) gels under denaturing and reducing conditions, these being performed in Laemmli's buffer system (Laenimli, U. K., *Nature* 227:680–685 (1970)). Proteins were visualized by silver staining (Morrissey, J. H., *Anal. Biochem.* 117:307–310 (1981)).

Preparation of crude extracts. *F. intermedia* stems (20 kg) were harvested, cut into 3–6 cm sections, and stored at −20° C. until needed. Batches of stems (2 kg) were frozen in liquid nitrogen and pulverized in a Waring Blendor. The resulting powder was homogenized with potassium phosphate buffer (0.1 mM, pH 7.0, 4 L), containing 5 mM dithiothreitol. The homogenate was filtered through four layers of cheesecloth into a beaker containing 10% (w/v) polyvinylpolypyrolidone. The filtrate was centrifuged (12, 000×g, 15 min). The resulting supernatant was fractionated with $(NH_4)_2SO_4$, with proteins precipitating between 40 and 60% saturation recovered by centrifugation (10,000×g, 1 h). The pellet was next reconstituted in a minimum amount of Tris-HCl buffer (20 mM, pH 8.0), containing 5 mM dithiothreitol (buffer A) and desalted using prepacked PD-10 columns (Sephadex G-25 medium) equilibrated with buffer A.

Affinity (Affi Blue Gel) Chromatography. The crude enzyme preparation (191 mg in buffer A, 5 nmol h$^{-1}$ mg$^{-1}$) was applied to an Affi Blue Gel column (2.6×70 cm) equilibrated in buffer A. After washing the column with 200 ml of buffer A, pinoresinol/lariciresinol reductase was eluted with a linear NaCl gradient (1.5–5 M in 300 ml) in buffer A at a flow rate of 1 ml min$^{-1}$. Active fractions were stored (−80° C.) until needed.

Hydrophobic Interaction Chromatography (Phenyl Sepharose). After thawing, ten preparations resulting from the Affi Blue chromatography step (150 mg, 51 nmol h$^{-1}$ mg$^{-1}$) were combined and applied to a Phenyl Sepharose column (1×10 cm) equilibrated in buffer A, containing 5 M NaCl. The column was washed with two bed volumes of the same buffer. Pinoresinol/lariciresinol reductase was eluted using a linear gradient of decreasing concentration of NaCl (5–0 M in 40 ml) in buffer A at a flow rate of 1 ml min$^{-1}$. Fractions catalyzing pinoresinol/lariciresinol reduction were combined and pooled.

Hydroxyapatite I Chromatography. Active protein (31 mg, 91 nmol h$^{-1}$ mg$^{-1}$) from the phenyl sepharose purification step was applied to an hydroxyapatite column (1.6×70 cm) equilibrated in 10 mM potassium phosphate buffer, pH 7.0, containing 5 mM dithiothreitol (buffer B). Pinoresinol/lariciresinol reductase was eluted with a linear gradient of potassium phosphate buffer, pH 7.0 (0.01–0.4 M in 200 ml) at a flow rate of 1 ml min$^{-1}$. Active fractions were combined. The buffer was then exchanged with buffer A using PD-10 prepacked columns.

Affinity (2',5'-ADP Sepharose) Chromatography. The enzyme solution resulting from the hydroxyapatite purification step (6.5 mg, 463 nmol h$^{-1}$ mg$^{-1}$) was next loaded on a 2',5'-ADP Sepharose (1×10 cm) column, previously equilibrated in buffer A containing 2.5 mM EDTA (buffer A') and then washed with 25 ml of buffer A'. Pinoresinol/lariciresinol reductase was eluted with a step gradient of NADP+ (0.3 mM in 10 ml) in buffer A' at a flow rate of 0.5 ml min$^{-1}$. [NAD+ (up to 3 mM) did not elute pinoresinol/lariciresinol reductase activity.] Because of the interference of the absorbance of the NADP+, it was not possible to directly monitor the eluent at 280 nm. Protein concentrations for each fraction were determined spectrophotometrically according to Bradford (Bradford, M. M., *Anal. Biochem.* 72:248–254 (1976)).

Hydroxyapatite II Chromatography. Fractions from the 2',5'-ADP Sepharose column that exhibited pinoresinol/lariciresinol reductase activity (0.85 mg, 1051 nmol h$^{-1}$ mg$^{-1}$) were combined and directly applied to a second hydroxyapatite column (1×3 cm), equilibrated in buffer B, with the enzyme eluted with a linear gradient of potassium phosphate buffer, pH 7.0 (0.01–0.4 M in 45 ml) at a flow rate of 1 ml min$^{-1}$.

Affinity (Affi Yellow) Chromatography—Active fractions (160 μg, 7960 nmol h$^{-1}$ mg$^{-1}$) from the second hydroxyapatite column purification step were next applied to a Reactive Yellow 3 Agarose column (1×3 cm), equilibrated in buffer A. Pinoresinol/lariciresinol reductase was eluted with a linear NaCl gradient (0–2.5 M in 100 ml) at a flow rate of 1 ml min$^{-1}$.

Fast Protein Liquid Chromatography (Superose 12 Chromatography)—Combined fractions from the Affi Yellow purification step having the highest activity (50 μg, 10,940 nmol h$^{-1}$ mg$^{-1}$) were pooled and concentrated to 1 ml, using a Centricon 10 microconcentrator (Amicon, Inc.). The enzyme solution was then applied in portions of 200 μl to a fast protein liquid chromatography column (Superose 12, HR 10/30). Gel filtration was performed in a buffer containing 20 mM Tris-HCl, pH 8.0, 150 mM NaCl and 5 mM dithiothreitol at a flow rate of 0.4 ml min$^{-1}$. Pinoresinol/lariciresinol reductase was eluted with 12.8 ml of the mobile phase. The active fractions which coincided with the UV profile (absorbance at 280 nm) were pooled (20 μg, 15,300 nmol h$^{-1}$ mg$^{-1}$) and desalted (PD-10 prepacked columns).

The foregoing purification protocol resulted in a 3060-fold purification of (+)-pinoresinol/(+)-lariciresinol reductase. As for many of the enzymes involved in phenylpropanoid metabolism, the protein was in very low abundance, i.e. 20 kg *F. intermedia* stems yielded only ~20 μg of the purified (+)-pinoresinol/(+)-lariciresinol reductase.

EXAMPLE 9

Characterization of Purified Pinoresinol/lariciresinol Reductases from *Forsythia Intermedia*

Isoelectric Focussing and pI Determination. In all stages of the purification protocol, (+)-pinoresinol/(+)-lariciresinol reductase activities coeluted. Given this observation, it was essential to unambiguously ascertain whether more than one form of the protein existed, i.e., whether one form of the protein catalyzed the reduction of pinoresinol, and another form of the protein catalyzed the reduction of lariciresinol. To this end, the isoelectric point of pinoresinol/lariciresinol reductase was estimated by chromatofocussing on a MonoP HR 5/20 FPLC column.

Active fractions from the Superose 12 gel filtration column (Example 1) were pooled and the buffer exchanged with 25 mM Bis-Tris, pH 7.1, using prepacked PD-10 columns, equilibrated in the same buffer. The preparation so obtained was loaded on the chromatofocussing column and a pH gradient between 7.1 and 3.9 was formed, using Polybuffer 74 as eluent at a flow rate of 0.5 ml min$^{-1}$. Aliquots (200 μl) of each fraction were assayed for pinoresinol/lariciresinol reductase activities. The remainder of the fractions was used to determine the pH gradient.

Molecular Weight Determination. Application of the MonoP HR 5/20 FPLC column preparation of pinoresinol/lariciresinol reductase to SDS-gradient gel electrophoresis (4–15% polyacrylamide) revealed the presence of two protein bands of similar apparent molecular weight, whose separation was achieved via anion-exchange chromatography on a MonoQ HR 5/5 FPLC matrix. Pooled fractions from the Sepharose 12 purification step (Example 1) were applied to a MonoQ HR 5/5 column (Pharmacia), equilibrated in buffer A. The column was washed with 10 ml of buffer A and pinoresinol/lariciresinol reductase activity eluted using a linear NaCl gradient (0–500 mM in 50 ml) in buffer A at a flow rate of 0.5 ml min$^{-1}$. Aliquots (30 μl) of the collected fractions were analyzed by SDS polyacrylamide gel electrophoresis, using a gradient (4–15% acrylamide) gel. Proteins were visualized by silver staining. Active fractions 34 through 37 (27,760 nmol h$^{-1}$ mg$^{-1}$) and 38 through 41 (30,790 nmol h$^{-1}$ mg$^{-1}$) were pooled separately and immediately used for characterization.

The two protein bands thus resolved under denaturing conditions had apparent molecular masses of ~36 and ~35 kDa, respectively. Each of the two reductase forms had a pI~5.7.

Native molecular weights of each reductase isoform were estimated via comparison of their elution behavior on Superose 12, Superose 6 and Superdex 75 gel filtration FPLC columns with the elution behavior of calibrated molecular weight standards. Gel filtration was carried out as set forth in Example 8. For each reductase, an apparent native molecular weight of 59,000 was calculated based on its elution volume, in contrast to that of ~36,000 and ~35,000 by SDS-polyacrylamide gel electrophoresis. While the discrepancy between molecular weights from gel filtration and SDS-PAGE remains unknown, it can tentatively be proposed that although the native protein likely exists as a dimer, it could also be a monomer of asymmetric shape, thereby altering its effective Stokes radius (Cantor, C. R., and Shimmel, P. R., *Biophysical Chemistry*, Part II, W.H. Freeman and Company, San Francisco, Calif. (1980); Stellwagen, E., *Methods in Enzymology* 182:317–328 (1990)), as reported for human thioredoxin reductase (Oblong, J. E., et al., *Biochemistry* 32:7271–7277 (1993)) and yeast metalloendopeptidase (Hrycyna, C. A., and Clarke, S., *Biochemistry* 32:11293–11301 (1993)).

pH and Temperature Optima. To determine the pH-optimum of pinoresinol/lariciresinol reductase, the enzyme preparation from the gel Superose 12 filtration step (Example 8) was assayed utilizing standard assay conditions (Example 8), except that the buffer was replaced with 50 mM Bis-Tris Propane buffer in the pH range of 6.3 to 9.4. The pH optimum was found to be pH 7.4.

The temperature optimum of pinoresinol/lariciresinol reductase was examined in the range between 4° C. and 80° C. under standard assay conditions (Example 8) utilizing the enzyme preparation from the gel filtration step (Example 8). At optimum pH, the temperature optimum for the reductase activity was established to be ~30° C.

Kinetic Parameters. Velocity studies were carried out to ascertain whether the two reductase isoforms catalyzed distinct reductions, i.e., that of the conversion of (+)-pinoresinol to (+)-lariciresinol, and (+)-lariciresinol to (−)-secoisolariciresinol, respectively, or whether either displayed a preference for (+)-pinoresinol or (+)-lariciresinol as substrates. The initial velocity studies were carried out individually utilizing the two isoforms of the enzyme, and individually employing both (+)-pinoresinol and (+)-lariciresinol as substrates. Initial velocity studies were performed in triplicate experiments, using 50 mM Bis-Tris Propane buffer, pH 7.4 containing 5 mM dithiothreitol, pure enzyme (after MonoQ anion-exchange chromatography), ten different substrate concentrations (between 8.8 and 160 $\mu$M) at a constant NADPH concentration (80 $\mu$M). Incubations were carried out at 30° C. for 10 min (within the linear kinetic range). Kinetic parameters were determined from Lineweaver-Burk plots.

Importantly, the kinetic parameters were essentially the same for both the 35 kDa and the 36 kDa forms of the enzyme (i.e., Km for pinoresinol: 27±1.5 $\mu$m for the 35 kDa form of the enzyme, and 23±1.3 $\mu$M for the 36 kDa form of the enzyme; Km for lariciresinol: 121±5.0 $\mu$M for the 35 kDa form of the enzyme and 123±6.0 $\mu$M for the 36 kDa form of the enzyme). In an analogous manner, apparent maximum velocities (expressed as $\mu$mol h$^{-1}$ mg$^{-1}$ of protein) were also essentially identical (i.e., Vmax for pinoresinol: 16.2±0.4 for the 35 kDa form of the enzyme and 17.3±0.5 for the 36 kDa form of the enzyme; for lariciresinol: 25.2±0.7 for the 35 kDa form of the enzyme and 29.9±0.7 for the 36 kDa form of the enzyme). Thus, all available evidence suggests that (+)-pinoresinol/(+)-lariciresinol reductase exists as two isoforms, with each capable of catalyzing the reduction of both substrates. How this reduction is carried out, i.e., whether both reductions are done in tandem, in either quinone or furano ring form, awaits further study using a more abundant protein source.

Enzymatic Formation of (+)-[7'R-$^2$H]Lariciresinol. Since the two (+)-pinoresinol/(+)-lariciresinol reductase isoforms exhibited essentially identical catalytic characteristics, the Sepharose 12 enzyme preparation (Example 8), containing both isoforms, was used to examine the stereospecificity of the hydride transfer. The strategy adopted utilized selective deuterium labeling using NADP$^2$H as cofactor for the reduction of (+)-pinoresinol, with the enzymatic product, (+)-lariciresinol, being analyzed by $^1$H NMR and mass spectroscopy. Thus, a solution of (±)-pinoresinols (5.2 mM in MeOH, 4 ml) was added to Tris-HCl buffer (20 mM, pH 8.0, containing 5 mM dithiothreitol, 22 ml) and stereospecifically deutero-labeled [4R-$^2$H]NADPH (20 mM in H$_2$O, 4 ml) prepared via the method of Anderson and Lin (Anderson, J. A., and Lin B. K., *Phytochemistry* 32:811–812 (1993)), with the whole added to the enzyme preparation (20 ml). After incubation at 30° C. for 1 h with shaking, the assay mixture was extracted with EtOAc (2×50 ml). The EtOAc soluble fraction was combined, washed with saturated NaCl (50 ml), dried (Na$_2$SO$_4$), and evaporated to dryness in vacuo. The resulting extract was reconstituted in a minimum amount of EtOAc, applied to a silica gel column (0.5×7 cm), and eluted with EtOAc/hexanes (1:2). Fractions containing the enzymatic product were combined and evaporated to dryness.

The enzymatic product was established to be (+)-[7'R-$^2$H]lariciresinol, as evidenced by the disappearance of the 7'-proR proton at $\delta$ 2.51 ppm due to its replacement by deuterium and by its molecular ion at (m/z) 361 (M++1) corresponding to the presence of one deuterium atom at C-7. $^1$H NMR (300 MHz) (CDCl$_3$): 2.39 (m,$^1$H, C8H), 2.71 (m,$^1$H, C8'H), 2.88 ($\delta$,$^1$H, J7'S,8'=5.0 Hz, C7'HS), 3.73 ($\delta\delta$,$^1$H, J8',9'b=7.0 Hz, J9'a,9'b=8.5 Hz, C9'H$\beta$), 3.76 ($\delta\delta$, $^1$H, J8,9S=6.5 Hz, J9R,9S=8.5 Hz, C9HS), 3.86 (s,$^3$H, OCH$_3$), 3.88 (s,$^3$H, OCH$_3$), 3.92 ($\delta\delta$,$^1$H, J8,9R=6.0 Hz, J9R,9S=9.5 Hz, C9HR), 4.04 ($\delta\delta$,$^1$H, J8',9'a=7.0 Hz, J9'a9'b=8.5 Hz, C9'Ha), 4.77 ($\delta$,$^1$H, J7,8=6.6 Hz, C7H), 6.68–6.70 (m,$^2$H, ArH), 6.75–6.85 (m,4H, ArH); MS m/z (%): 361 (M++1, 71.2), 360 (M+, 31.1), 237 (11.1), 153 (41.5), 152 (20.2), 151 (67.0), 138 (100), 137 (71.1).

Thus, hydride transfer from (+)-pinoresinol to (+)-lariciresinol had occurred in a manner whereby only the 7'-proR hydrogen position of (+)-lariciresinol was deuterated. An analogous result was observed for the conversion of (+)-lariciresinol into (−)-secoisolariciresinol, thereby establishing that the overall hydride transfer was completely stereospecific.

EXAMPLE 10

Amino Acid Sequence Analysis of Purified Pinoresinol/Lariciresinol Reductase from Forsythia intermedia Pinoresinol/Lariciresinol Reductase Amino Acid Sequencing. The (+)-pinoresinol/(+)-lariciresinol reductase N-terminal amino acid sequence was obtained from each of the purified proteins, and a mixture of both, using an Applied Biosystems protein sequencer with on-line HPLC detection. The N-terminal sequence was the same for both isoforms (SEQ ID NO:36).

For trypsin digestion, 150 pmol of the enzyme purified from the Sepharose 12 column (Example 8) was suspended in 0.1 M Tris-HCl (50 $\mu$l, pH 8.5), with urea added to give a final concentration of 8 M in 77.5 $\mu$l. The mixture was incubated for 15 min at 50° C., then 100 mM iodoacetamide (2.5 $\mu$l) was added, with the whole kept at room temperature for 15 min. Trypsin (1 $\mu$g in 20 $\mu$l) was then added, with the mixture digested for 24 h at 37° C., after which TFA (4 $\mu$l) was added to stop the enzymatic reaction.

The resulting mixture was subjected to reversed phase HPLC analysis (C-8 column, Applied Biosytems), this being eluted with a linear gradient over 2 h from 0 to 100% acetonitrile (in 0.1% TFA) at a flow rate of 0.2 ml/min with detection at 280 nm. Fractions containing individual oligopeptide peaks were collected manually and directly submitted to amino acid sequencing. Four tryptic fragments were resolved in sufficient quantity to permit amino acid sequence determination. (SEQ ID Nos:37–40).

Cyanogen bromide digestion was performed by incubation of 150 pmol of the reductase purified from the Sepharose 12 column (Example 8) with 0.5 M cyanogen bromide in 70% formic acid for 40 h at 37° C., following which the cyanogen bromide and formic acid were removed by centrifugation under reduced pressure (SpeedVac). The resulting oligopeptide fragments were separated by HPLC and three were resolved in sufficient quantity to permit sequencing (SEQ ID Nos:41–43).

EXAMPLE 11

Cloning of Pinoresinol/Lariciresinol Reductase from *Forsythia intermedia*

Plant Materials. *Forsythia intermedia* plants were either obtained from Bailey's Nursery (var. Lynwood Gold, St., Paul, Minn.), and maintained in Washington State University greenhouse facilities, or were gifts from the local community.

Materials. All solvents and chemicals used were reagent or HPLC grade. UV RNA and DNA determinations at $OD_{260}$ were obtained on a Lambda 6 UV/VIS spectrophotometer. A Temptronic II thermocycler (Thermolyne) was used for all PCR amplifications. Taq thermostable DNA polymerase was obtained from Promega, whereas restriction enzymes were from Gibco BRL (HaeIII), Boehringer Mannheim (Sau3a) and Promega (TaqI). pT7Blue T-vector and competent NovaBlue cells were purchased from Novagen and radiolabeled nucleotides ([$\alpha$-$^{32}$P]dCTP and [$\gamma$-$^{32}$P]ATP) were from DuPont NEN.

Oligonucleotide primers for polymerase chain reaction (PCR) and sequencing were synthesized by Gibco BRL Life Technologies. GENECLEAN II® kits (BIO 101 Inc.) were used for purification of PCR fragments, with the gel-purified DNA concentrations determined by comparison to a low DNA mass ladder (Gibco BRL) in 1.5% agarose gels.

Forsythia RNA Isolation. Initial attempts to isolate functional *F. intermedia* RNA from fast-growing, green stem tissue were unsuccessful, due to difficulties encountered via facile oxidation by its plant phenolic constituents. This problem was, however, successfully overcome by utilization of an RNA isolation procedure, specifically designed for woody plant tissue, which uses low pH and reducing conditions in the extraction buffer to prevent oxidation (Dong, Z. D., and Dunstan, D. I., *Plant Cell Reports* 15: 516–521 (1996)).

*Forsythia intermedia* stem cDNA Library Synthesis. Total RNA (~300 μg/g fresh weight) was obtained from young green stems of greenhouse-grown *Forsythia intermedia* plants (var. Lynwood Gold) (Dong, Z. D., and Dunstan, D. I., *Plant Cell Reports* 15:516–521 (1996)). A *Forsythia intermedia* stem cDNA library was constructed using 5 μg of purified poly A+mRNA (Oligotex-dT™ Suspension, QIAGEN) with the ZAP-cDNA® synthesis kit, the Uni-ZAP™ XR vector and the Gigapack® II Gold packaging extract (Stratagene), with a titer of 1.2×10⁶ PFU for the primary library. A portion (30 ml) of the amplified library (1.2×10¹⁰ PFU/ml; 158 ml total) was used to obtain pure cDNA library DNA for PCR (Sambrook, J. et al., *Molecular Cloning: A Laboratory Manual*, 3 volumes, 3rd Ed., Cold Spring Harbor Laboratory, Cold Spring Harbor, N.Y. (1994); Ausubel, F. M. et al., *Current Protocols in Molecular Biology*, 2 volumes, Greene Publishing Associates and Wiley-Interscience, John Wiley & Sons, NY (1991)).

Pinoresinol/Lariciresinol Reductase DNA Probe Synthesis—The N-terminal and internal peptide amino acid sequences were used to construct the degenerate oligonucleotide primers. Specifically, the primer PLRN5 (SEQ ID NO:44) was based on the sequence of amino acids 7 to 13 of the N-terminal peptide (SEQ ID NO:36). The primer PLR14R (SEQ ID NO:45) was based on the sequence of amino acids 2 to 8 of the internal peptide sequence set forth in (SEQ ID NO:37). The primer PLR15R (SEQ ID NO:46) was based on the sequence of amino acids 9 to 15 of the internal peptide sequence set forth in (SEQ ID NO:37). The sequence of amino acids 9 to 15 of the internal peptide sequence set forth in SEQ ID NO:37, upon which the sequence of primer PLR15R (SEQ ID NO:46) was based, also corresponded to the sequence of amino acids 4 to 10 of the cyanogen bromide-generated, internal fragment set forth in SEQ ID NO:41.

Purified *F. intermedia* cDNA library DNA (5 ng) was used as the template in 100 μl PCR reactions (10 mM Tris-HCl [pH 9.0], 50 mM KCl, 0.1% Triton X-100, 2.5 mM MgCl₂, 0.2 mM each dNTP and 2.5 units Taq DNA polymerase) with primer PLRN5 (SEQ ID NO:44) (100 pmol) and either primer PLRI5R (SEQ ID NO:46) (20 pmol) or primer PLRI4R (SEQ ID NO:45) (20 pmol). PCR amplification was carried out in a thermocycler as follows: 35 cycles of 1 min at 94° C., 2 min at 50° C. and 3 min at 72° C.; with 5 min at 72° C. and an indefinite hold at 4° C. after the final cycle. Single-primer, template-only and primer-only reactions were performed as controls. PCR products were resolved in 1.5% agarose gels. The combination of primers PLRN5 (SEQ ID NO:44) and PLRI4R (SEQ ID NO:45) yielded a single band of 380-bp corresponding to bases 22 to 393 of SEQ ID NO:47. The combination of primers PLRN5 (SEQ ID NO:44) and PLRI5R (SEQ ID NO:46) yielded a single band of 400-bp corresponding to bases 22 to 423 of SEQ ID NO:47.

To determine the nucleotide sequence of the two amplified bands, five, 100 μl PCR reactions were performed as above with each of the following combinations of template and primers: 380 bp amplified product plus primers PLRN5 (SEQ ID NO:44) and PLRI4R (SEQ ID NO:45); 400 bp amplified product plus primers PLRN5 (SEQ ID NO:44) and PLRI5R (SEQ ID NO:46). The 5 reactions from each combination of primers and template were concentrated (Microcon 30, Amicon Inc.) and washed with TE buffer (10 mM Tris-HCl, pH 8.0, 1 mM EDTA; 2×200 μl), with the PCR products subsequently recovered in TE buffer (2×50 μl). These were resolved in preparative 1.5% agarose gels. Each gel-purified PCR product (~0.2 pmol) was then ligated into the pT7Blue T-vector and transformed into competent NovaBlue cells, according to Novagen's instructions. Insert sizes were determined using the rapid boiling lysis and PCR technique (utilizing R20mer (SEQ ID NO:74) and U19mer (SEQ ID NO:75) primers according to the manufacturer's (Novagen's) instructions.

Restriction analysis was performed to determine whether all inserts for each combination of primers and template were the same. Restriction analysis was carried out as follows: each of the inserts was amplified by PCR utilizing the R20 (SEQ ID NO:74) and U19 (SEQ ID NO:75) primers. To 20 μl each of a 100 μl PCR reaction were added 4 units HaeIII, 1.5 units Sau3a or 5 units TaqI restriction enzyme. Restriction digestions were allowed to proceed for 60 min at 37° C. for HaeIII and Sau3A and at 65° C. for TaqI reactions. Restriction products were resolved in 1.5% agarose gels giving one restriction group for all inserts tested.

Five of the resulting, recombinant plasmids were selected for DNA sequencing. The inserts from three of the recombinant plasmids (called pT7PLR1-pT7PLR3) were generated by a combination of primers PLRN5 (SEQ ID NO:44) and PLRI5R (SEQ ID NO:46) with the 400 bp PCR product as substrate. The inserts from the remaining two recombinant plasmids (called pT7PLR4 and pT7PLR5) were generated from a combination of primers PLRN5 (SEQ ID NO:44) and PLRI4R (SEQ ID NO:45) and the 380 bp PCR product as substrate. All of the five, sequenced PCR products contained the same open reading frame.

The (+)-pinoresinol/(+)-lariciresinol reductase probe was constructed as follows: five, 100 µl PCR reactions were performed as described above with 10 ng pT7PLR3 DNA with primers PLRN5 (SEQ ID NO:44) and PLRI5R (SEQ ID NO:46). Gel-purified pT7PLR3 cDNA insert (50 ng) was used with Pharmacia's T7QuickPrime® kit and [$\alpha$-$^{32}$P] dCTP, according to kit instructions, to produce a radiolabeled probe (in 0.1 ml), which was purified over BioSpin 6 columns (Bio-Rad) and added to carrier DNA (0.9 ml of 0.5 mg/ml sheared salmon sperm DNA obtained from Sigma).

Library Screening. 600,000 PFU of *F. intermedia* amplified cDNA library were plated for primary screening, according to Stratagene's instructions. Plaques were blotted onto Magna Nylon membrane circles (Micron Separations Inc.), which were then allowed to air dry. The membranes were placed between two layers of Whatman® 3MM Chr paper. cDNA library phage DNA was fixed to the membranes and denatured in one step by autoclaving for 2 min at 100° C. with fast exhaust. The membranes were washed for 30 min at 37° C. in 6×standard saline citrate (SSC) and 0.1% SDS and prehybridized for 5 h with gentle shaking at 57–58° C. in preheated 6×SSC, 0.5% SDS and 5×Denhardt's reagent (hybridization solution, 300 ml) in a crystallization dish (190×75 mm).

The [$^{32}$P]radiolabeled probe was denatured (boiling, 10 min), quickly cooled (ice, 15 min) and added to a preheated fresh hybridization solution (60 ml, 58° C.) in a crystallization dish (150×75 mm). The prehybridized membranes were next added to this dish, which was then covered with plastic wrap. Hybridization was performed for 18 h at 57–58° C. with gentle shaking. The membranes were washed in 4×SSC and 0.5% SDS for 5 min at room temperature, transferred to 2×SSC and 0.5% SDS (at room temperature) and incubated at 57–58° C. for 20 min with gentle shaking, wrapped with plastic wrap to prevent drying and finally exposed to Kodak X-OMAT AR film for 24 h at −80° C. with intensifying screens.

This screening procedure resulted in more than 350 positive plaques, with twenty (of different signal intensities) being subjected to two additional rounds of screening. After final purification, six of the twenty cDNAs were subcloned by in vivo excision into pBluescript. These six cDNAs were called plr-Fi1 to plr-Fi6 (SEQ ID Nos:47, 49, 51, 53, 55, 57).

In vivo Excision and Sequencing of plr-Fi1-plr-Fi6 Phagemids. The six purified cDNA clones were rescued from the phage following Stratagene's in vivo excision protocol. Both strands of the six different cDNAs (plr-Fi1 to plr-Fi6) that coded for (+)-pinoresinol/ (+)-lariciresinol reductase were completely sequenced using overlapping sequencing primers.

Purification of DNA for sequencing employed a QIAwell Plus plasmid purification system (QIAGEN) followed by PEG precipitation (Sambrook, J., *Molecular Cloning: A Laboratory Manual*, 3 volumes, 3rd Ed., Cold Spring Harbor Laboratory, Cold Spring Harbor, N.Y. (1994)), with DNA sequences determined using an Applied Biosystems Model 373A automated sequencer. DNA and amino acid sequence analyses were performed using the Unix-based GCG Wisconsin Package (Program Manual for the Wisconsin Package, Version 8, September 1994, Genetics Computer Group, 575 Science Drive, Madison, Wis., USA 53711; Rice, P., Program Manual for the EGCG Package, Peter Rice, The Sanger Centre, Hinxton Hall, Cambridge, CB10 1Rq, England (1996)) and the ExPASy World Wide Web molecular biology server (Geneva University Hospital and University of Geneva, Geneva, Switzerland).

All six cDNAs had the same coding but different 5'-untranslated regions. On the other hand, analysis of the 3'-untranslated region of each of the six cDNAs established that all were truncated versions of the longest cDNA's 3'-region. Preliminary RNA gel blot analysis with total RNA from greenhouse-grown plant stem tips confirmed a single transcript with a length of approximately 1.2 kb.

RNA gel blot analysis. For RNA gel blot analysis, total RNA (30 µg per lane) from *F. intermedia* stem tips was separated by size by denaturing agarose gel electrophoresis. The RNA was transferred to charged nylon membranes (GeneScreen Plus®, Dupont NEN), cross-linked to the membrane (Stratalinker from Stratagene), prehybridized, hybridized with the same probe used to screen the cDNA library during cDNA cloning and washed according to the manufacturer's instructions for aqueous hybridization conditions. The membrane was then exposed to Kodak X-OMAT film for 48 hr at −80° C. with intensifying screens.

EXAMPLE 12

Expression of (+)-Pinoresinol/(+)-Lariciresinol Reductase cDNA plr-Fi1 (SEQ ID NO:47) in *E. coli*

Expression in *Escherichia coli*. In order to confirm that the putative (+)-pinoresinol/(+)-lariciresinol reductase cDNAs encoded functional (+)-pinoresinol/(+)-lariciresinol reductase, the cDNAs putatively encoding (+)-pinoresinol/ (+)-lariciresinol reductase were heterologously expressed in *E. coli*. Heterologous expression was also necessary in order to obtain sufficient protein to enable the systematic study of the precise biochemical mechanism of (+)-pinoresinol/(+)-lariciresinol reductase at a future date.

Examination of the six putative (+)-pinoresinol/(+)-lariciresinol reductase clones revealed that one, plr-Fi1 (SEQ ID NO:47), was in frame with the α-complementation particle of β-galactosidase in pBluescript. This was fortuitous, since it potentially provided a facile means to express the fully functional fusion protein, and hence to provide proof that the cloned sequence was correct.

Purified plasmid DNA from plr-Fi1 (SEQ ID NO:47) was transformed into NovaBlue cells according to Novagen's instructions. Transformed cells (5 ml cultures) were grown at 37° C. with shaking (225 rpm) to mid log phase ($OD_{600}$= 0.5) in LB medium (Sambrook, J., *Molecular Cloning: A Laboratory Manual*, 3 volumes, 3rd Ed., Cold Spring Harbor Laboratory, Cold Spring Harbor, N.Y. (1994)) supplemented with 12.5 µg ml$^{-1}$ tetracycline and 50 µg ml$^{-1}$ ampicillin. IPTG (isopropyl β-D-thioglucopyranoside) was then added to a final concentration of 10 mM, and the cells were allowed to grow for 2 h. Cells were collected by centrifugation and resuspended in 500 µl (per 5 ml culture tube) buffer (20 mM Tris-HCl, pH 8.0, 5 mM dithiothreitol). Lysozyme (5 µl of 0.1 mg ml$^{-1}$, Research Organics, Inc.) was next added and following incubation for 10 min, the cells were lysed by sonication (3×15 s). After centrifugation at 14,000×g at 4° C. for 10 min, the supernatant was removed and assayed for (+)-pinoresinol/(+)-lariciresinol reductase activity (210 µl supernatant per assay) as described in Example 8.

Catalytic activity was established by incubating cell-free extracts for 2 h at 30° C. with (±)-pinoresinols (0.4 mM) and [4R-$^3$H]NADPH (0.8 mM) under standard conditions. Following incubation, unlabeled (±)-lariciresinols and (±)-secoisolariciresinols were added as radiochemical carriers, with each lignan isolated by reversed-phase HPLC. Controls included assays of a pinoresinol/lariciresinol reductase cDNA which contains an out-of-frame cDNA insert, with all assay components, as well as plr-Fi1 (SEQ ID NO:47) and an out-of-frame pinoresinol/lariciresinol reductase cDNA with no substrate except [4R-$^3$H]NADPH. Separation of products and chiral identification were performed by HPLC as previously described (Chu, A., et al., *J. Biol. Chem.* 268:27026–27033 (1993)).

Subsequent chiral HPLC analysis revealed that both (+)-lariciresinol and (−)-secoisolariciresinol, but not the corresponding antipodes, were radiolabeled (total activity: 54 nmol h$^{-1}$ mg$^{-1}$). By contrast, no catalytic activity was detected either in the absence of (±)-pinoresinols, or when control cells were used which contained a plasmid in which the cDNA insert was not in-frame with the β-galactosidase gene. Thus, the heterologously expressed (+)-pinoresinol/(+)-lariciresinol reductase and the plant protein function in precisely the same enantiospecific manner.

EXAMPLE 13

Sequence and Homology Analysis of the cDNA Insert of Clone plr-Fi1 (SEQ ID NO:47) Encoding (+)-pinoresinol/(+)-lariciresinol reductase Sequence Analysis. The full length sequence of the cloned (+)-pinoresinol/(+)-lariciresinol reductase plr-Fi1 (SEQ ID NO:47) contained all of the peptide sequences determined by Edman degradation of digest fragments.

The single ORF predicts a polypeptide of 312 amino acids (SEQ ID NO:48) with a calculated molecular mass of 34.9 kDa, in close agreement with the value (~35 or ~36 kDa) estimated previously by SDS-PAGE for the two isoforms of (+)-pinoresinol/(+)-lariciresinol reductase. An equal number of acidic and basic residues are also present, with a theoretical isoelectric point (pI) of 7.09, in contrast to that experimentally obtained by chromatofocussing (pI~5.7).

The amino acid composition reveals seven methionine residues. Interestingly, the N-terminus of the plant-purified enzyme lacks the initial methionine, this being the most common post-translational protein modification known. Consequently, the first methionine in the cDNA can be considered to be the site of translational initiation. The sequence analysis also reveals a possible N-glycosylation site at residue 215 (although no secretory targeting signal is present), and seven possible protein phosphorylation sites at residues 50 and 228 (protein kinase C-type), residues 228, 250, 302 and 303 (casein kinase II-type ) and residue 301 (tyrosine kinase type).

Regions of the pinoresinol/lariciresinol polypeptide chain (SEQ ID NO:48) were also identified that contained conserved sequences associated with NADPH binding (Jörnvall, H., in *Dehydrogenases Requiring Nicotinamide Coenzymes* (Jeffery, J., ed) pp. 126–148, Birkhäuser Verlag, Basel (1980); Branden, C., and Tooze, J., *Introduction to Protein Structure*, pp. 141–159, Garland Publishing, Inc., New York and London (1991); Wierenga, R. K. et al.,*J. Mol. Biol.* 187:101–108 (1986)). There is a limited number of invariant amino acids in the sequences of different reductases which are viewed as indicative of NADPH binding sites. These include three conserved glycine residues with the sequence G-X-G-X-X-G (SEQ ID NO:76), where X is any residue, and six conserved hydrophobic residues. The glycine-rich region is considered to play a central role in positioning the NADPH in its correct conformation. In this regard, a comparison of the N-terminal region of (+)-pinoresinol/(+)-lariciresinol reductase with that of the conserved, NADPH-binding regions of *Drosophila melanogaster* alcohol dehydrogenase (Branden, C., and Tooze, J., *Introduction to Protein Structure*, pp. 141–159, Garland Publishing, Inc., New York and London (1991)), *Pinus taeda* cinnamyl alcohol dehydrogenase (MacKay J. J. et al., *Mol. Gen. Genet.* 247:537–545 (1995)), dogfish muscle lactate dehydrogenase (Branden, C., and Tooze, J., *Introduction to Protein Structure*, pp. 141–159, Garland Publishing, Inc., New York and London (1991)) and human erythrocyte glutathione reductase (Branden, C., and Tooze, J., Introduction to Protein Structure, pp. 141–159, Garland Publishing, Inc., New York and London (1991)), revealed some interesting parallels. The invariant glycine residues are aligned in every case, as are four of the six hydrophobic residues required for the correct packaging in the formation of the domain. Hence, the NADPH-binding site of (+)-pinoresinol/(+)-lariciresinol reductase isoforms is localized close to the N-terminus.

Homology Analysis: Comparison to Isoflavone Reductase. A BLAST search (Altschul, S. F, et al., *J. Mol. Biol.* 215:403–410 (1990)) was conducted with the translated amino acid sequence of (+)-pinoresinol/(+)-lariciresinol reductase (SEQ ID NO:48) against the non-redundant peptide database at the National Center for Biotechnology Information. Significant homology was noted for (+)-pinoresinol/(+)-lariciresinol reductase with various isoflavone reductases from the legumes, Cicer arietinum (Tiemann, K., et al., *Eur. J. Biochem.* 200:751–757 (1991)) (63.5% similarity, 44.4% identity), *Medicago sativa* (Paiva, N. L., et al., *Plant Mol. Biol.* 17:653–667 (1991)) (62.6% similarity, 42.0% identity) and *Pisum sativum* (Paiva, N. L., et al.,*Arch. Biochem. Biophys.* 312:501–510 (1994)) (61.6% similarity, 41.3% identity). This observation is of considerable interest since isoflavonoids are formed via a related branch of phenylpropanoid-acetate pathway metabolism. Specifically, isoflavone reductases catalyze the reduction of α,β-unsaturated ketones during isoflavonoid formation. For example, the *Medicago sativa* L. isoflavone reductase catalyzes the stereospecific conversion of 2'-hydroxyformononetin to (3R)-vestitone in the biosynthesis of the phytoalexin, (−)-medicarpin (Paiva, N. L. et al., *Plant Mol. Biol.* 17:653–667 (1991)). This sequence similarity may be significant given that both lignans and isoflavonoids are offshoots of general phenylpropanoid metabolism, with comparable plant defense functions and pharmacological roles, e.g., as "phytoestrogens". Consequently, since both reductases catalyze very similar reactions, it is tempting to speculate that the isoflavone reductases may have evolved from (+)-pinoresinol/(+)-lariciresinol reductase. This is considered likely since the lignans are present in the pteridophytes, hornworts, gymnosperms and angiosperms; hence their pathways apparently evolved prior to the isoflavonoids (Gang et al., In *Phy-* tochemicals for Pest Control, Hedin et al., eds, ACS Symposium Series, Washington D.C., 658:58–59 (1997)).

Comparable homology was also observed with putative isoflavone reductase "homologs" from *Arabidopsis thaliana* (Babiychuk, E., et al., Direct Submission (May 25, 1995) to the EMBL/GenBank/DDBJ databases (1995)) (65.9% similarity, 50.8% identity), *Nicotiana tabacum* (Hibi, N., et al., *Plant Cell* 6:723–735 (1994)) (64.6% similarity, 47.2% identity), *Solanum tuberosum* (van Eldik, G. J., et al., (1995) Direct submission (Oct. 6, 1995) to the EMBL/GenBank/ DDBJ databases) (65.5% similarity, 47.7% identity) *Zea mays* (Petrucco, S., et al., *Plant Cell* 8:69–80 (1996)) (61.6% similarity, 44.9% identity) and especially *Lupinus albus* (Attuci, S., et al., Personal communication and direction submission (Jun. 6, 1996) to the EMBL/Genbank/DDBJ databases (1996)) (85.9% similarity, 66.2% identity).

By contrast, homology with other NADPH-dependent reductases was significantly lower: for example, dihydroflavonol reductases from *Petunia hybrida* (Beld, M. et al., *Plant Mol. Biol.* 13:491–502 (1989)) (43.2% similarity, 21.5% identity) and *Hordeum vulgare* (Kristiansen, K. N., and Rhode, W., *Mol. Gen. Genet.* 230:49–59 (1991)) (46.2% similarity, 21.1% identity), chalcone reductase from *Medicago sativa* (Ballance, G. M. and Dixon, R. A., *Plant Physiol.* 107:1027–1028 (1995)) (39.5% similarity, 15.8% identity), chalcone reductase "homolog" from *Sesbania rostrata* (Goormachtig, S., et al., (1995) Direct Submission (Mar. 13, 1995) to the EMBL/GenBank/DDBJ databases) (47.6% similarity, 24.1% identity), cholesterol dehydrogenase from *Nocardia* sp. (Horinouchi, S., et al., *Appl. Environ. Microbiol.* 57:1386–1393 (1991)) (46.6% similarity, 21.0% identity) and 3-β-hydroxy-5-ene steroid dehydrogenase from *Rattus norvegicus* (Zhao, H.-F., et al., *Journal Endocrinology* 127:3237–3239 (1990)) (43.5% similarity, 20.6% identity).

Thus, sequence analysis establishes significant homology between (+)-pinoresinol/(+)-lariciresinol reductase, isoflavone reductases and putative isoflavone reductase "homologs" which do not possess isoflavone reductase activity.

EXAMPLE 14 cDNA Cloning of *Thuja plicata* (–)-Pinoresinol/(–)-Lariciresinol Reductases

Plant Materials. Western red cedar plants (*Thuja plicata*) were maintained in Washington State University greenhouse facilities.

Materials. All solvents and chemicals used were reagent or HPLC grade. Taq thermostable DNA polymerase and restriction enzymes (SacI and XbaI) were obtained from Promega. pT7Blue T-vector and competent NovaBlue cells were purchased from Novagen and radiolabeled nucleotide ([α-$^{32}$P]dCTP) was purchased from DuPont NEN.

Oligonucleotide primers for polymerase chain reaction (PCR) and sequencing were synthesized by Gibco BRL Life Technologies. GENECLEAN II® kits (BIO 101 Inc.) were used for purification of PCR fragments, with the gel-purified DNA concentrations determined by comparison to a low DNA mass ladder (Gibco BRL) in 1.3% agarose gels.

Instrumentation. UV (including RNA and DNA determinations at $OD_{260}$) spectra were recorded on a Lambda 6 UV/VIS spectrophotometer. A Temptronic II thermocycler (Thermolyne) was used for all PCR amplifications. Purification of plasmid DNA for sequencing employed a QIAwell Plus plasmid purification system (Qiagen) followed by PEG precipitation (Sambrook, J., et al., *Molecular Cloning. A Laboratory Manual*, 3 volumes, 3rd Ed., Cold Spring Harbor Laboratory, Cold Spring Harbor, N.Y. (1994)) or Wizard® Plus SV Minipreps DNA Purification System (Promega), with DNA sequences determined using an Applied Biosystems Model 373A automated sequencer.

*Thuja plicata* cDNA Library Synthesis. Total RNA (6.7 μg/g fresh weight) was obtained from young green leaves (including stems) of greenhouse-grown western red cedar plants (*Thuja plicata*) according to the method of Lewinsohn et al (Lewinsohn, E., et al., *Plant Mol. Biol. Rep.* 12:20–25 (1994)). A *T. plicata* cDNA library was constructed using 3 μg of purified poly(A)+mRNA (Oligotex-dT™ Suspension, Qiagen) with the ZAP-cDNA® synthesis kit, the Uni ZAP™ XR vector, and the Gigapack® II Gold packaging extract (Stratagene), with a titer of 1.2×10$^5$ pfu for the primary library. The amplified library (7.1×10$^8$ pfu /ml; 28 ml total) was used for screening (Sambrook, J., et al., *Molecular Cloning: A Laboratory Manual*, 3 volumes, 3rd Ed., Cold Spring Harbor Laboratory, Cold Spring Harbor, N.Y. (1994)).

*T. plicata* (–)-Pinoresinol/(–)-Lariciresinol Reductase cDNA Synthesis. *T. plicata* (–)-pinoresinol/(–)-lariciresinol reductase cDNA was obtained from mRNA by a reverse transcription-polymerase chain reaction (RT-PCR) strategy (Sambrook, J., et al., *Molecular Cloning: A Laboratory Manual*, 3 volumes, 3rd Ed., Cold Spring Harbor Laboratory, Cold Spring Harbor, N.Y. (1994)). First-strand cDNA was synthesized from the purified mRNA previously used for the synthesis of the *T. plicata* cDNA library, described above. Purified mRNA (150 ng) was mixed with linker-primer (1.4 μg) from ZAP-cDNA® synthesis kit (Stratagene), heated to 70° C. for 10 min, and quickly chilled on ice. The mixture of denatured mRNA template and linker-primer was then mixed with First Strand Buffer (Life Technologies), 10 mM DTT, 0.5 mM each dNTP, and 200 units of Super Script™II (Life Technologies) in a final volume of 20 μl. The reaction was carried out at 42° C. for 50 min and then stopped by heating (70° C., 15 min). *E. coli* RNase H (1.5 units, 1 μl) was added to the solution and incubated at 37° C. for 20 min.

The first-strand reaction (2 μl) was next used as the template in 100-μl PCR reactions (10 mM Tris-HCl, pH 9.0, 50 mM KCl, 0.1% Triton X-100, 1.5 mM MgCl$_2$, 0.2 mM each dNTP, and 5 units of Taq DNA polymerase) with primer CR6-NT (5'GCACATAAGAGTATGGATAAG3') (SEQ ID NO:60) (10 pmol) and primer XhoI-Poly(dT) (5'GTCTCGAGTTTTTTTTTTTTTTTTT3')(SEQ ID NO:59) (10 pmol). PCR amplification was carried out in a thermocycler as described in (Dinkova-Kostova, A. T., et al., *J. Biol. Chem.* 271:29473–29482 (1996)) except for the annealing temperature at 52° C. PCR products were resolved in 1.3% agarose gels, where at least two bands possessing the expected length (about 1,200-bp) were observed. The bands were extracted from the gel. The gel-purified PCR products (56 ng) were then ligated into the pT7Blue T-vector (50 ng) and transformed into competent NovaBlue cells, according to Novagen's instructions.

The size and orientation of the inserted cDNAs were determined using the rapid boiling lysis and PCR technique, following the manufacturer's (Novagen's) instructions, with the following primer combinations: R20-mer (SEQ ID NO:74) with U19-mer (SEQ ID NO:75); R20-mer (SEQ ID NO:74) with CR6-NT (SEQ ID NO:60); U19-mer (SEQ ID NO:75) with CR6-NT (SEQ ID NO:60). The CR6-NT primer end of the inserted DNAs was located next to the U19-mer primer site of the T-vector. The T-vectors containing the inserted cDNAs were purified with Wizard® Plus SV Minipreps DNA Purification System. Five inserted cDNAs were completely sequenced using overlapping sequencing primers and were shown to be identical except that polyadenylation sites were different. Therefore, the longest cDNA, designated plr-Tp1, (SEQ ID NO:61) was used for detection of enzyme activity using the pBluescript expression system.

Sequence Analysis—DNA and amino acid sequence analyses were performed using the Unix-based GCG Wisconsin Package (Program Manual for the Wisconsin Package, Version 8, September 1994, Genetics Computer Group, 575 Science Drives Madison, Wisconsin, USA 53711 (1996); Rice, P., Program Manual for the EGCG Package, Peter Rice, The Sanger Centre, Hinxton Hall, Cambridge, CB10 1Rq, England) and the ExPASy World Wide Web molecular biology server (Geneva University Hospital and University of Geneva, Geneva, Switzerland).

EXAMPLE 15 cDNA Cloning and Expression of *Thuja plicata* (+)-Pinoresinol/(+)-Lariciresinol Reductase

*T. plicata* (+)-Pinoresinol/(+)-Lariciresinol Reductase cDNA cloning. After plr-Tp1 (SEQ ID NO:61) was cloned and sequenced, the full-length clone was used to screen the *T. plicata* cDNA library as described in Example 11, except that the entire plr-Tp1 cDNA insert (SEQ ID NO:61) was used as a probe. Several positive clones were sequenced, revealing one new, unique cDNA which was called plr-Tp2 (SEQ ID NO:63). This cDNA encodes a reductase (SEQ ID NO:64) with high sequence similarity to plr-Tp1 (SEQ ID NO:62) (~81% similarity at the amino acid level), but with substrate specificity properties identical to the original *Forsythia intermedia* reductase, as described below.

Enzyme Assays. Pinoresinol and lariciresinol reductase activities were assayed by monitoring the formation of [$^3$H]lariciresinol and [$^3$H]secoisolariciresinol as set forth in Example 8, with the following modifications. Briefly, each assay for pinoresinol reductase activity consisted of (±)-pinoresinols (5 mM in MeOH, 20 μl) and the enzyme preparation (i.e., total protein extract from *E. coli*, 210 μl). The enzymatic reaction was initiated by addition of [4R-$^3$H]NADPH (10 mM, 6.79 kBq/mmol in distilled H$_2$O, 20 μl). After 3 hour incubation at 30° C. with shaking, the assay mixture was extracted with EtOAc (500 μl) containing (±)-lariciresinols (20 μg) and (±)-secoisolariciresinols (20 μg) as radiochemical carriers. After centrifugation (13,800× g, 5 min), the EtOAc solubles were removed and the extraction procedure was repeated. For each assay, the EtOAc solubles were combined with an aliquot (100 μl) removed for determination of its radioactivity using liquid scintillation counting. The remainder of the combined EtOAc solubles was evaporated to dryness in vacuo, reconstituted in MeOH/H$_2$O (30:70, 100 μl) and subjected to reversed phase and chiral column HPLC.

Lariciresinol reductase activity was assayed by monitoring the formation of (+)-[$^3$H]secoisolariciresinol. These assays were carried out exactly as described above, except that (±)-lariciresinols (5 mM in MeOH, 20 μl) were used as substrates, with (±)-secoisolariciresinols (20 μg) added as radiochemical carriers.

Expression of plr-Tp1 (SEQ ID NO:61) in *E. coli*—In order for the open reading frame (ORF) of plr-Tp1 (SEQ ID NO:61) to be in frame with the β-galactosidase gene α-complementation particle in pBluescript SK(−), plr-Tp1 (SEQ ID NO:61) was excised out of pT7Blue T-vector with SacI and XbaI, gel-purified, and then ligated into the expression vector digested with these same enzymes. This plasmid, pPCR-Tp1, was transformed into NovaBlue cells according to Novagen's instructions. The transformed cells (5-ml cultures) were grown at 37° C. in LB medium (Sambrook, J., et al., *Molecular Cloning: A Laboratory Manual*, 3 volumes, 3rd Ed., Cold Spring Harbor Laboratory, Cold Spring Harbor, N.Y. (1994)) supplemented with 50 μg ml$^{-1}$ carbenicillin with shaking (225 rpm) to mid log phase ($A_{600}$=0.5–0.7). The cells were next collected by centrifugation (1000 × g, 10 min) and resuspended in fresh LB medium supplemented with 10 mM IPTG (isopropyl β-D-thioglucopyranoside) and 50 μg ml$^{-1}$ carbenicillin to an absorbance of 0.6 (at 600 nm). The cells, allowed to grow overnight, were collected by centrifugation and resuspended in 500–700 μl of (per 5 ml culture tube) of buffer (50 mM Tris-HCl, pH 7.5, 2 mM EDTA, and 5 mM DTT). Next, the cells were lysed by sonication (5×45 s) and after centrifugation (17500×g, 4° C., 10 min) the supernatant was removed and assayed for (−)-pinoresinol/(−)-lariciresinol reductase activity as described above. Controls included assays of pBluescript (SK(−)) without insert DNA (as negative control) or with pPLR-Fi1 (SEQ ID NO:47) (cDNA of authentic *F. intermedia* (+)-pinoresinol/(+)-lariciresinol reductase in frame) as stereospecific control, as well as pPLR-Tp1 (SEQ ID NO:61) with no substrate except (4R)-$^3$HNADPH.

The results showed that both (−)-lariciresinol and (+)-secoisolariciresinol were radiolabeled and that no incorporation of radioactivity was found in (−)-secoisolariciresinol. However, accumulation of radiolabel into (+)-lariciresinol was also observed, although at a much slower rate than that observed for (−)-lariciresinol. These results indicate that plr-Tp1(SEQ ID NO:62) can use both (−)-pinoresinol and (+)-pinoresinol as substrates, with the former being converted via (−)-lariciresinol completely to (+)-secoisolariciresinol, and the latter being converted much more slowly to (+)-lariciresinol, but not further to (−)-secoisolariciresinol.

Expression of plr-Tp2 (SEQ ID NO:63) in *E. coli*. The plr-Tp2 cDNA (SEQ ID NO:63) was found to be in frame with the β-galactosidase gene α-complementation particle in pBluescript SK(−). When evaluated for activity and substrate specificity, as described above, plr-Tp2 (SEQ ID NO:64) was found to possess the same substrate specificity and product formation as the original *Forsythia intermedia* reductase (Dinkova-Kostova, A. T., et al., *J. Biol. Chem.* 271:29473–29482 (1996)) except that a small amount of (−)-lariciresinol was also detected. This is interesting, because plr-Tp2 (SEQ ID NO:64) has a higher sequence similarity to plr-Tp1 (SEQ ID NO:62) than it does to the Forsythia reductase.

All the above observations were confirmed using deutero-labeled substrates (±)-[9,9'-$^2$H$_2$, OC$^2$H$_3$]pinoresinols with isolation of the corresponding lignans; each was then subjected to chiral column chromatography and HPLC-mass spectral analysis to confirm these findings.

EXAMPLE 16

Cloning of Additional Pinoresinol/Lariciresinol Reductases from *Thuja plicata* and *Tsuga heterophylla*

Two additional pinoresinol/lariciresinol reductases were cloned from a *Thuja plicata* young stem cDNA library as described in Example 15 for the cloning of plr-Tp2 (SEQ ID NO:63). The two additional pinoresinol/lariciresinol reductases were designated plr-Tp3 (SEQ ID NO:65) and plr-Tp4 (SEQ ID NO:67).

Two additional pinoresinol/lariciresinol reductases were cloned from a *Tsuga heterophylla* young stem cDNA library as described in Example 15 for the cloning of plr-Tp2 (SEQ ID NO:63). The two additional pinoresinol/lariciresinol reductases from *Tsuga heterophylla* were designated plr-Tp3 (SEQ ID NO:69) and plr-Tp4 (SEQ ID NO:71).

EXAMPLE 17

Cloning Additional Dirigent Protein cDNAs from *Thuja plicata*

An additional cDNA, called Tp9 (SEQ ID NO:77), encoding a dirigent protein (SEQ ID NO:78) was cloned from mRNA extracted from Western red cedar (*Thuja plicata*) in the following manner. First strand cDNA was synthesized from Western red cedar cambium RNA using primer CS1-895N (5'-AGAGTGGAGATTGTTGTCAAGAGTA-3') (SEQ ID NO:79) derived from highly conserved sequence motifs found in other Western red cedar dirigent protein isoforms. SuperScript™II RNase H Reverse Transcriptase (Life Technologies, Rockville, Md.) was used to synthesize first strand cDNA following the manufacturer's protocol. Then the 3' end of the first strand cDNA was tailed with dATP using terminal transferase (Boehringer Mannheim, Indianapolis, Ind.). The tailed cDNA was amplified via Expand™ High Fidelity PCR system (Boehringer Mannheim, Indianapolis, Ind.) using the following primers: first round of PCR utilized the oligo dT-anchor primer (5'-GACCACGCGTATCGATGTCGACTTTTTTTTTTT-TTTTV-3')(SEQ ID NO:80)(wherein "V" at the 3'-end of the oligo-dT anchor primer represents A, C or G) as the 5'-sense primer, and primer CS1-895N (SEQ ID NO:79) as the 3'-antisense primer; second round of PCR utilized PCR anchor primer (5'-GACCACGCGTATCGATGTCGAC-3') (SEQ ID NO:81) as the 5'-sense primer, and primer CS1-874N (5'-AGTAATAGGATCATCAAACAC-3')(SEQ ID NO:82) as the 3'-antisense primer. The PCR conditions were as follows: first cycle, 94° C. for 1 minute; second thru twenty sixth cycles, 94° C. for 30 seconds, then 56° C. for 45 seconds, then 72° C. for two minutes; the twenty seventh cycle, 72° C. for seven minutes. The resulting PCR product (that corresponded to nucleic acid residues 1–253 of SEQ ID NO:77) was gel purified and cloned using a TA cloning kit (Invitrogen, Carlsbad, Calif.), and sequenced to identify the dirigent protein gene.

To complete the 3-region of the PCR product (that corresponded to nucleic acid residues 1–253 of SEQ ID NO:77), the oligo dT-anchor primer (SEQ ID NO:80) was used to generate first strand eDNA. The full length Tp9 cDNA (SEQ ID NO:77) was cloned using the following PCR primers: the first round of PCR utilized primer RT-CS-C1(–)50s (5'-CCAACTTCTTTCTCTACTTCAGAA-3') (SEQ ID NO:83) as the 5'-sense primer, and the oligo dT anchor primer (SEQ ID NO:80) as the 3'-antisense primer; the second round of PCR utilized primer RT-CS-C1(–)31s (5'-CAGAACCCTGTTTTCTGATTTATT-3')(SEQ ID NO:84) as the 5'-sense primer, and the PCR anchor primer (SEQ ID NO:81) as the 3'-antisense primer; and the third round of PCR utilized primer RT-CS-C1(–)13s (5'-TTTATTTTTGCACAATGGCAATCT-3')(SEQ ID NO:85) as the 5'-sense primer, and the PCR anchor primer (SEQ ID NO:81) as the 3'-antisense primer. The reaction conditions for each round of PCR were as follows: first cycle, 94° C. for 1 minute; second thru twenty sixth cycles, 94° C. for 30 seconds, then 56° C. for 45 seconds, then 72° C. for two minutes; the twenty seventh cycle, 72° C. for seven minutes. The full length Tp9 cDNA sequence (SEQ ID NO:77) was confirmed by direct PCR amplification of the Tp9 gene using Expand™ High Fidelity PCR system.

EXAMPLE 18

Completing the 5'-Ends of Dirigent Protein Clones Tp3 (SEQ ID NO:24) and Tp4 (SEQ ID NO:26) from *Thuja plicata*

The nucleotide sequences of the *Thuja plicata* dirigent protein clones Tp3 (SEQ ID NO:24) and Tp4 (SEQ ID NO:26) were incomplete at their 5' ends. Genomic DNA analysis indicated that Western red cedar dirigent protein genes do not contain introns. Consequently, it was possible to complete the partial cDNA sequences of Tp3 (SEQ ID NO:24) and Tp4 (SEQ ID NO:26) by utilizing the Advantage Genomic PCR Kit (Clonetech, Palo Alto, Calif.) following the manufacturer's instructions.

The cDNA clone (SEQ ID NO:86) encoding a full-length, Tp3 dirigent protein (SEQ ID NO:87) was cloned by PCR using *Thuja plicata* genomic DNA as template and the following primers: the first round of PCR utilized primer AP1 (5'-GTAATACGACTCACTATAGGGC-3')(SEQ ID NO:88) as the 5'-sense primer, and primer TpS4-213n (5'-AGATTAGCTCCTTGAGGGGCTGAAACAA-3')(SEQ ID NO:89) as the 3'-antisense primer; the second round of PCR utilized primer AP2 (5'-ACTATAGGGCACGCGTGGT-3') (SEQ ID NO:90) as the 5'-sense primer, and primer TpS4-199n (5'-AGGGGCTGAAACAAGTGCAGATGTTGCA-3')(SEQ ID NO:91) as the 3'-antisense primer; the third round of PCR utilized primer AP2 (SEQ ID NO:90) as the 5'-sense primer, and primer TpS4-188n (5'-CAAGTGTGCAGATGTTGCATTCTCTGCAT-3')(SEQ ID NO:92) as the 3'-antisense primer.

The cDNA clone (SEQ ID NO:93) encoding a full-length, Tp4 dirigent protein (SEQ ID NO:94) was cloned by PCR using *Thuja plicata* genomic DNA as template and the following primers: the first round of PCR utilized primer AP1 (SEQ ID NO:88) as the 5'-sense primer, and primer CS10-826N (5'-CAGTCATAATGGTGAGATTGGCTCCCT-3')(SEQ ID NO:95) as the 3'-antisense primer; the second round of PCR utilized primer AP2 (SEQ ID NO:90) as the 5'-sense primer, and primer CS10-814N (5'-TGAGATTGGCTCCCTCAGGGGCTGCAA-3')(SEQ ID NO:96) as the 3'-antisense primer; the third round of PCR utilized primer AP2 (SEQ ID NO:90) as the 5'-sense primer, and primer CS10-795N (5'-GGCTGCAACAAGTGCAGATGTTGCATT-3')(SEQ ID NO:97) as the 3'-antisense primer.

The PCR reaction conditions for cloning the full-length, Tp3 and Tp4 dirigent protein clones having the nucleic acid sequences set forth in SEQ ID NO:86 and SEQ ID NO:93 were identical and were as follows: the first round of PCR included primary PCR consisting of a first cycle at 94° C. for 1 minute and second thru eighth cycles at 94° C. for 25 seconds, then 72° C. for 12 minutes, followed by secondary PCR consisting of a first cycle at 94° C. for 1 minute, second thru thirty three cycles at 94° C. for 20 seconds, then 72° C. for 6 minutes, and finally a thirty fourth cycle at 68° C. for 12 minutes; the second and third rounds of PCR each consisted of a first cycle at 94° C. for one minute, then second thru twenty sixth cycles at 94° C. for 30 seconds, then 60° C. for 45 seconds, then 72° C. for two minutes, then a twenty seventh cycle at 72° C. for seven minutes.

The ability to complete the full-length Tp3 (SEQ ID NO:86) and Tp4 (SEQ ID NO:93) sequences from genomic DNA overcomes the difficulty in completing a full-length sequence from a cDNA pool. Incomplete synthesis of the first strand cDNA of target cDNAs often occurs due to instability of RNA or secondary structure of RNA, and results in the incomplete synthesis of the first strand cDNA.

EXAMPLE 19

Cloning a Dirigent Protein cDNA from *Eucommia ulmoides*

A cDNA (SEQ ID NO:98) encoding a dirigent protein (SEQ ID NO:99) was isolated from *Eucommia ulmoides* utilizing the strategy used for the cloning of the Tp9 cDNA (SEQ ID NO:77) of Western red cedar. First strand cDNA was synthesized with SuperScript™II RNase H Reverse Transcriptase from *E. ulmoides* leaf RNA using the oligo dT anchor primer (SEQ ID NO:80). From the first strand cDNA, a 300 bp cDNA fragment (corresponding to nucleotides 152 thru 452 of SEQ ID NO:98) was amplified using N-terminal primer 5'-GARTTGGTGTTCTATTTCCACGACATMC-3' (SEQ ID NO:100)(wherein "R" represents A or G and "M" represents A or C) and C-terminal primer 5'-CAAAGTGGCAACCCCTGTCGCCATG-3' (SEQ ID NO:101), derived from a highly conserved sequence among the other dirigent protein isoforms. The PCR reaction conditions were as follows: first cycle, 94° C. for 1min, second thru twenty sixth cycles, 94° C. for 30 seconds, then 50° C. for 45 seconds, then 72° C. for 2 min, and a twenty seventh cycle at 72° C. for 7 min.

The PCR product was gel purified and cloned using a TA cloning kit. Then this fragment was used to design gene specific primers to clone a complete sequence. In order to clone the missing 5' region, first strand cDNA was synthesized with SuperScript™II RNase H Reverse Transcriptase using the gene specific, 3'-antisense Sp2 primer (5'-CCCCCGTTCCTCCAACCACCGG-3')(SEQ ID NO:102), and the 3' end of the first strand cDNA was tailed with dATP using terminal transferase. The tailed cDNA was amplified via Expand TM High Fidelity PCR system using the oligo dT-anchor primer (SEQ ID NO:80) and the Sp2 primer (SEQ ID NO:102). Then the second round of PCR was conducted using the PCR-anchor primer (SEQ ID NO:81) and the Sp2 primer (SEQ ID NO:102). The PCR product was gel purified, and cloned using the TA cloning kit. The resulting, partial cDNA corresponded to nucleic acid residues 1 thru 413 of SEQ ID NO:98. The PCR reaction conditions were the same for the first and second rounds of PCR and were as follows: first cycle, 94° C. for 1 min, second thru twenty sixth cycles, 94° C. for 30 seconds, then 50° C. for 45 seconds, then 72° C. for 2 min, and a twenty seventh cycle at72° C. for 7 min.

To obtain the missing 3' sequence, the oligo dT-anchor primer (SEQ ID NO:80) was used to generate first strand cDNA. The full length Eucommia cDNA (SEQ ID NO:98) was amplified through two consecutive rounds of PCR using a set of nested primers: 5'-sense primers SpN1 (5'-GGCCCATGCGGTTAAGCATATTCTCC-3')(SEQ ID NO:103) and SpN2 (5'-CCTCTATAAAAACATAATTCTTTTCCCCC-3')(SEQ ID NO:104), and the primers having the nucleic acid sequences set forth in SEQ ID NO:80 and SEQ ID NO:81 as 3'-antisense primers. The reaction conditions for both the first and the second rounds of PCR were as follows: first cycle, 94° C. for 1 minute, second thru twenty sixth cycles, 94° C. for 30 seconds, then 60° C. for 45 seconds, then 72° C. for 2 minutes, a twenty seventh cycle at 72° C. for 7 minutes.

The PCR product was gel purified, and cloned using a TA cloning kit. The identity of the full length cDNA (SEQ ID NO:98) was confirmed by sequencing and by direct PCR amplification of the corresponding Eucommia dirigent protein gene.

EXAMPLE 20

Cloning a Dirigent Protein cDNA from *Schisandra chinensis*

A cDNA (SEQ ID NO:105), encoding a dirigent protein (SEQ ID NO:106) was cloned from mRNA extracted from *Schisandra chinensis* in the following manner. A cDNA library was made from *Schisandra chinensis* leaf and stem tissues. The cDNA library was probed for a homologous dirigent protein clone using the $^{32}$P-CTP-labelled *F. intermedia* dirigent protein gene (Psd-Fi1) (SEQ ID NO:12) as a probe. Three rounds of screening were utilized. For each screen, plaques were lifted onto nylon transfer membrane for 3 minutes, the transferred DNA was then fixed to the membrane by autoclaving for 3 minutes at 100° C., and debris were washed off the membranes with 2×SSC for 30 minutes at 37° C. Prehybridization solution consisted of 6×SSC, 5×Denhardt's reagent, and 0.5% SDS. 50 µl probe (SEQ ID NO:12) was made with T7 Quick-Prime Kit. 100 µl 5 mg/ml salmon sperm DNA and 850 µl deionized, distilled water were then added to the probe. Hybridization solution consisted of 6×SSC, 5×Denhardt's reagent, 0.5% SDS, and probe (SEQ ID NO:12).

For the primary screen, nylon membrane filters bearing plaques were prehybridized for seven and a half hours at 48–49° C. The filters were then hybridized overnight (approximately 17 hours) at 49° C. in the presence of 1.13×10$^7$ cpm radiolabelled probe (SEQ ID NO:12). After hybridization, the filters were washed with 4×SSC, 0.5% SDS, for 10 min, then with 2×SSC, 0.5% SDS, for 9 min at room temperature (from about 20° C. to about 24° C.), then with 2×SSC, 0.5% SDS, for 50 minutes, warming from room temperature (from about 20° C. to about 24° C.) to 49° C. Finally the filters were rinsed with 6×SSC briefly before being exposed to film for one and a half days.

For the secondary screen, nylon membrane filters bearing plaques were prehybridized for 8 hours at 49° C. The filters were then hybridized overnight (approximately 16 hours) at 49° C. in the presence of 3.9×10$^6$ cpm radiolabelled probe (SEQ ID NO:12). After hybridization, the filters were washed with 4×SSC, 0.5% SDS, at room temperature for 5–20 minutes, then rinsed briefly in 6×SSC before being exposed to film overnight.

For the tertiary screen, nylon membrane filters bearing plaques were prehybridized overnight at 45° C. The filters were then hybridized overnight (approximately 18 hours) at 45° C. in the presence of 1.2×10$^6$ cpm radiolabelled probe (SEQ ID NO:12). After hybridization, the filters were washed with 4×SSC, 0.5% SDS, for 10 minutes, then with 2×SSC, 0.5% SDS, for 2 minutes at room temperature (from about 20° C. to about 24° C.). Finally the filters were rinsed with 6×SSC briefly before being exposed to film for 4 days.

After three rounds of screening, one positive plaque was isolated. The cDNA from this plaque was subsequently excised and cloned into SOLR cells (Stratagene Cloning Systems, 11011 North Torrey Pines Road, La Jolla, Calif. 92037). Sequence analysis showed it to be a full-length clone, and homology analysis established it to be 51–72% identical and 63–80% similar to other known dirigent proteins at the amino acid level.

EXAMPLE 21

Cloning a Pinoresinol/Lariciresinol Reductase cDNA from *Linum usitatissimum*

A cDNA (SEQ ID NO:107), encoding a pinoresinol/lariciresinol reductase protein (SEQ ID NO:108), was cloned from mRNA extracted from *Linum usitatissimum* (Flax) in the following manner. Total RNA was obtained from two week old whorls (each containing 10 developing flax seeds) of green house grown *L. usitatissimum* plants. Poly(A)$^+$mRNA was purified using the Promega PolyATract® mRNA Isolation System. A *L. usitatissimum* seed cDNA library was constructed using 5 µg of purified mRNA with the Stratagene ZAP-cDNA® Synthesis Kit and the ZAP-cDNA® Gigapack® III Gold cloning kit, with a titer of $2.8 \times 10^5$ pfu (plaque forming units) for the primary library. Approximately 35 ml of liquid phage lysate from the amplified library ($2.8 \times 10^9$ pfu/ml) was used to obtain pure cDNA library DNA for PCR screening.

The following degenerate primers were designed based on N-terminal, C-terminal and internal regions of similarity found in the *Forsythia intermedia* and *Thuja plicata* (Western red cedar) pinoresinol/lariciresinol reductase clones: PLR4 forward primer (5'-CCITCIGAGTTCGGIATGGATCCI-3')(SEQ ID NO:109), and PLR6 reverse primer (5'-IGTATATTTIACTTCIGGGTA-3')(SEQ ID NO:110). Pure *L. usitatissimum* cDNA library DNA (~5 ng) was used as the template in 45 µl PCR reactions with various primer combinations. PCR amplification was carried out in an Amplitron® II thermocycler as follows: 5 cycles of 1 minute at 94° C., then 1 minute at 37° C., then 3 minutes at 72° C., followed by 25 cycles of 25 seconds at 94° C., then I minute at 48° C., and 2 minutes at 72° C.; with 10 minutes at 72° C. and an indefinite hold at 4° C. after the final cycle. PCR products were resolved in 1% agarose gels. Reactions producing single bands with an accurate size predicted by their respective primer combination were cloned using Invitrogen's Topo-TA cloning® Kit and sequenced. This round of PCR yielded a partial-length cDNA clone of about 600 bp (SEQ ID NO:111).

The partial length clone (SEQ ID NO:111) was used as a $^{32}$P-radiolabeled probe with the aim of isolating the full length sequence. 500,000 pfu of *L. usitatissimum* amplified cDNA library were plated, plaques were blotted onto Magna Nylon membrane circles, and the library was screened as follows. The blotted membranes were placed between two layers of Whatman 3MM Chr. Paper. cDNA library phage DNA was fixed to the membranes and denatured in one step by autoclaving for 4 min at 100° C. with fast exhaust. The membranes were washed for 30 min with gentle shaking at 37° C. in 6×SSC and 0.1% SDS, and prehybridized for 5 h with gentle shaking at 57° C. in preheated 6×SSC, 0.5% SDS, and 5×Denhardt's reagent (hybridization solution, 220 ml) in a crystallization dish (190×75 mm).

The $^{32}$P-radiolabeled probe (SEQ ID NO:111) was denatured (98° C. for 10 minutes), quickly cooled (on ice for 15 minutes), and added to a preheated hybridization solution (50 ml at 57° C.) in a crystallization dish (150×75 mm). The prehybridized membranes were next added to this dish, which was then covered with plastic wrap. Hybridization was performed for 17 h at 57° C. with gentle shaking. The membranes were washed in 4×SSC and 0.5% SDS (250 ml) for 5 min at room temperature, transferred to preheated 2×SSC and 0.5% SDS (250 ml), and incubated at 57° C. for 20 min with gentle shaking. After the membranes were removed from the dish and wrapped with plastic wrap, they were exposed to Kodak X-OMAT AR film for 24 h at −80° C. between intensifying screens. A larger cDNA clone (SEQ ID NO:112) was attained, but in comparison to *F. intermedia* cDNA plr-Fi1 (SEQ ID NO:47) it still lacked ~258 bp at the N-terminal.

To achieve a full length clone, gene specific primer 1 (5'-AACATTTCCGGCCTCTTTGATGGCCTCGAC-3') (SEQ ID NO:113) and gene specific primer 2 (5'-AAGGTAGATCATCAGATAATCTTTCATACG-3')(SEQ ID NO:114) were designed and used in combination with the Stratagene Uni-ZAP® XR vector T7 (5'-GTAATACGACTCACTATAGGGC-3')(SEQ ID NO:115) and T3 (5'-AATTAACCCTCACTAAAGGG-3')(SEQ ID NO:116) primers. A 936 bp gene (SEQ ID NO:107), containing identical sequence information from all previous truncated clones, displayed an ~74% similarity and ~61% identity to *F. intermedia* cDNA plr-Fi1 (SEQ ID NO:47) at the amino acid level.

EXAMPLE 22

Cloning a Pinoresinol/Lariciresinol Reductase cDNA from *Schisandra chinensis*

A cDNA (SEQ ID NO:117), encoding a pinoresinol/lariciresinol reductase protein (SEQ ID NO:118) was cloned from mRNA extracted from *Schisandra chinensis* in the following manner. Degenerate primers PLR4 (SEQ ID NO:109) and PLR6 (SEQ ID NO:110) were made from regions of high homology between known reductase clones, and these were used to screen a *Schisandra chinensis* leaf and stem tissue cDNA library using a PCR-guided strategy. The *Schisandra chinensis* leaf cDNA library was first used as a template under the following conditions: five cycles of 95° C. for 1 minute, 37° C. for 1 minute and 72° C. for 3 minutes, then 25 cycles of 94° C. for 25 minutes, 48° C. for 1 minute and 72° C. 2 minutes. No cDNA bands were found upon gel analysis of the resulting products which were then used as template for another round of PCR under the following conditions: five cycles of 95° C. for 1 minute, 37° C. 1 minute, 72° C. 3 minutes, then 25 cycles of 94° C. for 25 minutes, 48° C. for 1 minute, 72° C. for 2 minutes.

A 600 bp PCR product was obtained, which was then cloned into a TOPO-TA vector and partially sequenced to yield the sequence of SEQ ID NO:119. Sequence analysis showed it to be 55.7% identical and 67.0% similar to *F. intermedia* cDNA plr-Fi1 (SEQ ID NO:47) at the amino acid level. This PCR product (including the nucleic acid sequence set forth in SEQ ID NO:119) was then used to make a $^{32}$P-CTP probe, and the cDNA library was once again probed using three rounds of screening.

For the primary screen, cDNA library plaques were transferred onto nylon transfer membrane for 3 minutes, then fixed to the membranes by autoclaving for 3 minutes at 100° C. Debris was washed off membranes with 2×SSC for 30 minutes at 37° C., then the membranes were incubated in prehybridization solution consisting of 6×SSC, 5×Denhardt's reagent, and 0.5% SDS, for 6 hours at 48° C. The filters were then hybridized for 24 hours at 45° C. in hybridization solution (6×SSC, 5×Denhardt's reagent, 0.5% SDS), including 100 μl 5 mg/ml salmon sperm DNA, 850 μl ddH$_2$O and 9.6×10$^5$ cpm probe. The filters were then washed (at room temperature) with 4×SSC, 0.5% SDS, for 5 minutes, then with 2×SSC, 0.5% SDS, for 20 minutes, then rinsed briefly with 4×SSC and exposed to autoradiography film 5 days.

The secondary screen was conducted under the same conditions as the primary screen except that the filters were prehybridized for 24 hours at 48° C., then hybridized for 24 hours at 48° C. in the presence of 1.37×10$^6$ cpm probe. The filters were washed at room temperature with 4×SSC, 0.5% SDS, for 5 minutes then briefly rinsed in 6×SSC at room temperature and exposed to film overnight.

The tertiary screen was conducted under the same conditions as the primary screen except that the filters were prehybridized for 24 hours at 48° C., then hybridized for 37 hours at 48° C. in the presence of 2.2×10$^6$ cpm probe. The filters were washed at room temperature under the following conditions: 4×SSC, 0.5% SDS, for 5 minutes, then with 2×SSC, 0.5% SDS, for 5 minutes, rinsed briefly in 6×SSC and exposed to film overnight.

One positive plaque was identified and isolated after the foregoing three rounds of screening. The plaque was excised into a pBluescript plasmid, cloned into SOLR cells, and sequenced (SEQ ID NO:119). Sequence analysis showed this clone (SEQ ID NO:119) encoded a partial length reductase protein (SEQ ID NO:120) which was 57.4% identical and 78.7% similar to *F. intermedia* PLR at the peptide level. However, a one-base frame-shift mutation (deletion of an adenine at position 579) was present in the full-length clone (SEQ ID NO:119) which prevented expression of full-length protein.

This full-length clone (SEQ ID NO:119) was next used to make a $^{32}$P-dCTP probe, and the library was further screened in the following manner. For the primary screen, cDNA library plaques were transferred onto nylon transfer membrane for 3 minutes, then fixed to the membranes by autoclaving for 3 minutes at 100° C. Debris was washed off membranes with 2×SSC for 30 minutes at 37° C., then the membranes were incubated in prehybridization solution consisting of 6×SSC, 5×Denhardt's reagent, and 0.5% SDS, for 18 hours at 47° C. The filters were then hybridized for 24 hours at 47° C. in hybridization solution (6×SSC, 5×Denhardt's reagent, 0.5% SDS), including 100 μl 5 mg/ml salmon sperm DNA, 850 μl deionized, distilled H$_2$O and 9.3×10$^6$ cpm probe. The filters were then washed at room temperature with 4×SSC, 0.5% SDS, for 5–10 minutes, then rinsed briefly at room temperature with 6×SSC and exposed to autoradiography film overnight.

The secondary screen was conducted under the same conditions as the primary screen except that the filters were prehybridized for eight and a third hours at 45–47° C., then hybridized overnight at 40–47° C. in the presence of 7.5×10$^6$ cpm probe. The filters were washed with 4×SSC, 0.5% SDS, for 10 minutes, then with 2.5×SSC, 0.5% SDS for 10 minutes at room temperature, then washed with 2.5×SSC, 0.5% SDS, for 10 minutes with the temperature rising to 42° C. during that period, and finally rinsing in 6×SSC briefly at room temperature and exposed to film overnight.

The tertiary screen was conducted under the same conditions as the primary screen except that the filters were prehybridized for 11 hours at 47° C., then hybridized overnight (approximately 14 hours) at 47° C. in the presence of 1.8×10$^6$ cpm probe. The filters were washed at room temperature with 4×SSC, 0.5% SDS, for 10 minutes, then rinsed at room temperature in 6×SSC briefly and exposed to film for approximately 24 hours.

Two positive plaques were identified after the foregoing three rounds of screening. Each was excised, transformed into SOLR cells, and sequenced. Of these, one clone (SEQ ID NO:117) was a full-length reductase identical to the clone having the sequence set forth in SEQ ID NO:119, with the exception that it was in frame. The other clone was not full-length. The full-length reductase cDNA (SEQ ID NO:119) was cloned into a pBad-TOPO-TA expression vector.

Based on the characterization and sequence comparison of the foregoing pinoresinol/lariciresinol reductase cDNAs and proteins, presently preferred pinoresinol/lariciresinol reductase proteins of the invention utilize NADPH as a cofactor and include the conserved amino acid sequence domain Gly Xaa Gly Xaa Xaa Gly (SEQ ID NO:76).

EXAMPLE 23

Cloning Additional Nucleic Acid Molecules that Encode a Dirigent Protein

Additional nucleic acid molecules encoding a dirigent protein can be cloned utilizing a variety of strategies. In one approach, genomic DNA or cDNA can be amplified by PCR using the following primer pair: primer PS-6For 5'-KGTGTTYGAYGATCCYATTACYBTWGACAAC-3' (SEQ ID NO:120) and primer PS-2Rev 5'-TGRCTAMGTAWACTYCCTCTACAAATAAAG-3' (SEQ ID NO:121). The sequence of PCR reactions is set forth in Table 4 below. Representative PCR reaction conditions are as set forth in Table 6 below, except that primers PS-6For (SEQ ID NO:120) and PS-6Rev (SEQ ID NO:121) are utilized instead of primers PLR4 forward (SEQ ID NO:109) and PLR6 reverse (SEQ ID NO:110).

TABLE 4

| I | |
|---|---|
| Temp. (° C.) | Time |
| 94 | 1 min |
| 60 | 2 min |
| 72 | 3 min |
| 35 cycles | |
| 72 | 10 min |

The resulting nucleic acid molecule(s) can be used to screen a cDNA library or genomic DNA library to isolate a full-length, or substantially full-length, dirigent protein cDNA or gene. Representative library screening conditions are hybridization in 6×SSC, 5×Denhardt's, 0.5% SDS at 55–58° C. for 12 hours, followed by washing in 2×SSC, 0.5% SDS at 55–58° C. for 30 minutes. An optional further wash can be conducted in 1×SSC, 0.5% SDS at 55–58° C. for 30 minutes, followed, if so desired, by an additional, optional, wash in 0.5×SSC, 0.5% SDS at 55–58° C. for 30 minutes.

In another approach, genomic DNA molecules encoding a dirigent protein can be cloned by PCR utilizing either primer PS-6For (SEQ ID NO:120) or primer PS-2Rev (SEQ ID NO:121) and an adapter primer that is complementary to one strand of an oligonucleotide adapter ligated to the ends of the genomic DNA fragments that form the target population of nucleic acid molecules in the PCR reaction. Adapter molecules are well known to those of ordinary skill in the art and are described, for example, in Molecular Cloning, A Laboratory Manual (2$^{nd}$ edition), Sambrook et al (eds), Chapter 8, which chapter is incorporated herein by reference. Table 5 sets forth three, representative PCR cycling regimes that can be utilized in this aspect of the invention to clone genomic DNA molecules encoding a dirigent protein. Representative PCR reaction conditions are set forth in Table 6, except that primers PS-6For (SEQ ID NO:120) or primer PS-2Rev (SEQ ID NO:121) and an adapter primer are utilized instead of primers PLR4 forward (SEQ ID NO:109) and PLR6 reverse (SEQ ID NO:110).

TABLE 5

| Temp. (° C.) | Time |
|---|---|
| I | |
| 94 | 1 min |
| 60 | 2 min |
| 72 | 3 min |
| 35 cycles | |
| 72 | 10 min |
| II | |
| 94 | 20 sec |
| 72 | 3 min |
| 7 cycles | |
| 94 | 20 sec |
| 67 | 3 min |
| 32 cycles | |
| 67 | 7 min |
| III | |
| 94 | 15 sec |
| 72 | 12 min |
| 7 cycles | |
| 94 | 20 sec |
| 68 | 6 min |
| 32 cycles | |
| 67 | 6 min |

In yet another approach, nucleic acid molecules encoding a dirigent protein can be cloned by PCR utilizing genomic DNA or cDNA as template and pools of degenerate primers. Exemplary PCR cycling regimes useful in this aspect of the invention are those set forth as Program I in Table 5 above, except that the annealing temperature is 45° C. to 50° C. Representative PCR reaction conditions are set forth in Table 6, except that pools of degenerate primers are utilized instead of primers PLR4 forward (SEQ ID NO:109) and PLR6 reverse (SEQ ID NO:110).

In a further approach, cDNA molecules encoding a dirigent protein can be cloned by initially cloning a target population of cDNA molecules into a vector that includes binding sites for the T3 primer (SEQ ID NO:116) and the T7 primer (SEQ ID NO:117) flanking each cDNA insert. The cloned population of cDNA molecules is then utilized as template in a PCR reaction that utilizes either primer PS-6For (SEQ ID NO:120) or primer PS-2Rev (SEQ ID NO:121) and either the T3 primer (SEQ ID NO:116) or the T7 primer (SEQ ID NO:117). A representative PCR cycling regime is set forth as Program I in Table 5 above. Representative PCR reaction conditions are set forth in Table 6, except that primers PS-6For (SEQ ID NO:120) or primer PS-2Rev (SEQ ID NO:121) and either the T3 primer (SEQ ID NO:116) or the T7 primer (SEQ ID NO:117) are utilized instead of primers PLR4 forward (SEQ ID NO:109) and PLR6 reverse (SEQ ID NO:110).

Thus, in one aspect, the present invention provides isolated nucleotide sequences encoding dirigent proteins, the nucleotide sequences being capable of remaining hybridized to the antisense complement of a nucleotide sequence selected from the group consisting of SEQ ID NOS:12, 14, 16, 18, 20, 22, 28, 30, 32, 34, 77, 86, 93, 98 and 105 under wash conditions of 1xSSC at 58° C. The present invention also provides vectors, such as replicable expression vectors, that include one or more nucleic acid molecules of the invention, and host cells that include one or more vectors of the invention.

The present invention also provides methods of enhancing the expression of dirigent protein in a host cell. The methods of enhancing the expression of dirigent protein in a suitable host cell include the steps of (a) introducing into the host cell a replicable expression vector that comprises a nucleic acid sequence encoding a dirigent protein, the nucleic acid sequence being capable of remaining hybridized to the antisense complement of a nucleic acid sequence selected from the group consisting of SEQ ID NOS:12, 14, 16, 18, 20, 22, 28, 30, 32, 34, 77, 86, 93, 98 and 105 under stringent wash conditions, and (b) expressing the encoded dirigent protein.

The present invention also provides methods of inhibiting the expression of dirigent protein in a host cell. The methods include the steps of (a) introducing into the host cell a replicable vector that includes a nucleic acid sequence capable of hybridizing to a nucleic acid sequence selected from the group consisting of SEQ ID NOS:12, 14, 16, 18, 20, 22, 28, 30, 32, 34, 77, 86, 93, 98 and 105 under stringent wash conditions, and (b) transcribing the nucleic acid sequence.

In another aspect, the present invention provides methods of producing optically-pure lignans. The methods include the steps of (a) introducing into a host cell an expression vector that includes a nucleic acid sequence encoding a dirigent protein capable of directing a bimolecular phenoxy coupling reaction to produce an optically pure lignan, the nucleic acid sequence being capable of remaining hybridized to the antisense complement of a nucleic acid sequence selected from the group consisting of SEQ ID NOS:12, 14, 16, 18, 20, 22, 28, 30, 32, 34, 77, 86, 93, 98 and 105 under stringent wash conditions, (b) expressing the encoded dirigent protein and (c) purifying optically pure lignan from the host cell.

EXAMPLE 24

Cloning Additional Nucleic Acid Molecules That Encode a Pinoresinol/Lariciresinol Reductase Additional nucleic acid molecules encoding a pinoresinol/lariciresinol reductase can be cloned utilizing a variety of strategies. In one approach, a DNA probe is generated from cDNA or genomic DNA by PCR, and the probe is then used to screen a cDNA or genomic DNA library. Representative PCR reaction conditions are set forth in Table 6 below. The primers utilized are PLR4 forward (SEQ ID NO:109) and PLR6 reverse (SEQ ID NO:110)

TABLE 6

| Ingredients | Volume (μl) | Supplier |
|---|---|---|
| H₂O | 27.75 | |
| 25 mM MgCl₂ | 5.0 | Fischer Scientific |
| 10 X assay buffer: 100 mM Tris-HCl pH 8.3 (25° C.) 500 mM KCl | 5.0 | Fischer Scientific |
| Taq DNA polymerase | 0.125 | Fischer Scientific |
| dNTPs (20 mM) | 0.5 | Sigma |
| 10 X PLR4 forward (10 pmol/μl) (SEQ ID NO: 109) | 5.0 | Gibco BRL Life Technologies |
| 10 X PLR6 reverse (10 pmol/μl) (SEQ ID NO: 110) | 5.0 | Gibco BRL Life Technologies |
| Genomic/cDNA template (5 ng) | X | |
| Total volume | 45.0 | |

A representative PCR thermocycler program useful in this aspect of the invention is set forth in Table 7.

TABLE 7

| Temp. (° C.) | Time |
|---|---|
| 94 | 1 min |
| 37 | 1 min |
| 72 | 3 min |
| 5 cycles | |
| 94 | 25 sec |
| 48 | 1 min |
| 72 | 2 min |
| 25 cycles | |
| 72 | 10 min |
| 4 | hold |

The DNA fragment generated by the foregoing PCR reactions can be used as a probe to screen a cDNA or genomic DNA library in order to isolate a full-length, or substantially full-length, pinoresinol/lariciresinol reductase clone. Representative hybridization conditions are hybridization in 6×SSC, 5×Denhardt's and 0.5% SDS at 57° C. Representative wash conditions are one wash in 4×SSC, 0.5% SDS, at room temperature (typically 20° C. to 30° C.) for 5 minutes, followed by one wash in 2×SSC, 0.5% SDS at 57 ° C. for 20 minutes. An optional further wash can be conducted in 1×SSC, 0.5% SDS at 57° C. for 30 minutes, followed, if so desired, by an additional, optional, wash in 0.5×SSC, 0.5% SDS at 57° C. for 30 minutes.

In another approach, DNA molecules encoding a pinoresinol/lariciresinol reductase protein can be cloned from mRNA by RT-PCR, i.e., a PCR reaction that utilizes mRNA as the initial substrate. First-strand DNA is synthesized from the purified mRNA of interest. Purified mRNA (150 ng) is mixed with 1.4 μg linker-primer (5'-CTCGAGTTTTTTTTTTTT-3') (SEQ ID NO:122) from ZAP-cDNA® synthesis kit (Stratagene), heated to 70° C. for 10 min, and quickly chilled on ice. The mixture of denatured mRNA template and linker-primer (SEQ ID NO:122) is then mixed with First Strand Buffer (Life Technologies), 10 mM DTT, 0.5 mM each dNTP, and 200 units of SuperScript™ II (Life Technologies) in a final volume of 20 μl. The reaction is carried out at 42° C. for 50 minutes and then stopped by heating (70° C., 15 min). E. coli Rnase H (1.5 units, 1 μl) is added to the solution and incubated at 37° C. for 20 min.

The first-strand reaction (2 μl) is next used as the template in 100-μl PCR reactions (10 mM Tris-HCl, pH 9.0, 50 mM KCl, 0.1% Triton X-100, 1.5 mM MgCl₂, 0.2 mM each dNTP, and 5 units of Taq DNA polymerase) with primer CR6-NT (5'GCACATAAGAGTATGGATAAG3') (SEQ ID NO:60) (10 pmol) and primer XhoI-Poly(dT) (5'GTCTCGAGTTTTTTTTTTTTTTTTT3')(SEQ ID NO:59)(10 pmol). PCR amplification is carried out in a thermocycler as described in Dinkova-Kostova, A. T., et al., J. Biol. Chem. 271:29473–29482 (1996)(which publication is incorporated herein by reference), except for the annealing temperature at 52° C. In brief, the PCR amplification regime includes: 35 cycles, each cycle including one minute at 94° C., two minutes at 52° C., and three minutes at 72° C.; followed by 5 minutes at 72° C. and an indefinite hold at 4° C. after the final cycle. PCR products are resolved in 1.3% agarose gels to reveal a band of about 1,200-bp. The gel-purified PCR product (~50 ng) is then ligated into the pT7Blue T-vector (50 ng) and transformed into competent NovaBlue cells, according to Novagen's instructions. The inserted cDNA is next sequenced using overlapping sequencing primers.

The cDNA so obtained can be used to screen cDNA or genomic DNA libraries for full-length, or substantially full-length, pinoresinol/lariciresinol reductase clones. Representative hybridization conditions for screening cDNA or genomic DNA libraries are 6×SSC, 5×Denhardt's, 0.5% SDS at 57–58° C. Representative wash conditions are one wash in 4×SSC, 0.5% SDS at room temperature (typically 20° C. to 30° C.) for 5 minutes, followed by one wash in 2×SSC, 0.5% SDS at 57–58° C. for 20 minutes. An optional further wash can be conducted in 1×SSC, 0.5% SDS at 57–58° C. for 30 minutes, followed, if so desired, by an additional, optional, wash in 0.5×SSC, 0.5% SDS at 57–58° C. for 30 minutes.

In yet another approach, the entire Forsythia intermedia plr_Fi1 cDNA (SEQ ID NO:47) can be used as a probe to screen cDNA or genomic DNA libraries for full-length, or substantially full-length, pinoresinol/lariciresinol reductase clones. Representative hybridization conditions are 6×SSC, 5×Denhardt's, 0.5% SDS (Sigma) at 47° C. for 3 hours, followed by one wash at 6×SSC, 0.5% SDS (Sigma) at room temperature (typically 20° C. to 30° C.) for 3 minutes, then 4×SSC, 0.5% SDS (Sigma) at 47° C. for 2 minutes. An optional further wash can be conducted in 1×SSC, 0.5% SDS at 55° C. for 30 minutes, followed, if so desired, by an additional, optional, wash in 0.5×SSC, 0.5% SDS at 55° C. for 30 minutes.

Thus, in one aspect the present invention provides isolated nucleotide sequences encoding pinoresinol/lariciresinol reductase proteins, the nucleotide sequences being capable of remaining hybridized to the antisense complement of a nucleotide sequence selected from the group consisting of SEQ ID NOS:47, 49, 51, 53, 55, 57, 61, 63, 65, 67, 69, 71, 107 and 117 under wash conditions of 1×SSC at 55° C. The present invention also provides vectors, such as replicable expression vectors, that include one or more nucleic acid molecules of the invention, and host cells that include one or more vectors of the invention.

The present invention also provides methods of enhancing the expression of pinoresinol/lariciresinol reductase protein in a host cell. The methods include the steps of (a) introducing into the host cell a replicable expression vector comprising a nucleic acid sequence encoding a pinoresinol/lariciresinol reductase protein, said nucleic acid sequence being capable of remaining hybridized to the antisense complement of a nucleotide sequence selected from the group consisting of SEQ ID NOS:47, 49, 51, 53, 55, 57, 61, 63, 65, 67, 69, 71, 107 and 117, under stringent wash conditions, and (b) expressing the encoded pinoresinol/lariciresinol reductase protein.

The present invention also provides methods of inhibiting the expression of pinoresinol/lariciresinol reductase protein in a host cell. The methods include the steps of (a) introducing into the host cell a replicable vector that comprises a nucleic acid sequence capable of remaining hybridized to a nucleic acid sequence selected from the group consisting of SEQ ID NOS:47, 49, 51, 53, 55, 57, 61, 63, 65, 67, 69, 71, 107 and 117 under stringent wash conditions and (b) transcribing said nucleic acid sequence.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated nucleotide sequence encoding a dirigent protein, wherein said nucleotide sequence hybridizes to a nucleotide sequence selected from the group consisting of SEQ ID NOS: 12, 14, 16, 18, 20, 22, 28, 30, 32, 34, 98, and 105, or to the antisense complement of a nucleotide sequence selected from the group consisting of SEQ ID NOS: 12, 14, 16, 18, 20, 22, 28, 30, 32, 34, 98, and 105, under stringent wash conditions.

2. An isolated nucleotide sequence of claim 1, wherein said isolated nucleotide sequence hybridizes to a nucleotide sequence selected from the group consisting of SEQ ID NO:12 and SEQ ID NO:14, or to the antisense complement of a nucleotide sequence selected from the group consisting of SEQ ID NO:12 and SEQ ID NO:14, under stringent wash conditions.

3. An isolated nucleotide sequence of claim 2 wherein said nucleotide sequence encodes an amino acid sequence selected from the group consisting of SEQ ID NO:13 and SEQ ID NO:15.

4. An isolated nucleotide sequence of claim 2 consisting of a nucleotide sequence selected from the group consisting of SEQ ID NO:12 and SEQ ID NO:14.

5. An isolated nucleotide sequence of claim 1, wherein said isolated nucleotide sequence hybridizes to a nucleotide sequence selected from the group consisting of SEQ ID NO:16 and SEQ ID NO:18, or to the antisense complement of a nucleotide sequence selected from the group consisting of SEQ ID NO:16 and SEQ ID NO:18, under stringent wash conditions.

6. An isolated nucleotide sequence of claim 5 wherein said nucleotide sequence encodes an amino acid sequence selected from the group consisting of SEQ ID NO:17 and SEQ ID NO:19.

7. An isolated nucleotide sequence of claim 5 consisting of a nucleotide sequence selected from the group consisting of SEQ ID NO:16 and SEQ ID NO:18.

8. An isolated nucleotide sequence of claim 1, wherein said isolated nucleotide sequence hybridizes to a nucleotide sequence selected from the group consisting of SEQ ID NOS:20, 22, 28, 30, 32, and 34, or to the antisense complement of a nucleotide sequence selected from the group consisting of SEQ ID NOS:20, 22, 28, 30, 32, and 34, under stringent wash conditions.

9. An isolated nucleotide sequence of claim 8 wherein said nucleotide sequence encodes an amino acid sequence selected from the group consisting of SEQ ID NOS:21, 23, 29, 31, 33, 35, 78, 87 and 94.

10. An isolated nucleotide sequence of claim 8 consisting of a nucleotide sequence selected from the group consisting of SEQ ID NOS:20, 22, 28, 30, 32, 34, 77, 86 and 93.

11. An isolated nucleotide sequence of claim 1, wherein said isolated nucleotide sequence hybridizes to the nucleotide sequence of SEQ ID NO:98, or to the antisense complement of the nucleotide sequence of SEQ ID NO:98, under stringent wash conditions.

12. An isolated nucleotide sequence of claim 11 wherein said nucleotide sequence encodes the amino acid sequence of SEQ ID NO:99.

13. An isolated nucleotide sequence of claim 11 wherein said nucleotide sequence consists of the nucleotide sequence of SEQ ID NO:98.

14. An isolated nucleotide sequence of claim 1, wherein said isolated nucleotide sequence hybridizes to the nucleotide sequence of SEQ ID NO:105, or to the antisense complement of the nucleotide sequence of SEQ ID NO:105, under stringent wash conditions.

15. An isolated nucleotide sequence of claim 14 wherein said nucleotide sequence encodes the amino acid sequence of SEQ ID NO:106.

16. An isolated nucleotide sequence of claim 14 wherein said nucleotide sequence consists of the nucleotide sequence of SEQ ID NO:105.

17. A double stranded nucleic acid molecule encoding a dirigent protein, said double stranded nucleic acid molecule comprising a coding strand and a complementary non-coding strand, wherein the coding strand hybridizes to the oligonucleotide molecule of SEQ ID NO:120 in 50 mM KCL at 60° C., and the non-coding strand hybridizes to the oligonucleotide molecule of SEQ ID NO:121 in 50 mM KCL at 60° C.

18. An isolated nucleotide sequence encoding a dirigent protein, wherein said isolated nucleotide sequence hybridizes to the antisense complement of a nucleotide sequence selected from the group consisting of SEQ ID NOS:12, 14, 16, 18, 20, 22, 28, 30, 32, 34, 98 and 105 under wash conditions of 1×SSC at 58° C.

19. A replicable vector comprising a nucleotide sequence encoding a dirigent protein, wherein said nucleotide sequence hybridizes to a nucleotide sequence selected from the group consisting of SEQ ID NOS: 12, 14, 16, 18, 20, 22, 28, 30, 32, 34, 98, and 105, or to the antisense complement of a nucleotide sequence selected from the group consisting of SEQ ID NOS: 12, 14, 16, 18, 20, 22, 28, 30, 32, 34, 98, and 105, under stringent wash conditions.

20. A replicable vector of claim 19 wherein said nucleotide sequence hybridizes to a nucleotide sequence selected from the group consisting of SEQ ID NO:12 and SEQ ID NO:14, or to the antisense complement of a nucleotide sequence selected from the group consisting of SEQ ID NO:12 and SEQ ID NO:14, under stringent wash conditions.

21. A replicable vector of claim 19 wherein said nucleotide sequence hybridizes to a nucleotide sequence selected from the group consisting of SEQ ID NO:16 and SEQ ID NO:18, or to the antisense complement of a nucleotide sequence selected from the group consisting of SEQ ID NO:16 and SEQ ID NO:18, under stringent wash conditions.

22. A replicable vector of claim 19 wherein said nucleotide sequence hybridizes to a nucleotide sequence selected from the group consisting of SEQ ID NOS:20, 22, 28, 30, 32, and 34, or to the antisense complement of a nucleotide sequence selected from the group consisting of SEQ ID NOS:20, 22, 28, 30, 32, and 34, under stringent wash conditions.

23. A replicable vector comprising a nucleotide sequence encoding a dirigent protein comprising an amino acid sequence selected from the group consisting of SEQ ID NO:78, 87 and 94.

24. A replicable vector of claim 23 wherein said nucleotide sequence encoding a dirigent protein is selected from the group consisting of SEQ ID NO:77, 86 and 93.

25. A replicable vector of claim 19 wherein said nucleotide sequence hybridizes to the nucleotide sequence of SEQ ID NO:98, or to the antisense complement of the nucleotide sequence of SEQ ID NO:98, under stringent wash conditions.

26. A replicable vector of claim 19 wherein said nucleotide sequence hybridizes to the nucleotide sequence of SEQ ID NO:105, or to the antisense complement of the nucleotide sequence of SEQ ID NO:105, under stringent wash conditions.

27. A host cell comprising a replicable vector comprising a nucleotide sequence encoding a dirigent protein, wherein said nucleotide sequence hybridizes to a nucleotide sequence selected from the group consisting of SEQ ID NOS: 12, 14, 16, 18, 20, 22, 28, 30, 32, 34, 98, and 105, or to the antisense complement of a nucleotide sequence selected from the group consisting of SEQ ID NOS: 12, 14, 16, 18, 20, 22, 28, 30, 32, 34, 98, and 105, under stringent wash conditions.

28. A host cell of claim 27 wherein said nucleotide sequence hybridizes to a nucleotide sequence selected from the group consisting of SEQ ID NO:12 and SEQ ID NO:14, or to the antisense complement of a nucleotide sequence selected from the group consisting of SEQ ID NO:12 and SEQ ID NO:14, under stringent wash conditions.

29. A host cell of claim 27 wherein said nucleotide sequence hybridizes to a nucleotide sequence selected from the group consisting of SEQ ID NO:16 and SEQ ID NO:18, or to the antisense complement of a nucleotide sequence selected from the group consisting of SEQ ID NO:16 and SEQ ID NO:18, under stringent wash conditions.

30. A host cell of claim 27 wherein said nucleotide sequence hybridizes to a nucleotide sequence selected from the group consisting of SEQ ID NOS:20, 22, 28, 30, 32, and 34, or to the antisense complement of a nucleotide sequence selected from the group consisting of SEQ ID NOS:20, 22, 28, 30, 32, and 34, under stringent wash conditions.

31. A host cell comprising a replicable vector of claim 23.

32. A host cell comprising a replicable vector of claim 24.

33. A host cell of claim 27 wherein said nucleotide sequence hybridizes to the nucleotide sequence of SEQ ID NO:98, or to the antisense complement of the nucleotide sequence of SEQ ID NO:98, under stringent wash conditions.

34. A host cell of claim 27 wherein said nucleotide sequence hybridizes to the nucleotide sequence of SEQ ID NO:105, or to the antisense complement of the nucleotide sequence of SEQ ID NO:105, under stringent wash conditions.

35. A method of expressing of dirigent protein in a suitable host cell comprising introducing into the host cell a replicable expression vector that comprises a nucleic acid sequence encoding a dirigent protein, wherein said nucleic acid sequence hybridizes to the antisense complement of a nucleic acid sequence selected from the group consisting of SEQ ID NOS:12, 14, 16, 18, 20, 22, 28, 30, 32, 34, 98 and 105, under stringent wash conditions, and expressing said encoded dirigent protein.

36. A method of producing a dirigent protein comprising culturing a host cell of claim 27, under conditions suitable for expression of the dirigent protein by the host cell, and then recovering the dirigent protein.

37. A method of producing a dirigent protein comprising culturing a host cell of claim 31 under conditions suitable for expression of the dirigent protein by the host cell, and then recovering the dirigent protein.

38. A method of producing a dirigent protein comprising culturing a host cell of claim 32 under conditions suitable for expression of the dirigent protein by the host cell, and then recovering the dirigent protein.

* * * * *

UNITED STATES PATENT AND TRADEMARK OFFICE
CERTIFICATE OF CORRECTION

PATENT NO. : 6,210,942 B1
DATED : April 3, 2001
INVENTOR(S) : N.G. Lewis et al.

It is certified that error appears in the above-identified patent and that said Letters Patent is hereby corrected as shown below:

Column 1,
Lines 16-26, reads
"GOVERNMENT RIGHTS
This invention was funded in part by grant number DE-FG03-97ER20259 from the United States Department of Energy, by grant number MCB09631980 from the National Science Foundation, by grant number NAG100164 from the National Aeronautics and Space Administration, and by grant number 96-35103-3358 from the United States Department of Agriculture. The government has certain rights in this invention." should read
-- GOVERNMENT RIGHTS
This invention was funded in part by grant numbers DE-FG03-97ER20259 and DE-FG06-91ER20022 from the United States Department of Energy, by grant numbers MCB09631980 and MCB-9219586 from the National Science Foundation, by grant number NAG100164 from the National Aeronautics and Space Administration, and by grant numbers 96-35103-3358 and 91-3710-36638 from the United States Department of Agriculture. The government has certain rights in this invention. --

Signed and Sealed this

Seventh Day of May, 2002

Attest:

Attesting Officer

JAMES E. ROGAN
Director of the United States Patent and Trademark Office